US012163140B2

(12) United States Patent
Zhou et al.

(10) Patent No.: US 12,163,140 B2
(45) Date of Patent: Dec. 10, 2024

(54) NUCLEOTIDE SEQUENCES AND CORRESPONDING POLYPEPTIDES CONFERRING MODULATED GROWTH RATE AND BIOMASS IN PLANTS GROWN IN SALINE CONDITIONS

(71) Applicant: CERES, INC., Thousand Oaks, CA (US)

(72) Inventors: Fasong Zhou, Oxnard, CA (US); Kenneth A. Feldmann, Tucson, AZ (US); Julissa Sosa, Northridge, CA (US)

(73) Assignee: Ceres, Inc., Thousand Oaks, CA (US)

( * ) Notice: Subject to any disclaimer, the term of this patent is extended or adjusted under 35 U.S.C. 154(b) by 0 days.

(21) Appl. No.: 18/495,560

(22) Filed: Oct. 26, 2023

(65) Prior Publication Data

US 2024/0102041 A1 Mar. 28, 2024

Related U.S. Application Data

(62) Division of application No. 17/831,156, filed on Jun. 2, 2022, now Pat. No. 11,840,699, which is a division of application No. 17/002,713, filed on Aug. 25, 2020, now Pat. No. 11,421,245, which is a division of application No. 16/554,199, filed on Aug. 28, 2019, now Pat. No. 10,968,461, which is a division of application No. 16/275,537, filed on Feb. 14, 2019, now Pat. No. 10,428,346, which is a division of application No. 15/487,287, filed on Apr. 13, 2017, now Pat. No. 10,233,460, which is a division of application No. 13/663,204, filed on Oct. 29, 2012, now Pat. No. 9,637,756, which is a division of application No. 12/282,342, filed as application No. PCT/US2007/006544 on Mar. 14, 2007, now Pat. No. 8,324,454.

(60) Provisional application No. 60/782,735, filed on Mar. 14, 2006.

(51) Int. Cl.
| | |
|---|---|
| *C12N 15/82* | (2006.01) |
| *A23K 10/30* | (2016.01) |
| *A23L 19/00* | (2016.01) |
| *C07K 14/415* | (2006.01) |
| *C12N 9/88* | (2006.01) |

(52) U.S. Cl.
CPC ......... *C12N 15/8273* (2013.01); *A23K 10/30* (2016.05); *A23L 19/00* (2016.08); *C07K 14/415* (2013.01); *C12N 9/88* (2013.01); *C12N 15/8261* (2013.01); *C12Y 208/02015* (2013.01); *A23V 2002/00* (2013.01); *Y02A 40/146* (2018.01)

(58) Field of Classification Search
None
See application file for complete search history.

(56) References Cited

U.S. PATENT DOCUMENTS

| | | | |
|---|---|---|---|
| 6,281,411 B1 | 6/2001 | Adams et al. | |
| 8,222,482 B2 | 7/2012 | Bobzin et al. | |
| 8,324,454 B2 | 12/2012 | Zhou et al. | |
| 9,637,756 B2 | 5/2017 | Zhou et al. | |
| 10,233,460 B2 | 3/2019 | Zhou et al. | |
| 10,428,346 B2 | 10/2019 | Zhou et al. | |
| 10,696,978 B2 | 6/2020 | Zhou et al. | |
| 10,968,461 B2 | 4/2021 | Zhou et al. | |
| 11,421,244 B2 | 8/2022 | Zhou et al. | |
| 11,421,245 B2 | 8/2022 | Zhou et al. | |
| 11,466,284 B2 | 10/2022 | Zhou et al. | |
| 11,655,479 B2 | 5/2023 | Zhou et al. | |
| 11,814,636 B2 | 11/2023 | Zhou et al. | |
| 11,840,699 B2 | 12/2023 | Zhou et al. | |
| 2002/0016980 A1 | 2/2002 | Alberte et al. | |
| 2007/0039067 A1 | 2/2007 | Feldmann et al. | |
| 2009/0324797 A1 | 12/2009 | Bobzin et al. | |
| 2015/0259699 A1* | 9/2015 | Nadzan ............... | C07K 14/415 800/267 |
| 2016/0369294 A9 | 12/2016 | Nadzan et al. | |
| 2020/0297716 A1 | 9/2020 | Zhou et al. | |
| 2020/0299715 A1 | 9/2020 | Zhou et al. | |
| 2021/0254089 A1 | 8/2021 | Zhou et al. | |
| 2022/0403405 A1 | 12/2022 | Zhou et al. | |
| 2024/0102040 A1 | 3/2024 | Zhou et al. | |

FOREIGN PATENT DOCUMENTS

| | | | | |
|---|---|---|---|---|
| EP | | 1033405 A2 * | 9/2000 | ............ C07H 21/04 |
| WO | WO 99/61616 A2 | | 12/1999 | |
| WO | WO 2004/092326 A2 | | 10/2004 | |

(Continued)

OTHER PUBLICATIONS

Wells (Biochemistry 29:8509-8517, 1990).*
Guo et al. (PNAS, 101: 9205-9210, 2004 ).*
Ngo et al., (The Protein Folding Problem and Tertiary Structure Prediction, K. Merz., and S. Le Grand (eds.) pp. 492-495, 1994).*
Thornton et al. (Nature structural Biology, structural genomics supplement, Nov. 2000).*
Keskin et al. (Protein Science, 13:1043-1055, 2004).*
Doerks et al., (TIG, 14:248-250, 1998).*
Smith et al. (Nature Biotechnology, 15:1222-1223, 1997).*
Bork et al. (TIG, 12:425-427, 1996).*
U.S. Appl. No. 17/170,347, filed Feb. 8, 2021, Zhou et al.
U.S. Appl. No. 17/831,146, filed Jun. 2, 2022, Zhou et al.

(Continued)

*Primary Examiner* — Vinod Kumar
(74) *Attorney, Agent, or Firm* — Dentons US LLP

(57) ABSTRACT

The present invention relates to isolated nucleic acid molecules and their corresponding encoded polypeptides able confer the trait of improved plant size, vegetative growth, growth rate, seedling vigor and/or biomass in plants challenged with saline conditions. The present invention further relates to the use of these nucleic acid molecules and polypeptides in making transgenic plants, plant cells, plant materials or seeds of a plant having plant size, vegetative growth, growth rate, seedling vigor and/or biomass that are improved in saline conditions with respect to wild-type plants grown under similar conditions.

15 Claims, 16 Drawing Sheets

Specification includes a Sequence Listing.

(56) References Cited

FOREIGN PATENT DOCUMENTS

WO    WO 2004/092326 A3    10/2004

OTHER PUBLICATIONS

Bustos et al. "Regulation of beta-glucuronidase expression in transgenic tobacco plants by an A/T-rich, cis-acting sequence," *Plant Cell*; 1(9);839-853; 1989.

Guo et al., "Protein tolerance to random amino acid change," PNAS 101:9205-9210; 2004.

Keskin et al. A new, structurally nonredundant, diverse data set of protein-protein interfaces and its implications; *Protein Sci*; 13:1043-1055; 2004.

Klein et al., The multi-protein family of *Arabidopsis sulphotransferases* and their relatives in other plant species; *J of Experimental Botarny*; vol. 55; No. 404; 2004.

Maniatis et al.; Molecular Cloning: A laboratory manual, Cold Spring Harbor Laboratory; 1982.

Ngo et al., "Computational Complexity, Protein Structure Prediction, and the Levinthal Paradox," *The Protein Folding Problem and Tertiary Structure Prediction*; pp. 492-495; 1994.

Rabbani et al., "Monitoring Expression Profiles of Rice Genes under Cold, Drought, and High-Salinity Stresses and Abscisic Acid Application Using cDNA Microarray and RNA Gel-Blot Analyses," *Plant Physio*; vol. 133; pp. 1755-1767; 2003.

Thornton et al.; "From structure to function: Approaches and limitations," Nature Structural Biology, Structural Genomics supplement; Nov. 2000.

Wells, "Additivity of Mutational Effects in Proteins," *Biochemistry* 29:8509-8517; 1990.

Yamamoto et al., "The Promoter of a Pine Photosynthetic Gene Allows Expression of a β-Glucuronidase Reporter Gene in Transgenic Rice Plants in a Light-Independent but Tissue-Specific Manner," *Plant Cell Physiol* 35: 773-778; 1995.

NCBI GenBank Accession No. NP_179785; Aug. 21, 2001.
NCBI GenBank Accession No. NP_565906; Jan. 29, 2002.
NCBI GenBank Accession No. NP_565305; Jan. 29, 2002.
NCBI GenBank Accession No. NP_567957; Jan. 30, 2002.
NCBI GenBank Accession No. NP_566785; Jan. 29, 2002.
NCBI GenBank Accession No. NP_567754; Jan. 29, 2002.
NCBI GenBank Accession No. NM_129505; Aug. 21, 2001.
NCBI GenBank Accession No. NM_119581, Jan. 30, 2002.
NCBI GenBank Accession No. BT018295; Oct. 27, 2004.
NCBI GenBank Accession No. NM_127763; Nov. 4, 2005.
NCBI GenBank Accession No. BT003928; Feb. 14, 2003.
NCBI GenBank Accession No. AY086786; Jan. 27, 2006.
NCBI GenBank Accession No. AY092961; Apr. 21, 2002.
NCBI GenBank Accession No. AF410323; Aug. 27, 2001.

Bork et al., Go hunting is sequence databases but watch for traps, TIG 12(10):425-427, 1996.

Doerks et al., Protein annotation: detective work for function prediction, TIG 14(6): 248-250, 1998.

Hirschmann et al., The multi-protein family of sulfotransferases in plants: composition, occurrence, substrate specificity, and functions, Frontiers in Plant Science 5:1-13, 2014.

Smith et al., The challenges of genome sequence annotation or "The devil is in the details," Nature Biotechnology 15:1222-1223, 1997.

Wang et al., STV11 encodes a sulphotransferase and confers durable resistance to rice stripe virus, Nature Communications DOI:10:1038/ncomms5768, 2014.

GenBank Accession No. AY099809.1, dated May 6, 2002.

Kang et al., AtBAG6, a novel calmodulin-binding protein, induces programmed cell death in yeast and plants, Cell Death and Differentiation 13:84-95, 2006.

Rhoads and Friedberg, Sequence motifs for calmodulin recognition, FASEB J. 11:331-340, 1997.

U.S. Appl. No. 18/483,428, filed Oct. 9, 2023, Zhou, et al.

\* cited by examiner

| SEQ ID NO | | | | | |
|---|---|---|---|---|---|
| SEQ ID NO:90-CLONE-554272 | VENTDI KLV | GI DYLSVAAY | DHIT PAHLVF | KGREIT LVE | GLKLDDVAAG | 226 |
| SEQ ID NO:92-CLONE-881632 | LVDNTDI KLV | GI DYLSVAAF | DDLI PSHLVL | ENRDI LVE | GLKLENVI PG | 240 |
| SEQ ID NO:93-GI-50944095 | LVDNTDI KLV | GI DYLSVAAF | DDLI PSHLVL | KNRDI LVE | GLKLENI MPG | 244 |
| SEQ ID NO:80-CLONE-8686 | LVENTDI KLI | GLDYLSFAAF | EESPAT HRVI | KGRDI FVE | ALKLDGVEVG | 230 |
| SEQ ID NO:84-CLONE-954851 | LVENTDI KLI | GLDYLSFAAY | EEAPEI HKFI | GERDI I PVE | ALKLDGVEVG | 208 |
| SEQ ID NO:85-CLONE-1064137 | LVDNTDI KLV | SVDYLSVAAY | DDLI PSHLVF | KGREFI LVE | GLKLDDVKAG | 245 |
| SEQ ID NO:95-ANNOT-1494052 | LVDNTDI KLV | GI DYLSVAAW | SDLI PSHLVF | EGREIT LVE | ALKLDDI QPG | 249 |

| SEQ ID NO:90-CLONE-554272 | YTVHCLPLR | LAGAEGSPI R | CI LI K | 251 |
| SEQ ID NO:92-CLONE-881632 | YSLHCLPLR | LRCAEGSPI R | CI LI K | 265 |
| SEQ ID NO:93-GI-50944095 | YSLHCLPLR | LRCAEGSPI R | CI LI K | 269 |
| SEQ ID NO:80-CLONE-8686 | TYSLHCLPLR | LVGAEGAPI R | CI LI K | 255 |
| SEQ ID NO:84-CLONE-954851 | VYSLHCLPLR | LPCAEGAPI R | CI LI K | 233 |
| SEQ ID NO:85-CLONE-1064137 | VYSVHCLPLR | LVGAEGSPI R | CI LI 6 | 271 |
| SEQ ID NO:95-ANNOT-1494052 | VYSVHCLPLR | LF GAEGSPI R | CVLI K | 274 |

Figure 2

```
SEQ-ID-252:                     MGKRGKWFSA VKKVFSSSDP DGKEEAKAQKA DKSKSKRRWP FGKSKHSEPS  50
SEQ-ID-NO-301-CLONE-228069      MCKKCKWF GA VKKVFSPESK EKKEERL----  ---------- ---KSAASNPA  37
SEQ-ID-NO-302-CLONE-335348      MGKKGKWF GA VKKVFSPESK EKKEE------ ---------- ---------- 25
SEQ-ID-NO-100-GI-56202321       MGKKGMFSA VKKVFSSSDP DGREAK---EKA ---------- KMPFGKSK  45
SEQ-ID-NO-303-GI-54306075       MGKKGKWF GA VKKVFSPESK EKKEERL---- ---------RR ---KLAASNPN  37
SEQ-ID-NO-312-CLONE-1727738     MGKKGKWF GA VKKVFSPESK EKKEERQ---- ---------RR ---KSAASNPT  37
SEQ-ID-NO-298-CLONE-1792902     MGKKGKWF GA VKKVFSPESK EKKEERQ---- ---------RR ---KSAASNPT  37

SEQ-ID-252:                     -ISTVPGITAP AVA--PLPSPP A--------- -QPHSLEIKDI VNPVETDSEQ  89
SEQ-ID-NO-301-CLONE-228069      PVDLTPSTL EE EVNVSVPPPP A--T------ -PPVPRQIFDE VRVPEAEQEQ  78
SEQ-ID-NO-302-CLONE-335348      ---------- ---------- ---------- ---------- ---------- 25
SEQ-ID-NO-100-GI-56202321       KSDPWTSTL-V AVPTSTAPPP QPPPPPPTHP IQPPPEETKD VKAVETDSEQ  94
SEQ-ID-NO-303-GI-54306075       PPDLTPSASL EVNVSVPPPP P--P------ PPVQQIEE VKVPEVEQEQ  77
SEQ-ID-NO-312-CLONE-1727738     PRDLTPSTL EE EVNVSVPPPP A--P------ PALHQIEE RAPEAEQEQ  77
SEQ-ID-NO-298-CLONE-1792902     PJDLTPSTL EE EVNVSVPPPP A--P------ PALHQIKE VRIPEAEQEQ  77

SEQ-ID-252:                     NKHAYSVALA SA---VAAEA AAVAAQAAAE VVRLTAVTTA APKMPVSSRE  136
SEQ-ID-NO-301-CLONE-228069      SKHVT--LEEA PAAAAPAQA ---------- ----SV---- --PPGAPTE  107
SEQ-ID-NO-302-CLONE-335348      ---------- ---------- ---------- ---------- ---------- 25
SEQ-ID-NO-100-GI-56202321       NKHAYSVALA SA---VAAEA AAVAAQAAAE VVRLTTATTA VPKSPVSSKD  141
SEQ-ID-NO-303-GI-54306075       SKHVT--VEAV PEAVPVPAQI ---------- ----SS---- --PPGVSRE  106
SEQ-ID-NO-312-CLONE-1727738     SKHVT--VEEA PA---APAQA ---------- ----SV---- --PPGVPSE  103
SEQ-ID-NO-298-CLONE-1792902     SKHIT--VEEA PA---APAQA ---------- ----SV---- --PPGVPSE  103

SEQ-ID-252:                     ELAAIKIQTA FRGYLARRAL RALRGLVRLK SLVDGNAVKR QTAHFLQCIQ  186
SEQ-ID-NO-301-CLONE-228069      ELAAIKIQTA FRGYLARRAL RALRGLVRLK SLVEGNSVKR QSASTLRCMQ  157
SEQ-ID-NO-302-CLONE-335348      ---------- ---------- ---------- ---------- ---------- 25
SEQ-ID-NO-100-GI-56202321       ELAAIKIQTA FRGYLARRAL RALRGLVRLK SLVDGNAVKR QTAHFLHCIQ  191
SEQ-ID-NO-303-GI-54306075       ELAAIKIQTA FRGYLARRAL RALRGLVRLK SLVEGNSVKR QASTLRCMQ  156
SEQ-ID-NO-312-CLONE-1727738     ELAAIKIQTA FRGYLARRAL RALRGLVRLK SLVEGDSVRR QSASTLRCMQ  153
SEQ-ID-NO-298-CLONE-1792902     ELAAIKIQTA FRGYLARRAL RALRGLVRLK SLVEGDSVRR QSASTLRCMQ  153
```

Figure 2 - continued

| | | | | | |
|---|---|---|---|---|---|
| SEQ:ID-252 | AMTRVQTQIY | SRRVKLEEEK | QALQRQLQLK | HQRELEKMKI | DEDWDHSHQS | 236 |
| SEQ-ID-NO-301-CLONE-228069 | LSRVQSQIR- | SRRVKMEEEK | QALQRQLLLK | —QELENFRM | GENWDDSTQS | 205 |
| SEQ-ID-NO-302-CLONE-335348 | — | — | — | — | — | 25 |
| SEQ-ID-NO-100-GI-56202321 | NTRVQTQIY- | SRRLKMSEEN | QALQRQLLLK | HQRELEKMKI | DEDWDHSHQS | 241 |
| SEQ-ID-NO-303-GI-54306075 | LARVQSQIR- | SRRAKMSEEN | QALQRQLLLK | —QELESLRM | GENWDDSTQS | 204 |
| SEQ-ID-NO-312-CLONE-1727738 | LSRVQSQIR- | SRRAKMSEEN | QALQRQLLLK | —QELENFRM | GENWDDSTQS | 201 |
| SEQ-ID-NO-298-CLONE-1792902 | LSRVQSQIR- | SRRAKMSEEN | QALQRQLLLK | —QELENFRM | GENWDDSTQS | 201 |

| | | | | | |
|---|---|---|---|---|---|
| SEQ:ID-252 | KEQIEANLMM | RQEAALRRER | ALAYAFSHQW | RNSGRTITPT | FLEPGNPNWG | 286 |
| SEQ-ID-NO-301-CLONE-228069 | KEQIEASLIS | RQEAAIRRER | ALAYAFSHQW | KSTSRSANPM | FVDPNNLQWG | 255 |
| SEQ-ID-NO-302-CLONE-335348 | — | — | — | — | — | 25 |
| SEQ-ID-NO-100-GI-56202321 | KEQVEISLMM | RQEAAVRRER | ALAYAFSHQW | KNSGRTITPT | FLDQGNPNWG | 291 |
| SEQ-ID-NO-303-GI-54306075 | KEQIEASLIS | RQEAAIRRER | ALAYAFSHQW | KSTSRSVNPM | FVDPNNPQWG | 254 |
| SEQ-ID-NO-312-CLONE-1727738 | KEQIEASLIS | RQEAAIRRER | ALAYAFSHQW | KSTSRSVNPM | FVDPNNLQWG | 251 |
| SEQ-ID-NO-298-CLONE-1792902 | KEQIEASLIS | RQEAAIRRER | ALAYAFSHQW | KSTSRSVNPM | FVDPNNLQWG | 251 |

| | | | | | |
|---|---|---|---|---|---|
| SEQ:ID-252 | MSWMERWMIR | RPWESRLAAA | SDKDP-KERA | VTKNASTSA- | —YRVPVSRA | 333 |
| SEQ-ID-NO-301-CLONE-228069 | MSWLERWMAA | KPWEGRNG— | DKESNIDRG | SVKNMSLNL- | VGEGEITKAF | 303 |
| SEQ-ID-NO-302-CLONE-335348 | — | — | SNIDRG | SVKSMSLNL- | —GEGEITKAF | 49 |
| SEQ-ID-NO-100-GI-56202321 | MSWMERWMIS | RPWESRM— | SDKDP-KIDHY | STKNPSTSA- | SRTYVPRAI | 336 |
| SEQ-ID-NO-303-GI-54306075 | MSWLERWMAA | KPWEGRAG— | DKESNLDRA | SAKSASLNL- | —GEGEITKAF | 300 |
| SEQ-ID-NO-312-CLONE-1727738 | MSWLERWMAA | KPWEGCNG— | ADKESNIDRG | SVKSMSLNL- | —GEGEITKAF | 297 |
| SEQ-ID-NO-298-CLONE-1792902 | MSWLERWMAA | KPWEGRNG— | TDKESNVDRG | SVKSMSLNL- | —GEGEITKAF | 297 |

| | | | | | |
|---|---|---|---|---|---|
| SEQ:ID-252 | —SIQRPI | ATPN-KSSRP | PSRQSLSTPP | SKITPSASGKA | RPASPRNSWL | 377 |
| SEQ-ID-NO-301-CLONE-228069 | NRRDSKPEKP | SPPTPKPARP | ASRQSPSTPS | ARVAPIPARR | KSSTPKNGLS | 353 |
| SEQ-ID-NO-302-CLONE-335348 | —EKPI | SPPTPRPARP | TSRQSPLTPS | ARVAPIPARR | KSWTPKNGLS | 99 |
| SEQ-ID-NO-100-GI-56202321 | —SIQRPI | ATPN-KSSRP | PSRQSPSTPP | SRVPSWTGK | RPASPRDSWL | 380 |
| SEQ-ID-NO-303-GI-54306075 | NRRGSKPDKS | SPPTPKLTRP | ASRQSPSTPS | AKVSPIFAKK | KSATPENGLS | 350 |
| SEQ-ID-NO-312-CLONE-1727738 | NRRDSKPEKP | SPPTPKLTRP | ASRQSPSTPS | AKVAPIPARR | KSATPENGLS | 347 |
| SEQ-ID-NO-298-CLONE-1792902 | NRRDSKPEKP | SPPTPKLTRP | ASRQSPSTPS | AKVAPIPVRR | KSWTPKNGLS | 347 |

Figure 2 - continued

```
SEQ-ID-252              MKEDDLRSIT SIRSERPRRQ SIGG-GSVRD DISLISTPPL PSYMQSIIESA  426
SEQ-ID-NO-301-CLONE-228069  QVDDDMRSVL SVQSERPRRH SIATISTMRD DESLASSPSL PSYMVPTESA  403
SEQ-ID-NO-302-CLONE-335348  QVDDDARSVL SVQSERPRRH SIATISTVRD DESLISSPSL PSYMVPTESA  148
SEQ-ID-NO-100-GI-56202321   SIRSERPRRQ SIRSERPRRQ SIATISTVRD DASLISTPAL PSYMQSIIESA  429
SEQ-ID-NO-303-GI-54306075   QVDDDAKSVF SVQSERPRRH SIEG-ASVRD DESLASSPSV PSYMAPTKSA  399
SEQ-ID-NO-312-CLONE-1727738 HVDDDARSVF SVQSERPRRH SIATISTVQD NESLASSPSL PSYMVPTESA  396
SEQ-ID-NO-298-CLONE-1792902 HVDDDARSVF SVQSERPRRH SIATISTVRD DESLASSPSL PSYMVPTESA  396

SEQ-ID-252              RAKSRMRSLL LTEKLEMPLE RAPLAHSVVK KRLSFPVVEK PSVVPTEKPR  475
SEQ-ID-NO-301-CLONE-228069  RAKSRL---A TANGAETPLE KGGSA-GPVK KRLSFQGGIA A         440
SEQ-ID-NO-302-CLONE-335348  RAKSRLQGSA MANGAETPLE KGGSIT-GPAK KRLSFQGGIA A         188
SEQ-ID-NO-100-GI-56202321   RAKSRPRSL  LTDRFEKPLE RVPLVHSSIK KRLSFPVADK PNGEHADKLM  477
SEQ-ID-NO-303-GI-54306075   RAKLRLQGSA VTDGAETPPE KVASV-GSVK KKLSFQAGMA P         440
SEQ-ID-NO-312-CLONE-1727738 RAKSRLQGSA LTNGAETPLE KGSSA-GPVK KRLSFQGGIA A         436
SEQ-ID-NO-298-CLONE-1792902 RAKSRLQGSA LNGAETPLE  KGSSA-GPVK KRLSFQGGIA A         436

SEQ-ID-252              ERVRRHSDPP KVDPATLKDA                     PAA ANG-GSK  498
SEQ-ID-NO-301-CLONE-228069  SPMRRHSGPP KVESA-VKDI APPQPEALV        ANG-GSK  475
SEQ-ID-NO-302-CLONE-335348  SPMRRHSGPP KYEL--VKDI -APPQPEALV       VNG-GSK  217
SEQ-ID-NO-100-GI-56202321   ERGRRHSDPP KVDPASLKDV                     PVS      500
SEQ-ID-NO-303-GI-54306075   SPMRRHSGPP KVEV--VKDI AEPPQPEALV       ING-GSK  474
SEQ-ID-NO-312-CLONE-1727738 SPMRRHSGPP KVDSA-VKDI VAPPQPEALV       NG-GSK   471
SEQ-ID-NO-298-CLONE-1792902 SPMRRHSGPP KVGSA-VKDI VAPPQPEALV       NG-GSK   471
```

Figure 3

| SEQ ID | Sequence | Pos |
|---|---|---|
| SEQ-ID-NO-106-CLONE-105319 | MEA_TOR_Q YPS_WDCRKV ECK_PQRGSLR YSQQVKV_DER F--RG_E_AR | 48 |
| SEQ-ID-NO-107-CLONE-463638 | ------M--- ---------- ---------- --------- ---------- | 4 |
| SEQ-ID-NO-115-GI-76782196 | MDGK_ANGL_V VSPRIGSERF ARR_CGSVRV SRRFREQ_DRL P--VLNSAQL | 48 |
| SEQ-ID-NO-113-GI-56805577 | MEAC_V_LALQ SRA_GFGGSD RRR_ALYGGE GRAR__----- -GSL_RVAE- | 42 |
| SEQ-ID-NO-112-CLONE-749796 | MDAC_V_LRPR PR_AWAG--- RRK_PQGFPPA TVPAV_RL_DQN PARRPL_VLRS | 47 |
| SEQ-ID-NO-114-CLONE-294723 | ---------- ---------- ---------- ---------- ---------- | 0 |

| SEQ-ID-NO-106-CLONE-105319 | LQPE_RRI_DQR_ RA_VS_PA_VSCS DN_RSSA-_LLE_ _GSV-_YPFDE_ D--_LKRKAEE_ | 95 |
| SEQ-ID-NO-107-CLONE-463638 | ---------- R_T_ALEVSCS_ _GN_SASK_LE_ SGSV_RAP_LDE EL_ LKNRSQE | 44 |
| SEQ-ID-NO-115-GI-76782196 | QQK_FRNSN_WH KI_ASLEVSCS_ _KNF_PA_SVLE_ SGD_RAPF_DD ALI_LKNKSQE | 98 |
| SEQ-ID-NO-113-GI-56805577 | PAVAKAA_WA RGSKP_VAPLR AK_KSS_--- HEI_LHNSVDE ALLLKRK_SEE | 89 |
| SEQ-ID-NO-112-CLONE-749796 | QAQ_SRSTDPI _GA_SLR_LC HKSA_------ G TEK_VHYSADE ALV_LKQKAED | 92 |
| SEQ-ID-NO-114-CLONE-294723 | ---------- ---------- ---------- ---------- ---------- | 0 |

| SEQ-ID-NO-106-CLONE-105319 | VKPYLNGRSM YLVGMMGSGK TVGKLMSKV LGYTFFDCQT_ _TEDAMNGTS_ | 145 |
| SEQ-ID-NO-107-CLONE-463638 | QPYLNGRCI YLVGMMGSGK TVGKI MSQV LGYSFFDSDA LVEEEVCGNS | 94 |
| SEQ-ID-NO-115-GI-76782196 | EPYLSGRCI YLVGMMGSGK TVGKVLSQV LSYAFFDSDF LVEQD_DANS | 146 |
| SEQ-ID-NO-113-GI-56805577 | VCFYLNGRCI YLVGMMGSGK STVGKI MSEV LGYSFFDSDK RPVAV_GMPS | 139 |
| SEQ-ID-NO-112-CLONE-749796 | VI_PYLNDRCV YLVGMMGSGK TVGKI AEV LGYSFFDSDK LVEQSVGI PSI | 142 |
| SEQ-ID-NO-114-CLONE-294723 | ---------- --MMGSGK TVGKI LSEV LGYSFFDSDKI LVEKAVGI SS | 36 |

| SEQ-ID-NO-106-CLONE-105319 | VAEI FV_H_GE NF_FRC_KETDA KKLSSR_YQV_ VVSTGGGAVI_ RPI NWKYW_HK | 195 |
| SEQ-ID-NO-107-CLONE-463638 | VAQI FKQHGE TFFRNKETEV HKLSL_MHQL VI STGGGAV_ RPI NWKYMHK | 144 |
| SEQ-ID-NO-115-GI-76782196 | VAEI FN_LYCE GFFRDKETEV LRKLSLMHRL VVSTGGGAVV RPI NWKYMQK | 195 |
| SEQ-ID-NO-113-GI-56805577 | VAQI FKVHSE AFFRDNESEV LRDLSSMHRL VVATGGGAVI RPVNWKYMKK | 189 |
| SEQ-ID-NO-112-CLONE-749796 | VAEI FQVHSE AFFRDNESEV LRDLSSMHRL I VATGGGAVI RPI NWSY_MKKI | 192 |
| SEQ-ID-NO-114-CLONE-294723 | VAEI FQLHSE TFFRDNESEV L_TDLSSMHRL VVATGGGAVI RPI NWSY_MKK | 86 |

| SEQ-ID-NO-106-CLONE-105319 | GI SI WLDVPL EALA_HRI AAV _STD_SRPLLHD ESGDA_YSVA_F KRLSAI WDER | 245 |
| SEQ-ID-NO-107-CLONE-463638 | GVSVWLDVPV EALAQRI AAV GTN_SRPLLHY EAGDPYTRAF MRLSALFEER | 194 |
| SEQ-ID-NO-115-GI-76782196 | SI SVWLDVPL EALARRI AAV CTG_SRPLLHH DSGDA_YTKI TF MRLTSLMEER | 248 |
| SEQ-ID-NO-113-GI-56805577 | GLSVWLDVPL DALARRI AK_M GTASRPLL_DC_ PSGDPYT_MAF SKLSM_L_AEQR | 239 |
| SEQ-ID-NO-112-CLONE-749796 | GLTI WLDVPL DALARRI AAV GTASRPLLHQ ESGDPYAKAY AKLTALFEQR | 242 |
| SEQ-ID-NO-114-CLONE-294723 | GLTVWLDVPL DALARRI AAV GTASRPLLHQ ESGDPYAKAY AKLTSLFEQR | 136 |

Figure 3 - continued

| SEQ ID NO | | | | | |
|---|---|---|---|---|---|
| SEQ ID NO:106-CLONE:105319 | GEAYI NANANAR | VSLENI AAKR | GYKNVSDLTP | TEI EI EAFEQ | VLSFL EKEET | 295 |
| SEQ ID NO:107-CLONE:463638 | GEAYANANANAR | VSLKNI AIKE | GKRDVSELSP | TDI AI EALEQ | DNFL KGEG | 243 |
| SEQ ID NO:115-GI:76782196 | SEAYANANANAR | VSLEDVAAKL | CHRDVSNLTP | TRI AI EALEQ | EGFL KEEN | 297 |
| SEQ ID NO:113-GI:56805577 | GDAYANADNR | VSLEEI ASKQ | GHDDVSKLTP | TDI AI ESFHK | ENFV TEHI | 288 |
| SEQ ID NO:112-CLONE:749796 | MDSYANADAR | VSLEWI ALKQ | GHNDVNWLTP | SI AI EALLK | MESFL TEKA | 291 |
| SEQ ID NO:114-CLONE:294723 | MDSYANADAR | VSLEHI ALKQ | GHNDVTI LTP | SI AI EALLKI | MESFL TEKT | 185 |

| | | |
|---|---|---|
| SEQ ID NO:106-CLONE:105319 | ME PDGDL | 303 |
| SEQ ID NO:107-CLONE:463638 | GRYAEC | 249 |
| SEQ ID NO:115-GI:76782196 | GDFAL | 302 |
| SEQ ID NO:113-GI:56805577 | VDNPVGDSQA DSRAQRI QTL | 308 |
| SEQ ID NO:112-CLONE:749796 | MVRN | 295 |
| SEQ ID NO:114-CLONE:294723 | MVRN | 189 |

Figure 4

```
SEQ-ID-NO:130-GI:505152        ------------------  ---MADQIT  DDQISEFKEA  FSLFDKDGDG  CITIKELGIV   36
SEQ-ID-NO:123                  ------------------  ---MASTKP  TDQIKQLKDI  FARFDMDKDG  SLTQLELAAL   36
SEQ-ID-NO:126-CLONE:651548     ------------------  -------ME  TDQIKQLNDI  FKRFDMDQDG  SLTHLELAAL   33
SEQ-ID-NO:125-ANNOT:1464081    ------------------  --------- ----------  ----MDSDG   SLTQLELAAL   15
SEQ-ID-NO:129-CLONE:759217     MTKPSPSPSP  APAKGAGSIR  GSDLKQLRSL  FDRFDMDGDG  SLTQLELAAL   50
SEQ-ID-NO:127-GI:50932815      MTTMAARRSE  -AAPAPQDLR  GSDLKQLREL  FRRFDMNGDG  SLTQLELAAL   49
SEQ-ID-NO:128-CLONE:287120     MTRSAPPASP  -PAPKP-VLR  GSDLEQLREI  ERKFDMDGDG  SLTQLELGAL   48

SEQ-ID-NO:130-GI:505152        MRSLGQNPTE  AELQDMINEV  DADGNGTIDF  PEFLNLMARK  MKDID------   82
SEQ-ID-NO:123                  LRSLGIKPRS  DQISLLNQI   DRNGNGSVEF  DELVVAILPD  LNEEM-----   84
SEQ-ID-NO:126-CLONE:651548     LRSLGIKPTG  DEIALLSNM   DENGNGYI-EF DELVHAILPD  LIESV-----   81
SEQ-ID-NO:125-ANNOT:1464081    LRSLGIKPTG  DQLFVLLSNM  DANGNGYVEF  DELVSAILPD  LNEEM-----   63
SEQ-ID-NO:129-CLONE:759217     LRSLGLRPTG  DESRALLLA-  DADGSGTVEF  DELARAIAPV  LTAHAPRLVD  100
SEQ-ID-NO:127-GI:50932815      LRSLGLRPTG  DEVHALLAGM  DANGNGSVEF  DELAKAIAPV  LTIQT-HLVD   98
SEQ-ID-NO:128-CLONE:287120     LRSLGLRPTG  EEARALLAAM  DSNGNGAVEF  GELAAAIAPL  LTIQT-HLVD   97

SEQ-ID-NO:130-GI:505152        EEELKEAFRV  FDKDQNGFIS  AAELRHVMTN  LGEKLTDEEV  DEMIREADVD  132
SEQ-ID-NO:123                  QEQLMEVFRS  FDRDGNGSIT  AAELAPSMAK  MGHPLTYREL  DEMMTEADSN  134
SEQ-ID-NO:126-CLONE:651548     QEQLLEVFRS  FDRDGNGFIT  ASELAPSMAK  MGQPLTYREL  ASMMREADSN  131
SEQ-ID-NO:125-ANNOT:1464081    QEQLLEVFRS  FDRDGNGYIT  AAELAPSMAK  MGHPLTYREL  SDMMREADTN  113
SEQ-ID-NO:129-CLONE:759217     QAQLLEVFRA  FDRDGNGYIS  AAELAPSMAR  LGQPLTFEEL  RTMMRDADAD  150
SEQ-ID-NO:127-GI:50932815      QAQLLEVFRA  FDRDGNGFIS  AAELAPSMAR  LGQPLTFEEL  TRMMRDADTD  148
SEQ-ID-NO:128-CLONE:287120     QAQLLEVFRA  FDRDGNGYIS  AAELAPSMAR  IGQPLTFEEL  TRMMRDADAD  147

SEQ-ID-NO:130-GI:505152        GDGQI  NYEEF  VKVMMAK   ---------  149
SEQ-ID-NO:123                  SFNEF  SHIMAKSAAD  FLGLTAS  161
SEQ-ID-NO:126-CLONE:651548     GDGVI  SFNEF  AALMAKSAAE  FLGVKVA  158
SEQ-ID-NO:125-ANNOT:1464081    GDGVI  SFNEF  ANVMAKSAPD  FLGIKVP  140
SEQ-ID-NO:129-CLONE:759217     GDGVL  SFGEF  AAVMARSALD  FLGVPAA  177
SEQ-ID-NO:127-GI:50932815      GDGVI  SFKEF  AAVMAKSALD  FLGVA--  173
SEQ-ID-NO:128-CLONE:287120     GDGVI  SFNEF  AAVMAKSALD  FLGVA--  172
```

Figure 5

```
                                                                                                    50
SEQ-ID-NO-143-CLONE-1272732   METAAVAASS  AGRRIMVAVD  EGEEFSLHALN  WCLANVSPA   GGDTLVLVHA          46
SEQ-ID-NO-139-CLONE-684584    MAAQAPPPPP  PEQKMWVAID  ESEQSHYALE   MAIRNL----  APRRLILFTV          35
SEQ-ID-NO-142-CLONE-1059727   ----------  --AVAID     DSDQSKHALR   WTLSYLKDSI  ADSDPILFTA          35
SEQ-ID-NO-134-ANNOT-1486744   ----------  -MVTLD      ESEYSHSFM    MVVDNLKEFI  TESPLVLAA           39
SEQ-ID-NO-132-CLONE-2767      ----------  -MKMWMLID   ESNASYDLL    MALENQKDT   ESSKMLFAK

90
SEQ-ID-NO-143-CLONE-1272732   RRPRPV----Y  AAMDSAG---  ---YMMISD   VLASVERHAN  AVSPAAVDKA          89
SEQ-ID-NO-139-CLONE-684584    QPFSPLSY-L   PVGSPLG---  ----PSVASPE  LIRSVIEHQR  OLAQALVDKA         75
SEQ-ID-NO-142-CLONE-1059727   QPQLDLS---S  VYASSYG---  AAPIE-----  LINSMQQNYK   NAALNRIEEG         83
SEQ-ID-NO-134-ANNOT-1486744   LPAPNCK---F  FYGAQFGTAA  LCCFVSPILD   LICALQEKNK   KITLGFLEKA         89
SEQ-ID-NO-132-CLONE-2767      QPQNSFTPPT   VLSSSVGFAQ  IFYPFSPNSE   LIRLAQEKNM   KIALGILEKA

139
SEQ-ID-NO-143-CLONE-1272732   KRVCADHPHM   KMETIVESGD  PRDVICDAAN   KMAADLLVMG  SHG--YGFIQR        137
SEQ-ID-NO-139-CLONE-684584    KIA-CAEH-GV  DAETVIEVGD  PKEFICEAAE   KLNVDLLILG  SHS--RGPVQR        123
SEQ-ID-NO-142-CLONE-1059727   TKI-CAES-GV  TPFKMEFGN   PKEALCDAVE   KLGVDLLIVG  SHG--KGALER        132
SEQ-ID-NO-134-ANNOT-1486744   VNI-CASR-GV  KAETLEASE    PIELTCNAVQ   KNNINLLVIG  NTSINGTLKR         135
SEQ-ID-NO-132-CLONE-2767      KKI-CLNH-GI  KAETFTNVGD  PKDLIRKILQ   ERNINLIVTS  DQQ---SLKK

162
SEQ-ID-NO-143-CLONE-1272732   ----AFLGS--  VSNHCADNCK  CPVLIVKR   ----------  ----------           160
SEQ-ID-NO-139-CLONE-684584    ----FFLGS--  VSNYCSHIAK  CPVLVVKK   ----------  ----------           146
SEQ-ID-NO-142-CLONE-1059727   ----TFLGS--  VSNYCVNKAK  CPVLVVRT   ----------  ----------           182
SEQ-ID-NO-134-ANNOT-1486744   ----------   SFALESRIN   CMNLIQNELF  QELEHAGMVV  NPINSCNKLH          150
SEQ-ID-NO-132-CLONE-2767      LGNFFVTSKI   CTONID       CSLLVVKK    ----------  ---------R

SEQ-ID-NO-143-CLONE-1272732   --PKE        165
SEQ-ID-NO-139-CLONE-684584    --KE         162
SEQ-ID-NO-142-CLONE-1059727   --KA         148
SEQ-ID-NO-134-ANNOT-1486744   YQKH         186
SEQ-ID-NO-132-CLONE-2767      LRKD         154
```

Figure 6

| SEQ:ID:NO:151-GI:50944591 | MAI HSI APA | APAFSAFPLA | AANRFPCASA | TSNI CAFSLA | EHI TREGMF F | 50 |
| SEQ:ID:NO:152-CLONE:1551032 | MAI AVPAAC | LRAPCSSPAR | VARR LGA | GGP SLRKRH | CAVAPVAAAC | 45 |
| SEQ:ID:NO:146-CLONE:16403 | MAVSSLSI RC | CGFSPTLS | HRTEI LC | PNPSL KAC | CLLSSGGKAD | 43 |
| SEQ:ID:NO:147-CLONE:611156 | MI VSSESL | SWI SPCLS | HKTNLPH | TN CLPRNI | ATSSNI VFC | 41 |
| SEQ:ID:NO:149-ANNOT:1464944 | MAI SSLSL | SWASI TLS | QKLSVPG | SNEI LPRVA | AFSGNNSVI K | 42 |

| SEQ:ID:NO:151-GI:50944591 | DLQ SI KR | EI AEER-SRRR | MLI AAGAAMF | LSMPNPAATA | AEAKKGFL PV | 96 |
| SEQ:ID:NO:152-CLONE:1551032 | GPAPPRLL DN | EEAVCL-SVRR | RVLVAGAI AAF | LSRPNPAAFA | AEAKKGFL PV | 94 |
| SEQ:ID:NO:146-CLONE:16403 | SSES TYQK | GSGNNWKRRQ | ALVGVGI LVA | TSI PATI LLA | EEI FKSYSPI | 91 |
| SEQ:ID:NO:147-CLONE:611156 | ELD I TPSI | GESHC-RRRP | LLLGI GALI A | NLQPI NLVFA | DEKPDRYRAF | 87 |
| SEQ:ID:NO:149-ANNOT:1464944 | TAE ATFN | EESNC-KRRL | LLLGVCALI T | SLVPANFLFA | EEI PKNYI SF | 88 |

| SEQ:ID:NO:151-GI:50944591 | I DKKDGYSFL | YPF GWQEVVV | DGQDKVYKDV | I EPLESVSVN | TI PTSKQDI R | 146 |
| SEQ:ID:NO:152-CLONE:1551032 | VDKKAGYSFL | YPF GWEEVAV | EGQDKVYKDV | I EPLESVSVN | SI PTSKEDI R | 144 |
| SEQ:ID:NO:146-CLONE:16403 | VDREDGYSYL | YPI DWREFDF | RAHDSAFKDR | YLQL QNVRVR | FI PTEKNDI H | 141 |
| SEQ:ID:NO:147-CLONE:611156 | VDFEDGYSYV | YPI DWKEFDF | RAHDSAFKDR | YLQL QNVRVR | FI PTEKKDI R | 137 |
| SEQ:ID:NO:149-ANNOT:1464944 | VDFEDGYSYN | DFDF | RGHDSAFKDR | TKQLQNVRVR | FI PTEKKDI H | 138 |

| SEQ:ID:NO:151-GI:50944591 | ELGPPDQVI AE | AI TRKVLAAP | TQKTKLI EAK | ENDVDGRI YY | TFEFTAQAPN | 196 |
| SEQ:ID:NO:152-CLONE:1551032 | DLGPPDKVAE | ALI KKVLAPS | TQKTKLI EAK | ENDVDGRAYY | TFEFTAQAPN | 194 |
| SEQ:ID:NO:146-CLONE:16403 | EVGPMEEVM | DLVKFKFAAP | NQVATI FDMK | ERVEDGKNYY | TFEYGLRTPL | 191 |
| SEQ:ID:NO:147-CLONE:611156 | DLGPMEEVYI | DLVKHRYAAP | NQRPTI NDMQ | EKTI DGKHYY | TFEYLI SPN | 187 |
| SEQ:ID:NO:149-ANNOT:1464944 | ELGPMEEF K | DSHMQQEI MN | VKLDNFLE-N | QKTVEGKNYY | TFEYELI SPN | 185 |

| SEQ:ID:NO:151-GI:50944591 | FTRHAL CAI A | ANGKFYTLT | TGANERRWEK | KDRLHTVND | SFKI EAREVR | 246 |
| SEQ:ID:NO:152-CLONE:1551032 | YTRHAL GAI V | ANGKFYTLT | TGANERRWEK | MKDRLHI VVD | SFKI ENRI | 242 |
| SEQ:ID:NO:146-CLONE:16403 | YATI SFATVAI | VGNNRYYTLI | VGANERRWKR | VKKQLQVVAD | SI KI LQ | 238 |
| SEQ:ID:NO:147-CLONE:611156 | YSSASFATI A | GNGRYYTLI | VGANERRWKR | FRDQLKVVAQ | SFRLLDI | 234 |
| SEQ:ID:NO:149-ANNOT:1464944 | YSSVSFATI V | ANGRFYTLI | VGANERRWRR | YRSQLKVVAD | SFKVLDI | 232 |

| SEQ:ID:NO:151-GI:50944591 | FNGKCREHGS Y | 257 |
| SEQ:ID:NO:152-CLONE:1551032 | - | 242 |
| SEQ:ID:NO:146-CLONE:16403 | - | 238 |
| SEQ:ID:NO:147-CLONE:611156 | - | 234 |
| SEQ:ID:NO:149-ANNOT:1464944 | - | 232 |

| SEQ ID | Sequence | # |
|---|---|---|
| SEQ-ID-NO-168-CLONE-1064128 | VSLWHFMAKF T------PWD DEAHGRFCEG VSLYGPFWEH VLSYWRWHVD | 222 |
| SEQ-ID-NO-161-CLONE-703785 | VSLWHFMNRF AP-----SPWDL GEALQQFCDG VSLFGPFWEH VLGYWRWHVE | 222 |
| SEQ-ID-NO-169-GI-775529975 | VSLWHFMNRF M------PWNL DDAHRQFCNG VSLFGLYWEH VLSYWNWHVE | 152 |
| SEQ-ID-NO-160-GI-68067679 | VSTYHFLRQI VKLSVEEAPF EEAFDEFCQG ISSCGPYWEH KGYWKASLE | 197 |
| SEQ-ID-NO-163-GI-1706738 | VSMYHFLRQI VKLSVEEAPF ELMFDAYCQG ISSCGPYWEH LGYWKASLE | 197 |
| SEQ-ID-NO-154-CLONE-3964 | VSGMHYRNML HRTKMDQATF ETAVAAFCKG VLYGPYWEH VLSYWKDSLE | 240 |
| SEQ-ID-NO-164-GI-342004 | VSLWHFGRKL APEKTAEYP APEKTAEYP KFLGGPFWDH VLEYWYESLK | 215 |
| SEQ-ID-NO-157-ANNOT-1448303 | RSETVPLL EEIFKMVCEG VVGFGPFWDH MLGYWKEFSLE | 223 |
| SEQ-ID-NO-168-CLONE-1064128 | RPIGQVLFTY EELSADPLGG LRRLAEFIGR PFTPGEQEAG VDREIAEACA | 272 |
| SEQ-ID-NO-161-CLONE-703785 | RPEQVLFTY EELAADFLGQ KRRLAAFLGR PFTSEEREAR VDREIVEACA | 272 |
| SEQ-ID-NO-169-GI-775529975 | RPSEVLFTY EELAADILGH LRRLAEFVGR PFTPEEEQDAR VDRKIVETCA | 202 |
| SEQ-ID-NO-160-GI-68067679 | KPEIFLFLKY EDMKKDPVPS VKKLADFIGH PFTPKEEEAG VIEDIVKLCS | 247 |
| SEQ-ID-NO-163-GI-1706738 | KPEIFLFLKY EDMKKDPVPS VKKLADFIGH PFTPKEEEAG VIENIKLCS | 247 |
| SEQ-ID-NO-154-CLONE-3964 | AKENVLFMKY EEIEEPRVQ VKRLAEFLEG PFTKEEEESG SVEEILKLCS | 290 |
| SEQ-ID-NO-164-GI-342004 | NPKRVLFVTY EELKKOTEVE VKRIAEFLGC GFTAEEEI VSEIVKLCS | 261 |
| SEQ-ID-NO-157-ANNOT-1448303 | RDKVLFLKY EDMKADVTFY LKKIAKFLGC PFSVEEEKEG VVEKIASLCS | 273 |
| SEQ-ID-NO-168-CLONE-1064128 | MKSMNQEVN QSRTIEI VEL MPJFNGIFFR RGMVGDWNY LTPEMAGRID | 321 |
| SEQ-ID-NO-161-CLONE-703785 | MESLASLEVN RSGKIDMTE SSVANNIFFR RGVGDWKNH LTPEMARRID | 321 |
| SEQ-ID-NO-169-GI-775529975 | MESLSGLEVN RSGMINFTK KOMPNNISFR RGMVGDWRNH LTPEMARRID | 254 |
| SEQ-ID-NO-160-GI-68067679 | FERLSSLEVN KSGMHRPEEA HSIENRLYFR KGKDGDWKNY FTDEMTQKID | 297 |
| SEQ-ID-NO-163-GI-1706738 | FEKLSSLEVN KSGMHRPEEA HSIENRLYFR KGKDGDWKNY FTDEMLEKID | 297 |
| SEQ-ID-NO-154-CLONE-3964 | LRNLSNLEVN KNGITR----- IGVDSQVFFR KGEVGDWKNH LTPOMAKTFD | 336 |
| SEQ-ID-NO-164-GI-342004 | FESLSSLEVN RGCKLP----- NGLESNAFFR KGETGDWRDF SESLADVF D | 307 |
| SEQ-ID-NO-157-ANNOT-1448303 | FEKMKNLEVN KSGRS----- TNFENKHLFR KAEVGDWNY SPISMVKDLS | 319 |
| SEQ-ID-NO-168-CLONE-1064128 | EITKSKFEGS GLMLPKTISE ISKI--------- --------- --------- | 345 |
| SEQ-ID-NO-161-CLONE-703785 | EITDSKFRGS GLALTPATAD QN---------- --------- --------- | 343 |
| SEQ-ID-NO-169-GI-775529975 | EITEVKFKGS GLLLHPPFLQ VKRELNEL--- --------- --------- | 279 |
| SEQ-ID-NO-160-GI-68067679 | KLIDEKLGAT GLVLK------ --------- --------- --------- | 312 |
| SEQ-ID-NO-163-GI-1706738 | KLIDEKLGAT GLVLK------ --------- --------- --------- | 312 |
| SEQ-ID-NO-154-CLONE-3964 | EIIDYRLGDS GLIFQ------ --------- --------- --------- | 351 |
| SEQ-ID-NO-164-GI-342004 | RTIFEQKFGGS GLKFSS----- --------- --------- --------- | 323 |
| SEQ-ID-NO-157-ANNOT-1448303 | QLIEEKLGGS GNQAAAAAAA SSSSSVIKKK FELQRYGENK NTNVN | 364 |

FIGURE 8

```
SEQ:ID:NO:172-CLONE-965405    MSADDSSNAI DVDGKLDSDL NMSDGEDAA  DNDSSKILT-  PAPAVCLVR   49
SEQ:ID:NO:173-CLONE-5367      MAADSSNAI  DIDGNLDSDS NLMDGEAT   DNDSSKALVT  PAPAVCLER   50
SEQ:ID:NO:174-GI:79537394     MAAENSSNAI NVDISLDSDS KPNRDANDMT DHDSSKALV   PAPAVCLVR   50
SEQ:ID:NO:175-GI:9758183      MAAENSSNAI NVDISLDSDS KPNRDANDMT DHDSSKALV   PAPAVCLVR   50
SEQ:ID:NO:176-CLONE-1060894   MAAENPSNCM DVDISLASDS NDNRKASDI  NHDSS-MALI  VPSIAVCLGR  49
SEQ:ID:NO:179-ANNOT-1494390   MATANSPNIS NNSDSDVEDP NPNPSSN-   NMASTIPSAE  SSTPSVCLIR  48
SEQ:ID:NO:177-CLONE-639280    MAAR-SENES DGDVG      NPAEGGS    SLSLPPL     AAGPAVCVLR  39

SEQ:ID:NO:172-CLONE-965405    FAGDAAGGAV MGSIFGYGSG LFKKKGFKGS FADAGQSAKT  FAVLSGVHSL  99
SEQ:ID:NO:173-CLONE-5367      FAGDAAGGAV MGSIFGYGSG LFKKKGFKGS FADAGQSAKT  FAVLSGVHSL  100
SEQ:ID:NO:174-GI:79537394     FAGDAASAF  MGSVFGYGSG LFKKKGFKGS FVDAGQSAKT  FAVLSGVHSL  100
SEQ:ID:NO:175-GI:9758183      FAGDAASAF  MGSVFGYGSG LFKKKGFKGS FVDAGQSAKT  FAVLSGVHSL  98
SEQ:ID:NO:176-CLONE-1060894   FAGDAASAFL MGSIFGYGSG LFKKKGFKGS FADAGQSAKN  FAILSGVHSL  99
SEQ:ID:NO:179-ANNOT-1494390   FAGDSAGAFI MGSIFGYGSG LKKKGFKGS  FEAGSAKT    FAVLSGVHSL  98
SEQ:ID:NO:177-CLONE-639280    SAGDFAGGAFL VGSIFGYGQ  LLSKKGIKGS  LGNAGSAKS  FAVLSGYQSL  89

SEQ:ID:NO:172-CLONE-965405    VVCLLKQLRG KDDAINVGVA GCCTGLALSF PGAPQALLQS  CLTFGAFSFI  149
SEQ:ID:NO:173-CLONE-5367      VVCLLKQIRG KDDAINVGVA GCCTGLALSF PGAPQALLQS  CLTFGAFSFI  150
SEQ:ID:NO:174-GI:79537394     VVCLLKQIRG KDDAINVGVA GCCTGLALSF PGAPQAMLQS  CLTFGAFSFI  150
SEQ:ID:NO:175-GI:9758183      VVCLLKQIRG KDDAINVGVA GCCTGLALSF PGAPQAMLQS  CLTFGAFSFI  148
SEQ:ID:NO:176-CLONE-1060894   VVCLLKKLRG KDDAINVGIA GCCTGLALSY PGAPQAMLQS  CVTFGAFSFI  149
SEQ:ID:NO:179-ANNOT-1494390   VVCELKRLRG KDDMNAGVA  GCCTGLALSF PGAPQALLQS  CLTFGAFSFI  148
SEQ:ID:NO:177-CLONE-639280    VLCLLRKLRG LNSGIAI    GCCTGLALSF PGTPQALLQN  CAIFAAFSCL  139

SEQ:ID:NO:172-CLONE-965405    LEGLNKRQTA LAHSVSLR-H QTGNFGDHQD RPLQLSLALPI  HEEIKGLFS   197
SEQ:ID:NO:173-CLONE-5367      EGLNKRQTA  LAHSVSLR-H QTGLFQDHH-  RALPLSLALP  PEEIKGLFS   198
SEQ:ID:NO:174-GI:79537394     LEGLNKRQTA LAHSVSFR-Q QTRSP-     QH          DLPLLSLAIP  HDEIKGAFS   196
SEQ:ID:NO:175-GI:9758183      LEGLNKRQTA LAHSVSFR-Q QTRSP-     QH          DLPLLSLAIP  HDEIKGAFS   194
SEQ:ID:NO:176-CLONE-1060894   LEGLNKRQTA LAHSVSSRHD QTRSL-     KD          DLP-LSLALP  HEEIKGAFS   195
SEQ:ID:NO:179-ANNOT-1494390   EGLNKKQAA  LAHSISSR-N KCDYHS     KP          CPLALPLSVPL LPELKGAFS  195
SEQ:ID:NO:177-CLONE-639280    MEGLNKQQTA MAHTLTGN-A LIFAH-     DN          GAGVLPPSLP  PQSSMLPMLS  185
```

Figure 8 - continued

| | | | |
|---|---|---|---|
| SEQ:ID:NO:172:CLONE:965405 | SFCKSLTKPK | KT------- | 209 |
| SEQ:ID:NO:173:CLONE:5367 | SFCKSLAKPR | KF------- | 210 |
| SEQ:ID:NO:174:GI:79537394 | SFCNSLTKPK | KL-KFPHAR- | 214 |
| SEQ:ID:NO:175:GI:97581833 | SFCNSLTKPK | KL-KFPHAR- | 212 |
| SEQ:ID:NO:176:CLONE:1060894 | SFCKSLTKPK | KL-AFPSSR- | 213 |
| SEQ:ID:NO:179:ANNOT:1494390 | FFCKSLRKPK | KLASNFPAAAP | 214 |
| SEQ:ID:NO:177:CLONE:639280 | PHAARPWSPS | LRSTRQQH  | 203 |

| | | | |
|---|---|---|---|
| SEQ-ID-NO-304-CLONE-335348-T | PQPEALVVNG | -GSK | 193 |
| SEQ-ID-NO-305-CLONE-228069-T | PQPEALVANG | GGSK | 200 |
| SEQ-ID-NO-306-CLONE-375578-T | ----TLKDA | -PAA | 189 |
| SEQ-ID-NO-307-CLONE-229668-T | PQPEALVVNG | -GSK | 193 |
| SEQ-ID-NO-308-GI-54306075-T | PQPEALVING | -GSK | 199 |
| SEQ-ID-NO-309-GI-56202321-T | ----SLKDV | -PVS | 188 |
| SEQ-ID-NO-310-CLONE-1792902-T | PQPEALVING | -GSK | 199 |
| SEQ-ID-NO-311-CLONE-1727738-T | PQPEALVING | -GSK | 200 |

NUCLEOTIDE SEQUENCES AND CORRESPONDING POLYPEPTIDES CONFERRING MODULATED GROWTH RATE AND BIOMASS IN PLANTS GROWN IN SALINE CONDITIONS

This application is a Divisional of U.S. patent application Ser. No. 17/831,156, filed Jun. 2, 2022, which is a Divisional of U.S. patent application Ser. No. 17/002,713, filed Aug. 25, 2020, now U.S. Pat. No. 11,421,245, which is a Divisional of U.S. patent application Ser. No. 16/554,199, filed Aug. 28, 2019, now U.S. Pat. No. 10,968,461, which is a Divisional of U.S. patent application Ser. No. 16/275,537, filed Feb. 14, 2019, now U.S. Pat. No. 10,428,346, which is a Divisional of U.S. patent application Ser. No. 15/487,287, filed Apr. 13, 2017, now U.S. Pat. No. 10,233,460, which is a Divisional of U.S. patent application Ser. No. 13/663,204, filed Oct. 29, 2012, now U.S. Pat. No. 9,637,756, which is a Divisional of U.S. patent application Ser. No. 12/282,342, filed on Nov. 17, 2008, now U.S. Pat. No. 8,324,454, and for which priority is claimed under 35 U.S.C. § 120. U.S. patent application Ser. No. 12/282,342 is a National Phase application under 35 U.S.C. § 371 of PCT International Application No. PCT/US2007/006544, which has the International filing date of Mar. 14, 2007, which designated the United States of America, and which claims priority under 35 U.S.C. § 119(e) of U.S. Provisional Application No. 60/782,735, filed Mar. 14, 2006, the entire contents of each of which are hereby incorporated by reference.

INCORPORATION OF SEQUENCE LISTING

The sequence listing that is contained in the XML file named "CRES002USD12_ST26," which is 788 kilobytes as measured in Microsoft Windows operating system and was created on Sep. 14, 2023, is filed electronically herewith and incorporated herein by reference.

FIELD OF THE INVENTION

The present invention relates to isolated nucleic acid molecules and their corresponding encoded polypeptides able to enhance plant growth under saline conditions. The present invention further relates to using the nucleic acid molecules and polypeptides to make transgenic plants, plant cells, plant materials or seeds of a plant having improved growth rate, vegetative growth, seedling vigor and/or biomass under saline conditions as compared to wild-type plants grown under similar conditions.

BACKGROUND OF THE INVENTION

Plants specifically improved for agriculture, horticulture, biomass conversion, and other industries (e.g. paper industry, plants as production factories for proteins or other compounds) can be obtained using molecular technologies. As an example, great agronomic value can result from enhancing plant growth in saline conditions.

A wide variety agriculturally important plant species demonstrate significant sensitivity to saline water and/or soil. Upon salt concentration exceeding a relatively low threshold, many plants suffer from stunted growth, necrosis, and death that results in an overall stunted appearance and reduced yields of plant material, seeds, fruit and other valuable products. Physiologically, plants challenged with salinity experience disruption in ion and water homeostasis, inhibition of metabolism, and damage to cellular membranes that result in developmental arrest and cell death (Huh et al. (2002) *Plant J,* 29(5):649-59).

In many of the world's most productive agricultural regions, agricultural activities themselves lead to increased water and soil salinity, which threatens their sustained productivity. One example is crop irrigation in arid regions that have abundant sunlight. After irrigation water is applied to cropland, it is removed by the processes of evaporation and evapotranspiration. While these processes remove water from the soil, they leave behind dissolved salts carried in irrigation water. Consequently, soil and groundwater salt concentrations build over time, rendering the land and shallow groundwater saline and thus damaging to crops.

In addition to human activities, natural geological processes have created vast tracts of saline land that would be highly productive if not saline. In total, approximately 20% of the irrigated lands in are negatively affected by salinity. (Yamaguchi and Blumwald, 2005, *Trends in Plant Science,* 10: 615-620). For these and other reasons, it is of great interest and importance to identify genes that confer improved salt tolerance characteristics to thereby enable one to create transgenic plants (such as crop plants) with enhanced growth and/or productivity characteristics in saline conditions.

The availability and sustainability of a stream of food and feed for people and domesticated animals has been a high priority throughout the history of human civilization and lies at the origin of agriculture. Specialists and researchers in the fields of agronomy science, agriculture, crop science, horticulture, and forest science are even today constantly striving to find and produce plants with an increased growth potential to feed an increasing world population and to guarantee a supply of reproducible raw materials. The robust level of research in these fields of science indicates the level of importance leaders in every geographic environment and climate around the world place on providing sustainable sources of food, feed and energy.

Manipulation of crop performance has been accomplished conventionally for centuries through selection and plant breeding. The breeding process is, however, both time-consuming and labor-intensive. Furthermore, appropriate breeding programs must be specially designed for each relevant plant species.

On the other hand, great progress has been made in using molecular genetic approaches to manipulate plants to provide better crops. Through the introduction and expression of recombinant nucleic acid molecules in plants, researchers are now poised to provide the community with plant species tailored to grow more efficiently and yield more product despite suboptimal geographic and/or climatic environments. These new approaches have the additional advantage of not being limited to one plant species, but instead being applicable to multiple different plant species (Zhang et al. (2004) *Plant* 15 *Physiol.* 135:615; Zhang et al. (2001) *Proc. Natl. Acad. Sci. USA* 98:12832).

Despite this progress, today there continues to be a great need for generally applicable processes that improve forest or agricultural plant growth to suit particular needs depending on specific environmental conditions. To this end, the present invention is directed to advantageously manipulating plant tolerance to salinity in order to maximize the benefits of various crops depending on the benefit sought, and is characterized by expression of recombinant DNA molecules in plants. These molecules may be from the plant itself, and simply expressed at a higher or lower level, or the molecules may be from different plant species.

SUMMARY OF THE INVENTION

The present invention, therefore, relates to isolated nucleic acid molecules and polypeptides and their use in making transgenic plants, plant cells, plant materials or seeds of plants having improved growth characteristics in saline conditions compared to wild-type plants under similar or identical conditions.

The present invention also relates to processes for increasing the growth potential of plants challenged with saline conditions due to salt tolerance derived from recombinant nucleic acid molecules and polypeptides. The phrase "increasing growth potential" refers to continued growth in saline conditions, better yield after exposure to saline conditions and/or increased vigor in saline conditions.

Unless otherwise defined, all technical and scientific terms used herein have the same meaning as commonly understood by one of ordinary skill in the art to which this invention belongs.

BRIEF DESCRIPTION OF THE FIGURES

FIG. 1 Amino acid sequence alignment of homologues of Ceres clone 8686 (SEQ ID NO: 80). Conserved regions are enclosed in a box.

FIG. 2. Amino acid sequence alignment of homologues of Ceres clone 375578 (SEQ ID NO: 252). Conserved regions are enclosed in a box.

FIG. 3. Amino acid sequence alignment of homologues of Ceres clone 105319 (SEQ ID NO: 106). Conserved regions are enclosed in a box.

FIG. 4 Amino acid sequence alignment of homologues of Ceres clone 29658 (SEQ ID NO: 123). Conserved regions are enclosed in a box.

FIG. 5 Amino acid sequence alignment of homologues of Ceres clone 2767 (SEQ ID NO: 132). Conserved regions are enclosed in a box.

FIG. 6 Amino acid sequence alignment of homologues of Ceres clone 16403 (SEQ ID NO: 146). Conserved regions are enclosed in a box.

FIG. 7 Amino acid sequence alignment of homologues of Ceres clone 3964 (SEQ ID NO: 154). Conserved regions are enclosed in a box.

FIG. 8. Amino acid sequence alignment of homologues of Ceres clone 965405 (SEQ ID NO: 172). Conserved regions are enclosed in a box.

FIG. 9. Amino acid sequence alignment of a conserved region of Ceres clones 375578 (SEQ ID NO: 306) and 335348 (SEQ ID NO: 304) and homologues. Conserved regions are enclosed in a box.

DETAILED DESCRIPTION OF THE INVENTION

1. The Invention

The present invention discloses novel isolated nucleic acid molecules, nucleic acid molecules that interfere with these nucleic acid molecules, nucleic acid molecules that hybridize to these nucleic acid molecules, and isolated nucleic acid molecules that encode the same protein due to the degeneracy of the DNA code. Additional embodiments of the present application further include the polypeptides encoded by the isolated nucleic acid molecules of the present invention.

Figure 1:
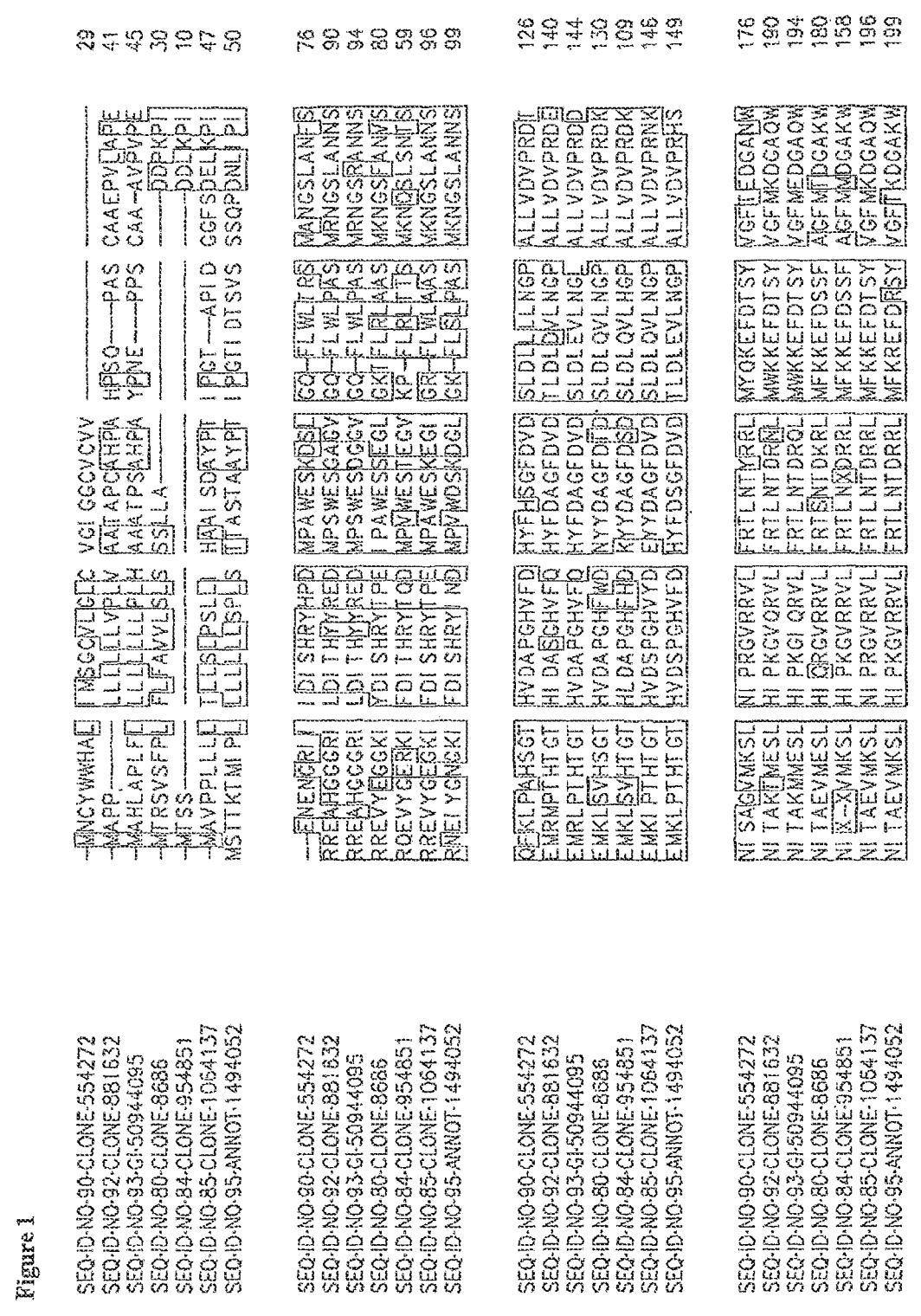

More particularly, the nucleic acid molecules of the present invention comprise: (a) a nucleotide sequence that encodes an amino acid sequence and that is at least 85% identical to any one of SEQ ID Nos. 80, 99, 106, 123, 132, 146, 154 and 172 respectively, (b) a nucleotide sequence that is complementary to any one of the nucleotide sequences according to (a), (c) a nucleotide sequence according to any one of SEQ ID NOs. 79, 98, 105, 122, 131, 145, 153 and 171, (d) a nucleotide sequence able to interfere with any one of the nucleotide sequences according to (a), (e) a nucleotide sequence able to form a hybridized nucleic acid duplex with the nucleic acid according to any one of paragraphs (a)-(d) at a temperature from about 5° C. to about 10° C. below a melting temperature of the hybridized nucleic acid duplex, (f) a nucleotide sequence encoding any one of amino acid sequences of SEQ ID NOS. 80, 99, 106, 123, 132, 146, 154 and 172, (g) a nucleotide sequence encoding any one of the amino acid sequences with an HMM bit score greater than 20 that fits an HMM based on the sequences aligned in any one of FIGS. 1-8, and (h) a nucleotide sequence encoding an amino acid sequence having a fragment that fits an HMM based on the sequences aligned in FIG. 9 and which has an HMM bit score greater than 400.

Additional embodiments of the present invention include those polypeptide and nucleic acid molecule sequences disclosed in SEQ ID NOs: 81-97, 100-104, 107-121, 124-130, 133-144, 147-152, 155-170, 173-252 and 269-315.

The present invention further embodies a vector comprising a first nucleic acid having a nucleotide sequence encoding a plant transcription and/or translation signal, and a second nucleic acid having a nucleotide sequence according to the isolated nucleic acid molecules of the present invention. More particularly, the first and second nucleic acids may be operably linked. Even more particularly, the second nucleic acid may be endogenous to a first organism, and any other nucleic acid in the vector may be endogenous to a second organism. Most particularly, the first and second organisms may be different species.

In a further embodiment of the present invention, a host cell may comprise an isolated nucleic acid molecule according to the present invention. More particularly, the isolated nucleic acid molecule of the present invention found in the host cell of the present invention may be endogenous to a first organism and may be flanked by nucleotide sequences endogenous to a second organism. Further, the first and second organisms may be different species. Even more particularly, the host cell of the present invention may comprise a vector according to the present invention, which itself comprises nucleic acid molecules according to those of the present invention.

In another embodiment of the present invention, the isolated polypeptides of the present invention may additionally comprise amino acid sequences that are at least 85% identical to any one of SEQ ID Nos. 80, 99, 106, 123, 132, 146, 154 and 172.

Other embodiments of the present invention include methods of introducing an isolated nucleic acid of the present invention into a host cell. More particularly, an isolated nucleic acid molecule of the present invention may be contacted to a host cell under conditions allowing transport of the isolated nucleic acid into the host cell. Even more particularly, a vector as described in a previous embodiment of the present invention may be introduced into a host cell by the same method.

Methods of detection are also available as embodiments of the present invention. Particularly, methods for detecting a nucleic acid molecule according to the present invention in a sample. More particularly, the isolated nucleic acid molecule according to the present invention may be contacted with a sample under conditions that permit a comparison of the nucleotide sequence of the isolated nucleic acid molecule with a nucleotide sequence of nucleic acid in the sample. The results of such an analysis may then be considered to determine whether the isolated nucleic acid molecule of the present invention is detectable and therefore present within the sample.

A further embodiment of the present invention comprises a plant, plant cell, plant material or seeds of plants comprising an isolated nucleic acid molecule and/or vector of the present invention. More particularly, the isolated nucleic acid molecule of the present invention may be exogenous to the plant, plant cell, plant material or seed of a plant.

A further embodiment of the present invention includes a plant regenerated from a plant cell or seed according to the present invention. More particularly, the plant, or plants derived from the plant, plant cell, plant material or seeds of a plant of the present invention preferably has increased size (in whole or in part), increased vegetative growth and/or increased biomass (sometimes hereinafter collectively referred to as increased biomass) in saline conditions, as compared to a wild-type plant cultivated under identical conditions. Furthermore, the transgenic plant may comprise a first isolated nucleic acid molecule of the present invention, which encodes a protein involved in improving growth and phenotype characteristics in saline conditions, and a second isolated nucleic acid molecule which encodes a promoter capable of driving expression in plants, wherein the growth and phenotype improving component and the promoter are operably linked. More preferably, the first isolated nucleic acid may be mis-expressed in the transgenic plant of the present invention, and the transgenic plant exhibits improved characteristics as compared to a progenitor plant devoid of the polynucleotide, when the transgenic plant and the progenitor plant are cultivated under identical, saline conditions. In another embodiment of the present invention the improved growth and phenotype characteristics may be due to the inactivation of a particular sequence, using for example an interfering RNA.

A further embodiment consists of a plant, plant cell, plant material or seed of a plant according to the present invention which comprises an isolated nucleic acid molecule of the present invention, wherein the plant, or plants derived from the plant, plant cell, plant material or seed of a plant, has the improved growth and phenotype characteristics in saline conditions as compared to a wild-type plant cultivated under identical conditions.

The polynucleotide conferring increased biomass or vigor in saline conditions may be mis-expressed in the transgenic plant of the present invention, and the transgenic plant exhibits an increased biomass or vigor as compared to a progenitor plant devoid of the polynucleotide, when the transgenic plant and the progenitor plant are cultivated under identical saline conditions. In another embodiment of the present invention increased biomass or vigor phenotype may be due to the inactivation of a particular sequence, using for example an interfering RNA.

Another embodiment consists of a plant, plant cell, plant material or seed of a plant according to the present invention which comprises an isolated nucleic acid molecule of the present invention, wherein the plant, or plants derived from the plant, plant cell, plant material or seed of a plant, has increased biomass or vigor in saline conditions as compared to a wild-type plant cultivated under identical conditions.

Another embodiment of the present invention includes methods of enhancing biomass or vigor in plants challenged with saline conditions. More particularly, these methods comprise transforming a plant with an isolated nucleic acid molecule according to the present invention. Preferably, the method is a method of enhancing biomass or vigor in the transgenic plant, whereby the plant is transformed with a nucleic acid molecule encoding the polypeptide of the present invention.

Polypeptides of the present invention include sequences belonging to the consensus sequence families shown in FIGS. 1-9 as delineated by Hidden Markov Models (HMMs).

2. Definitions

The following terms are utilized throughout this application:

Functionally Comparable Proteins or Functional Homologs: This phrase describes a set of proteins that perform similar functions within an organism. By definition, perturbation of an individual protein within that set (through misexpression or mutation, for example) is expected to confer a similar phenotype as compared to perturbation of any other individual protein. Such proteins typically share sequence similarity resulting in similar biochemical activity. Within this definition, homologs, orthologs and paralogs are considered to be functionally comparable.

Functionally comparable proteins will give rise to the same characteristic to a similar, but not necessarily the same, degree. Typically, comparable proteins give the same characteristics where the quantitative measurement due to one of the comparables is at least 20% of the other, more typically, between 30 to 40%; even more typically, between 50-60%; even more typically between 70 to 80%; even more typically between 90 to 100% of the other.

Heterologous sequences: "Heterologous sequences" are those that are not operatively linked or are not contiguous to each other in nature. For example, a promoter from corn is considered heterologous to an *Arabidopsis* coding region sequence. Also, a promoter from a gene encoding a growth factor from corn is considered heterologous to a sequence encoding the corn receptor for the growth factor. Regulatory element sequences, such as UTRs or 3' end termination sequences that do not originate in nature from the same gene as the coding sequence, are considered heterologous to said coding sequence. Elements operatively linked in nature and contiguous to each other are not heterologous to each other. On the other hand, these same elements remain operatively linked but become heterologous if other filler sequence is placed between them. Thus, the promoter and coding sequences of a corn gene expressing an amino acid transporter are not heterologous to each other, but the promoter and coding sequence of a corn gene operatively linked in a novel manner are heterologous.

Hidden Markov Model (HMM): HMM is a statistical description of a sequence family's consensus. The model is indicative of similarity of a polypeptide sequence to a group of structurally and functionally related polypeptides (Durbin, R., Eddy, S. R., Krogh, A. & Mitchison, G. J. *Biological Sequence Analysis: Probabilistic Models of Proteins and Nucleic Acids* Cambridge University Press, Cambridge UK, 1998).

HMM based on specified sequences: An HMM profile based on specified sequences is the output model generated by the program HMMER 2.3.2 (released Oct. 3, 2003 under a GNU general public license, and available from various sources, such as the HMMER website on the internet) configured with default parameters, the model being built by the program using as input the specified sequences. The program outputs the model as a text file.

HMM bit score: An HMM bit score is a probabilistic indication of confidence that a sequence fits the model. The bit score reflects whether the sequence is a better fit to an HMM of interest than to a null model of nonhomologous sequences. A significant HMM bit score is greater than zero, but is typically greater than 20. The HMM bit score of a polypeptide sequence fitted to an HMM profile can be determined by fitting the polypeptide to the HMM with program HMMER 2.3.2 configured for glocal alignments.

Misexpression: The term "misexpression" refers to an increase or a decrease in the transcription of a coding region into a complementary RNA sequence as compared to the wild-type. This term also encompasses expression and/or translation of a gene or coding region or inhibition of such transcription and/or translation for a different time period as compared to the wild-type and/or from a non-natural location within the plant genome, including a gene or coding region from a different plant species or from a non-plant organism.

Percentage of sequence identity: As used herein, the term "percent sequence identity" refers to the degree of identity between any given query sequence and a subject sequence. A subject sequence typically has a length that is from about 80 percent to 250 percent of the length of the query sequence, e.g., 82, 85, 87, 89, 90, 93, 95, 97, 99, 100, 105, 110, 115, or 120, 130, 140, 150, 160, 170, 180, 190, 200, 210, 220, 230, 240, or 250 percent of the length of the query sequence. A query nucleic acid or amino acid sequence is aligned to one or more subject nucleic acid or amino acid sequences using the computer program ClustalW (version 1.83, default parameters), which allows alignments of nucleic acid or protein sequences to be carried out across their entire length (global alignment). Chenna et al. (2003) *Nucleic Acids Res.* 31(13):3497-500.

ClustalW calculates the best match between a query and one or more subject sequences, and aligns them so that identities, similarities and differences can be determined. Gaps of one or more residues can be inserted into a query sequence, a subject sequence, or both, to maximize sequence alignments. For fast pairwise alignment of nucleic acid sequences, the following default parameters are used: word size: 2; window size: 4; scoring method: percentage; number of top diagonals: 4; and gap penalty: 5. For an alignment of multiple nucleic acid sequences, the following parameters are used: gap opening penalty: 10.0; gap extension penalty: 5.0; and weight transitions: yes. For fast pairwise alignment of protein sequences, the following parameters are used: word size: 1; window size: 5; scoring method: percentage; number of top diagonals: 5; gap penalty: 3. For multiple alignment of protein sequences, the following parameters are used: weight matrix: blosum; gap opening penalty: 10.0; gap extension penalty: 0.05; hydrophilic gaps: on; hydrophilic residues: Gly, Pro, Ser, Asn, Asp, Gln, Glu, Arg, and Lys; residue-specific gap penalties: on. The output is a sequence alignment that reflects the relationship between sequences. ClustalW can be run, for example, at the Baylor College of Medicine Search Launcher website and at the European Bioinformatics Institute website on the World Wide Web.

To determine a percent identity for polypeptide or nucleic acid sequences between a query and a subject sequence, the sequences are aligned using Clustal W and the number of identical matches in the alignment is divided by the query length, and the result is multiplied by 100. The output is the percent identity of the subject sequence with respect to the query sequence. It is noted that the percent identity value can be rounded to the nearest tenth. For example, 78.11, 78.12, 78.13, and 78.14 are rounded down to 78.1, while 78.15, 78.16, 78.17, 78.18, and 78.19 are rounded up to 78.2.

Photosynthetic efficiency: photosynthetic efficiency, or electron transport via photosystem II, is estimated by the relationship between Fm, the maximum fluorescence signal and the variable fluorescence, Fv. Here, a reduction in the optimum quantum yield (Fv/Fm) indicates stress and can be used to monitor the performance of transgenic plants compared to non-transgenic plants under salt stress conditions.

Regulatory Regions: The term "regulatory region" refers to nucleotide sequences that, when operably linked to a sequence, influence transcription initiation or translation initiation or transcription termination of said sequence and the rate of said processes, and/or stability and/or mobility of a transcription or translation product. As used herein, the term "operably linked" refers to positioning of a regulatory region and said sequence to enable said influence. Regulatory regions include, without limitation, promoter sequences, enhancer sequences, response elements, protein recognition sites, inducible elements, protein binding sequences, 5' and 3' untranslated regions (UTRs), transcriptional start sites, termination sequences, polyadenylation sequences, and introns. Regulatory regions can be classified in two categories, promoters and other regulatory regions.

Salt tolerance: Plant species vary in their capacity to tolerate salinity. "Salinity" can be defined as the set of environmental conditions under which a plant will begin to suffer the effects of elevated salt concentration, such as ion imbalance, decreased stomatal conductance, decreased photosynthesis, decreased growth rate, increased cell death, loss of turgor (wilting), or ovule abortion. For these reasons, plants experiencing salinity stress typically exhibit a significant reduction in biomass and/or yield.

Elevated salinity may be caused by natural, geological processes and by human activities, such as irrigation. Since plant species vary in their capacity to tolerate water deficit, the precise environmental salt conditions that cause stress cannot be generalized. However, under saline conditions, salt tolerant plants produce higher biomass, yield and survivorship than plants that are not salt tolerant. Differences in physical appearance, recovery and yield can be quantified and statistically analyzed using well known measurement and analysis methods.

Seedling area: The total leaf area of a young plant about 2 weeks old.

Seedling vigor: As used herein, "seedling vigor" refers to the plant characteristic whereby the plant emerges from soil faster, has an increased germination rate (i.e., germinates faster), has faster and larger seedling growth and/or germinates faster under salt conditions as compared to the wild-type or control under similar conditions. Seedling vigor has often been defined to comprise the seed properties that determine "the potential for rapid, uniform emergence and development of normal seedlings under a wide range of field conditions".

Stringency: "Stringency," as used herein is a function of nucleic acid molecule probe length, nucleic acid molecule probe composition (G+C content), salt concentration, organic solvent concentration and temperature of hybridization and/or wash conditions. Stringency is typically measured by the parameter $T_m$, which is the temperature at which 50% of the complementary nucleic acid molecules in the hybridization assay are hybridized, in terms of a temperature differential from $T_m$. High stringency conditions are those providing a condition of $T_m$–5° C. to $T_m$–10° C. Medium or moderate stringency conditions are those providing $T_m$–20° C. to $T_m$–29° C. Low stringency conditions are those providing a condition of $T_m$–40° C. to $T_m$–48° C. The relationship between hybridization conditions and $T_m$ (in ° C.) is expressed in the mathematical equation:

$$T_m = 81.5 - 16.6(\log_{10}[\text{Na}^+]) + 0.41(\% \, G+C) - (600/N) \qquad (I)$$

where N is the number of nucleotides of the nucleic acid molecule probe. This equation works well for probes 14 to 70 nucleotides in length that are identical to the target sequence. The equation below, for $T_m$ of DNA-DNA hybrids, is useful for probes having lengths in the range of 50 to greater than 500 nucleotides, and for conditions that include an organic solvent (formamide):

$$T_m = 81.5 + 16.6 \log\{[\text{Na}^+]/(1+0.7[\text{Na}^+])\} + 0.41(\% \, G+C) - 500/L \, 0.63(\% \text{ formamide}) \qquad (II)$$

where L represents the number of nucleotides in the probe in the hybrid (Bonner et al. (1973) *J. Mol. Biol.* 81:123). The $T_m$ of Equation II is affected by the nature of the hybrid: for DNA-RNA hybrids, $T_m$ is 10-15° C. higher than calculated; for RNA-RNA hybrids, $T_m$ is 20-25° C. higher. Because the $T_m$ decreases about 1° C. for each 1% decrease in homology when a long probe is used (Frischauf et al. (1983) *J. Mol Biol,* 170: 827-842), stringency conditions can be adjusted to favor detection of identical genes or related family members.

Equation II is derived assuming the reaction is at equilibrium. Therefore, hybridizations according to the present invention are most preferably performed under conditions of probe excess and allowing sufficient time to achieve equilibrium. The time required to reach equilibrium can be shortened by using a hybridization buffer that includes a hybridization accelerator such as dextran sulfate or another high volume polymer.

Stringency can be controlled during the hybridization reaction, or after hybridization has occurred, by altering the salt and temperature conditions of the wash solutions. The formulas shown above are equally valid when used to compute the stringency of a wash solution. Preferred wash solution stringencies lie within the ranges stated above; high stringency is 5-8° C. below $T_m$, medium or moderate stringency is 26-29° C. below $T_m$ and low stringency is 45-48° C. below $T_m$.

For example, the hybridization step may be performed in aqueous hybridization solution at a temperature between 63° C. and 70° C., more preferably at a temperature between 65° C. and 68° C. and most preferably at a temperature of 65° C. Alternatively, the high stringency hybridization step may be performed in formamide hybridization solution at a temperature between 40° C. and 46° C., at a temperature between 41° C. and 44° C. and most preferably at a temperature of 42° C.

A wash step follows hybridization, and an initial wash is performed with wash solution 1 at 25° C. or 37° C. Following the initial wash, additional washes are performed with wash solution 1 at a temperature between 63° C. and 70° C., more preferably at a temperature between 65° C. and 68° C. and most preferably at a temperature of 65° C. The number of additional wash steps can be 1, 2, 3, 4, 5 or more. The time of both the initial and additional wash steps may be 5 minutes, 10 minutes, 15 minutes, 20 minutes, 25 minutes, 30 minutes, 45 minutes, 1 hour, 1.5 hours, 2 hours or more.

Set forth below are the composition of the hybridization and wash solutions and their components. A person of ordinary skill in the art will recognize that these solutions are typical and exemplary of high stringency hybridization solutions.

Aqueous Hybridization Solution: 6×SSC or 6×SSPE
    0.05% Blotto or 5×Denhardt's Reagent
    100 µg/ml denatured salmon sperm DNA
    0.05% SDS
Formamide Hybridization Solution: 50% Formamide
    6×SSC or 6×SSPE
    0.05% Blotto or 5×Denhardt's Reagent
    100 µg/ml denatured salmon sperm DNA
    0.05% SDS
Wash Solution 1: 2×SSC or SSPE
    0.1% SDS
Wash Solution 2: 0.1×SSC or SSPE
    0.5% SDS
20×SSC: 175.3 g NaCl
    88.2 g Sodium Citrate
    Bring to 800 ml with $H_2O$
    Adjust to pH 7 with 10 n NaOH
    Bring to 1 L with $H_2O$
20×SSPE: 175.3 g NaCl
    27.6 g $NaH_2PO_4$
    Bring to 800 ml with $H_2O \cdot H_2O$
    7.4 g EDTA
    Adjust to pH 7.4 with 10 n NaOH
    Bring to 1 L with $H_2O$
1×BLOTTO: 5% Non-fat dry milk
    0.02% Sodium azide
50×Denhardts's Reagent: 5 g Ficoll
    5 g Polyvinylpyrrolidone
    5 g BSA
    Adjust to 500 ml with $H_2O$ Superpool: As used in the context of the current invention, a "superpool" contains an equal amount of seed from 500 different events, representing 100 distinct exogenous nucleotide sequences. An event is a plant carrying a unique insertion of a distinct exogenous sequence which misexpresses that sequence. Transformation of a single polynucleotide sequence can result in multiple events because the sequence can insert in a different part of the genome with each transformation.

$T_0$: The term "$T_0$" refers to the whole plant, explant or callus tissue, inoculated with the transformation medium.

$T_1$: The term $T_1$ refers to either the progeny of the $T_0$ plant, in the case of whole-plant transformation, or the regenerated seedling in the case of explant or callous tissue transformation.

$T_2$: The term $T_2$ refers to the progeny of the $T_1$ plant. $T_2$ progeny are the result of self-fertilization or cross-pollination of a $T_1$ plant.

$T_3$: The term $T_3$ refers to second generation progeny of the plant that is the direct result of a transformation experiment. $T_3$ progeny are the result of self-fertilization or cross-pollination of a $T_2$ plant.

$T_4$: As used in the current application, the term $T_4$ refers to third generation progeny of the plant that is the direct result of a transformation experiment. $T_4$ progeny are the result of self-fertilization or cross pollination of a $T_3$ plant.

Transformation: Examples of means by which this can be accomplished are described below and include *Agrobacterium*-mediated transformation (of dicots (Needleman and Wunsch (1970) *J. Mol. Biol.* 48:443; Pearson and Lipman (1988) 10 *Proc. Natl. Acad. Sci.* (USA) 85: 2444), of monocots (Yamauchi et al. (1996) *Plant Mol Biol.* 30:321-9;

Xu et al. (1995) *Plant MoL Biol.* 27:237; Yamamoto et al. (1991) *Plant Cell* 3:371), and biolistic methods (P. Tijessen, "Hybridization with Nucleic Acid Probes" In Laboratory Techniques in Biochemistry and Molecular Biology, P. C. vand der Vliet, ed., c. 1993 by Elsevier, Amsterdam), electroporation, in planta techniques and the like. Such a plant containing the exogenous nucleic acid is referred to here as a $T_0$ for the primary transgenic plant and $T_1$ for the first generation.

3. Important Characteristics of the Polynucleotides and Polypeptides of the Invention The nucleic acid molecules and polypeptides of the present invention are of interest because when the nucleic acid molecules are mis-expressed (i.e., when expressed at a non-natural location or in an increased or decreased amount relative to wild-type) they produce plants that exhibit improved salt tolerance as compared to wild-type plants, as evidenced by the results of various experiments disclosed below. In particular, plants transformed with at least one of the nucleic acid molecules and polypeptides of the present invention have increased salt growth index values as compared to wild-type plants. For example, plants transformed with the sequences of the present invention can exhibit increases in SGI values of at least 25%, at least 50%, at least 75%, at least 100%, at least 200%, at least 300%, at least 400%, or even at least 500%. This trait can be used to exploit or maximize plant products. For example, the nucleic acid molecules and polypeptides of the present invention are used to increase the expression of genes that cause the plant to have improved biomass, growth rate and/or seedling vigor in saline conditions.

Because the disclosed sequences and methods increase vegetative growth and growth rate in saline conditions, the disclosed methods can be used to enhance plant growth in plants irrigated with saline water and/or grown in saline soil. For example, plants of the invention show, under saline conditions, increased photosynthetic efficiency and increased seedling area as compared to a plant of the same species that is not genetically modified for substantial vegetative growth. Examples of increases in biomass production include increases of at least 5%, at least 20%, or even at least 50%, when compared to an amount of biomass production by a wild-type plant of the same species under identical conditions.

Seed or seedling vigor is an important characteristic that can greatly influence successful growth of a plant, such as crop plants. Adverse environmental conditions, such as saline conditions, can affect a plant growth cycle, germination of seeds and seedling vigor (i.e. vitality and strength under such conditions can differentiate between successful and failed crop growth). Seedling vigor has often been defined to comprise the seed properties that determine "the potential for rapid, uniform emergence and development of normal seedlings under a wide range of field conditions". Hence, it would be advantageous to develop plant seeds with increased vigor, particularly in elevated salinity.

For example, increased seedling vigor would be advantageous for cereal plants such as rice, maize, wheat, etc. production. For these crops, germination and growth can often be slowed or stopped by salination. Genes associated with increased seed vigor and/or salination tolerance have therefore been sought for producing improved crop varieties. (Walia et al. (2005) *Plant Physiology* 139:822-835).

4. The Polypeptides/Polynucleotides of the Invention

The polynucleotides of the present invention and the proteins expressed via translation of these polynucleotides are set forth in the Sequence Listing, specifically SEQ ID NOs. 79-253 and 269-315. The Sequence Listing also consists of functionally comparable proteins. Polypeptides comprised of a sequence belonging to the consensus sequence families shown in FIGS. 1 to 9 as delineated by HMMs can be utilized for the purposes of the invention, namely to make transgenic plants with improved biomass, growth rate and/or seedling vigor in saline conditions.

5. Use of the Polypeptides to Make Transgenic Plants

To use the sequences of the present invention or a combination of them or parts and/or mutants and/or fusions and/or variants of them, recombinant DNA constructs are prepared that comprise the polynucleotide sequences of the invention inserted into a vector and that are suitable for transformation of plant cells. The construct can be made using standard recombinant DNA techniques (see, Sambrook et al., Molecular Cloning: A Laboratory Manual, Second Edition, Cold Spring Harbor Laboratory Press, 1989, New York.) and can be introduced into the plant species of interest by, for example, *Agrobacterium*-mediated transformation, or by other means of transformation, for example, as disclosed below.

The vector backbone may be any of those typically used in the field such as plasmids, viruses, artificial chromosomes, BACs, YACs, PACs and vectors such as, for instance, bacteria-yeast shuttle vectors, lambda phage vectors, T-DNA fusion vectors and plasmid vectors (see, Shizuya et al. (1992) *Proc. Natl. Acad. Sci. USA* 89: 8794-8797; Hamilton et al. (1996) *Proc. Natl. Acad. Sci. USA* 93: 9975-9979; Burke et al. (1987) *Science* 236:806-812; Sternberg N. et al. (1990) *Proc Natl Acad Sci USA.* 87:103-7; Bradshaw et al. (1995) *Nucl Acids Res* 23: 4850-4856; Frischauf et al. (1983) *J. Mol Biol* 170: 827-842; Huynh et al., Glover N M (ed) DNA Cloning: A practical Approach, Vol. 1 Oxford: IRL Press (1985); Walden et al. (1990) *Mol Cell Biol* 1: 175-194).

Typically, the construct comprises a vector containing a nucleic acid molecule of the present invention with any desired transcriptional and/or translational regulatory sequences such as, for example, promoters, UTRs, and 3' end termination sequences. Vectors may also include, for example, origins of replication, scaffold attachment regions (SARs), markers, homologous sequences, and introns. The vector may also comprise a marker gene that confers a selectable phenotype on plant cells. The marker may preferably encode a biocide resistance trait, particularly antibiotic resistance, such as resistance to, for example, kanamycin, bleomycin, or hygromycin, or herbicide resistance, such as resistance to, for example, glyphosate, chlorosulfuron or phosphinotricin.

It will be understood that more than one regulatory region may be present in a recombinant polynucleotide, e.g., introns, enhancers, upstream activation regions, transcription terminators, and inducible elements. Thus, more than one regulatory region can be operably linked to said sequence.

To "operably link" a promoter sequence to a sequence, the translation initiation site of the translational reading frame of said sequence is typically positioned between one and about fifty nucleotides downstream of the promoter. A promoter can, however, be positioned as much as about 5,000 nucleotides upstream of the translation initiation site, or about 2,000 nucleotides upstream of the transcription start site. A promoter typically comprises at least a core (basal) promoter. A promoter also may include at least one control element, such as an enhancer sequence, an upstream element or an upstream activation region (UAR). For example, a suitable enhancer is a cis-regulatory element (−212 to −154) from the upstream region of the octopine synthase (ocs) gene. Fromm et al. (1989) *Plant Cell* 1:977-984.

Some suitable promoters initiate transcription only, or predominantly, in certain cell types. For example, a promoter that is active predominantly in a reproductive tissue (e.g., fruit, ovule, pollen, pistils, female gametophyte, egg cell, central cell, nucellus, suspensor, synergid cell, flowers, embryonic tissue, embryo sac, embryo, zygote, endosperm, integument, or seed coat) can be used. Thus, as used herein a cell type- or tissue-preferential promoter is one that drives expression preferentially in the target tissue, but may also lead to some expression in other cell types or tissues as well. Methods for identifying and characterizing promoter regions in plant genomic DNA include, for example, those described in the following references: Jordano, et al. (1989) *Plant Cell* 1:855-866; Bustos et al. (1989) *Plant Cell* 1:839-854; Green et al. (1988) *EMBO J.* 7: 4035-4044; Meier et al. (1991) *Plant Cell* 3: 309-316; and Zhang et al. (1996) *Plant Physiology* 110: 1069-1079.

Examples of various classes of promoters are described below. Some of the promoters indicated below are described in more detail in U.S. Patent application Ser. Nos. 60/505,689; 60/518,075; 60/544,771; 60/558,869; 60/583,691; 60/619,181; 60/637,140; 10/950,321; 10/957,569; 11/058,689; 11/172,703; 11/208,308; and PCT/US05/23639. It will be appreciated that a promoter may meet criteria for one classification based on its activity in one plant species, and yet meet criteria for a different classification based on its activity in another plant species.

Other Regulatory Regions: A 5' untranslated region (UTR) can be included in nucleic acid constructs described herein. A 5' UTR is transcribed, but is not translated, and lies between the start site of the transcript and the translation initiation codon and may include the +1 nucleotide. A 3' UTR can be positioned between the translation termination codon and the end of the transcript. UTRs can have particular functions such as increasing mRNA stability or attenuating translation. Examples of 3' UTRs include, but are not limited to, polyadenylation signals and transcription termination sequences, e.g., a nopaline synthase termination sequence.

Various promoters can be used to drive expression of the polynucleotides of the present invention. Nucleotide sequences of such promoters are set forth in SEQ ID NOS: 1-78. Some of them can be broadly expressing promoters, others may be more tissue preferential.

A promoter can be said to be "broadly expressing" when it promotes transcription in many, but not necessarily all, plant tissues or plant cells. For example, a broadly expressing promoter can promote transcription of an operably linked sequence in one or more of the shoot, shoot tip (apex), and leaves, but weakly or not at all in tissues such as roots or stems. As another example, a broadly expressing promoter can promote transcription of an operably linked sequence in one or more of the stem, shoot, shoot tip (apex), and leaves, but can promote transcription weakly or not at all in tissues such as reproductive tissues of flowers and developing seeds. Non-limiting examples of broadly expressing promoters that can be included in the nucleic acid constructs provided herein include the p326 (SEQ ID NO: 76), YP0144 (SEQ ID NO: 55), YP0190 (SEQ ID NO: 59), p13879 (SEQ ID NO: 75), YP0050 (SEQ ID NO: 35), p32449 (SEQ ID NO: 77), 21876 (SEQ ID NO: 1), YP0158 (SEQ ID NO: 57), YP0214 (SEQ ID NO: 61), YP0380 (SEQ ID NO: 70), PT0848 (SEQ ID NO: 26), and PT0633 (SEQ ID NO: 7). Additional examples include the cauliflower mosaic virus (CaMV) 35S promoter, the mannopine synthase (MAS) promoter, the 1' or 2' promoters derived from T-DNA of *Agrobacterium tumefaciens*, the figwort mosaic virus 34S promoter, actin promoters such as the rice actin promoter, and ubiquitin promoters such as the maize ubiquitin-1 promoter. In some cases, the CaMV 35S promoter is excluded from the category of broadly expressing promoters.

Root-active promoters drive transcription in root tissue, e.g., root endodermis, root epidermis, or root vascular tissues. In some embodiments, root-active promoters are root-preferential promoters, i.e., drive transcription only or predominantly in root tissue. Root-preferential promoters include the YP0128 (SEQ ID NO: 52), YP0275 (SEQ ID NO: 63), PT0625 (SEQ ID NO: 6), PT0660 (SEQ ID NO: 9), PT0683 (SEQ ID NO: 14), and PT0758 (SEQ ID NO: 22). Other root-preferential promoters include the PT0613 (SEQ ID NO: 5), PT0672 (SEQ ID NO: 11), PT0688 (SEQ ID NO: 15), and PT0837 (SEQ ID NO: 24), which drive transcription primarily in root tissue and to a lesser extent in ovules and/or seeds. Other examples of root-preferential promoters include the root-specific subdomains of the CaMV 35S promoter (Lam et al. (1989) *Proc. Natl. Acad. Sci. USA* 86:7890-7894), root cell specific promoters reported by Conkling et al. (1990) *Plant Physiol.* 93:1203-1211 and the tobacco RD2 gene promoter.

In some embodiments, promoters that drive transcription in maturing endosperm can be useful. Transcription from a maturing endosperm promoter typically begins after fertilization and occurs primarily in endosperm tissue during seed development and is typically highest during the cellularization phase. Most suitable are promoters that are active predominantly in maturing endosperm, although promoters that are also active in other tissues can sometimes be used. Non-limiting examples of maturing endosperm promoters that can be included in the nucleic acid constructs provided herein include the napin promoter, the Arcelin-5 promoter, the phaseolin gene promoter (Bustos et al. (1989) *Plant Cell* 1(9):839-853), the soybean trypsin inhibitor promoter (Riggs et al. (1989) *Plant Cell* 1(6):609-621), the ACP promoter (Baerson et al. (1993) *Plant Mol Biol,* 22(2):255-267), the stearoyl-ACP desaturase gene (Slocombe et al. (1994) *Plant Physiol* 104(4):167-176), the soybean α' sub-unit of β-conglycinin promoter (Chen et al. (1986) *Proc Natl Acad Sci USA* 83:8560-8564), the oleosin promoter (Hong et al. (1997) *Plant Mol Biol* 34(3):549-555), and zein promoters, such as the 15 kD zein promoter, the 16 kD zein promoter, 19 kD zein promoter, 22 kD zein promoter and 27 kD zein promoter. Also suitable are the Osgt-1 promoter from the rice glutelin-1 gene (Zheng et al. (1993) *Mol. Cell Biol.* 13:5829-5842), the beta-amylase gene promoter, and the barley hordein gene promoter. Other maturing endosperm promoters include the YP0092 (SEQ ID NO: 38), PT0676 (SEQ ID NO: 12), and PT0708 (SEQ ID NO: 17).

Promoters that drive transcription in ovary tissues such as the ovule wall and mesocarp can also be useful, e.g., a polygalacturonidase promoter, the banana TRX promoter, and the melon actin promoter. Other such promoters that drive gene expression preferentially in ovules are YP0007 (SEQ ID NO: 30), YP0111 (SEQ ID NO: 46), YP0092 (SEQ ID NO: 38), YP0103 (SEQ ID NO: 43), YP0028 (SEQ ID NO: 33), YP0121 (SEQ ID NO: 51), YP0008 (SEQ ID NO: 31), YP0039 (SEQ ID NO: 34), YP0115 (SEQ ID NO: 47), YP0119 (SEQ ID NO: 49), YP0120 (SEQ ID NO: 50) and YP0374 (SEQ ID NO: 68).

In some other embodiments of the present invention, embryo sac/early endosperm promoters can be used in order drive transcription of the sequence of interest in polar nuclei and/or the central cell, or in precursors to polar nuclei, but not in egg cells or precursors to egg cells. Most suitable are promoters that drive expression only or predominantly in polar nuclei or precursors thereto and/or the central cell. A pattern of transcription that extends from polar nuclei into early endosperm development can also be found with embryo sac/early endosperm-preferential promoters, although transcription typically decreases significantly in later endosperm development during and after the cellularization phase. Expression in the zygote or developing embryo typically is not present with embryo sac/early endosperm promoters.

Promoters that may be suitable include those derived from the following genes: *Arabidopsis* viviparous-1 (see, GenBank No. U93215); *Arabidopsis* atmyc1 (see Urao (1996) *Plant Mol. Biol.*, 32:571-57; Conceicao (1994) *Plant*, 5:493-505); *Arabidopsis* FIE (GenBank No. AF129516); *Arabidopsis* MEA; *Arabidopsis* FIS2 (GenBank No. AF096096); and FIE 1.1 (U.S. Pat. No. 6,906,244). Other promoters that may be suitable include those derived from the following genes: maize MAC1 (see, Sheridan (1996) *Genetics*, 142: 1009-1020); maize Cat3 (see, GenBank No. L05934; Abler (1993) *Plant Mol. Biol.*, 22:10131-1038). Other promoters include the following *Arabidopsis* promoters: YP0039 (SEQ ID NO: 34), YP0101 (SEQ ID NO: 41), YP0102 (SEQ ID NO: 42), YP0110 (SEQ ID NO: 45), YP0117 (SEQ ID NO: 48), YP0119 (SEQ ID NO: 49), YP0137 (SEQ ID NO: 53), DME, YP0285 (SEQ ID NO: 64), and YP0212 (SEQ ID NO: 60). Other promoters that may be useful include the following rice promoters: p530c10, pOsFIE2-2, pOsMEA, pOsYp102, and pOsYp285.

Promoters that preferentially drive transcription in zygotic cells following fertilization can provide embryo-preferential expression and may be useful for the present invention. Most suitable are promoters that preferentially drive transcription in early stage embryos prior to the heart stage, but expression in late stage and maturing embryos is also suitable. Embryo-preferential promoters include the barley lipid transfer protein (Ltp1) promoter (*Plant Cell Rep* (2001) 20:647-654, YP0097 (SEQ ID NO: 40), YP0107 (SEQ ID NO: 44), YP0088 (SEQ ID NO: 37), YP0143 (SEQ ID NO: 54), YP0156 (SEQ ID NO: 56), PT0650 (SEQ ID NO: 8), PT0695 (SEQ ID NO: 16), PT0723 (SEQ ID NO: 19), PT0838 (SEQ ID NO: 25), PT0879 (SEQ ID NO: 28) and PT0740 (SEQ ID NO: 20).

Promoters active in photosynthetic tissue in order to drive transcription in green tissues such as leaves and stems are of particular interest for the present invention. Most suitable are promoters that drive expression only or predominantly such tissues. Examples of such promoters include the ribulose-1,5-bisphosphate carboxylase (RbcS) promoters such as the RbcS promoter from eastern larch (*Larix laricina*), the pine cab6 promoter (Yamamoto et al. (1994) *Plant Cell Physiol.* 35:773-778), the Cab-1 gene promoter from wheat (Fejes et al. (1990) *Plant Mol. Biol.* 15:921-932), the CAB-1 promoter from spinach (Lubberstedt et al. (1994) *Plant Physiol.* 104:997-1006), the cab1R promoter from rice (Luan et al. (1992) *Plant Cell* 4:971-981), the pyruvate orthophosphate dikinase (PPDK) promoter from corn (Matsuoka et al. (1993) *Proc Natl Acad. Sci USA* 90:9586-9590), the tobacco Lhcb1*2 promoter (Cerdan et al. (1997) *Plant Mol. Biol.* 33:245-255), the *Arabidopsis thaliana* SUC2 sucrose-H+ symporter promoter (Truernit et al. (1995) *Planta* 196:564-570), and thylakoid membrane protein promoters from spinach (psaD, psaF, psaE, PC, FNR, atpC, atpD, cab, rbcS. Other promoters that drive transcription in stems, leafs and green tissue are PT0535 (SEQ ID NO: 3), PT0668 (SEQ ID NO: 2), PT0886 (SEQ ID NO: 29), PR0924 (SEQ ID NO: 265), YP0144 (SEQ ID NO: 55), YP0380 (SEQ ID NO: 70) and PT0585 (SEQ ID NO: 4).

In some other embodiments of the present invention, inducible promoters may be desired. Inducible promoters drive transcription in response to external stimuli such as chemical agents or environmental stimuli. For example, inducible promoters can confer transcription in response to hormones such as giberellic acid or ethylene, or in response to light or drought. Examples of drought inducible promoters are YP0380 (SEQ ID NO: 70), PT0848 (SEQ ID NO: 26), YP0381 (SEQ ID NO: 71), YP0337 (SEQ ID NO: 66), PT0633 (SEQ ID NO: 7), YP0374 (SEQ ID NO: 68), PT0710 (SEQ ID NO: 18), YP0356 (SEQ ID NO: 67), YP0385 (SEQ ID NO: 73), YP0396 (SEQ ID NO: 74), YP0384 (SEQ ID NO: 72), PT0688 (SEQ ID NO: 15), YP0286 (SEQ ID NO: 65), YP0377 (SEQ ID NO: 69), and PD1367 (SEQ ID NO: 78). Examples of promoters induced by nitrogen are PT0863 (SEQ ID NO: 27), PT0829 (SEQ ID NO: 23), PT0665 (SEQ ID NO: 10) and PT0886 (SEQ ID NO: 29). An example of a promoter induced by salt is rd29A (Kasuga et al. (1999) *Nature Biotech* 17: 287-291).

Other Promoters: Other classes of promoters include, but are not limited to, leaf-preferential, stem/shoot-preferential, callus-preferential, guard cell-preferential, such as PT0678 (SEQ ID NO: 13), and senescence-preferential promoters. Promoters designated YP0086 (SEQ ID NO: 36), YP0188 (SEQ ID NO: 58), YP0263 (SEQ ID NO: 62), PT0758 (SEQ ID NO: 22), PT0743 (SEQ ID NO: 21), PT0829 (SEQ ID NO: 23), YP0119 (SEQ ID NO: 49), and YP0096 (SEQ ID NO: 39), as described in the above-referenced patent applications, may also be useful.

Alternatively, misexpression can be accomplished using a two component system, whereby the first component consists of a transgenic plant comprising a transcriptional activator operatively linked to a promoter and the second component consists of a transgenic plant that comprise a nucleic acid molecule of the invention operatively linked to the target-binding sequence/region of the transcriptional activator. The two transgenic plants are crossed and the nucleic acid molecule of the invention is expressed in the progeny of the plant. In another alternative embodiment of the present invention, the misexpression can be accomplished by having the sequences of the two component system transformed in one transgenic plant line.

Another alternative consists in inhibiting expression of a biomass or vigor-modulating polypeptide in a plant species of interest under saline conditions. The term "expression" refers to the process of converting genetic information encoded in a polynucleotide into RNA through transcription of the polynucleotide (i.e., via the enzymatic action of an RNA polymerase), and into protein through translation of mRNA. "Up-regulation" or "activation" refers to regulation that increases the production of expression products relative to basal or native states, while "down-regulation" or "repression" refers to regulation that decreases production relative to basal or native states.

A number of nucleic-acid based methods, including antisense RNA, ribozyme directed RNA cleavage, and interfering RNA (RNAi) can be used to inhibit protein expression in plants. Antisense technology is one well-known method. In this method, a nucleic acid segment from the endogenous gene is cloned and operably linked to a promoter so that the antisense strand of RNA is transcribed. The recombinant vector is then transformed into plants, as described above, and the antisense strand of RNA is produced. The nucleic acid segment need not be the entire sequence of the endogenous gene to be repressed, but typically will be substantially identical to at least a portion of the endogenous gene to be repressed. Generally, higher homology can be used to compensate for the use of a shorter sequence. Typically, a sequence of at least 30 nucleotides is used (e.g., at least 40, 50, 80, 100, 200, 500 nucleotides or more).

Thus, for example, an isolated nucleic acid provided herein can be an antisense nucleic acid to one of the aforementioned nucleic acids encoding a polypeptide modulates biomass under saline conditions. A nucleic acid that decreases the level of a transcription or translation product of a gene encoding a biomass-modulating polypeptide is transcribed into an antisense nucleic acid similar or identical to the sense coding sequence of the biomass- or growth rate-modulating polypeptide. Alternatively, the transcription product of an isolated nucleic acid can be similar or identical to the sense coding sequence of a biomass growth rate-modulating polypeptide, but is an RNA that is unpolyadenylated, lacks a 5' cap structure, or contains an uspliceable intron.

In another method, a nucleic acid can be transcribed into a ribozyme, or catalytic RNA, that affects expression of an mRNA. (See, U.S. Pat. No. 6,423,885). Ribozymes can be designed to specifically pair with virtually any target RNA and cleave the phosphodiester backbone at a specific location, thereby functionally inactivating the target RNA. Heterologous nucleic acids can encode ribozymes designed to cleave particular mRNA transcripts, thus preventing expression of a polypeptide. Hammerhead ribozymes are useful for destroying particular mRNAs, although various ribozymes that cleave mRNA at site-specific recognition sequences can be used. Hammerhead ribozymes cleave mRNAs at locations dictated by flanking regions that form complementary base pairs with the target mRNA. The sole requirement is that the target RNA contains a 5'-UG-3' nucleotide sequence. The construction and production of hammerhead ribozymes is known in the art. See, for example, U.S. Pat. No. 5,254,678 and WO 02/46449 and references cited therein. Hammerhead ribozyme sequences can be embedded in a stable RNA such as a transfer RNA (tRNA) to increase cleavage efficiency in vivo. Perriman, et al. (1995) *Proc. Natl. Acad. Sci. USA,* 92(13):6175-6179; de Feyter and Gaudron, Methods in Molecular Biology, Vol. 74, Chapter 43, "Expressing Ribozymes in Plants", Edited by Turner, P. C, Humana Press Inc., Totowa, NJ. RNA endoribonucleases such as the one that occurs naturally in *Tetrahymena thermophila*, and which have been described extensively by Cech and collaborators can be useful. See, for example, U.S. Pat. No. 4,987,071.

Methods based on RNA interference (RNAi) can be used. RNA interference is a cellular mechanism to regulate the expression of genes and the replication of viruses. This mechanism is thought to be mediated by double-stranded small interfering RNA molecules. A cell responds to such a double-stranded RNA by destroying endogenous mRNA having the same sequence as the double-stranded RNA. Methods for designing and preparing interfering RNAs are known to those of skill in the art; see, e.g., WO 99/32619 and WO 01/5164. For example, a construct can be prepared that includes a sequence that is transcribed into an interfering RNA. Such an RNA can be one that can anneal to itself, e.g., a double stranded RNA having a stem-loop structure. One strand of the stem portion of a double stranded RNA comprises a sequence that is similar or identical to the sense coding sequence of the polypeptide of interest, and that is from about 10 nucleotides to about 2,500 nucleotides in length. The length of the sequence that is similar or identical to the sense coding sequence can be from 10 nucleotides to 500 nucleotides, from 15 nucleotides to 300 nucleotides, from 20 nucleotides to 100 nucleotides, or from 25 nucleotides to 100 nucleotides. The other strand of the stem portion of a double stranded RNA comprises an antisense sequence of the biomass-modulating polypeptide of interest, and can have a length that is shorter, the same as, or longer than the corresponding length of the sense sequence. The loop portion of a double stranded RNA can be from 10 nucleotides to 5,000 nucleotides, e.g., from 15 nucleotides to 1,000 nucleotides, from 20 nucleotides to 500 nucleotides, or from 25 nucleotides to 200 nucleotides. The loop portion of the RNA can include an intron. See, e.g., WO 99/53050.

Transcriptional silencing of the target gene can also be achieved via the promoter through expression of an RNAi construct. This results in the synthesis of double stranded RNA molecules of which the nucleotides sequence is identical to a part of the promoter region of the target gene.

Another alternative method for suppression of the target gene may be achieved through a methodology generally referred to as Virus Induced Gene Silencing or VIGS (Ratcliff et al (2001) Plant J. 25, 237-245). Here, effective and specific gene silencing is achieved by infection of a plant with a plant virus carrying an insert which is homologous to the target gene. The advantage of the VIGS system is that there is no need to develop a plant transformation protocol for the plant species in which the target gene resides.

In all of these silencing methods, the silencing construct (antisense RNA, co-suppression, RNAi or hairpin construct or VIGs vector) preferably contains a DNA fragment that is identical to the target sequence (gene or promoter) that needs to be silenced. The percentage of identity may, however, range between 50-100%, preferably between 60-100%, more preferably between 70-100%, even more preferably between 80-100% and most preferably between 90-100%.

In some nucleic-acid based methods for inhibition of gene expression in plants, a suitable nucleic acid can be a nucleic acid analog. Nucleic acid analogs can be modified at the base moiety, sugar moiety, or phosphate backbone to improve, for example, stability, hybridization, or solubility of the nucleic acid. Modifications at the base moiety include deoxyuridine for deoxythymidine, and 5-methyl-2'-deoxycytidine and 5-bromo-2'-deoxycytidine for deoxycytidine. Modifications of the sugar moiety include modification of the 2' hydroxyl of the ribose sugar to form 2'-O-methyl or 2'-O-allyl sugars. The deoxyribose phosphate backbone can be modified to produce morpholino nucleic acids, in which each base moiety is linked to a six-membered morpholino ring, or peptide nucleic acids, in which the deoxyphosphate backbone is replaced by a pseudopeptide backbone and the four bases are retained. See, for example, Summerton and Weller, 1997, *Antisense Nucleic Acid Drug Dev.,* 7:187-195; Hyrup et al., 1996, *Bioorgan. Med. Chem.,* 4: 5-23. In addition, the deoxyphosphate backbone can be replaced with, for example, a phosphorothioate or phosphorodithioate backbone, a phosphoroamidite, or an alkyl phosphotriester backbone.

Transformation

Nucleic acid molecules of the present invention may be introduced into the genome or the cell of the appropriate host plant by a variety of techniques. These techniques, able to transform a wide variety of higher plant species, are well known and described in the technical and scientific literature (see, e.g., Weising et al. (1988) *Ann. Rev. Genet.*, 22:421 and Christou (1995) *Euphytica*, 85:13-27).

A variety of techniques known in the art are available for the introduction of DNA into a plant host cell. These techniques include transformation of plant cells by injection (Newell (2000) *Mol Biotech* 16:53-65), microinjection (Griesbach (1987) *Plant Sci.* 50:69-77), electroporation of DNA (Fromm et al. (1985) *Proc. Natl. Acad Sci. USA* 82:5824), PEG (Paszkowski et al. (1984) *EMBO J.* 3:2717), use of biolistics (Klein et al. (1987) *Nature* 327:773), fusion of cells or protoplasts (Willmitzer, L (1993) Transgenic Plants. In: Iotechnology, A Multi-Volume Comprehensive treatise (H J. Rehm, G. Reed, A. Püler, P. Stadler, eds., Vol. 2, 627-659, VCH Weinheim-New York-Basel-Cambridge), and via T-DNA using *Agrobacterium tumefaciens* (*Crit. Rev. Plant. Sci.* 4:1-46; Fromm et al. (1990) *Biotechnology* 8:833-844) or *Agrobacterium rhizogenes* (Cho et al. (2000) *Planta* 210:195-204) or other bacterial hosts (Brootghaerts et al. (2005) *Nature* 433:629-633), for example.

In addition, a number of non-stable transformation methods that are well known to those skilled in the art may be desirable for the present invention. Such methods include, but are not limited to, transient expression (Lincoln et al. (1998) *Plant Mol. Biol. Rep.* 16:1-4) and viral transfection (Lacomme et al. (2001), "Genetically Engineered Viruses" (C. J. A. Ring and E. D. Blair, Eds). Pp. 59-99, BIOS Scientific Publishers, Ltd. Oxford, UK).

Seeds are obtained from the transformed plants and used for testing stability and inheritance. Generally, two or more generations are cultivated to ensure that the phenotypic feature is stably maintained and transmitted.

A person of ordinary skill in the art recognizes that after the expression cassette is stably incorporated in transgenic plants and confirmed to be operable, it can be introduced into other plants by sexual crossing. Any of a number of standard breeding techniques can be used, depending upon the species to be crossed.

In aspects related to making transgenic plants, a typical step involves selection or screening of transformed plants, e.g., for the presence of a functional vector as evidenced by expression of a selectable marker. Selection or screening can be carried out among a population of recipient cells to identify transformants using selectable marker genes such as herbicide resistance genes. Physical and biochemical methods can be used to identify transformants. These include Southern analysis or PCR amplification for detection of a polynucleotide; Northern blots, Si RNase protection, primer-extension, or RT-PCR amplification for detecting RNA transcripts; enzymatic assays for detecting enzyme or ribozyme activity of polypeptides and polynucleotides; and protein gel electrophoresis, Western blots, immunoprecipitation, and enzyme-linked immunoassays to detect polypeptides. Other techniques such as in situ hybridization, enzyme staining, and immunostaining also can be used to detect the presence or expression of polypeptides and/or polynucleotides. Methods for performing all of the referenced techniques are known.

A population of transgenic plants can be screened and/or selected for those members of the population that have a desired trait or phenotype conferred by expression of the transgene. For example, a population of progeny of a single transformation event can be screened for those plants having a desired level of expression of a heterologous salt tolerance polypeptide or nucleic acid. As an alternative, a population of plants comprising independent transformation events can be screened for those plants having a desired trait, such as salt tolerance. Selection and/or screening can be carried out over one or more generations, which can be useful to identify those plants that have a statistically significant difference in a protein level as compared to a corresponding level in a control plant. Selection and/or screening can also be carried out in more than one geographic location. In some cases, transgenic plants can be grown and selected under conditions which induce a desired phenotype or are otherwise necessary to produce a desired phenotype in a transgenic plant. In addition, selection and/or screening can be carried out during a particular developmental stage in which the phenotype is expected to be exhibited by the plant. Selection and/or screening can be carried out to choose those transgenic plants having a statistically significant difference in salt tolerance relative to a control plant that lacks the transgene. Selected or screened transgenic plants have an altered phenotype as compared to a corresponding control plant, as described elsewhere in this specification.

The nucleic acid molecules of the present invention may be used to confer the trait of improved tolerance to saline conditions. The invention has utility in improving important agronomic characteristics of crop plants, for example enabling plants to be productively cultivated in saline conditions. As noted above, transgenic plants that exhibit overexpression of the polynucleotides of the invention grow well under high salt conditions.

The nucleic acid molecules of the present invention encode appropriate proteins from any organism, but are preferably found in plants, fungi, bacteria or animals.

Transgenic Plant Phenotypes

Information that the polypeptides disclosed herein can modulate salt tolerance is useful in breeding of crop plants. Based on the effect of the disclosed polypeptides on salt tolerance, one can search for and identify polymorphisms linked to genetic loci for such polypeptides. Polymorphisms that can be identified include simple sequence repeats (SSRs), amplified fragment length polymorphisms (AFLPs) and restriction fragment length polymorphisms (RFLPs).

If a polymorphism is identified, its presence and frequency in populations is analyzed to determine if it is statistically significantly correlated to an increase in salt tolerance. Those polymorphisms that are correlated with an increase in salt tolerance can be incorporated into a marker assisted breeding program to facilitate the development of lines that have a desired increase in salt tolerance. Typically, a polymorphism identified in such a manner is used with polymorphisms at other loci that are also correlated with a desired increase in salt tolerance or other desired trait.

The methods according to the present invention can be applied to any plant, preferably higher plants, pertaining to the classes of Angiospermae and Gymnospermae. Plants of the subclasses of the Dicotylodenae and the Monocotyledonae are particularly suitable. Dicotyledonous plants belonging to the orders of the Magniolales, Illiciales, Laurales, Piperales Aristochiales, Nymphaeales, Ranunculales, Papeverales, Sarraceniaceae, Trochodendrales, Hamamelidales, Eucomiales, Leitneriales, Myricales, Fagales, Casuarinales, Caryophyllales, Batales, Polygonales, Plumbaginales, Dilleniales, Theales, Malvales, Urticales, Lecythidales, Violales, Salicales, Capparales, Ericales, Diapensales, Ebenales, Primulales, Rosales, Fabales, Podostemales, Haloragales, Myrtales, Cornales, Proteales, Santales, Rafflesiales, Celastrales, Euphorbiales, Rhamnales, Sapindales, Juglandales, Geraniales, Polygalales, Umbellales, Gentianales, Polemoniales, Lamiales, Plantaginales, Scrophulariales, Campanulales, Rubiales, Dipsacales, and Asterales, for example, are also suitable. Monocotyledonous plants belonging to the orders of the Alismatales, Hydrocharitales, Najadales, Triuridales, Commelinales, Eriocaulales, Restionales, Poales, Juncales, Cyperales, Typhales, Bromeliales, Zingiberales, Arecales, Cyclanthales, Pandanales, Arales, Lilliales, and Orchidales also may be useful in embodiments of the present invention. Further examples include, but are not limited to, plants belonging to the class of the Gymnospermae are Pinales, Ginkgoales, Cycadales and Gnetales.

The methods of the present invention are preferably used in plants that are important or interesting for agriculture, horticulture, biomass for bioconversion and/or forestry. Non-limiting examples include, for instance, tobacco, oilseed rape, sugar beet, potatoes, tomatoes, cucumbers, peppers, beans, peas, citrus fruits, avocados, peaches, apples, pears, berries, plumbs, melons, eggplants, cotton, soybean, sunflowers, roses, poinsettia, petunia, guayule, cabbages, spinach, alfalfa, artichokes, sugarcane, mimosa, *Servicea lespedera*, corn, wheat, rice, rye, barley, sorghum and grasses such as switch grass, giant reed, Bermuda grass, Johnson grasses or turf grass, millet, hemp, bananas, poplars, eucalyptus trees and conifers. Of interest are plants grown for energy production, so called energy crops, such as broadleaf plants like alfalfa, hemp, Jerusalem artichoke and grasses such as sorghum, switchgrass, Johnson grass and the likes. Thus, the described materials and methods are useful for modifying biomass characteristics, such as characteristics of biomass renewable energy source plants. A biomass renewable energy source plant is a plant having or producing material (either raw or processed) that comprises stored solar energy that can be converted to fuel. In general terms, such plants comprise dedicated energy crops as well as agricultural and woody plants. Examples of biomass renewable energy source plants include: switchgrass, elephant grass, giant chinese silver grass, energycane, giant reed (also known as wild cane), tall fescue, bermuda grass, sorghum, napier grass, also known as uganda grass, triticale, rye, winter wheat, shrub poplar, shrub willow, big bluestem, reed canary grass and corn.

Homologues Encompassed by the Invention

It is known in the art that one or more amino acids in a sequence can be substituted with other amino acid(s), the charge and polarity of which are similar to that of the substituted amino acid, i.e. a conservative amino acid substitution, resulting in a biologically/functionally silent change. Conservative substitutes for an amino acid within the polypeptide sequence can be selected from other members of the class to which the amino acid belongs. Amino acids can be divided into the following four groups: (1) acidic (negatively charged) amino acids, such as aspartic acid and glutamic acid; (2) basic (positively charged) amino acids, such as arginine, histidine, and lysine; (3) neutral polar amino acids, such as serine, threonine, tyrosine, asparagine, and glutamine; and (4) neutral nonpolar (hydrophobic) amino acids such as glycine, alanine, leucine, isoleucine, valine, proline, phenylalanine, tryptophan, cysteine, and methionine.

Nucleic acid molecules of the present invention can comprise sequences that differ from those encoding a protein or fragment thereof selected from the group consisting of SEQ ID NOs. 80, 99, 106, 123, 132, 146, 154 and 172, respectively, due to the fact that the different nucleic acid sequence encodes a protein having one or more conservative amino acid changes.

Biologically functional equivalents of the polypeptides, or fragments thereof, of the present invention can have about 10 or fewer conservative amino acid changes, more preferably about 7 or fewer conservative amino acid changes, and most preferably about 5 or fewer conservative amino acid changes. In a preferred embodiment of the present invention, the polypeptide has between about 5 and about 500 conservative changes, more preferably between about 10 and about 300 conservative changes, even more preferably between about 25 and about 150 conservative changes, and most preferably between about 5 and about 25 conservative changes or between 1 and about 5 conservative changes.

Identification of Useful Nucleic Acid Molecules and their Corresponding Nucleotide Sequences The nucleic acid molecules, and nucleotide sequences thereof, of the present invention were identified by use of a variety of screens that are predictive of nucleotide sequences that provide plants with improved vegetative growth, growth rate, and/or biomass under saline conditions. One or more of the following screens were, therefore, utilized to identify the nucleotide (and amino acid) sequences of the present invention.

The present invention is further exemplified by the following examples. The examples are not intended to in any way limit the scope of the present application and its uses.

6. Experiments Confirming the Usefulness of the Polynucleotides and Polypeptides of the Invention General Protocols
*Agrobacterium*-Mediated Transformation of *Arabidopsis*

Host Plants and Transgenes: Wild-type *Arabidopsis thaliana* Wassilewskija (WS) plants are transformed with $T_1$ plasmids containing nucleic acid sequences to be expressed, as noted in the respective examples, in the sense orientation relative to the 35S promoter in a $T_1$ plasmid. A $T_1$ plasmid vector useful for these constructs, CRS 338, contains the Ceres-constructed, plant selectable marker gene phosphinothricin acetyltransferase (PAT), which confers herbicide resistance to transformed plants.

Ten independently transformed events are typically selected and evaluated for their qualitative phenotype in the $T_1$ generation.

Preparation of Soil Mixture: 24 L Sunshine Mix #5 soil (Sun Gro Horticulture, Ltd., Bellevue, WA) is mixed with 16 L Therm-O-Rock vermiculite (Therm-0-Rock West, Inc., Chandler, AZ) in a cement mixer to make a 60:40 soil mixture. To the soil mixture is added 2 Thsp Marathon 1% granules (Hummert, Earth City, MO), 3 Thsp OSMO-COTE® 14-14-14 (Hummert, Earth City, MO) and 1 Tbsp Peters fertilizer 20-20-20 (J. R. Peters, Inc., Allentown, PA), which are first added to 3 gallons of water and then added to the soil and mixed thoroughly. Generally, 4-inch diameter pots are filled with soil mixture. Pots are then covered with 8-inch squares of nylon netting.

Planting: Using a 60 mL syringe, 35 mL of the seed mixture is aspirated. 25 drops are added to each pot. Clear propagation domes are placed on top of the pots that are then placed under 55% shade cloth and subirrigated by adding 1 inch of water.

Plant Maintenance: 3 to 4 days after planting, lids and shade cloth are removed. Plants are watered as needed. After 7-10 days, pots are thinned to 20 plants per pot using forceps. After 2 weeks, all plants are subirrigated with Peters fertilizer at a rate of 1 Tsp per gallon of water. When bolts are about 5-10 cm long, they are clipped between the first node and the base of stem to induce secondary bolts. Dipping infiltration is performed 6 to 7 days after clipping.

Preparation of *Agrobacterium*: To 150 mL fresh YEB is added 0.1 mL each of carbenicillin, spectinomycin and rifampicin (each at 100 mg/ml stock concentration). *Agrobacterium* starter blocks are obtained (96-well block with *Agrobacterium* cultures grown to an $OD_{600}$ of approximately 1.0) and inoculated one culture vessel per construct by transferring 1 mL from appropriate well in the starter block. Cultures are then incubated with shaking at 27° C. Cultures are spun down after attaining an $OD_{600}$ of approximately 1.0 (about 24 hours). 200 mL infiltration media is added to resuspend *Agrobacterium* pellets. Infiltration media is prepared by adding 2.2 g MS salts, 50 g sucrose, and 5 µL 2 mg/ml benzylaminopurine to 900 ml water.

Dipping Infiltration: The pots are inverted and submerged for 5 minutes so that the aerial portion of the plant is in the *Agrobacterium* suspension. Plants are allowed to grow normally and seed is collected.

High-throughput Phenotypic Screening of Misexpression Mutants: Seed is evenly dispersed into water-saturated soil in pots and placed into a dark 4° C. cooler for two nights to promote uniform germination. Pots are then removed from the cooler and covered with 55% shade cloth for 4-5 days. Cotyledons are fully expanded at this stage. FINALE® (Sanofi Aventis, Paris, France) is sprayed on plants (3 ml FINALE® diluted into 48 oz. water) and repeated every 3-4 days until only transformants remain.

Screening: Screening is routinely performed by high-salt agar plate assay and also by high-salt soil assay. Traits assessed in high-salt conditions include: seedling area, photosynthesis efficiency, salt growth index, and regeneration ability.

Seedling area: the total leaf area of a young plant about 2 weeks old.

Photosynthesis efficiency (Fv/Fm): Seedling photosynthetic efficiency, or electron transport via photosystem II, is estimated by the relationship between Fm, the maximum fluorescence signal and the variable fluorescence, Fv. Here, a reduction in the optimum quantum yield (Fv/Fm) indicates stress, and so can be used to monitor the performance of transgenic plants compared to non-transgenic plants under salt stress conditions.

Salt growth index=seedling area×photosynthesis efficiency (*Fv/Fm*).

PCR was used to amplify the DNA insert in one randomly chosen $T_2$ plant. This PCR product was then sequenced to confirm the sequence in the plants.

Assessing Tolerance to Salt Stress: Initially, independently transformed plant lines are selected and qualitatively evaluated for their tolerance to salt stress in the $T_1$ generation. The transformed lines that qualitatively show the strongest tolerance to salt stress in the $T_1$ generation are selected for further evaluation in the $T_2$ and $T_3$ generations. This evaluation involves sowing seeds from the selected transformed plant lines on MS agar plates containing either 100 mM or 150 mM NaCl and incubating the seeds for 5 to 14 days to allow for germination and growth.

Calculating SGI: After germination and growth, seedling area and photosynthesis efficiency of transformed lines and a wild-type control are determined. From these measurements, the Salt Growth Index (SGI) is calculated and compared between wild-type and transformed seedlings. The SGI calculation is made by averaging seedling area and photosynthesis efficiency measurements taken from two replicates of 36 seedlings for each transformed line and a wild-type control and performing a t-test.

Determining Transgene Copy Number: $T_2$ generation transformed plants are tested on BASTA™ plates in order to determine the transgene copy number of each transformed line. A BASTA™ resistant:BASTA™ sensitive segregation ratio of 3:1 generally indicates one copy of the transgene.

Results:

The following Examples provide information for polynucleotides and their encoded polypeptides useful for increasing tolerance to salt stress. Enhanced salt tolerance gives the opportunity to grow crops in saline conditions without stunted growth and diminished yields due to salt-induced ion imbalance, disruption of water homeostasis, inhibition of metabolism, damage to membranes, and/or cell death. The ability to grow crops in saline conditions would result in an overall expansion of arable land and increased output of land currently marginally productive due to elevated salinity Example 1: ME03807 (Ceres Clone 8686: SEO ID No. 79)

Wild-type *Arabidopsis thaliana* Wassilewskija was transformed with a $T_1$ plasmid carrying the 35S promoter operatively linked to Ceres Clone 8686. Two transformed lines, ME03807-02 and ME03807-03, showed the strongest qualitative tolerance to salt stress in a prevalidation assay (Table 1-1). Their tolerance to 150 mM NaCl was further evaluated in a validation assay for two generations. Segregation ratios (BASTA™ resistant: BASTA™ sensitive) indicated that ME03807-02 contains two copies of the transgene and that ME03807-03 carries one copy of the transgene.

TABLE 1-1

Prevalidation assay of ME03807 salt tolerance as compared to wild-type Ws

|  | WS Wild-type | ME03807-02 | ME03807-03 |
|---|---|---|---|
| Mean* | 0.0268 | 0.0397 | 0.0506 |
| Standard Error | 0.0006 | 0.0041 | 0.0038 |

*Average seedling area of 36 plants grown on MS agar plates containing 150 mM NaCl for 14 days When grown on MS agar plates containing 150 mM NaCl, ME03807-02 and ME03807-03 transgenic plants showed significantly increased seedling area and SGI relative to non-transgenic plants. As shown in Table 1-2, the T2-generation SGI value for ME03807-02 seedlings increased by 74.4% while ME03807-03 seedlings increased by 87.6% compared to non-transgenic control seedlings. In the $T_3$ generation, the SGI increase was 134.2% for ME03807-02 and 141.8% for ME03807-03. The differences between transgenic and non-transgenic seedlings are statistically significant under the t-test, and clearly demonstrate that the enhanced tolerance to salt stress is a result of the ectopic expression of Ceres Clone 8686 in the ME03807 transformant lines.

TABLE 1-2

Validation assay of ME03807 salt stress tolerance in two generations

| ME Events | SGI* of transgenics | | | SGI of pooled non-transgenics | | | t-Test | | % of SGI |
|---|---|---|---|---|---|---|---|---|---|
| | Avg | SE | N | Avg | SE | N | t-value | $t_{0.05}$ | increase |
| ME03807-02T$_2$ | 0.952 | 0.126 | 32 | 0.546 | 0.087 | 24 | 2.66 | 1.68 | 74.4 |
| ME03807-03T$_2$ | 0.604 | 0.047 | 24 | 0.322 | 0.065 | 13 | 3.51 | 1.70 | 87.6 |
| ME03807-02T$_3$ | 0.965 | 0.111 | 19 | 0.412 | 0.031 | 11 | 5.95 | 1.70 | 134.2 |
| ME03807-03T$_3$ | 1.064 | 0.104 | 42 | 0.440 | 0.028 | 16 | 9.60 | 1.68 | 141.8 |

*SGI (Salt Growth Index) = seedling area × Fv/Fm (photosynthesis efficiency)

Summary of Results:

Ectopic expression of Ceres Clone 8686 under the control of the 35S promoter enhances tolerance to salt stress that causes necrotic lesions and stunted growth in wild-type WS seedlings.

The protein encoded by Ceres Clone 8686 is a 255-amino-acid putative cyclase (Susstrunk et al. (1998) *Mol Microbiol,* 30(1):33-46 and Kang et al. (1999) *Microbiology,* 145:1161-72. Cyclase is a large gene family that includes adenylyl cyclase, which converts ATP to cAMP. cAMP is an important signal molecule that is involved in signal transduction which conveys signals from a plasma membrane receptor to cytosol cascades. The ME03807 transgene is more closely related to cyclase enzymes that are involved in antibiotic synthesis.

Example 2: ME00774 (Cees Clone 2767; SEQ ID No. 131)

Wild-type *Arabidopsis thaliana* Wassilewskija was transformed with a T$_1$ plasmid carrying the 32449 promoter (SEQ ID No. 77) and Ceres Clone 2767. Two transformed lines, ME00774-03 and ME00774-04, showed the strongest qualitative tolerance to salt stress in a prevalidation assay (Table 2-1). Their tolerance to 150 mM NaCl was further evaluated in a validation assay for two generations. Segregation ratios (BASTA™ resistant:BASTA™ sensitive) indicated that ME00774-03 contains two copies of the transgene and that ME00774-04 carries one copy of the transgene.

TABLE 2-1

Prevalidation assay of ME00774 salt tolerance as compared to wild-type Ws

| | Ws wild-type | ME00774-01 | ME00774-02 | ME00774-03 | ME00774-04 | ME00774-05 |
|---|---|---|---|---|---|---|
| Mean* | 0.0286 | 0.0313 | 0.0333 | 0.0468 | 0.0384 | 0.0343 |
| Std Error | 0.0006 | 0.0015 | 0.0019 | 0.0037 | 0.0026 | 0.0024 |

*Average seedling area of 36 plants grown on MS agar plates containing 150 mM NaCl for 14 days When grown on MS agar plates containing 150 mM NaCl, ME00774-03 and ME00774-04 transgenic plants showed significantly greater seedling area and SGI relative to non-transgenic plants. As shown in Table 2-2, the T2-generation SGI value for ME00774-03 seedlings increased by 41.8% while ME00774-04 seedlings increased by 379.4% compared to non-transgenic control seedlings. In the T$_3$ generation, the SGI increase was 315.1% for ME00774-03 and 551.8% for ME00774-04. The differences between transgenic and non-transgenic seedlings are statistically significant under the t-test, and clearly demonstrate that the enhanced tolerance to salt stress was a result of the ectopic expression of Ceres Clone 2767 in the ME00774 transformant lines.

TABLE 2-2

Validation assay of ME00774 on salt tolerance in two generations

| ME Events | SGI* of transgenics | | | SGI of pooled non-transgenics | | | t-Test | | % of SGI |
|---|---|---|---|---|---|---|---|---|---|
| | Avg | SE | N | Avg | SE | N | t-value | $t_{0.05}$ | increase |
| ME00774-03T$_2$ | 1.462 | 0.122 | 51 | 1.031 | 0.127 | 18 | 2.45 | 1.67 | 41.8 |
| ME00774-04T$_2$ | 0.954 | 0.072 | 20 | 0.199 | 0.03 | 10 | 9.78 | 1.70 | 379.4 |
| ME00774-03T$_3$ | 1.598 | 0.081 | 48 | 0.385 | 0.05 | 23 | 12.79 | 1.67 | 315.1 |
| ME00774-04T$_3$ | 1.082 | 0.091 | 20 | 0.166 | 0.032 | 16 | 9.52 | 1.70 | 551.8 |

*SGI (Salt Growth Index) = seedling area × Fv/Fm (photosynthesis efficiency)

Summary of Results:

Ectopic expression of Clone 2767 under the control of the 32449 promoter enhances tolerance to salt stress.

Ceres Clone 2767 encodes a 154-amino-acid protein that belongs to a universal stress protein family (Kerk et al. (2003) *Plant Physiol.* 131(3):1209-19). The USP superfamily has its members conserved in bacteria, archaea, and eukaryotes. The expression of USP genes in *E. coli* is induced by a large variety of environmental insults. The uspA gene plays an important role for *E. coli* to survive in cellular growth arrest, but the molecular mechanism of the gene function is not known yet (Nachin et al. (2005) *J Bacteriol* 187(18):6265-72). In *Arabidopsis*, there are 44 family members of USP. However, their function has not been characterized yet (Kerk et al. 2003). A rice homolog, OsUsp1, has been found to be induced by submergence and ethylene (Sauter et al. (2002) *J Exp Bot* 53(379):2325-31).

The identification of an AtUsp gene in a salt screen suggests that the *Arabidopsis* USP family members may play a similar role in stress tolerance as observed in *E. coli*.

Example 3: ME0146 (Ceres Clone 16403: SEO ID No. 145)

Wild-type *Arabidopsis thaliana* Wassilewskija was transformed with a $T_1$ plasmid carrying the 35S promoter and Ceres Clone 16403. Two transformed lines, ME01468-01 and ME01468-04, showed the strongest qualitative tolerance to salt stress in a prevalidation assay (Table 3-1). Their tolerance to 100 mM NaCl was further evaluated in a validation assay for two generations. Segregation ratios (BASTA™ resistant: BASTA™ sensitive) indicated ME01468-01 and ME01468-04 transformed lines each carry one copy of the transgene.

TABLE 3-1

Prevalidation assay of ME00774 salt tolerance as compared to wild-type Ws

| | Ws Wild-type | ME01468-01 | ME01468-02 | ME01468-03 | ME01468-04 |
|---|---|---|---|---|---|
| Mean* | 0.0268 | 0.0424 | 0.0312 | 0.0215 | 0.0395 |
| Standard Error | 0.0006 | 0.0032 | 0.0018 | 0.0027 | 0.0031 |

*Average seedling area of 36 plants grown on MS agar plates containing 150 mM NaCl for 14 days When grown on MS agar plates containing 100 mM NaCl, ME01468-01 and ME01468-04 transgenic plants showed significantly greater seedling area and SGI relative to non-transgenic plants. As shown in Table 3-1, the T2-generation SGI value for ME01468-01 seedlings increased by 23.7% while ME01468-04 seedlings increased by 39.3% compared to non-transgenic control seedlings. In the $T_3$ generation, the SGI increase was 83.7% for ME01468-01 and 79.4% for ME01468-04. The differences between transgenic and non-transgenic seedlings are statistically significant under the t-test, and clearly demonstrate that the enhanced tolerance to salt stress was a result of the ectopic expression of Ceres Clone 16403 in the ME01468 transformant lines.

TABLE 3-2

Validation assay of ME01468 on salt tolerance in two generations

| ME Events | SGI* of transgenics | | | SGI of pooled non-transgenics | | | t-Test | | % of SGI increase |
|---|---|---|---|---|---|---|---|---|---|
| | Avg | SE | N | Avg | SE | N | t-value | $t_{0.05}$ | |
| ME01468-01$T_2$ | 3.842 | 0.146 | 39 | 3.105 | 0.307 | 29 | 2.162 | 1.67 | 23.7 |
| ME01468-04$T_2$ | 3.143 | 0.179 | 35 | 2.256 | 0.261 | 32 | 2.795 | 1.67 | 39.3 |
| ME01468-01$T_3$ | 5.939 | 0.416 | 33 | 3.233 | 0.296 | 37 | 5.293 | 1.67 | 83.7 |
| ME01468-04$T_3$ | 7.508 | 0.524 | 13 | 4.186 | 0.469 | 21 | 4.719 | 1.70 | 79.4 |

*SGI (Salt Growth Index) = seedling area × Fv/Fm (photosynthesis efficiency)

Summary of Results:

Ectopic expression of Ceres Clone 16403 under the control of the 35S promoter enhances tolerance to high salt stress.

Ceres Clone 16403 encodes a 238-amino-acid calcium-binding protein that also shows similarity to an oxygen evolving complex from rice (Sanchez-Barrena et al. (2005) *J Mol Biol.* 345(5):1253-64). It is worth noting that SOS3, an important gene involved in salt tolerance, has been molecularly characterized as a $Ca^{++}$ binding protein.

Example 4: ME02064 (Ceres Clone 375578: SEO ID No. 98)

Wild-type *Arabidopsis thaliana* Wassilewskija was transformed with a $T_1$ plasmid carrying the 35S promoter and Ceres Clone 375578. Three transformed lines, ME02064-01 and ME02064-03, ME02064-04, showed the strongest qualitative tolerance to salt stress in a prevalidation assay (Table 4-1). Their tolerance to 150 mM NaCl was further evaluated in a validation assay for two generations. Segregation ratios (BASTA™ resistant: BASTA™ sensitive) indicated ME02064-01 and ME02064-03, ME02064-04 transformed lines each carry one copy of the transgene.

TABLE 4-1

Prevalidation assay of ME02064 salt tolerance as compared to wild-type Ws

|  | Ws Wild-type | ME02064-01 | ME02064-02 | ME02064-03 | ME02064-04 | ME02064-05 |
|---|---|---|---|---|---|---|
| Mean* | 0.0359 | 0.0435 | 0.0346 | 0.0441 | 0.0438 | 0.0305 |
| Standard Error | 0.0016 | 0.0048 | 0.004 | 0.0041 | 0.0035 | 0.0019 |

*Average seedling area of 36 plants grown on MS agar plates containing 150 mM NaCl for 14 days When grown on MS agar plates containing 150 mM NaCl, ME02064-01 and ME02064-03, ME02064-04 transgenic plants showed significantly greater seedling area and SGI relative to non-transgenic plants. As shown in Table 4-2, the T2-generation SGI value for ME02064-01 seedlings increased by 110% while ME02064-03 seedlings increased by 131% and ME02064-04 seedlings increased by 72% compared to non-transgenic control seedlings. In the $T_3$ generation, the SGI increase was 43% for ME02064-01, 47% for ME02064-03, and 64% for ME02064-04. The differences between transgenic and non-transgenic seedlings are statistically significant, and clearly demonstrate that the enhanced tolerance to salt stress was a result of the ectopic expression of Ceres Clone 375578 in the ME02064 transformant lines.

TABLE 4-2

Validation assay of ME02064 on salt tolerance in two generations

| ME Events | SGI* of transgenics | | | SGI of pooled non-transgenics | | | t-Test | | % of SGI |
|---|---|---|---|---|---|---|---|---|---|
|  | Avg | SE | N | Avg | SE | N | t-value | $t_{0.05}$ | increase |
| ME02064-01-$T_2$ | 2.057 | 0.249 | 12 | 0.977 | 0.205 | 17 | 3.35 | 1.70 | 110.5 |
| ME02064-03-$T_2$ | 2.237 | 0.371 | 5 | 0.968 | 0.140 | 24 | 3.20 | 1.70 | 131.1 |
| ME02064-04-$T_2$ | 1.810 | 0.146 | 14 | 1.055 | 0.135 | 13 | 3.81 | 1.70 | 71.6 |
| ME02064-01-$T_3$ | 2.438 | 0.170 | 21 | 1.708 | 0.289 | 9 | 2.18 | 1.70 | 42.7 |
| ME02064-03-$T_3$ | 2.837 | 0.257 | 20 | 1.927 | 0.271 | 14 | 2.43 | 1.70 | 47.2 |
| ME02064-04-$T_3$ | 2.770 | 0.318 | 16 | 1.688 | 0.188 | 19 | 2.93 | 1.70 | 64.1 |

*SGI (Salt Growth Index) = seedling area × Fv/Fm (photosynthesis efficiency)

Summary of Results:
Ectopic expression of Ceres Clone 375578 under the control of the 35S promoter enhances tolerance to salt stress that causes necrotic lesions and stunted growth in wild-type Ws seedlings.

Ceres Clone 375578 encodes a 311-amino-acid protein that belongs to the calmodulin binding family (Sanchez-Bafrena et al. (2005) *J Mol Biol.* 345(5):1253-64). $Ca^{++}$ homeostasis is an important signaling cascade in abiotic and biotic resistance. A critical gene, SOS3, involved in salt tolerance has been previously identified to be a $Ca^{++}$ binding protein. Understanding the connection between SOS3 and the transgene in ME02064 will help to better engineer resistance to salt stress.

Example 5: ME04074 (Ceres Clone 105319; SEO ID No. 105)

Wild-type *Arabidopsis thaliana* Wassilewskija was transformed with a $T_1$ plasmid carrying the 35S promoter and Ceres Clone 105319. Two transformed lines, ME04074-02 and ME04074-05, showed the strongest qualitative tolerance to salt stress in a prevalidation assay (Table 5-1). Their tolerance to 150 mM NaCl was further evaluated in a validation assay for two generations. Segregation ratios (BASTA™ resistant: BASTA™ sensitive) indicate ME04074-02 and ME04074-05 transformed lines each carry one copy of the transgene.

TABLE 5-1

Prevalidation assay of ME04074 salt tolerance as compared to wild-type Ws

|  | Ws Wild-type | ME04074-01 | ME04074-02 | ME04074-03 | ME04074-04 | ME04074-05 |
|---|---|---|---|---|---|---|
| Mean* | 0.0301 | 0.0332 | 0.0423 | 0.0351 | 0.039 | 0.0448 |
| Standard Error | 0.0032 | 0.0027 | 0.0033 | 0.0026 | 0.0025 | 0.0027 |

*Average seedling area of 36 plants grown on MS agar plates containing 150 mM NaCl for 14 days When grown on MS agar plates containing 150 mM NaCl, ME04074-02 and ME04074-05 transgenic plants showed significantly greater seedling area and SGI relative to non-transgenic plants. As shown in Table 5-2, the T2-generation SGI value for ME04074-02 seedlings increased by 40.6% while ME04074-05 seedlings increased by 52.2% compared to non-transgenic control seedlings. In the $T_3$ generation, the SGI increase was 18.5% for ME04074-02 and 60.6% for ME04074-05. The differences between transgenic and non-transgenic seedlings are statistically significant under the t-test, and clearly demonstrate that the enhanced tolerance to salt stress was a result of the ectopic expression of Ceres Clone 105319 in the ME04074 transformant lines.

TABLE 5-2

Validation assay of ME04074 on salt tolerance in two generations

| ME Events | SGI* of transgenics | | | SGI of pooled non-transgenics | | | t-Test | | % of SGI |
|---|---|---|---|---|---|---|---|---|---|
| | Avg | SE | N | Avg | SE | N | t-value | $t_{0.05}$ | increase |
| ME04074-$0_2$-$T_2$ | 2.432 | 0.212 | 23 | 1.730 | 0.155 | 40 | 2.68 | 1.67 | 40.6 |
| ME04074-$0_5$-$T_2$ | 2.707 | 0.212 | 26 | 1.778 | 0.171 | 38 | 3.41 | 1.67 | 52.2 |
| ME04074-$0_2$-$T_3$ | 2.257 | 0.156 | 34 | 1.905 | 0.190 | 34 | 1.43 | 1.67 | 18.5 |
| ME04074-$0_5$-$T_3$ | 2.851 | 0.158 | 32 | 1.775 | 0.147 | 52 | 4.98 | 1.67 | 60.6 |

*SGI (Salt Growth Index) = seedling area × Fv/Fm (photosynthesis efficiency)

Summary of Results:

Ectopic expression of Ceres Clone 105319 under the control of the 35S promoter enhances tolerance to salt stress that causes necrotic lesions and stunted growth in wild-type Ws seedlings.

The protein encoded by Ceres Clone 105319 encodes a putative shikimate cyclase (Griffen et al. (1995) *DNA Seq* 5(3):195-197). The enzyme has ATP binding activity and catalyzes the fifth step in the biosynthesis of aromatic amino acids from chorismate. The protein is found in bacteria, fungi and plants. How this protein is involved in stress response is not yet known. However, aromatic acids, such as L-phenylalanine, are important substrates for the phenylpropanoid biosynthesis pathway, which produces many compounds related to stress responses.

TABLE 6-1

Prevalidation assay of ME02907 salt tolerance as compared to wild-type Ws

| | Ws Wild-type | ME02907-01 | ME02907-03 | ME02907-04 | ME02907-05 |
|---|---|---|---|---|---|
| Mean* | 0.0268 | 0.034483 | 0.0315 | 0.0224 | 0.0368 |
| Standard Error | 0.0006 | 0.002016 | 0.0029 | 0.0031 | 0.0039 |

*Average seedling area of 36 plants grown on MS agar plates containing 150 mM NaCl for 14 days When grown on MS agar plates containing 150 mM NaCl, ME02907-03 and ME02907-05 transgenic plants showed significantly greater seedling area and SGI relative to non-transgenic plants. As shown in Table 6-2, the T2-generation SGI value for ME02907-03 seedlings increased by 59% while ME02907-05 seedlings increased by 67% as compared to non-transgenic control seedlings. In the $T_3$ generation, the SGI increase was 110% for ME02907-03 and 99% for ME02907-05. The differences between transgenic and non-transgenic seedlings are statistically significant under the t-test, and clearly demonstrate that the enhanced tolerance to salt stress was a result of the ectopic expression of Ceres Clone 29658 in the ME02907 transformant lines.

TABLE 6-2

Validation assay of ME02907 on salt tolerance in two generations

| ME Events | SGI* of transgenics | | | SGI of pooled non-transgenics | | | t-Test | | % of SGI |
|---|---|---|---|---|---|---|---|---|---|
| | Avg | SE | N | Avg | SE | N | t-value | $t_{0.05}$ | increase |
| ME02907-03-$T_2$ | 1.252 | 0.115 | 31 | 0.787 | 0.121 | 18 | 2.79 | 1.68 | 59.1 |
| ME02907-05-$T_2$ | 1.235 | 0.120 | 34 | 0.738 | 0.100 | 28 | 3.18 | 1.67 | 67.3 |
| ME02907-03-$T_3$ | 1.039 | 0.100 | 26 | 0.495 | 0.023 | 15 | 7.40 | 1.69 | 109.9 |
| ME02907-05-$T_3$ | 1.157 | 0.064 | 37 | 0.582 | 0.070 | 17 | 7.53 | 1.70 | 98.8 |

*SGI (Salt Growth Index) = seedling area × Fv/Fm (photosynthesis efficiency)

Example 6: ME02907 (Ceres Clone 29658: SEO ID No. 122)

Wild-type *Arabidopsis thaliana* Wassilewskija was transformed with a $T_1$ plasmid carrying the 35S promoter and Ceres Clone 29658. Three transformed lines, ME02907-01, ME02907-03 and ME02907-05, showed the strongest qualitative tolerance to salt stress in a prevalidation assay (Table 6-1). Their tolerance to 150 mM NaCl was further evaluated in a validation assay using ME02907-03 and ME02907-05 for two generations. Segregation ratios (BASTA™ resistant: BASTA™ sensitive) indicated ME02907-03 and ME02907-05 transformed lines each carry one copy of the transgene.

Summary of Results:

Ectopic expression of Ceres Clone 29658 under the control of the 35S promoter enhances tolerance to salt stress that causes necrotic lesions and stunted growth in wild-type Ws seedlings.

The protein encoded by Ceres Clone 29658 is a putative calmodulin. Sanchez-Barrena et al. *J Mol Biol.* 345(5): 1253-64. $Ca^{++}$-mediated signaling is critical in salt tolerance. SOS3 has been demonstrated to confer salt tolerance in *Arabidopsis* and it has $Ca^{++}$-binding activity.

Example 7: ME00199 (Ceres Clone 3964: SEQ ID No. 153)

Wild-type *Arabidopsis thaliana* Wassilewskija was transformed with a $T_1$ plasmid carrying the 32499 promoter and Ceres Clone 3964. Two transformed lines, ME00199-02 and ME00199-03, showed the strongest qualitative tolerance to salt stress in a prevalidation assay (Table 7-1). Their tolerance to 100 mM NaCl was further evaluated in a validation assay for two generations. Segregation ratios (BASTA™ resistant: BASTA™ sensitive) indicated ME00199-02 and ME00199-03 transformed lines each carry one copy of the transgene.

TABLE 7-1

Prevalidation assay of ME00199 salt tolerance as compared to wild-type Ws

|  | Ws wild-type | ME00199-01-01 | ME00199-02-01 | ME00199-03-01 |
|---|---|---|---|---|
| Mean* | 0.0268 | 0.0244 | 0.0401 | 0.0307 |
| Standard Error | 0.0006 | 0.0025 | 0.0052 | 0.0037 |

*Average seedling area of 36 plants grown on MS agar plates containing 150 mM NaCl for 14 days When grown on MS agar plate containing 100 mM NaCl, ME00199-02 and ME00199-03 transgenic plants showed significantly greater seedling area and SGI relative to non-transgenic plants. As shown in Table 7-2, the SGI value of T2-generation ME00199-02 seedlings increased by 106.6% and the SGI value of $T_2$-generation ME00199-03 seedlings increased by 48.2% as compared to non-transgenic control seedlings. In the $T_3$ generation, the SGI increase was 174.3% for ME00199-02 and 205.9% for ME00199-03. The differences between transgenic and non-transgenic seedlings are statistically significant under the t-test, and clearly demonstrate that the enhanced tolerance to salt stress was a result of the ectopic expression of Ceres Clone 3964 in the ME00199 transformant lines.

TABLE 7-2

Validation assay of ME00199 on salt tolerance in two generations

|  | SGI* of transgenics | | | SGI of pooled non-transgenics | | | t-Test | | % of SGI |
|---|---|---|---|---|---|---|---|---|---|
| ME Events | Avg | SE | N | Avg | SE | N | t-value | $t_{0.05}$ | increase |
| ME00199-02$T_3$ | 4.6025 | 0.3400 | 43 | 2.2277 | 0.2159 | 28 | 5.90 | 1.67 | 106.6 |
| ME00199-03$T_3$ | 3.8795 | 0.3444 | 40 | 2.6182 | 0.3855 | 28 | 2.44 | 1.67 | 48.2 |
| ME00199-02$T_4$ | 6.8743 | 0.5132 | 45 | 2.5058 | 0.5904 | 12 | 5.58 | 1.68 | 174.3 |
| ME00199-03$T_4$ | 7.4472 | 0.7392 | 30 | 2.4343 | 0.5283 | 15 | 5.52 | 1.68 | 205.9 |

SGI (Salt Growth Index) = seedling area × Fv/Fm (photosynthesis efficiency)

Summary of Results:
Ectopic expression of Ceres Clone 3964 under the control of the 32499 promoter enhances tolerance to salt stress that causes necrotic lesions and stunted growth in wild-type Ws seedlings.
The protein encoded by Ceres Clone 3964 is a putative steroid sulfotransferase (351 AA).

Example 8: ME09814 (Ceres Clone 965405: SEQ ID No. 171)

Wild-type *Arabidopsis thaliana* Wassilewskija was transformed with a $T_1$ plasmid carrying the 35S promoter and Ceres Clone 965405. Two transformed lines, ME09814-01 and ME09814-02, showed the strongest qualitative tolerance to salt stress in a prevalidation assay. Their tolerance to 100 mM NaCl was further evaluated in a validation assay for two generations. Segregation ratios (BASTA™ resistant: BASTA™ sensitive) indicated ME09814-01 and ME09814-02 transformed lines each carry one copy of the transgene originated from *Brassica napus* subsp. *napus* (canola).

Grown on MS agar plates containing 100 mM NaCl, ME09814-01 and ME09814-02 transgenic plants showed significantly greater seedling area and SGI relative to non-transgenic plants. As shown in Table 8-1, the SGI value of T2-generation ME09814-01 seedlings increased by 29% and the SGI value of T2-generation ME09814-02 seedlings increased by 69% as compared to non-transgenic control seedlings. In the $T_3$ generation, the SGI increase was 80% for ME09814-01 and 49% for ME09814-02. The differences between transgenic and non-transgenic seedlings are statistically significant under the t-test, and clearly demonstrate that the enhanced tolerance to salt stress was a result of the ectopic expression of Ceres Clone 965405 in the ME09814 transgenic lines.

TABLE 8-1

Validation assay of ME09814 on salt tolerance in two generations

| ME Events | SGI* of transgenics | | | SGI of pooled non-transgenics | | | t-Test | | % of SGI increase |
|---|---|---|---|---|---|---|---|---|---|
| | Avg | SE | N | Avg | SE | N | t-value | $t_{0.05}$ | |
| ME09814-01T$_2$ | 2.6841 | 0.2346 | 37 | 2.0812 | 0.1830 | 34 | 2.03 | 1.67 | 29.0 |
| ME09814-02T$_2$ | 2.6985 | 0.2438 | 32 | 1.5942 | 0.1909 | 38 | 3.57 | 1.67 | 69.3 |
| ME09814-01T$_3$ | 3.0664 | 0.2934 | 29 | 1.6996 | 0.1724 | 42 | 4.02 | 1.67 | 80.4 |
| ME09814-02T$_3$ | 2.6878 | 0.2350 | 36 | 1.8087 | 0.1743 | 34 | 3.00 | 1.67 | 48.6 |

*SGI (Salt Growth Index) = seedling area × Fv/Fm (photosynthesis efficiency)

Summary of Results:
Ectopic expression of Ceres Clone 965405 under the control of the 35S promoter enhances tolerance to sat stress that causes necrotic lesions and stunted growth in wild-type Ws seedlings.
The protein encoded by Ceres Clone 965405 is an unknown protein.

Example 9: ME07361 (Ceres Clone 5367: SEQ ID NO: 245)

Wild-type *Arabidopsis thaliana* Wassilewskija was transformed with a $T_1$ plasmid carrying the 35S promoter and Ceres Clone 5367. Ceres Clone 5367 is a functional homolog of Ceres clone 965405.

Grown on MS agar plates containing 100 mM NaCl, ME07361-04 transgenic plants showed significantly greater seedling area and SGI relative to non-transgenic plants. As shown in Table 9-1, the SGI value of T2-generation ME07361-03 seedlings increased by 30.34% and the SGI value of T2-generation ME07361-04 seedlings increased by 52% as compared to non-transgenic control seedlings. The differences between transgenic and non-transgenic seedlings are statistically significant under the t-test, and clearly demonstrate that the enhanced tolerance to salt stress was a result of the ectopic expression of Ceres Clone 5367 in the ME07361 transgenic lines.

TABLE 9-1

Results of ME07361 on salt tolerance assay in T2 generations

| ME Events | SGI* of transgenics | | | SGI of pooled non-transgenics | | | t-Test | SGI increase |
|---|---|---|---|---|---|---|---|---|
| | Avg | SE | N | Avg | SE | N | p-value | |
| ME07361-01 | 0.89 | 0.103 | 16 | 0.89 | 0.105 | 20 | 0.489 | −0.45% |
| ME07361-02 | 1.30 | 0.160 | 17 | 1.22 | 0.132 | 18 | 0.357 | 06.29% |
| ME07361-03 | 1.58 | 0.195 | 21 | 1.21 | 0.151 | 15 | 0.073 | 30.34% |
| ME07361-04 | 1.98 | 0.369 | 15 | 1.30 | 0.145 | 21 | 0.049 | 52.00% |

*SGI (Salt Growth Index) = seedling area × Fv/Fm (photosynthesis efficiency)

Transgenic plants of ME07361-04 showed significant better tolerance to high salt than pooled non-transgenics.
Summary of Results:
Ectopic expression of Ceres Clone 5367 under the control of the 35S promoter enhances tolerance to salt stress that causes necrotic lesions and stunted growth in wild-type Ws seedlings.

Example 10: ME09594 (Annot ID 566551: SEO ID NO: 290)

Wild-type *Arabidopsis thaliana* Wassilewskija was transformed with a $T_1$ plasmid carrying the 35S promoter and Annot ID 566551. Annot ID 566551 is a functional homolog of Ceres clone 965405.

Grown on MS agar plates containing 100 mM NaCl, ME09594-03 transgenic plants showed significantly greater seedling area and SGI relative to non-transgenic plants. As shown in Table 10-1, the SGI value of T2-generation ME09594-03 seedlings increased by 60.09% as compared to non-transgenic control seedlings. The differences between transgenic and non-transgenic seedlings are statistically significant under the t-test, and clearly demonstrate that the enhanced tolerance to salt stress was a result of the ectopic expression of Annot ID 566551 in the ME09594 transgenic lines.

TABLE 10-1

Results of ME09594 on salt tolerance assay in T2/T3 generation

| ME Events | SGI* of transgenics | | | SGI of pooled non-transgenics | | | t-Test | SGI |
|---|---|---|---|---|---|---|---|---|
| | Avg | SE | N | Avg | SE | N | p-value | increase |
| ME09594-01 | 2.17 | 0.357 | 19 | 2.36 | 0.352 | 16 | 0.357 | −7.87% |
| ME09594-02-99 | 1.83 | 1.109 | 4 | 1.72 | 0.252 | 24 | 0.463 | 6.20% |
| ME09594-03 | 2.32 | 0.380 | 24 | 1.45 | 0.280 | 9 | 0.038 | 60.09% |
| ME09594-04-99 | 0.71 | 0.110 | 16 | 0.79 | 0.082 | 17 | 0.288 | −9.82% |
| ME09594-05 | 2.38 | 0.465 | 13 | 2.69 | 0.392 | 21 | 0.305 | −11.66% |

*SGI (Salt Growth Index) = seedling area × Fv/Fm (photosynthesis efficiency)

Transgenic plants of ME09594-03 showed significant better tolerance to high salt than pooled non-transgenics.
Summary of Results:
Ectopic expression of Annot ID 566551 under the control of the 35S promoter enhances tolerance to salt stress that causes necrotic lesions and stunted growth in wild-type Ws seedlings.

Example 11: ME23428 (Annot ID 842118: SEQ ID NO: 289)

Wild-type *Arabidopsis thaliana* Wassilewskija was transformed with a T₁ plasmid carrying the 35S promoter and Annot ID 842118. Annot ID 842118 is a functional homolog of Ceres clone 29658.

Grown on MS agar plates containing 100 mM NaCl, ME23428-02 transgenic plants showed significantly greater seedling area and SGI relative to non-transgenic plants. As shown in Table 11-1, the SGI value of T2-generation ME23428-02 seedlings increased by 81.77% as compared to non-transgenic control seedlings. The differences between transgenic and non-transgenic seedlings are statistically significant under the t-test, and clearly demonstrate that the enhanced tolerance to salt stress was a result of the ectopic expression of Annot ID 842118 in the ME23428 transgenic lines.

Transgenic plants of ME23428-02 showed significant better tolerance to high salt than pooled non-transgenics.
Summary of Results:
Ectopic expression of Annot ID 842118 under the control of the 35S promoter enhances tolerance to salt stress that causes necrotic lesions and stunted growth in wild-type Ws seedlings.

Example 12: ME24903 (Clone 295570: SEQ ID NO: 275)

Wild-type *Arabidopsis thaliana* Wassilewskija was transformed with a T₁ plasmid carrying the 35S promoter and Ceres clone 295570. Ceres clone 295570 is a functional homolog of Ceres clone 8686.

Grown on MS agar plates containing 100 mM NaCl, ME24903-04, ME24903-05 ME24903-07 and ME24903-09 transgenic plants showed significantly greater seedling area and SGI relative to non-transgenic plants. As shown in Table 12-1, the SGI value of T2-generation ME24903-04 seedlings increased by 68.42%, the SGI value of T2-generation ME24903-05 seedlings increased by 55.99%, the SGI value of T2-generation ME24903-07 seedlings increased by 140.73% and the SGI value of T2-generation ME24903-09 seedlings increased by 121.46% as compared to non-transgenic control seedlings. The differences between transgenic and non-transgenic seedlings are statistically significant under the t-test, and clearly demonstrate that the enhanced tolerance to salt stress was a result of the ectopic expression of Ceres clone 295570 in the ME24903 transgenic lines.

TABLE 11-1

Results of ME23428 on salt tolerance assay in T2 generation

| ME Events | SGI* of transgenics | | | SGI of pooled non-transgenics | | | t-Test | SGI |
|---|---|---|---|---|---|---|---|---|
| | Avg | SE | N | Avg | SE | N | p-value | increase |
| ME23428-01 | 1.26 | 0.166 | 9 | 1.76 | 0.283 | 26 | 0.069 | −28.36% |
| ME23428-02 | 1.17 | 0.134 | 18 | 0.65 | 0.139 | 11 | 0.005 | 81.77% |
| ME23428-03 | 0.63 | 0.036 | 13 | 0.64 | 0.039 | 19 | 0.386 | −2.43% |
| ME23428-04 | 0.93 | 0.108 | 18 | 0.84 | 0.222 | 13 | 0.371 | 9.72% |
| ME23428-05 | 0.99 | 0.144 | 19 | 0.97 | 0.166 | 14 | 0.466 | 1.96% |

*SGI (Salt Growth Index) = seedling area × Fv/Fm (photosynthesis efficiency)

TABLE 12-1

Results of ME24903 on salt tolerance assay in T2 generation

| ME Events | SGI* of transgenics | | | SGI of pooled non-transgenics | | | t-Test | SGI |
|---|---|---|---|---|---|---|---|---|
| | Avg | SE | N | Avg | SE | N | p-value | increase |
| ME24903-04 | 0.97 | 0.141 | 19 | 0.58 | 0.091 | 15 | 0.0123 | 68.42% |
| ME24903-05 | 1.72 | 0.221 | 18 | 1.10 | 0.160 | 17 | 0.0153 | 55.99% |
| ME24903-07 | 1.51 | 0.229 | 21 | 0.63 | 0.112 | 12 | 0.0008 | 140.73% |
| ME24903-08 | 0.89 | 0.087 | 18 | 0.79 | 0.208 | 12 | 0.3241 | 13.22% |
| ME24903-09 | 1.86 | 0.303 | 14 | 0.84 | 0.104 | 20 | 0.0016 | 121.46% |

*SGI (Salt Growth Index) = seedling area × Fv/Fm (photosynthesis efficiency)

Transgenic plants of ME24903-04, -5, -7 and -09 showed significant better tolerance to high salt than pooled non-transgenics.

Summary of Results:

Ectopic expression of Ceres clone 295570 under the control of the 35S promoter enhances tolerance to salt stress that causes necrotic lesions and stunted growth in wild-type Ws seedlings.

Example 13: ME10681 (Clone 335348: SEQ ID NO: 314)

Wild-type *Arabidopsis thaliana* Wassilewskija was transformed with a $T_1$ plasmid carrying the 35S promoter and Ceres clone 335348. Ceres clone 335348 is a functional homolog of Ceres clone 375578.

Grown on MS agar plates containing 100 mM NaCl, ME10681-02, ME10681-04, and ME10681-05 transgenic plants showed significantly greater seedling area and SGI relative to non-transgenic plants. As shown in Table 13-1, the SGI value of T2-generation, the SGI value of T2-generation ME10681-02 seedlings increased by 119.17%, the SGI value of T2-generation ME10681-04 seedlings increased by 113.51% and the SGI value of T2-generation ME10681-05 seedlings increased by 103.98% as compared to non-transgenic control seedlings. The differences between transgenic and non-transgenic seedlings are statistically significant under the t-test, and clearly demonstrate that the enhanced tolerance to salt stress was a result of the ectopic expression of Ceres clone 335348 in the ME10681 transgenic lines.

TABLE 13-1

Results of ME10681 on salt tolerance assay in T2 generation

| ME Events | SGI* of transgenics | | | SGI of pooled non-transgenics | | | t-Test | SGI |
|---|---|---|---|---|---|---|---|---|
| | Avg | SE | N | Avg | SE | N | p-value | increase |
| ME10681-01 | 3.87 | 0.6837 | 9 | 2.78 | 0.4324 | 24 | 0.0940 | 39.17% |
| ME10681-02 | 4.13 | 0.3354 | 25 | 1.89 | 0.5752 | 11 | 0.0009 | 119.17% |
| ME10681-04 | 6.22 | 0.4787 | 12 | 2.91 | 0.5671 | 15 | 7.66E−05 | 113.51% |
| ME10681-05 | 5.25 | 0.3916 | 20 | 2.57 | 0.6140 | 15 | 0.0004 | 103.98% |

*SGI (Salt Growth Index) = seedling area × Fv/Fm (photosynthesis efficiency)

Transgenic plants of ME10681-02, -04 and -05 showed significant better tolerance to high salt than pooled non-transgenics.

Summary of Results:

Ectopic expression of Ceres clone 335348 under the control of the 35S promoter enhances tolerance to salt stress that causes necrotic lesions and stunted growth in wild-type Ws seedlings.

Example 14: Determination of Functional Homolog Sequences

The sequences described in the above Examples are utilized as query sequences to identify functional homologs of the query sequences and, together with those sequences, are utilized to define consensus sequences for a given group of query and functional homolog sequences. Query sequences and their corresponding functional homolog sequences are aligned to illustrate conserved amino acids consensus sequences that contain frequently occurring amino acid residues at particular positions in the aligned sequences, as shown in FIGS. 1-9.

A subject sequence is considered a functional homolog of a query sequence if the subject and query sequences encode proteins having a similar function and/or activity. A process known as Reciprocal BLAST (Rivera et al. (1998) *Proc. Natl Acad. Sci. USA* 95:6239-6244) is used to identify potential functional homolog sequences from databases consisting of all available public and proprietary peptide sequences, including NR from NCBI and peptide translations from Ceres clones.

Before starting a Reciprocal BLAST process, a specific query polypeptide is searched against all peptides from its source species using BLAST in order to identify polypeptides having sequence identity of 80% or greater to the query polypeptide and an alignment length of 85% or greater along the shorter sequence in the alignment. The query polypeptide and any of the aforementioned identified polypeptides are designated as a cluster.

The main Reciprocal BLAST process consists of two rounds of BLAST searches; forward search and reverse search. In the forward search step, a query polypeptide sequence, "polypeptide A," from source species $S^A$ is BLASTed against all protein sequences from a species of interest. Top hits are determined using an E-value cutoff of $10^{-5}$ and an identity cutoff of 35%. Among the top hits, the sequence having the lowest E-value is designated as the best hit, and considered a potential functional homolog. Any other top hit that had a sequence identity of 80% or greater to the best hit or to the original query polypeptide is considered a potential functional homolog as well. This process is repeated for all species of interest.

In the reverse search round, the top hits identified in the forward search from all species are used to perform a BLAST search against all protein or polypeptide sequences from the source species $S^4$. A top hit from the forward search that returned a polypeptide from the aforementioned cluster as its best hit is also considered as a potential functional homolog.

Functional homologs are identified by manual inspection of potential functional homolog sequences. Representative functional homologs are shown in FIGS. 1-9. The Figures represents a grouping of a query sequence aligned with the corresponding identified functional homolog subject sequences. Query sequences and their corresponding functional homolog sequences are aligned to identify conserved amino acids and to determine a consensus sequence that contains a frequently occurring amino acid residue at particular positions in the aligned sequences, as shown in FIGS. 1-9.

An HMM was made based on SEQ ID NOs: 80, 84, 85, 90, 92, 93 and 95, aligned in FIG. 1. When fit to the HMM, SEQ ID NOs: 80, 81, 82, 83, 84, 85, 86, 87, 89, 90, 91, 92, 93, 95, 97, 182, 184, 186, 188, 190, 191, and 192 gave HMM bit scores of 576.8, 394.8, 231.4, 382.2, 523.7, 632.7, 39.3, 409.6, 386.4, 569.7, 551.4, 621.4, 635.3, 633.5, 573.9, 543.4, 594.6546.7, 493.1, 613.4, and 635.3, respectively.

An HMM was made based on SEQ ID NOs: 100, 252, 298, 301, 302, 303 and 312 aligned in FIG. 2. When fit to the HMM, SEQ ID NOs: 100, 102, 103, 104, 252, 298, 300, 301, 302, 303 and 312 gave HMM bit scores of 1315.8, 208.1, 118.5, 173.9, 1272.1, 1235.9, 635.2, 1206.4, 225.6, 1212.9 and 1233.4, respectively.

An HMM was made based on SEQ ID NOs: 106, 107, 112, 113, 114 and 115, aligned in FIG. 3. When fit to the HMM, SEQ ID NOs: 106, 107, 109, 110, 111, 112, 113, 114, 115, 116, 117, 118, 119, 121, 194, 196, 197, 198 and 200 gave HMM bit scores of 593.7, 487.6, 238.4, 113.8, 492.6, 536.1, 524.8, 289.4, 624.9, 288.2, 476.4, 282.4, 489.3, 588.8, 545.8, 503.3, 491.5, 486, 504.9, respectively.

An HMM was made based on SEQ ID NOs: 123, 125, 126, 127, 128, 129 and 130, aligned in FIG. 4. When fit to the HMM, SEQ ID NOs: 123, 125, 126, 127, 128, 129. 130, 270 and 284 gave HMM bit scores of 390.1, 327.9, 392.3, 396.5, 394.8, 393.7, 323.8, 330.6 and 235.5, respectively.

An HMM was made based on SEQ ID NOs: 132, 134, 139, 142 and 143, aligned in FIG. 5. When fit to the HMM, SEQ ID NOs: 132, 134, 136, 138, 139, 141, 142, 143 and 144 gave HMM bit scores of 343.8, 454.5, 208, 197, 388.2, 144.1, 319.9, 375.2 and 295.2, respectively.

An HMM was made based on SEQ ID NOs: 146, 147, 149, 151 and 152, aligned in FIG. 6. When fit to the HMM, SEQ ID NOs: 146, 147, 149, 150, 151, 152, 202, 204 and 206 gave HMM bit scores of 593.1, 602.9, 570.8, 355.3, 633.9, 570.8, 369.3, 474.7 and 357.4, respectively.

Figure 7:
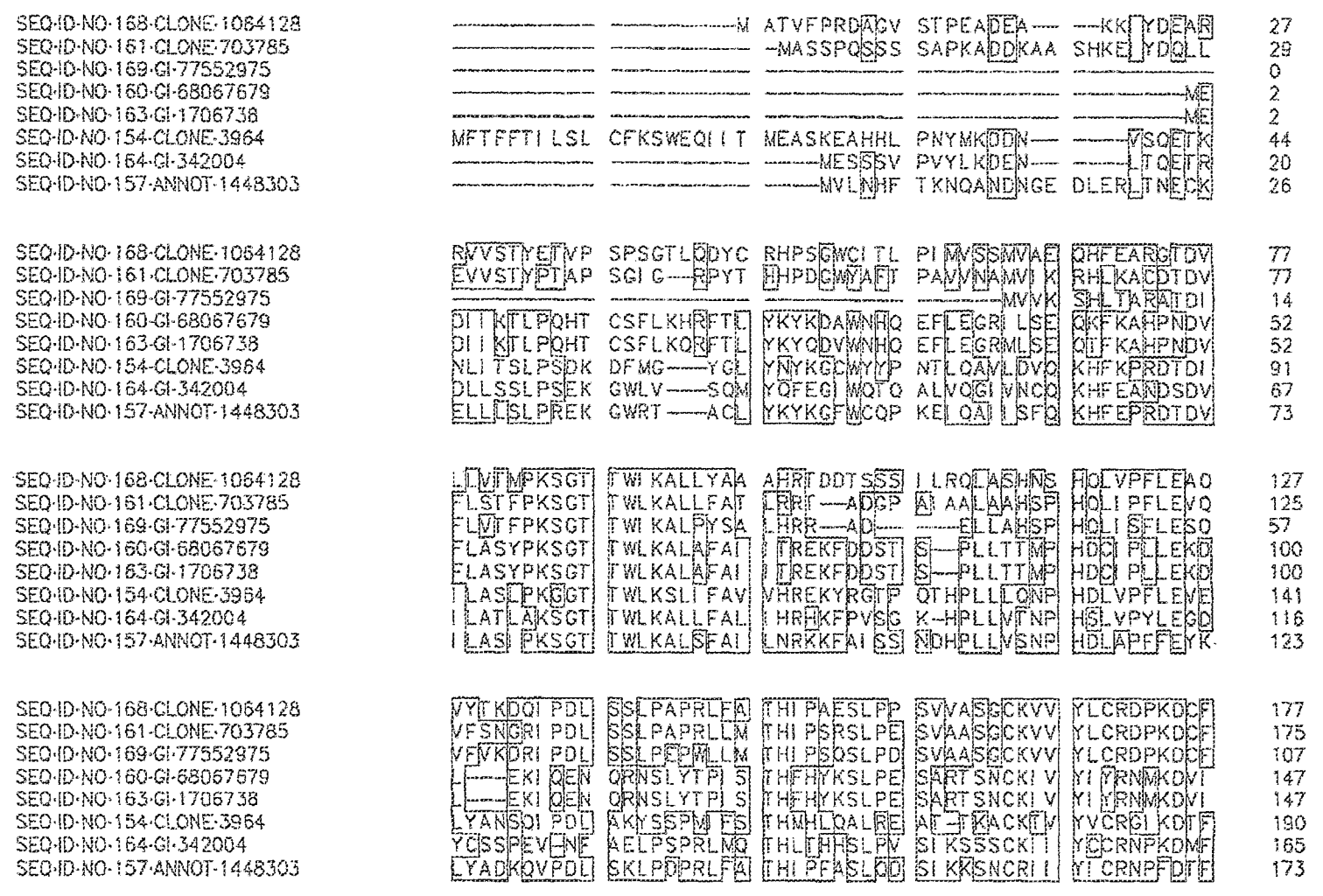

An HMM was made based on SEQ ID NOs: 154, 157, 160, 161, 163, 164, 168, and 169, aligned in FIG. 7. When fit to the HMM, SEQ ID NOs: 154, 155, 157, 159, 160, 161, 162, 163, 164, 165, 166, 167, 168, 169, 170, 274, 278, 282, 286 and 288 gave HMM bit scores of 894.1, 719.9, 901.3, 801.4, 747, 810.2, 692.7, 748.7, 779.9, 656.3, 603.6, 485.1, 816.9, 634.5, 149, 498, 510, 584.3, 455.2 and 670.6, respectively.

An HMM was made based on SEQ ID NOs: 172, 173, 174, 175, 176, 177 and 179, aligned in FIG. 8. When fit to the HMM, SEQ ID NOs: 172, 173, 174, 175, 176, 177, 179, 208, 210, 212 and 213 gave HMM bit scores of 533.9, 542, 570.8, 559.9, 547.5, 474.8, 531.3, 414.3, 447.1, 358.5 and 344, respectively.

Figure 9:
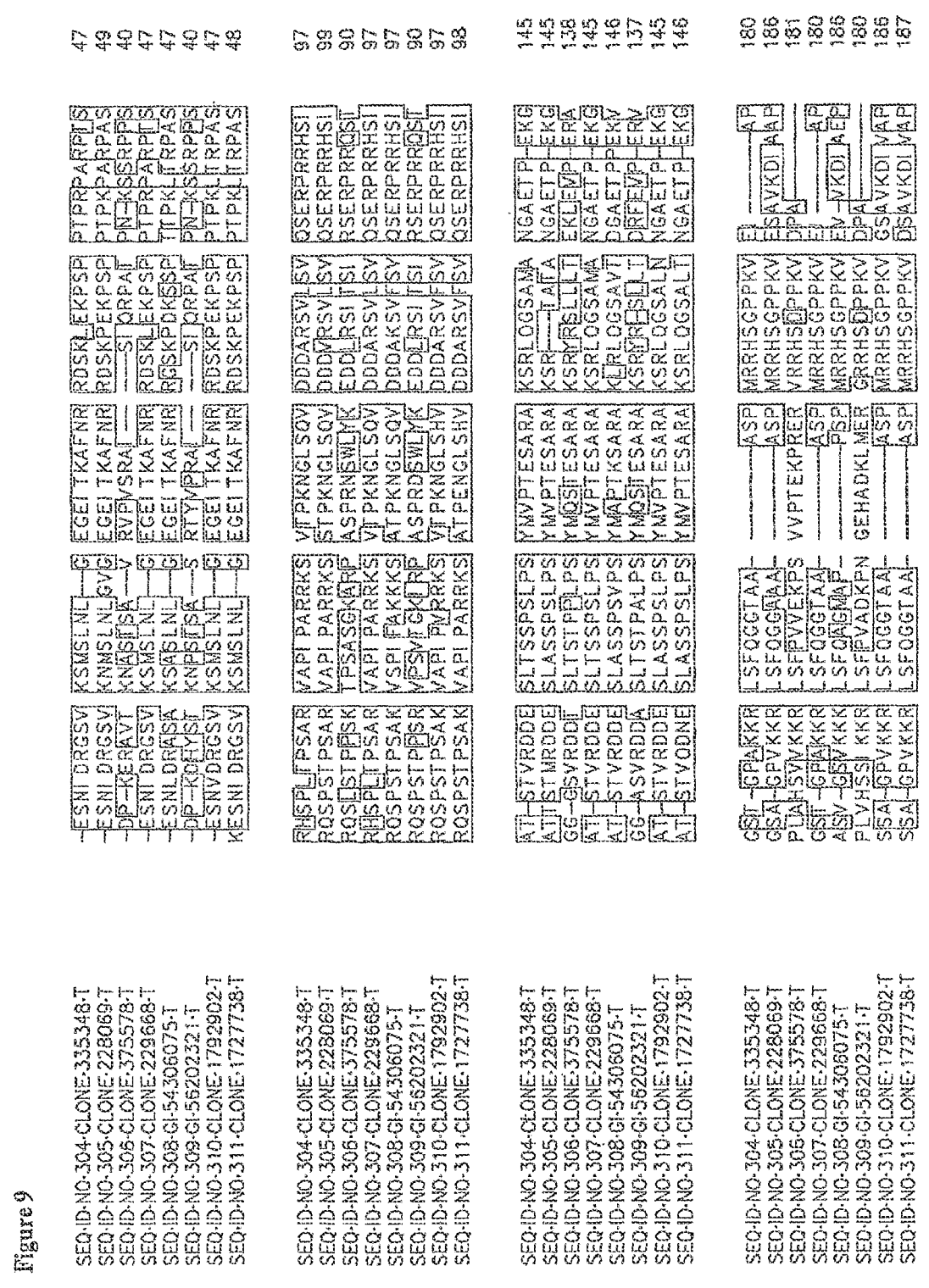

An HMM was made based on SEQ ID NOs: 304, 305, 306, 307, 308, 309, 310 and 311, aligned in FIG. 9. When fit to the HMM, SEQ ID NOs: 100, 102, 103, 104, 252, 298, 300, 301, 302, 303, 304, 305, 306, 307, 308, 309, 310, 311 and 312 gave HMM bit scores of 418.9, 208.1, 118.5, 173.9, 407.6, 490.5, 156.9, 461, 462, 469.6, 462, 461, 406.7, 462, 469.6, 418.9, 490.5 and 493.3, 493.3 respectively.

Useful polypeptides of the invention include each of the sequences and corresponding functional homolog sequences shown in the Figures and/or the Sequence Listing, as well as polypeptides belonging to the corresponding consensus sequence families as delineated by HMMs. In different embodiments, consensus sequence families have HMM bit score lower limits as about 50%, 60%, 70%, 80%, 90%, or 95% of any of the HMM bit scores of the family members presented in this application. In some embodiments the lower HMM bit score limits correspond approximately to the HMM bit score of any of the family members disclosed in this application. A sequence that has an HMM bit score of 20 means that it has a 95% likelihood of belonging to the consensus sequence defined by a particular HMM. Alternative HMM bit scores that are useful for the current invention are 50, 75, 100, 125, 150, 200, 250, 300, 350, 400, 450 and 500.

The present invention further encompasses nucleotides that encode the above described polypeptides, as well as the complements thereof, and including alternatives thereof based upon the degeneracy of the genetic code.

The invention being thus described, it will be apparent to one of ordinary skill in the art that various modifications of the materials and methods for practicing the invention can be made. Such modifications are to be considered within the scope of the invention as defined by the following claims.

The following references are cited in the Specification. Each of the references from the patent and periodical literature cited herein is hereby expressly incorporated in its entirety by such citation.

REFERENCES (1) Zhang et al. (2004) *Plant Physiol.* 135:615.
(2) Salomon et al. (1984) *EMBO J.* 3:141.
(3) Herrera-Estrella et al. (1983) *EMBO J.* 2:987.
(4) Escudero et al. (1996) *Plant J.* 10:355.
(5) Ishida et al. (1996) *Nature Biotechnology* 14:745.
(6) May et al. (1995) *Bio/Technology* 13:486)
(7) Armaleo et al. (1990) *Current Genetics* 17:97.
(8) Smith. T. F. and Waterman, M. S. (1981) *Adv. App. Math.* 2:482.
(9) Needleman and Wunsch (1970) *J. Mol. Biol.* 48:443.
(10) Pearson and Lipman (1988) *Proc. Natl. Acad Sci.* (USA) 85: 2444.
(11) Yamauchi et al. (1996) *Plant Mol Biol.* 30:321-9.
(12) Xu et al. (1995) *Plant Mol. Biol.* 27:237.
(13) Yamamoto et al. (1991) *Plant Cell* 3:371.
(14) P. Tijessen, "Hybridization with Nucleic Acid Probes" In Laboratory Techniques in Biochemistry and Molecular Biology, P. C. vand der Vliet, ed., c. 1993 by Elsevier, Amsterdam.
(15) Bonner et al., (1973) *J. Mol. Biol.* 81:123.
(16) Sambrook et al., Molecular Cloning: A Laboratory Manual, Second Edition, Cold Spring Harbor Laboratory Press, 1989, New York.

(17) Shizuya et al. (1992) *Proc. Natl. Acad. Sci. USA*, 89: 8794-8797.
(18) Hamilton et al. (1996) *Proc. Natl. Acad. Sci. USA*, 93: 9975-9979.
(19) Burke et al. (1987) *Science*, 236:806-812.
(20) Sternberg N. et al. (1990) *Proc Natl Acad Sci USA.*, 87:103-7.
(21) Bradshaw et al. (1995) *Nucl Acids Res*, 23: 4850-4856.
(22) Frischauf et al. (1983) *J. Mol Biol*, 170: 827-842.
(23) Huynh et al., Glover N M (ed) DNA Cloning: A practical Approach, Vol. 1 Oxford: IRL Press (1985).
(24) Walden et al. (1990) *Mol Cell Biol* 1: 175-194.
(25) Vissenberg et al. (2005) *Plant Cell Physiol* 46:192.
(26) Husebye et al. (2002) *Plant Physiol* 128:1180.
(27) Plesch et al. (2001) *Plant J* 28:455.
(28) Weising et al. (1988) *Ann. Rev. Genet.*, 22:421.
(29) Christou (1995) *Euphytica*, v. 85, n. 1-3:13-27.
(30) Newell (2000)
(31) Griesbach (1987) *Plant Sci.* 50:69-77.
(32) Fromm et al. (1985) *Proc. Natl. Acad Sci. USA* 82:5824.
(33) Paszkowski et al. (1984) *EMBO J.* 3:2717.
(34) Klein et al. (1987) *Nature* 327:773.
(35) Willmitzer, L. (1993) Transgenic Plants. In: iotechnology, A Multi-Volume Comprehensive treatise (H J. Rehm, G. Reed, A. Püler, P. Stadler, eds., Vol. 2, 627-659, VCH Weinheim-New York-Basel-Cambridge).
(36) *Crit. Rev. Plant. Sci.* 4:1-46.
(37) Fromm et al. (1990) *Biotechnology* 8:833-844.
(38) Cho et al. (2000) *Planta* 210:195-204.
(39) Brootghaerts et al. (2005) *Nature* 433:629-633.
(40) Lincoln et al. (1998) *Plant Mol. Biol. Rep.* 16:1-4.
(41) Lacomme et al. (2001), "Genetically Engineered Viruses" (C. J. A. Ring and E. D. Blair, Eds). Pp. 59-99, BIOS Scientific Publishers, Ltd. Oxford, UK.
(42) Huh G H, Damsz B, Matsumoto T K, Reddy M P, Rus A M, Ibeas J I, Narasimhan M L, Bressan R A, Hasegawa P M, 2002, Salt causes ion disequilibrium-induced programmed cell death in yeast and plants. *Plant J* 29(5): 649-59.
(43) Kang D K, Li X M, Ochi K, Horinouchi S, 1999, Possible involvement of cAMP in aerial mycelium formation and secondary metabolism in *Streptomyces griseus*. *Microbiology*, 145 (Pt 5):1161-72.
(44) Kerk D, Bulgrien J, Smith D W, Gribskov M, 2003, *Arabidopsis* proteins containing similarity to the universal stress protein domain of bacteria. *Plant Physiol.* 131(3): 1209-19.
(45) Zhu J K, 2001, Cell signaling under salt, water and cold stresses. *Curr Opin Plant Biol.* 4(5):401-6.
(46) Susstrunk U, Pidoux J, Taubert S, Ullmann A, Thompson C J, 1998, Pleiotropic effects of cAMP on germination, antibiotic biosynthesis and morphological development in *Streptomyces coelicolor. Mol Microbiol* 30(1):33-46.
(47) Davletova S, Schlauch K, Coutu J, Mittler R., 2005, The zinc-finger protein Zat12 plays a central role in reactive oxygen and abiotic stress signaling in *Arabidopsis. Plant Physiol* 139(2):847-56.
(48) Fowler S G, Cook D, Thomashow M F., 2005, Low temperature induction of *Arabidopsis* CBF1, 2, and 3 is gated by the circadian clock. *Plant Physiol* 137(3):961-8.
(49) Nachin L, Nannmark U, Nystom T (2005) Differential roles of the universal stress proteins of *Escherichia coli* in oxidative stress resistance, adhesion and motility *J Bacteriol* 187(18):6265-72.
(50) Rizhsky L, Davletova S, Liang H, Mittler R, 2004, The zinc finger protein Zat12 is required for cytosolic ascorbate peroxidase 1 expression during oxidative stress in *Arabidopsis. J Biol Chem.* 19; 279(12):11736-43.
(51) Vogel J T, Zarka D G, Van Buskirk H A, Fowler S G, Thomashow M F, 2005, Roles of the CBF2 and ZAT12 transcription factors in configuring the low temperature transcriptome of *Arabidopsis. Plant J.* 41(2):195-211.
(52) Sanchez-Barrena M J, Martinez-Ripoll M, Zhu J K, Albert A., 2005, The structure of the *Arabidopsis thaliana* SOS3: molecular mechanism of sensing calcium for salt stress response *J Mol Biol.* 345(5):1253-64.
(53) Griffen, H. G, and Gasson, M. J. (1995) The Gene (aroK) Encoding Shikimate Kinase I from *E. coli. DNA Seq.*, 5(3):195-197.
(54) Susstrunk et al. (1998) *Mol Microbiol*, 30(1):33-46
(55) Kang et al. (1999) *Microbiology*, 145:1161-72.
(56) Sauter M, Rzewuski G, Marwedel T, Lorbiecke R (2002) The novel ethylene-regulated gene OsUsp1 from rice encodes a member of a plant protein family related to prokaryotic universal stress proteins. *J Exp Bot* 53 (379): 2325-31.
(57) Kasuga et al. (1999) *Nature Biotech* 17: 287-291.
(58) Rus et al. (2001) PNAS 98:14150-14155.
(60) Shi et al. (2000) PNAS 97:6896-6901.
(61) Apse et al. (1999) Science 285:1256-1258.
(62) Zhang et al. (2001) PNAS 98:12832-12836.
(63) Berthomieu et al. (2003) EMBO J 22:2004-2014.
(64) Ren et al. (2005) Nat Genet. 37:1029-30
(65) Davletova et al (2005) Plant Physiol. 139:847-56

SEQUENCE LISTING

```
Sequence total quantity: 315
SEQ ID NO: 1          moltype = DNA  length = 1823
FEATURE               Location/Qualifiers
misc_feature          1..1823
                      note = Ceres Promoter 21876
source                1..1823
                      mol_type = unassigned DNA
                      organism = Arabidopsis thaliana
SEQUENCE: 1
gtctcttaaa aaggatgaac aaacacgaaa ctggtggatt atacaaatgt cgccttatac  60
atatatcggt tattggccaa aagagctatt ttacttatg  gataatggtg ctactatggt 120
tggagttgga ggtgtagttc aggcttcacc ttctggttta agccctccaa tgggtaatgg 180
taaatttccg gcaaaaggtc ctttgagatc agccatgttt tccaatgttg aggtcttata 240
ttccaagtat gagaaaggta aaataaatgc gtttcctata gtggagttgc tagatagtag 300
tagatgttat gggctacgaa ttggtaagag agttcgattt tggactagtc cactcggata 360
cttttcaat  tatggtggtc ctggaggaat ctcttgtgga gtttgatatt tgcgagtata 420
atctttgaac ttgtgtagat tgtacccaaa accgaaaaca tatcctatat aaatttcatt 480
atgagagtaa aattgtttgt tttatgtatc atttctcaac tgtgattgag ttgactattg 540
```

```
                                            -continued
aaaacatatc ttagataagt ttcgttatga gagttaatga tgattgatga catacacact     600
cctttatgat ggtggattcaa cgttttggag aaaatttatt tataatctct cataaattct    660
ccgttattag ttgaataaaa tcttaaatgt ctcctttaac catagcaaac caacttaaaa    720
atttagattt taaagttaag atggatattg tgattcaacg attaattatc gtaatgcata    780
ttgattatgt aaaataaaat ctaactaccg gaatttattc aataactcca ttgtgtgact    840
gcatttaaat atatgtttta tgtcccatta attaggctgt aatttcgatt tatcaattta    900
tatactagta ttaatttaat tccatagatt tatcaaagcc aactcatgac ggctagggtt    960
ttccgtcacc ttttcgatca tcaagagagt ttttttataa aaaaatttat acaattatac   1020
aatttcttaa ccaaacaaca cataattata agctatttaa catttcaaat tgaaaaaaaa   1080
aatgtatgag aattttgtgg atccatttt  gtaattcttt gttgggtaaa ttcacaacca   1140
aaaaaataga aaggcccaaa acgcgtaagg gcaaattagt aaaagtagaa ccacaaagag   1200
aaagcgaaaa ccctagacac ctcgtagcta taagtaccct cgagtcgacc aggattaggg   1260
tgcgctctca tatttctcac atttttcgtag ccgcaagact cctttcagat tcttacttgc  1320
aggttagata ttttctctct ttagtgtctc cgatcttcat cttcttatga ttattgtagc   1380
tgtttagggt ttagattctt agttttagct ctatattgac tgtgattatc gcttattctt   1440
tgctgttgtt atactgcttt tgattctcta gctttagatc cgtttactcg tcgatcaata   1500
ttgttcctat tgagtctgat gtataatcct ctgattaatt gatagcgttt agttttgata   1560
tcgtcttcgc atgtttttta tcatgtcgat ctgtatctgc tctggttata gttgattctg   1620
atgtatttgg ttggtgatgt tccttagatt tgatatacct gttgtctcgt ggtttgatat   1680
gatagctcaa ctggtgatat gtggttttgt ttcagtggat ctgtgtttga ttatattgtt   1740
gacgttttgg ttgttgtatg gttgatggtt gatgtatttt tgttgattct gatgtttcga   1800
ttttttgtttt tgttttgaca gct                                          1823

SEQ ID NO: 2             moltype = DNA  length = 1000
FEATURE                  Location/Qualifiers
misc_feature             1..1000
                         note = Ceres Promoter PT0668
source                   1..1000
                         mol_type = unassigned DNA
                         organism = Arabidopsis thaliana
SEQUENCE: 2
atagagtttt actatgcttt tggaatcttt cttctaatgt gccaactaca gagaaataca     60
tgtattacca ctaggaatcg gaccatatca tagatatcag gattagataa ctagttctcg    120
tcgctatcac ttcgcattaa gttctagtaa ttgttaaaga ttctaattt  ttactaaaca    180
aaaactaaat caacatcaaa tatgcaaagt gtgtgttgtc cacacaagtg actcaaagta    240
tacgcaggtg ggattggacc atattattgc aaatcgtttc cgaaccactc atatttcttt    300
ttttctctcc ttttttatc  cggagaatta tggaaccact tcatttcaac ttcaaaacta    360
attttttggt tcagtgatca aatacaaaaa aaaaaaaaaa gttatagata ttaaatagaa    420
aactattcca atcttaaaaa tacaaatgaa accataattt taatttatac aaaactattt    480
aattagctaa gggttgtctt aacgtttaga aaataaaaaa ttatgattgt ctgtttaaaa    540
ttacaatgaa tgaataaaaa aaatatgcaa tgaatgaaag aataaatttt gtacatccga    600
tagaatgaga aaatgaattt tgtacaaacc actcaagaat tcaaaacaat tgtcaaagtt    660
tcttcctcag ccgtgtgtcc tcctctccta gccgccacat ctcacacact aatgctaacc    720
acgcgatgta accgtaagcg ctgagttttt gcatttcaga tttcacttcc accaaacaaa    780
actcgccacg tcatcaatac gaatcattcc gtataaacgt ctagattctt tacagcctac    840
aatgttctct tctttggtcg gccattattt aacgctttga acctaaatct agcccagcca    900
acgaagaaga cgaagcaaat ccaaaccaaa gttctccatt ttcgtagctt ctttaagctt    960
tttcagtatc atagagacac ttttttttttt ttgattagaa                       1000

SEQ ID NO: 3             moltype = DNA  length = 1000
FEATURE                  Location/Qualifiers
misc_feature             1..1000
                         note = Ceres Promoter PT0535
source                   1..1000
                         mol_type = unassigned DNA
                         organism = Arabidopsis thaliana
SEQUENCE: 3
ttagtgaaat tatgacatta agtaaggttt tcttagttag ctaatgtatg gctattcaat     60
tgttatgtta ggctatttta gttagtatat gaatttaggc agtctatgca aatgatttcg    120
tttttcatttt ttcatatgta aacatcaaga tcaagtaacg ccattcgagt tgatatttt    180
tttttaaatt agtgtgtgta aattttggac cgcttatttg agtttgctaa tgaagttgca    240
tatatattac gttaaaccat aggcaaacta atttgaaaca tccgattcga tttcctgtaa    300
tttttcttgg ttaattgacc aaaatcaaga tcttcagaaa taaaataaaa gacgaaagaa    360
agctgtcgca aagcagattg tgttaaaaaa aagtggattg ggctcaaacg caacttgtca    420
agcccgtgac aattacccta tacgcaagta agagtaacgt atcactggca aaagttggta    480
ttagttacga tatctttgtc atgggggcat gcatgggcat ggcttaagag ttaagcctta    540
agaagagtcc cacactcgtg actctcatga tcacttgttg tttcttacgg gcaaatacat    600
ttaactttat tcttcattta ttcacctata tctttttgga taataacttt tctctatata    660
aaataacaaa catcgtacgt ttcatttatt tacaacaagc gatgagaatt aaaaggagac    720
cttaattgat gatactcttc ttttctctcg gttacaacgg gattattaca gataatgata    780
atctatatgg atgctgacgt ggaaaaacaa aatttggtga aacacgtcaa ttaagcacga    840
cttttccatg gctagtggct aagatcgttt catcacatgg ctatatcata taatacttgg    900
atgaattcaa aataaacgac tgagaaaatg tccacgtcac ggcgcaccgc tttggactta    960
agtctcctat aataaataca acaccaaaca ttgcattcca                        1000

SEQ ID NO: 4             moltype = DNA  length = 999
FEATURE                  Location/Qualifiers
misc_feature             1..999
                         note = Ceres Promoter PT0585
```

-continued

```
source                    1..999
                          mol_type = unassigned DNA
                          organism = Arabidopsis thaliana
SEQUENCE: 4
tgaagtcatt taatatgagt ttgacattag gtaaacctaa tctatgagat tatagaatgt   60
agcaaaacta tcaatgtttc ttttccaaaa tattttgtgg ttttttcttt tggttcatta  120
tgttttgtta tttgtgaatt attttaatat gaagtaatta tattgatttt atatgatata  180
catattattt tgatataaaa tttaacactt atccattaaa atagcatggg cataatcaaa  240
atcgggacta ttacgatgaa aaagatagtt aaattgtatg ataaaataaa atgtgtaaga  300
ttaaaatttt gggttttaga aaattactaa acaaaatata gacaaagtat gttgactatt  360
atttaaaatt taaatatcat caataagata tagttaaagt cattaagtgt atagcaaaat  420
gaaaattcta agattaaaat tcgattaaaa ttttttttac taaattaaat attttaaaat  480
agggattatc atttactatt tacaattcta atatcatggg taaaaattga taacttttt   540
taaacccgcc tatctaggtg ggcctaacct agtttactaa ttactatatg attaacttat  600
taccactttt acttcttctt ttttggtcaa attactttat tgtttttat aaagtcaaat   660
tactctttgc attgtaaata atagtagtaa ctaaaatctt aaaacaaaat attcaacctt  720
tcccattatt ggaatggtaa tgtcttcaac accattgacc aacgttaagg aatgtcttt   780
aatattttg gaacctaaat gctaaatactg tataccacaa tcacttatga gtattgaagt  840
tgagatagag gaggtacaag gagacccttat ctgcagaaga caaaaagcca ttttttagcaa 900
aactaaagaa agaaaaaaga ttgaaacaca aatatgcgcc actcgtagtc caccccctatc 960
tctttggcaa aagccacttc actctttttc ccttttat                           999

SEQ ID NO: 5              moltype = DNA  length = 1000
FEATURE                   Location/Qualifiers
misc_feature              1..1000
                          note = Ceres Promoter PT0613
source                    1..1000
                          mol_type = unassigned DNA
                          organism = Arabidopsis thaliana
SEQUENCE: 5
ttaatactaa cattgtagaa agccacaaaa aagaaattga aatgtgagta gatgctgagt    60
cagaggtttg gtcaatacac aacagctaat tgagataata ttatacacgt cacgatgact  120
tgtttttct cctcccaact tgttaatttc tttattctta aaattaaacc atcgcaaaaa   180
cagaagaaca cagctgtttt tctcgactcc caatttctat tttgctgcta aggacatttc  240
atttcattat ttcccaattc aggactcctt agatttttcct aaatttgttt tcctaacttg  300
ctctctctca ttcaacatt ttctcatttt tttagattat cttgtacttt ttagtagatt   360
attttatcag gttttacaaa catacattga cattctaaaa agggcttcta aaaattcagt  420
gtggaatgct gatatactaa aaaaaggtca tgcaaaatta tctacgattt atctaaaatt  480
agataatttg ccatatataa ctattaacta ataatcgatc ttttgattt ttgtttagat   540
aaaacgaaac agctatatct ttttttttg ttatcggatt ttaatcgaat aaaagctgaa   600
aataacagt tatatcttct tctttttaa ctaatgaaac agttatatct taaacaaaca   660
acagaaacag taaatatta atgcaaatcc gcgtcaagag ataaattta acaaactaat   720
aacaattgag ataagattag cgcaaaagaa actctcattt tagagcgtgt aaacacaaa   780
acgtcttgaa agtaaacgtg aattacacgc ttcaaaacg agcgtgagtt ttggttataa   840
cgaagatacg gtgaagtgtg acaccttttc acgttaattt cagtttgagg acacaactca  900
agttatgttt gatatctaag gacttgcact gtctccaaat ctgcaggaag gactttttga   960
ttggatcaat ataaatacca tctccattct cgtctccttc                        1000

SEQ ID NO: 6              moltype = DNA  length = 351
FEATURE                   Location/Qualifiers
misc_feature              1..351
                          note = Ceres Promoter PT0625
source                    1..351
                          mol_type = unassigned DNA
                          organism = Arabidopsis thaliana
SEQUENCE: 6
gatcatgatc agtttcaact cgctgtgccc acgtgtcgag agatcggcac gtgcctgagc    60
tctcagccgc tcataaatac acttgtttag tagcaacagt atactatagt agtcctctcc  120
tgtttggctt ttagcttgca tcgatggatg gatggatgga tcgcatgaga gggcttcgcg  180
aaggtacgga accttacaca acgcgtgtcc tttctacgtg gccatcgtgt aggcgtctcg  240
ccatgctacg tgtcccggag gatgtctcga tgccaacccct tataaatact gttccattcc  300
aatcccatcg ccacagccag tgcaaatctg atcgatcaag ataatcgagc a           351

SEQ ID NO: 7              moltype = DNA  length = 1022
FEATURE                   Location/Qualifiers
misc_feature              1..1022
                          note = Ceres Promoter PT0633
source                    1..1022
                          mol_type = unassigned DNA
                          organism = Arabidopsis thaliana
SEQUENCE: 7
cccgatcggc cttaatctga gtcctaaaaa ctgttatact taacagttaa cgcatgattt    60
gatggaggag ccatagatgc aattcaatca aactgaaatt tctgcaagaa tctcaaacac  120
ggagatctca aagtttgaaa gaaaatttat ttcttcgact caaaacaaac ttacgaaatt  180
taggtagaac ttatatacat tatattgtaa tttttttgtaa caaaatgttt ttattattat  240
tatagaattt tactggttaa attaaaaatg aatagaaaag gtgaattaag aggagagagg  300
aggtaaacat tttcttctat ttttttcatat tttcaggata aattattgta aaagtttaca  360
agatttccat ttgactagtg taaatgagga atattctcta gtaagatcat tatttcatct  420
acttcttta tcttctacca gtagaggaat aaacaatatt tagctccttt gtaaatacaa   480
```

```
attaatttc gttcttgaca tcattcaatt ttaattttac gtataaaata aaagatcata   540
cctattagaa cgattaagga gaaatacaat tcgaatgaga aggatgtgcc gtttgttata   600
ataaacagcc acacgacgta aacgtaaaat gaccacatga tgggccaata gacatggacc   660
gactactaat aatagtaagt tacatttag gatggaataa atatcatacc gacatcagtt    720
tgaaagaaaa gggaaaaaaa gaaaaaataa ataaaagata tactaccgac atgagttcca   780
aaaagcaaaa aaaagatca agccgacaca gacacgcgta gagagcaaaa tgactttgac    840
gtcacaccac gaaacagac gcttcatacg tgtccttta tctctctcag tctctctata     900
aacttagtga gaccctcctc tgttttactc acaaatatgc aaactagaaa acaatcatca   960
ggaataaagg gtttgattac ttctattgga aagaaaaaaa tctttggaaa aggcctgcag  1020
gg                                                                1022

SEQ ID NO: 8            moltype = DNA   length = 1000
FEATURE                 Location/Qualifiers
misc_feature            1..1000
                        note = Ceres Promoter PT0650
source                  1..1000
                        mol_type = unassigned DNA
                        organism = Arabidopsis thaliana
SEQUENCE: 8
catacttaat tctaaaaaaa caacacttat agtttataag cagctcttat gataaaaatc    60
tttctgagtt atagctctgt taaacttgta ttcaccccaa aaacgatgt ttcatttctt    120
atttttact tggagtattt tattgtaatt tgtaaaaaaa aatgtaaagt gggggatatc    180
atgaaaaca acgtcacttt gtttggtcac aatatacatt tgataaaata atggtcgtcg    240
cgtgatttag ttgattttg ttttatcaac cacgtgtttc acttgatgag tagtttatat    300
agttaacatg attcggccac ttcagatttg ggtttgccca catgacat accgacatag     360
aaggttaaat ccacgtggga aatgccaata ttcaatgttt ggttttcaaa agagaatcat   420
ttctttatat gatctcaaaa gtatggaatt gaaatgacta atgagcacat gcaattggtg   480
ctatcttaaa aaccgaacgt ctttgaattt aatttgtttt tcaccaaagg tacctaatga   540
aaccctttca ttaaaaaata aaggtaacaa acaaatttt gtattggaaa aacatttttt     600
tggaatatat aatttggtaa tagaattatg agcaaaaaag aaaaagaaaa gaaagaataa   660
tgagcataat aaagccttta cagtattact aattgggccg agcagttttg ggctcttgat   720
catgtctagt aatcttaaac agacgataaa gttaactgca atttagttgg ttcaggtgag   780
ctaccaaatc caaaaatacg cagattaggt tcaccgtacc ggaacaaacc ggatttatca   840
aaatccttaa gttatacgaa atcacgcttt ccttcgatt tctccgctct tctccactct    900
tcttctcgt tctatcgcag acatttttgt ttatatgcat acataataat aatacactct    960
tgtcaggatt tttgattctc tcttttggttt tctcggaaaa                       1000

SEQ ID NO: 9            moltype = DNA   length = 998
FEATURE                 Location/Qualifiers
misc_feature            1..998
                        note = Ceres Promoter PT0660
source                  1..998
                        mol_type = unassigned DNA
                        organism = Arabidopsis thaliana
SEQUENCE: 9
caagtcaagt tccaatattc taaggagaaa taatagtata ctaaacatac attagagagg    60
ttaaacttct ttttggattt aagtgtgtat gcataggcta ttattcttta agtataacta   120
ttaactgtag ctagatttat acaagaaata cataaaactt tatgcatgtg aggtagccat   180
gaatatacgt acatgttgca atcgattata catgttgtat ttggatttct ctatacatgt   240
tttaacttgt cattctctaa gtatatacat accattaata ctgtgggcat gagtttatga   300
taagacttttt cttttggaga ccagtttgt tttcctttcc acctatattt gtctataggc   360
ttcacggtac actagtttac aagtgttttt atatgttcta aataaaattg agattttccg   420
gaacggtatg atctgtttgc aaataaggac gtatatataa cagtatcaaa tatatttgtt   480
gttataaggc aataatatat tttctgagat attgcgtgtt acaaaaaaga aatatttgtt   540
aagaaaaaaa aagtgatggtcg aaaaaggggga gtaggtgggg gcggtcggct tttgattagt  600
aataaaagaa accacacgag tgacctaccg attcgactca acgagtgctac cgagctaaca   660
cagattcaac tcgctcgagc ttcgttttat gacaagttgg ttttttttt ttttttaat    720
tttttcatct tcttgggttt ggtttgggtca ctcttcaggt caggtgtgta aaaaagaaag    780
aagaaaaaga gagattgttg tgttgtaacc cctttgacta aaatctaatg aactttttta   840
acacaacaaa actccttcag atctgaaagg gttcttcttc tctcttagtc tcttcgtcct   900
tttattctcc gtcgtcgttt catgatctga ctctctggtc ttctcttctt cttcttcttc   960
ttctattttt tcttacttcg tcactgttgt gtctgaac                          998

SEQ ID NO: 10           moltype = DNA   length = 1000
FEATURE                 Location/Qualifiers
misc_feature            1..1000
                        note = Ceres Promoter PT0665
source                  1..1000
                        mol_type = unassigned DNA
                        organism = Arabidopsis thaliana
SEQUENCE: 10
aaaaaggatg ggtaatggga cctatttcc ccaacatccc acatgcacac ttccctctcc     60
attctctcac atttatttct ttcattcaa tttatccatt ccgtgtgtaa catattcact   120
aataatctca tctcactaac tcattcattg attgtgatat gtttatctag aattagtgtt   180
ttaacactgt gtctacatat gatttccttt tcattgtatg tgaacatgtt aactcactaa    240
tcatttgta ttttcgagtt aacatgagtc tccacttcgg tagactaaag taagatagg      300
tttgagtata ataagttta aaatttgctt taaaatcaat atttataaat aagtttttat   360
cataagtgat ttttgtatgt tatattggac cttgtataaa cagactacag aagaaaatta   420
tttatgagaa cttgtaatgt tagagtggac ctcgtataaa ctaattatgt gggcttttac   480
```

```
cataaactat ttatgaaaat tattatggcc cacaccacta taactaaagc ccacatattt      540
agcagcccag tttcattgta agagacatgt tcgctctgga actagaattt tctggttttt      600
gggtatttgt tttcttatgt gtagagaaat gatggtaacg attaaatgtt gtgtattaca      660
atttacaatg gtaagacgat taatatattt acacacaatt ttgttgttgc tgtaacacgt      720
tagtgtgtgt gatgatagaa tttcataaag ctttaactac gaggggcaaa atgttaattc      780
taaatagttg acagcagaaa aagatatgta tacataatat aaggattaaa acgtaaaataa     840
taataaataa ggcgagttaa attaaaaccc tgttaaaacc ctagcttgaa acacatgtat      900
aaaaacactt gcgagcgcag cttcatcgcc atcgccattc tctctctcat caaaagcttt      960
tctccttgat tttcgcattc tttagagtct taacgcaaag                            1000

SEQ ID NO: 11            moltype = DNA   length = 999
FEATURE                  Location/Qualifiers
misc_feature             1..999
                         note = Ceres Promoter PT0672
source                   1..999
                         mol_type = unassigned DNA
                         organism = Arabidopsis thaliana
SEQUENCE: 11
cagccgtaaa tcctccataa atttatttg caagttttgc tcattatata atgagcggaa       60
tttatgatat aatcgtttgt aataatgtta tgttttgatc aaaatttgaa attaaaagta      120
ggtgagaact tgttatacag tgtagataag gtggatcttg aatataaaaa taaaatttat      180
aagatgtatt taaagcagaa aagcataaaa ctttagataa aataatgtaa aaatgtgtta     240
gcatcaatgt tgggatattg gccgacccga acttaatcaa tgtcggaagc cattacttct      300
ctcccaaaag acctttttcc ttcggagaac taggaacttc ctcactacct ttcgcttaac     360
gtgaaagcca taaatttcat atattcataa aaatcagaaa atctaaaact gtttagtatc      420
acctgttttt ggtatagact attggttttg tgttacttcc taaactatat gatttcgtac      480
ttcattggat cttatagaga tgaatattcg taaaaagata agttatctgg tgaaacgtta      540
cttcagtcat gttgggtcta gatttacata ctactatgaa acatttttaag ataataatta     600
tcctagccaa ctatatgttc tatattatgg gccaagaaga tatagaacta aaagttcaga     660
atttaacgat ataaattact agtatattct aatacttgta tgattactgt tttagttgtt     720
tagaataaat agtagcgtgt tggttaagat accatctatc cacatctata tttgtgtggg     780
ttacataaaa tgtacataat attatataca tatatatgta tattttttgat aaagccatat    840
attactcctt gacctctgcc cccatttcct tttactataa ataggaatac tcatgatcct     900
ctaattcagc aatcaacacc aacgaacaca accttttcca aagccaataa taaaagaaca     960
aaagctttta gtttcatcaa agacgaagct gccttagaa                             999

SEQ ID NO: 12            moltype = DNA   length = 1000
FEATURE                  Location/Qualifiers
misc_feature             1..1000
                         note = Ceres Promoter PT0676
source                   1..1000
                         mol_type = unassigned DNA
                         organism = Arabidopsis thaliana
SEQUENCE: 12
aagatagtac agtttcagtg tttttgagaaa aaaagctgaa ctaaaactaa aatgtttaag    60
gacacaatat ttagtttcaa ttagataatt caacagtttg aacaatttt ttttttttt      120
tttgaagtca tttatttata caatgtttta aaacgcatta agcatttagg cagccgacaa     180
acgcctattg tctaactgta aataggcgct tccacttagg ttcatattgc atatttacta     240
tatgtgtata gtgacaaaaa ccaatatttc tcttatttg gatgaaggta tagtagttgt      300
taaatgttca atataattaa gcattaatga caaataaaat aaaattaatt tagttgataa     360
aaagataatc ttataaaaag atcgatgaat agatatagtg gtttactgaa ttctatagct    420
cttaccttgc acgactatgt cccaaggaga ggaagtacct taactataat tctgaacata    480
attttgtcta tcttggtgag tattatatga cctaaaccct ttaataagaa aagtataat     540
actggcgtaa cgtaataaat taacacaatc ataagttgtt gacaagcaaa aaaacataca     600
taatttgttt aatgagatat attagttata ttcttatgt caaagtacaa ttatgcctat     660
caaaattaat taatgatttc aacaggaagt ctgagatgat gggccgacgt gtagttacgt    720
ttcttgaatt gtgagagatg gtatttatta tactgaagaa aacattattt actaaataaa    780
ttttcatttc acatcttctg taatcaatgc gggtagatga agaagttgtt aatacgatgg    840
ccaaccatat ggatctcttt tttggcgttt ctatatatag taacctcgac tccaaaggca    900
ttacgtgact caataaaatc aagtcttttg tttccttta tccaaaaaaa aaaaaagtc      960
ttgtgtttct cttaggttgg ttgagaatca tttcatttca                            1000

SEQ ID NO: 13            moltype = DNA   length = 998
FEATURE                  Location/Qualifiers
misc_feature             1..998
                         note = Ceres Promoter PT0678
source                   1..998
                         mol_type = unassigned DNA
                         organism = Arabidopsis thaliana
SEQUENCE: 13
aattaaatga aaccgcccct aaattaggag ggatttgggt aagtggtaac acattcactg      60
gaaacatgtg aagaaaggag gatgtcaagt agctgaaaac tcagtatagt aaccaacggc     120
ttctcaccaa ccctttcatta ataatttggt catccctata ttttattca acattttgtt    180
tttcaatagc ttagagcacc ttaatacctt tcagtgtttt tttataaaaa aacaaaaat     240
tgggattaat catccaatccc caaatgtaac gtttacttag attatgttca ttttttctata    300
cacacaaatc atattctttt gttttaatct tcgaaaaacg agaggacatt aaatacccct     360
aaaaaaggag gggacattac taccaacgta cattaacatg tttgatagca aacgatttat     420
tttgttcgtt ttgaaaaggg gaaagtaatg tgtaaattat gtaaagatta ataaacttttt    480
atggtatagt aacattttcg aataataaga gagggaaaac actcgccatt gtcggcaatt     540
```

```
tagaaccaat attagaaggg ttttttttaga gaaaaaggac ttaaaagttt agagacctta    600
acaacaactt atttagaaat agacatgctt aagttgacaa cagcgagttt attttctata    660
tcgaagaaaa atacgaactt tttcttaatt agatttcgaa tgcatgcact atcgagaatc    720
gaccgtcaca agaaaaaact aatatacata ctgtacatat ctatattcaa tattggtggg    780
gatgggttta atgtgtattt ataattcatg gataaattca cacaataagg tccatgaaac    840
tagaaggtac caaaaataag cattaatgac tctttgccac ttatatatat gattctctca    900
tagtaccatt ttattctccc aaacctatct tcttcttcct ctcttgtctc tctcgctctc    960
tctcttctac attgtttctt gaggtcaatc tattaaaa                            998

SEQ ID NO: 14           moltype = DNA   length = 1000
FEATURE                 Location/Qualifiers
misc_feature            1..1000
                        note = Ceres Promoter PT0683
source                  1..1000
                        mol_type = unassigned DNA
                        organism = Arabidopsis thaliana
SEQUENCE: 14
gattgaatga tgagtgtgca cccttgtatt actaataaaa aatttagcaa cagttataag    60
ctaacgtcat ccatgagtca ttcattagat tcactatttg cgttctcaaa aatcgaattg    120
ttaaaatttg agaagctcta atatacgagt caatgagatg tggcaaaagc atgtccttga    180
ccataaaatt tcgaggggtc aactcattag ataaggacaa gaatcaacca attgaaggcg    240
tcttctataa caagtttctt tattactaat attaaagtcc aatggggtga gggggagaag    300
aacttaaata aaaggaaata attggtaagt gaataaaatc taaatacgat actagatgat    360
tgatttgtgc tagtgcatgg tattagatca gatatgtgtt actattcgaa ttcaaattgg    420
catattccat gttgttgata agaaaattgt agaagtgtaa aagctgagtt actatattca    480
aactagtggt ttacataaag tgagacaaca actgtttcac aaaaatgact ataaaatagt    540
aagtagtatt aggtcaattg attttaaaat tttaatcaaa ttcaaatttg tgatataatc    600
aaatttgttt atagaaaatg ttaagaaatc aattttggca gaactaattc agtgagaaac    660
aatcatttac aaaaacaatt ttaacattat ttaacagtaa gatttgacat ttaacccgtt    720
cgtgtgaacc catcatatct aacatggctc tacccatggc gcctccatgc catggacaat    780
tttgacagat cagaagttct gaacgtggac gaggtaagaa caccatgatg atacgattgg    840
agttagttat gtcgccaccg acatcactgc caatctcatt aataaaagtg gtactaaatc    900
tctaatctct attaactata aatataacaa agaaccaaaa gaaagtttct tatctctctt    960
atctttcata atttccaaga aacacaaacc ttttctacta                          1000

SEQ ID NO: 15           moltype = DNA   length = 1000
FEATURE                 Location/Qualifiers
misc_feature            1..1000
                        note = Ceres Promoter PT0688
source                  1..1000
                        mol_type = unassigned DNA
                        organism = Arabidopsis thaliana
SEQUENCE: 15
acgttcagag gcatcgcttt tgtacaaatt gaagcgggtt tgttcaatat ttaaaataac    60
acaggaaaca ttcaaatgta ttattgatgt tgcttaggtt tgtgaaatga tatgaaccat    120
atcgtatata ttactagatt tttcttatat gttttaaggg tagtggggct gacctatcat    180
tctgtttggc attaccaatc agactatcag agtattcacc attcaggatt cctaactag    240
aaaaagaagg ggtttacatt ttctcatact gtataatttt ctactatcag agattttatc    300
gattacatta atctcatagt gattattctg atttataaaa aagttgacaa ataattaaa    360
accagtattt tataacaaga ttgtctctct cccatggcca ttattttgac ctctgactta    420
tttaaatctt aattaacagc ataatactgt attaagcgta tttaaatgaa acaaaataaa    480
agaaaaaaag aacaaaacga aagagtggac cacatgcgtg tcaagaaagg ccggtcgtta    540
ccgttaaggt gtgtcgaact gtgattgggc cacgttaacg gcgtatccaa aagaaagaaa    600
gggcacgtgt atagatctag gaaaaaagaa agaatggacg gtttagattg tatctaggta    660
ccaggaaatg gaacgtcaca ccaaaacggta cgtgtcgata cctgccgtt gatgctgacg    720
gtcagcaact tccccttatt catgcccccc tgcccgttaa ttacgtgtaa cccttccatg    780
cgaaaatcaa acccttttt tttttgcgt tcttcttcaa cttttctttt taaatcaaac    840
ctttcttttt taaaatcaca ttgcatttcc taacgctcaa caaatctctc ctctactaat    900
atctctctct ctctctctct attgttgaag aagactcata atcggagatt gtttgttttt    960
ggtttgctct gtaaattgga gaagtttgt tagagatcaa                          1000

SEQ ID NO: 16           moltype = DNA   length = 1000
FEATURE                 Location/Qualifiers
misc_feature            1..1000
                        note = Ceres Promoter PT0695
source                  1..1000
                        mol_type = unassigned DNA
                        organism = Arabidopsis thaliana
SEQUENCE: 16
aacattttct ttaacttact cttaaatttt aatagtaagt tgatgcatgt tatgttgatc    60
cgtcttgatc acaaatattg ttttatggac gaattcttg acagtaaatg gctatagtga    120
ctcagcttgg agcatcccga tatgaaaaca aagtgcagta ttgtgtcgtg gtcatcacta    180
acgcactttc ctagaactat cgcgcgtgtt tgacctatgc aacacaccag atgtcatgaa    240
cgtatactta aatagaaaca atgatataga caattggcta tattctgtca tggaacgcaa    300
accggataac atgtctatta gattcatcgg acttgatcat ggtatgtct taatagacga    360
attcttgtt aacgattggt taaaacggct cacgttagag catcctacta tgacttcaaa    420
attgataaat attacatgga aatcacttta attttagtta gaaggtagtt aatttagata    480
ttcttatta ataaattaaa aatagaaga aaaaagatg agaagagttt tgttgtataa      540
aataagaaat atcttttatt gtaattttaa aattaaacaa atttaattta tattaaaatt   600
```

```
atctttgttt tattgttaag gcaataatta ttttttggt gggaattgtt aaaacaataa    660
ttagtatact gttaagtggt cctttaataa taagataacg tgatttaaaa aagaacgaga    720
caggctaata tagtagagag gaaaaaatac aatttaggcc caataaagcc caatatagag    780
ttgtgctcaa acacaggtct tcgccagatt tcctatgacg ccgtgtgtca atcatgacgc    840
caagtgtcat tcaagaccgt cacgtggcgt tgtttctaca cataggcgat ccatacaaat    900
cagtaacaaa cacgaaaaga gcattcatat gtacgaaagt agaaaagaag agactctttg    960
tgataaaact aagtaagaaa tagcataaaa gtaaaaggga                         1000

SEQ ID NO: 17           moltype = DNA  length = 1000
FEATURE                 Location/Qualifiers
misc_feature            1..1000
                        note = Ceres Promoter PT0708
source                  1..1000
                        mol_type = unassigned DNA
                        organism = Arabidopsis thaliana
SEQUENCE: 17
gtttccaaaa ctagtattct ttatttgctc tattcattat atttttatat ttgtaacgtc    60
ccgaccgtct ttattaggtt tcgacaatca cttctcggaa ggtcgtccat cctgaaatta   120
ctctatccta aacatgttta actataaaat tctctcgaaa cttttgtaac gtatataacc   180
acataaaattc tcttaaactt atttgcatac accattatat ttctgaaatc gatatgttac   240
aatattattt aatatttaga ttacttttac tgaatcgaat taaatatcaa atcgaaacaa   300
atctaatcta ccaaaaataa tttttgttata aacattctt gcctagttct acctcatata   360
catttttagtt aaagaaagaa atcacaacaa ttcccataat tcaataatta aatccacaaa   420
atcttggagt aagtaagaga aataaaaaga tagtatctta acataaacaa ttcaaagatg   480
ctctctcaca caattcacac acacttacaa aacaaaagac agaaacaatg ttttcattca   540
aatcaaaaga agttataaca ctagtacaaa aaaagctcaa attctaatag taactctttt   600
tatttcccaa ttacccaaag attctctctc acttcacaaa actagctttg agagtcgtgt   660
tccacaaaat ccattaaagc tgaaacggtt ttgctcacca ttcaaacaaa tacaaaattg   720
caaaaccccca aattataaca aataatata aaattaaac cgctaaaaag agtgaaccaa    780
caaaaatcgc cgaatgtgtg tgtaatgaga aaaccgaccc atcatcccaa tcatctctctc   840
ccgtgtcact ctcttcctct cccacgtttc ttctctcttc cctttatggg ttttaacttc    900
tccttcttct tcttcttcaa tcttcagttt tcaaattcaa caacaattca cattttgatt    960
tcttcatcat ctctctctct ctcgcttctc tctcaaatcg                         1000

SEQ ID NO: 18           moltype = DNA  length = 1000
FEATURE                 Location/Qualifiers
misc_feature            1..1000
                        note = Ceres Promoter PT0710
source                  1..1000
                        mol_type = unassigned DNA
                        organism = Arabidopsis thaliana
SEQUENCE: 18
tagtgcgcgt ggggagaggg aatggtgaaa ccttagtggt taagttatga ggaaaatgat    60
aaaaggataa aacaatcaaa tgcagcttga aacggccata acataaagta ccttatggtg   120
gtgcgaatat ttttgtgttt ctttcactct tttattgctg aaagctacga cacttgtctt   180
aatatatttgt ttccgcaagt cacatgatct acttttttatt taacgtctag aaacgccgag   240
atatgatg attagtatat cacgtctatg caaattgtta gttcgtgttt ggccaaaaga   300
tatcgagaca tgtctgaaga accgagtctg gttttgagat atttcttcaa gcattactat   360
acaatagaaa aaggagacac gcgaaatatg taatagcaaa aggcataaaa aggcgaaaat   420
taaagaaaaa cgtaaagtga tttggcctca atcaacggga acgtatctta attttagagg   480
ttcttctttt acttttgaga cgagagagtt tgcgtcttg cgagctgctt tggttgacta   540
aacattatca tattgaaaac caaaatacaa cggaggaata tttgtcacag tttcactttc   600
acattgttc cttaacgttt aatcaacctt gttcaaaatt tctatagttg taatcatcat   660
tgtttacaaa attttcgttc aaagatgatt ttaaataaaa ttgtgaaaga aaaccttttc   720
tgaaataagg attggatgat agtgttaaaa gaaaaatatg aactgaggca aaaagagggg   780
tggtccccgg aagattgtga aatgtgtcat ctaaaccagc cagacgtagt cacgtgttct   840
ctctagcttt atgaacttcc ttagccagca ccatcattgt gattgtagta tatatgtaac   900
cctaccttca tctctcccat tttccattct ccatatagac tcctttacaa tatacaaaac   960
ctatccaaaa gcgaagaagc caagcaaaca tattataaaa                        1000

SEQ ID NO: 19           moltype = DNA  length = 1002
FEATURE                 Location/Qualifiers
misc_feature            1..1002
                        note = Ceres Promoter PT0723
source                  1..1002
                        mol_type = unassigned DNA
                        organism = Arabidopsis thaliana
SEQUENCE: 19
gtcatatctt atcaacacgt caacgatcaa aacctttagc ctattaaatt caacggctta    60
gatcaaaacg aaactaggtg ggtcccactt ttaatatcgt ggctgcataa catttcctcg   120
ataactgaag ccgttgtggt cttttctcaga atctggtgct taaacactct ggtgagttct   180
agtacttctg ctatgatcga tctcattacc atttcttaaa tttctctccc taaatattcc   240
gagttcttga ttttttgataa cttcaggttt tctcttttttg ataaatctgg tctttccatt   300
tttttttttt tgtggttaat ttagtttcct atgttctcg atgttattat gcatgatctg   360
tgtttggatt ctgttagatt atgttattgg tgaatatgta tgtgtttttg catgtctggt   420
tttggtctta aaaatgttca aatctgatga tttgattgaa gctttttag tgttggtttg   480
attcttctca aaactactgt taatttacta tcatgttttc caactttgat tcatgatgac   540
acttttgttc tgctttgtta taaaattttg gttggttgga ttttgtaatt atagtgtaat   600
tttgttagga atgaacatgt tttaatactc tgttttrcga tttgtcacac attcgaatta   660
```

```
ttaatcgata atttaactga aaattcatgg ttctagatct tgttgtcatc agattatttg    720
tttcgataat tcatcaaata tgtagtcctt ttgctgattt gcgactgttt cattttttct    780
caaaattgtt ttttgttaag tttatctaac agttatcgtt gtcaaaagtc tctttcattt    840
tgcaaaatct tctttttttt tttgtttgta actttgtttt ttaagctaca catttagtct    900
gtaaaatagc atcgaggaac agttgtctta gtagacttgc atgttcttgt aacttctatt    960
tgtttcagtt tgttgatgac tgctttgatt tgtaggtca aa                       1002

SEQ ID NO: 20           moltype = DNA  length = 1001
FEATURE                 Location/Qualifiers
misc_feature            1..1001
                        note = Ceres Promoter PT0740
source                  1..1001
                        mol_type = unassigned DNA
                        organism = Arabidopsis thaliana
SEQUENCE: 20
tgtggccact aaagatttac ccttaaccgg gcccatataa gcccacgtca agtggcgctt     60
atacgctctc cgtaagagag ccaacatttg gtatgtaatg ttgcaaatta ttcttcaaga    120
caataaattc aaatatatt caatattgtc caaatatagt gatgtacttc agttgtgcac    180
atagaaactc cactaaacca acttttagat agatgcattc acaaattttc aacaatgtcg    240
cgaaagtcta atccatcacc agattctaac attttaatta ttatatttaa ctatacatac    300
tctaatcagc atgagtcaaa cgtgtacaat agcccaagca taataaga ccaaagtcaa    360
actcaaataa atgtctccaa actcaaaact tgaaaaagac ctaattatta catggtagat    420
atgactttgt cgacaagtaa accaactaat cctcgaagct accttctctt cccagttatt    480
atgtgtgatc gatttataaa tctcttcttc taataacacc tatattttc ttatgatgtg    540
aataaatata aaacttttaa ctttaaaaca tatttatccg aaatattgca cttagatttc    600
aaaatagataa ataatagtac tatctaactg atattgaaaa gacctaacac ggaaaacagt    660
tttataaaaa atcccaaatg tgggtaatta tcttgatttc ttgggggaaa cagaaaatgt    720
attaagatta atcggagtcg tgtcaagcag ctcgttaata actgtagcaa gttgactgag    780
taagcatcaa cgtgtcatct ccgtaaagcc cattatttct agtctcgccg cgtcttctct    840
tccacgtagc acttcacttt ttctctcctt ttgtttcctt tggaacacaa acgtttctat    900
ttataggaat aattacgtcg tccgtatctg tgtcggaaca tagatccaaa ttaaaagcga    960
cttacttaat tacatatcgt tcgtgttttt ttcttcaaaa a                       1001

SEQ ID NO: 21           moltype = DNA  length = 1024
FEATURE                 Location/Qualifiers
misc_feature            1..1024
                        note = Ceres Promoter PT0743
source                  1..1024
                        mol_type = unassigned DNA
                        organism = Arabidopsis thaliana
SEQUENCE: 21
tcgattggcc cgatcggccc caaaatcaag ctgagccgct tcaaacttca gcttttgaaa     60
tcaccccaa actcatgtcc tcttatcatt ataactaaag gatctttcat tttatttaac    120
tcatcgtctt gcactaccca acccaaaggt tccaactata cccgaagctt tctaaaggtc    180
caaagacttt cttttttcgag ccagactatt caagccaaga aaagccaaac cccacaagcc    240
agtactttc aattccatat tataaactta tctgtcttgt tttagtccca ctaaaaacaa    300
cagaatttaa tttaggttga gctaaaaccc ttgacaaaga tgtatagtcg tcgattcagt    360
agcacactca tcactcatca gatttgatag ttgacctaaa gtatgactac tccatttcaa    420
ctaacaaatg aaaataaaag agacctaagg gttagaggat tgaaactata ctctcaagtc    480
ttttatcact aggctactac cagctagtta acttgatgga tttaagcaag aaaacgtaga    540
atttatattc gagcagattg tttagctaaa aaagcttagg tttgaaattg cctttttctcc    600
catataagca cgtcggttcc taaataactc tttctagcgg agagtgtctt tccaataatt    660
taataaaaat ggtgtttgta tatcaaaaaa aaaagaaaaa agaaactgat cgagataaa    720
cgtttgcagt tttataaaca atttaaaaaa caaaaaaaat taaactcaat gtattttta    780
ttaattcaca aacaataata aatcatagga tcgaatattt acacggtatc aaaacctact    840
cgccgctact atataaaaat tgaagtcaaa tatcaaccgc aattattaaa ccagcaagac    900
aataattcat aaacttaata taaacataaa taaattaatg ttacacaacg atatatggtg    960
agggttatta ctatcttctt cctctcaaaa cacatctcct aaccttaagc tttagacggc   1020
ctgc                                                                1024

SEQ ID NO: 22           moltype = DNA  length = 1000
FEATURE                 Location/Qualifiers
misc_feature            1..1000
                        note = Ceres Promoter PT0758
source                  1..1000
                        mol_type = unassigned DNA
                        organism = Arabidopsis thaliana
SEQUENCE: 22
agctagccac atcagtgacc aaaaaagata attaacaaac caaataaaat aacaaatttt     60
gatcatttgg aataaaattt ataaaggaa cgaaagcgcc ttctcacggg tcccatccat    120
tgaaatatat tctctctttt tgctctatat aataataacg cgtactaatt tgtagtatat    180
attattacaa agtcgatatt tgattgtttt gtgaacgttg atatattaat tttcttggat    240
gatgacaaaa aaagtcatag aaagtaacgt gtgaacatag cattaacaaa atacaaacat    300
aatatataac caaatatg aaaataggat aaaatctcat tgaatagatc ttcttctatt    360
caaatatata aatatttgtt tgtctataaa attaacagag cattcacatt atctaaaata    420
atagtaaaat caaaataaaa ctaaataaaa ataactctgg ttttataacg attgatttta    480
aatattagtt tttgttgtaa agagatcatt atatatgtct gtaatatttt tatactgagt    540
tacatgatat ttagttatta tagcgtaatt aactaagata agaaattaac taagtgata    600
ttctgattat tattatttt gttaggacac gtacgtggaa aaactaaaca ctataggtta    660
```

```
caaaacggta taataaactc accattactg gaaaatgttt gcatttgact caataagtaa  720
cttattataa gttactgata taatgcatag ttttgaaatt cttaaataaa ttattttggt  780
ttcgcatgaa aatatgaaag gagagaaatt tattattgtc acttatatat atatacatcg  840
taatcatttt ttcgtaaata attctctctc ccattccatt atttctcagt atctctcttt  900
ctttccctta ctttattgtt gcttttaaac cttcaatttg ctcataaacc aaatatataa  960
tatcaaaaca aacaaacaaa aaatcagaat tcccctaata                       1000

SEQ ID NO: 23           moltype = DNA   length = 921
FEATURE                 Location/Qualifiers
misc_feature            1..921
                        note = Ceres Promoter PT0829
source                  1..921
                        mol_type = unassigned DNA
                        organism = Arabidopsis thaliana
SEQUENCE: 23
aaagttttga attattggga atcaatttcg aagttttgta attctttggg ggctaatagg   60
atattttatt ttcttggttt cgtctattgt tgttttttcta tttatggttg ggcttttaga  120
actctggaca ggcccatgtc atatgttttc ccttctccctt atatttttca tttttcattt  180
tgttaaatta atgcataata tccaaaaaca atttaaattt ttgaaggaac cctttagtta  240
cggctccgaa gctttcacaa gtgagaatgt gagatcaaag aaggcaaatg gaggatttta  300
aaagttaaaa tcatcttttta tctgcaaaag ttgacaattt ttttgtatca aatctaaatc  360
atcaaactct cttaaactac aagagcataa caacctctat gtaatccatg aaataatctg  420
cttgaaggac ataacataaa tcattatggc tagagtgact aacttcaatc aaatcctctt  480
aactctagct ccccttacaat ggtatcgtaa aacattatgc attagggatt gttgtcctag  540
gaaaataaaa taaaaatccc cacagaccaa ctaccattttt aacttaaaaa taagcttcgt  600
ccgcgacgaa ttgttttcca tcctaaaaat agaatgtgat aatctgctaa tggtttagtt  660
ccattaactt gcaagttcta ttgaaagcct aaatgtcaat aaagatatta aaattcggag  720
tcaaaagaca aatgaatcaa aagcaacaag acaagtcagc tccattcttc actacccatc  780
ttttacaata aatcatctct cttttcacaa atttcaaact actctcattg ccctttagct  840
tgttataga gccaacacta cagagagact cacacacttg tttcaataat taaatctgaa  900
tttggctctt cttataaact a                                            921

SEQ ID NO: 24           moltype = DNA   length = 763
FEATURE                 Location/Qualifiers
misc_feature            1..763
                        note = Ceres Promoter PT0837
source                  1..763
                        mol_type = unassigned DNA
                        organism = Arabidopsis thaliana
SEQUENCE: 24
aactacaagg gagacataat atccaccatct ggttcctgtt atcatctgaa gatttcttgt   60
tttaccttcc agtgataaaa tgatccttat aatacatata gatatattaa attgctgtat  120
tttaagatta tagatatata aggtacatga gagtgtttat ttaaaaaat tcacttggaa   180
ttcatgtttt gtgatacgtt agattggaat ccatttggga aaagaagaat catctgttct  240
tatgtctcaa attttgactt cattcacttttt tcttcttgtc ttttaagaaa gcttccacaa  300
tctaactgtt cgatgtgaaa actgagattc gagtaagaaa atgtgaactg tgttatactg  360
ttttttaatt agataaattta gattgcactc agataaatta ataacattcc tcgaatactt  420
ttatgtgatt ggatatatta ggtatatctg ccaaccaacc aataaactgc tatgtttaaa  480
caaattaaat aaaattagtat atgttactc aagaataaag aagatagaaa agaaaattct  540
atatgagcta aatttgctgg aggaggcatc ggacgtgggt accagacctt tccaagcaca  600
cgagtagtgc ttagccatgt catgctaaca tacaccattt ggttcatca aaatccaaat  660
caaaatctat ttttaaaatc tttttgcacac gtctttgaaa aacacctctc atactatagc  720
tacggaagct tcaatttcaa ggttttgtcta aaagctaacg att                   763

SEQ ID NO: 25           moltype = DNA   length = 751
FEATURE                 Location/Qualifiers
misc_feature            1..751
                        note = Ceres Promoter PT0838
source                  1..751
                        mol_type = unassigned DNA
                        organism = Arabidopsis thaliana
SEQUENCE: 25
atactggtat gcttaaggtt gaagccaaga tctctgtctt acccaagtaa ccactttcta   60
ttagaaggga tcaacactaa gaatatggag atttaagcct aagggctaag gcggttctca  120
acaatacatg atgtgaatac aatcacgac gatttactga ggtttgttga taagatcttg  180
atcagtctct gcatcatctg ttcaacaatc tcaatctttg actgttttgct ttcggagcca  240
taaacagagg aatcccttat tccctgttat aggagcaata caccaagtat tatttccatg  300
gctgaaattc tcttatggaa acctaattgt tccattgaag ctgtaaaatc gaatctggtg  360
aatattctcg agcaaaagccg catgctaatt atgtcaattc agaagagttt gattaggaga  420
ctcgaagcga gtttgatgat cttttcttgat gttcaactcc gattgtaagg gtataattga  480
cttttcatgt attacggctc cacccacctga cactaaggca ctctttgtcc atctcgttgg  540
tatcatcgga ttcggatggt aaaaataaaa agagcagagg aaacttgtta ctcatgcaag  600
cttctcaggt gccacgtcac tccattacgt gtcatcttca cacaccatct cgctcaaaac  660
cgatctcatt tttcaaacct taaggcaga agcaactgat taagttaaca ctcttgagaa  720
gctctcgatt aagcttgaac ttggaggatc a                                 751

SEQ ID NO: 26           moltype = DNA   length = 669
FEATURE                 Location/Qualifiers
misc_feature            1..669
```

```
                         note = Ceres Promoter PT0848
source                   1..669
                         mol_type = unassigned DNA
                         organism = Arabidopsis thaliana
SEQUENCE: 26
tctctttaaa tcagttaact aaccgtttat atatttacga taaggtttga agagattatt    60
gataaaataa tacatttcat aatcccgcgt tcaaccgttt aaagtaacat ttaagttgac   120
tatatctaat ttttttttcca ttaaatatgg agctggtaaa ctttatcaac ttctaaaaag   180
tgtaacaaca aaaattaggt caatcacaat tctgttttt ttattatttt ggattgactt    240
ccaattgcaa atagtcttag tgatcaccat tatcatacat atatacatca agtaggtttc    300
atcatgatat accacaaagt atttgacaag ccatatggtt ttggatcaaa aagtcggtcc    360
aaaattaatg ttttatgtgc aagaaccgac ccattgtaca cacgtgttaa catcttcaag    420
actttcatct ctattttttct tttggtcatt aagataccca ttgatccgaa tctgttacat    480
tcccacctac ttttttaatt tttactatcc actccaaatt aaacacaacc gatgattta    540
ataattggaa gcttttaaaa atatttcaaa acaagcctct ttgtgtttgt ctatatatat    600
acacgtaata agaaggtgaa tgaatctcac agcttacttg ttctaaggct tccaataacg    660
aaaacagta                                                           669

SEQ ID NO: 27           moltype = DNA   length = 702
FEATURE                 Location/Qualifiers
misc_feature            1..702
                        note = Ceres Promoter PT0863
source                  1..702
                        mol_type = unassigned DNA
                        organism = Arabidopsis thaliana
SEQUENCE: 27
cgggaaacga caatctgatc tctagtccag tcgattggcc cgatcggccg attataaact     60
tacatgagac aagtataaat aattattata aactattaa gttaagatc aaggcttttg    120
tgcaatgtat caatgaatgt tagatgtgat atgatgaaag caatgttta aacacataca    180
tagtcattga tcggaatgtg tgttattaga aatgcatgct taagccgata gggttatcta    240
tgtttggtct tggacattat agccaaattt cgaatctaat tcttccaata tatattttt    300
ttttttgct tagggccact actagtattg cttatcaatt ttaagagctc atgaaaatgc    360
aacaatatag tagttgcaaa tccttgtttc aagagaaatc aaagggccac ttgtgaattg    420
aataataata atatttgcaa ataacctttc actaaaccat accaacaaaa ccacacagat    480
ttggcaaaga cataacctt gggagacgtg aaaaggctca aaatttgaca attgtcctta    540
caaattcgct cattagtgca attgtgagat ttgtttgcat ccaaatccaa ttcataactc    600
acactcgtct caaattcgaa aaggcctgca gggccagtgc actgggatcc aacaatgtcc    660
tccgactcgt ccaagatcaa gaggaagcgg aaccgcaccg cg                      702

SEQ ID NO: 28           moltype = DNA   length = 435
FEATURE                 Location/Qualifiers
misc_feature            1..435
                        note = Ceres Promoter PT0879
source                  1..435
                        mol_type = unassigned DNA
                        organism = Arabidopsis thaliana
SEQUENCE: 28
ttctaggaag actggtcaag ctaagctgtt tctgttttt gttttgtac tttactttt      60
gtttgctagt gggaactggg tttattgggc cttgaagttg ataaaagatg aataaaagac   120
atatcgccta aagcccatat gagaagcaga agacaaaaac ctccaacttt gggcataaat   180
tttgattata gttaaaagtc cagacccaat ttggcacctg gcttagttac gattctaagg   240
catgacacct gcctaatatg tttattacag aaaataaaga gaatcagcta ggtgtccctt   300
attgaacaca ttaacaaact ccaacgacac tacgtgtctt cgtgactctt actatatcca   360
aaaacctata gctaaagctg aatttttcat gattagtata gtcccaacca aaaaaatact   420
gaagaaggca taagc                                                    435

SEQ ID NO: 29           moltype = DNA   length = 397
FEATURE                 Location/Qualifiers
misc_feature            1..397
                        note = Ceres Promoter PT0886
source                  1..397
                        mol_type = unassigned DNA
                        organism = Arabidopsis thaliana
SEQUENCE: 29
agtgtatttg aaaacgacat tgaagaatta atatatttt ttttaatttt agttttttat      60
agtacaaata ttaaaacaaa caatcctacc atatcataac atttgtaaat aacatttaa    120
gttttgtttt gagtttaat taatttttcta tgacaaaaaa atgaagtcaa tagactaagt   180
gaatcatata gtataaataa acacaattta aatagtttca aataaattta gaaagaataa   240
aacaaataga aatcagaagg tgtctgtttc ctcctcgcaa catacgcatca aagagaaaca   300
acttgacccct ttacattgct caagagctca tctcttccct ctacaaaaat ggccgcacgt   360
ctccaacctt ctcccaactc cttcttccgc catcatc                            397

SEQ ID NO: 30           moltype = DNA   length = 1024
FEATURE                 Location/Qualifiers
misc_feature            1..1024
                        note = Ceres Promoter YP0007
source                  1..1024
                        mol_type = unassigned DNA
                        organism = Arabidopsis thaliana
```

```
SEQUENCE: 30
agcagaacaa ctatatttat tgtgtcacat aaatctgaga tcatttataa ccaccaaaga    60
acctatacac agtaaatgac aaatgtatct ccctctatct ctattgccca tatgtagatg   120
ctaaagtaag atttctcttt tttttaatgt acttttttt gtataaagta tattccataa    180
gaaaaaggaa aagcttgttt attggatcaat tgaccccaaa aaaagttttt agatcaaagc  240
ccaatataaa aaaaaaacac agtagtgaca caaaggaact taaataaacc atgaattgat   300
ctataaacag tagagatcga taaggcgaac attttccatg tgaagtgtct tctttcatct   360
ataatatttt tgacatccaa taatttcctc tataatatca ttcacataat tgatagaaac   420
attatgttag aattgtccac atcatttgag ctgtaatata ttctgttta acaaattata    480
tggtagttgc ttaatcttat gtccatcttc ttctatgcat cgttttcgcg cctagttgtc   540
cagtccattt caactaccta cctctaaattc ttatcttaaa acaacatttt ttaatttaag  600
tattatgctc aaagactaac tagatagaaa accgttatta aacattaaac gaattaaaag   660
tcttacatgg aaaatgtagg tttataaacc acgagttatg attgacaata aaaaaaatgc   720
aaatcatcaa tcaaaagaga cttgagtgcg actctataa aaccattgca attaaatta    780
tctatcacaa aaattttaga cagattaagt taatttagtc taaattcact aatttatttt   840
ctataattag taattaacta tatttattta tttacacatt ttctgataat ttagaaattt   900
gcatgaataa caaatataag attttggaaa ttagtagcaa atttaattaa taattatttt   960
tgcctaaatg aaccaaacta taaaacctcc acatacacca gtcatcaaat ttacagagac  1020
aaca                                                                1024

SEQ ID NO: 31          moltype = DNA  length = 1000
FEATURE                Location/Qualifiers
misc_feature           1..1000
                       note = Ceres Promoter YP0008
source                 1..1000
                       mol_type = unassigned DNA
                       organism = Arabidopsis thaliana
SEQUENCE: 31
ctcgagagat gaagtcttag taatgtttga acaaacaata atcacgtttt ccatcaaatt    60
cgagcattta aagtttatat tactacatgc cccaagatga taccgtccat ctcatccgaa   120
aatatttctg aaattgcgct aagacaacaa tgtttgctca aattcgatca tttaaagttt   180
acaaatctct catcaatctt acaaacttct cacactaaac agaggtacat attttcttat   240
aaagacaaaa ggttcgaaca gctggcttct caactcgagt tgtttgtcag ggcctctctt   300
cactaactac aagttggtac ttcaaatatt ggtggctagc tcacgtgat attgtctaca   360
aattaaaccc atgaaaaagc tgcattaatt gttccaagtg aaccctgagg agtgtcaata   420
gtctttgctt tagtgtgatc attaaaccaa atctctaaat tcctaatttg tactaacatt   480
tggaacgtat ttcctactct tctccctgct ccaactccca aaaataagat tagttagatt   540
tctataacta atatacatgt atactcccaa aaacagtaaa accatattaa taaagctaat   600
tttgcataga tttatttcgg taaaccggcg gttcaagttg gggaaaaaaa agacaaacgg   660
tctaaagtca tccaaagaca aaaaaccaaa gacaagttga gagagacgag accaatcaca   720
acattgcttc gtagattgcg tgacatcatc cttgacggct actttcattt gtgtcttatt   780
tggataaaac gcacgtgttt aattcacgaa ccttcatagc aataagaaat ttccattact   840
ttcatatttt caactttttt tattacccat tacatgctta aatattaat tcacaagtct   900
ttgtcaaaat tcaatatttt ccaggttcat gaacccttt tatctcaatc tactctataa   960
tatctcccta taaattacaa caaaacctct ttatttttca                        1000

SEQ ID NO: 32          moltype = DNA  length = 999
FEATURE                Location/Qualifiers
misc_feature           1..999
                       note = Ceres Promoter YP0019
source                 1..999
                       mol_type = unassigned DNA
                       organism = Arabidopsis thaliana
SEQUENCE: 32
gatataagta gaatcatttt ttgccgccgt ttctcgctaa cacaccgaaa actgaatcaa    60
atctcctagc tcttctacgc aaaatcgagt gcatcgacaa tggcggaacg tggtgtcgaa   120
cgtggtggag atcgcggcga tttcggacgt ggattcggtg gtcgcggcgg tggaagaggt   180
ggtccgagag gtcgtggtcg ccgtgcaggt cgtgctccag aggaggagaa atgggtgcca   240
gtgactaagc ttggtcgtct cgtaaaggaa ggtaagatca caaagattga gcagatctac   300
ctccattctc tcccagtcaa ggagtaccag atcatagatt tactcgtcgg tccttcattg   360
aaagacgaag tgatgaaaat catgccggtt caaaaacaaa ccagagccgg tcagagaacg   420
agattcaagg ccttcatcgt cgtcggagat agtaacggtc acgtcggatt aggagtcaaa   480
tgctccaagg aagttgcgac ggcgatcaga ggcgcgatca ttctcgcgaa attgtctgtg   540
gttccgatac gaagaggtta ttggggtaac aagattgaaa aaccacatac ggttccgtgt   600
aaggtaaccg ggaaatgtgg atctgttact gtacgtatgg ttccagctcc gagaggttcc   660
ggtattgtgg cggctagagt tcctaagaag gttcttcaat tcgctggaat tgatgatgtc   720
tttacttctt ctagaggatc caccaaaact cttggaaact tcgtcaaggt atgtactttc   780
acaatggctg ttttggtttg atgaactctg aattaggcag tgaaaaagta atcattacca   840
gttaagtgaa tttatattga agattaggat ttagctgatt gtattggttt gagcagtgaa   900
gtttgtgttt aagattgctt gaattgaaat gctttaggtt gtttgattac gctaaattct   960
gactaatgta attcaaattg ttgttgtttt tttttggtc                          999

SEQ ID NO: 33          moltype = DNA  length = 1024
FEATURE                Location/Qualifiers
misc_feature           1..1024
                       note = Ceres Promoter YP0028
source                 1..1024
                       mol_type = unassigned DNA
                       organism = Arabidopsis thaliana
```

```
SEQUENCE: 33
gtcagtgaag tcgattggta gtacttgaaa cacttggttg gtttcatgta tttggcctat    60
atataaacaa acatcgtaat tatatacgga ttttttttcgg aattttacgc catatctgta   120
agtatatata acatgcatgt cgttttcaaa ttcatatgat gaacgatcca cgtaagtgct   180
actactccta caatattgca tgagagagat atgtatttat aaattttatt ttgaagaaga   240
aataagaggg aaggttactt gggtggatcg atgtgaaaac aaaagaagaa aaagcgaaac   300
ccactaagcc attacatgat atcgaccttc ttatcttttt cctctttatt ttattttttct  360
catcttcttt ttgtcaggac ttttttctac ttaatgaaac ctccaaacta tctaactaat   420
acactcccat gtagaataaa gaaaattata taagatattg ttgatatttt gtaactagaa   480
aatatatttg ctctgtaatt tttcgtaagt taaatcaaca ttttaaagta gaaacaaata   540
ttactgcaaa aagtaggatc attatttttg tccaaaatct cagttagcta tagggttgta   600
gtaaaaacaa aacacattct tgatttgccc caaaaaataa agagagagaa gaatattgtt   660
caaaagtggt ctcttctctc tctaattatg ttttcactaa acccaattag attcaaacag   720
tctacaaagt ccaaaagata aacatgggac aacaattcga tgcaaaaaat cctcttttca   780
tgctcttttt ttattctcta gtctttttaaa ttactaataa aaactcacaa atccaccaaa   840
cccattctct acaactcacc ttcatctaga tttacccact cccaccgaga aacacaagaa   900
aaaaaatata catatataaa tataacaagac aacacatgat gctgatgcaa tatacacaac   960
aaagtattaa atcttagata ttgtgggtct ccctttcttc tattcatttt cttattcatt  1020
aaaa                                                                1024

SEQ ID NO: 34             moltype = DNA  length = 1024
FEATURE                   Location/Qualifiers
misc_feature              1..1024
                          note = Ceres Promoter YP0039
source                    1..1024
                          mol_type = unassigned DNA
                          organism = Arabidopsis thaliana
SEQUENCE: 34
ccgttcgagt atttgaaaat ttcgggtaca cccgcctaaa taggcggacc ttatctagta    60
tatatataca tttgaactat attgtttact ttttagttga tttaggctat gtcatgacat   120
tgacataaat ctacctgtta tttatcacgt gtaattcgtg taaagtgtaa actagaaagt   180
tcaaatacgt atttgttttt gttctgttat ataggattgt catagttgta aatctacaat   240
ttattacaac atgaataagt acacaagcaa tgtaattgga tttaattgct aaactcttta   300
catggtcaat ctaaatttga taagaaatac gtcacatatt actaagactg atagttttttt  360
tgttgtcacc aattatttt gttaaattga cgaaaacaat tccaaaaact caaatgtaca   420
aaatcataca gtctcacaaa catctcatag agaaagatat aaatctccca tatgggaacg   480
ataacacgag gtcgaaatac tattcgtaaa actaaacgc cttagttata aatcgttagt    540
tgtaaccgcg gtcgagaata catacagatc cacgaaacta ctaccacaca tgctgctgaa   600
ttggaatttg gaaaagacca tcttctttag gaagagctca cccaatgagt gacaaaggtg   660
tcggtggctt gttttctacc catatgtata catcaaatgg tagttttcatt aacgttttggt  720
tttgagaaaa gtaagacttt ggctagtagc taggttcgta tataataaac tcttttgaga   780
aagttcatca ctggtggaaa atgttaaacc ggttttttct cattttttcc gccatgttaa   840
ccaccggttt aaaaagaccg taacacattg aaagattaat aagggtatat ttgtaattac   900
ggtttgctgg caatttttaa ttattattttt aattagagaa aatagagaag ccctatcaat   960
gtacatggta tatatataaa aggcaaaacc ctagaaaacg atactattcg actcagccgt  1020
cctt                                                                 1024

SEQ ID NO: 35             moltype = DNA  length = 1024
FEATURE                   Location/Qualifiers
misc_feature              1..1024
                          note = Ceres Promoter YP0050
source                    1..1024
                          mol_type = unassigned DNA
                          organism = Arabidopsis thaliana
SEQUENCE: 35
aatctgatct ctagtccagt cgattggtac ttgagggaaa catcatatttt ttaaaccttg    60
tctcagtaag ctaacacaca cccccttgtga ttacttatcc atgtttatcc acaagaatgc   120
agttggattg agatattttc ttctttgttg aaatcaggcc tcaaggtgtt catgtggtct   180
gcaaaaaaat tccaaaaaat aaagatagtg acatctgaaa tcgataatgg attagacgaa   240
gagtttcgtg ttattccttg gtatgggcgg gtttggggac agatattttg gcacagacga   300
ggactaggcc actgtggtcc tgcagcatta ggtgtcccctt ccatgtcctg cattacatttt  360
tattgatgga ttcatcaccc tatctactac aacggctaca caaactatga agagttttgt   420
ttactaataa atgcccaagt gaggggtcga tcgaacccgg gacacgtttt tcagtttacc   480
atatagaatt atccttggaa cccttgatac tccatagaac atcaccacct ctgttgtcat   540
ctcaggaatc caggttcaaa cctagtctct ctctccctag tgggaggtat atggccactg   600
ggccaatgat gacaaaatgc aaaaaaaata aaatacattt gggttcatta tctaaaatat   660
ctcttgtgtt tgtaagtttt ggttgcacac tcgtgtggtt gaagtgtgtg tgagaggtac   720
tatacaatac actctgcttt tgttttgtac ctatctcttt ctcttctcca catatccaag   780
actttgggga taaagctgag atcattggtt gccatttggt tgtgtagaag caatcaccca   840
tttgctttat ccgaggttga taaatttcct cgggttctcc ttctgacacg tatgacaaat   900
tctaatagta tattccctcgt agatattacc tatatattct caatagttgc aggtacttaa   960
ggctttgtct tggcatcctc gtcctcttca gcaaaactcg tctctcttgc actccaaaaa  1020
gcaa                                                                 1024

SEQ ID NO: 36             moltype = DNA  length = 999
FEATURE                   Location/Qualifiers
misc_feature              1..999
                          note = Ceres Promoter YP0086
source                    1..999
```

```
                         mol_type = unassigned DNA
                         organism = Arabidopsis thaliana
SEQUENCE: 36
cttatccttt aacaatgaac aggttttag aggtagcttg atgattcctg cacatgtgat    60
cttggcttca ggcttaattt tccaggtaaa gcattatgag atactcttat atctcttaca   120
tacttttgag ataatgcaca agaacttcat aactatatgc tttagtttct gcatttgaca   180
ctgccaaatt cattaatctc taatatcttt gttgttgatc tttggtagac atgggtacta   240
gaaaaagcaa actacaccaa ggtaaaatac ttttgtacaa acataaactc gttatcacgg   300
aacatcaatg gagtgtatat ctaacggagt gtagaaacat ttgattattg caggaagcta   360
tctcaggata ttatcggttt atatggaatc tcttctacgc agagtatctg ttattcccct   420
tcctctagct ttcaatttca tggtgaggat atgcagtttt ctttgtatat cattcttctt   480
cttctttgta gcttggagtc aaaatcggtt ccttcatgta catacatcaa ggatatgtcc   540
ttctgaattt ttatatcttg caataaaaat gcttgtacca attgaaacac cagctttttg   600
agttctatga tcactgactt ggttctaacc aaaaaaaaaa aaatgtttaa tttacatatc   660
taaaagtagg tttagggaaa cctaaacagt aaaatatttg tatattattc gaatttcact   720
catcataaaa acttaaattg caccataaaa ttttgtttta ctattaatga tgtaatttgt   780
gtaacttaag ataaaaataa tattccgtaa gttaaccggc taaaaccacg tataaaccag   840
ggaacctgtt aaaccggttc tttactggat aaagaaatga aagcccatgt agacagctcc   900
attagagccc aaaccctaaa tttctcatct atataaaagg agtgacatta gggttttgt    960
tcgtcctctt aaagcttctc gttttctctg ccgtctctc                         999

SEQ ID NO: 37           moltype = DNA  length = 1024
FEATURE                 Location/Qualifiers
misc_feature            1..1024
                         note = Ceres Promoter YP0088
source                  1..1024
                         mol_type = unassigned DNA
                         organism = Arabidopsis thaliana
SEQUENCE: 37
tcgattggga ttactacttc atctagtaag gttctgaaaa cgtttgttgt tgataaggaa    60
gattcgtctc aggttattac tgttgatctt caaggtttgt gattgtgacg cttatacatg   120
tgctgaaact gtggtgttta tttattgaaa acaaaaaaaa agtctctctt gtagtttcat   180
tgtactaaat agaaaacaag aaacgttttt ttctttaatc ttctacattg ataatattgg   240
atcaaaggat tgtttctgca agacacaaca caaacatact tatactagtt tacttctact   300
aagtactaac tacataccca tacacacact tgcacctaga ctttacttct agacatcatt   360
accctaaggt agaaccaagc ttacaagcaa gttttaccga caactcttac attacaactc   420
tagtctgtag tctttaacgt agacttacta actagtcatt agtggtttaa tttttttaaat  480
tttcatccat atgttttgt tgtagatata aactaaagtc ggtcacattt aataattgtc    540
attatgtccg cgtaaaagtc aattcagcta ttggacattt atgaaatgta agattttctc   600
tctcattcc ccgtgcgtga agacatgcat tggttttct gtaataatca acaaatccaa    660
acccctttc gatctttatt tggacattgt tagagacaaa atttctctat agtcttttc     720
ctaattttgat accatgtttt tgtttctgca caaatttact cactggttta actaactatc   780
cacttattta tgatttacc attaggcgtc agctagccct agtcaaattt gtaaacaagc    840
caagctatct acataaatcg agatgtcatt aacgttaatc gtcgttaatt cgaatttgaa   900
aacatagata gctttagcag tacaatgggc aatggtaaga agaatagcaa aaggcccaat   960
atttggtttg cagaaattaa agccttaaaa aaaagcccac agatatttgt caaagaaccc  1020
taat                                                               1024

SEQ ID NO: 38           moltype = DNA  length = 1024
FEATURE                 Location/Qualifiers
misc_feature            1..1024
                         note = Ceres Promoter YP0092
source                  1..1024
                         mol_type = unassigned DNA
                         organism = Arabidopsis thaliana
SEQUENCE: 38
aaagattgag ttgagagaga tggtggagac gcagaacaga caaagggagt ttaccatata    60
gtgctctaaa gggcaatgag attgcagtga tgtggctatc cggggaatca tcgcaggtta   120
ttccttccca tgagcaacaa tcaatggatg ggttccaatt cagaggagaa acagaagaag   180
aaacgtttcc agagaaccac agtagggatt ctcgatcctg cgagttgcag agagcctctg   240
aaactgcaat agaaaggaca ctgatgaaaa gaacacactg aaggagtatg ccaatcatgt   300
gaaaactcag agcttgtatt ggtcttgtgg ttgatgaagt tctcacaaaa cctttggctt   360
tgaatctccc ctcattagtc atggtgagaa caagaacaag acgagaaaca gacaaagaag   420
atgaaaaaac ttgttggcca gtgttgacta aggggaata gccccagaca taacaaaatt    480
agacttgtcg tacatcttta ataatttttt atctgtttct ttgtcctgac gctttcatta   540
ttcctgtgat caatttttctc ataccattgg tccatcgtta atcctttctt aatttcattt   600
tctacgtaac atgagaggag accaagtcct atgagaacag ttgacgtaac agtggttgtt   660
aagttaagtt aaaaaagagga agctagtgag agtgaccgtt aggtagagaa gtgagatctt   720
taaccactct tcttttctctc tctctctgct tttttcgtt cactactgttcg               780
caaactctct tatgcttcca ataatggtga taccaattga gacttgcagg agaatctcct   840
cttctccaca ctctataaac tggtcagcca tgaatggtc gtttcagttt caatattcct    900
ggattctttt taaggattcc tgtttctctt ctgttcctgg tatattctta acgacgaaat   960
tagtatcgga tcctggtaat acattttgaa gcttttaagt accattgcac tgggatccaa  1020
caat                                                               1024

SEQ ID NO: 39           moltype = DNA  length = 1020
FEATURE                 Location/Qualifiers
misc_feature            1..1020
                         note = Ceres Promoter YP0096
```

```
source                  1..1020
                        mol_type = unassigned DNA
                        organism = Arabidopsis thaliana
SEQUENCE: 39
gaggtcagtg agtcgattgg tgcaaaattg aaaaattgaa gggtgaaaca aatttaaaga    60
taatatctat taaatcctct aattttaaaa atttagcaaa aattgtattt tcttatggat   120
ctgttagttc acacgtatct taattagtac caaatcatat ctaatgatta gtgataaaac   180
tagttagata tctatatgtg tctttaccat ttaacttgaa tccttcttct tttttttacg   240
taaacaactt gaatccttcg ttaatacata aatttaaagc attttttctt taattctatt   300
gatcggtata tatttactat aagtttttagc tcatatgcaa tttcaaatga tatgcttta    360
aattttgtct aggtgtgata gttgtatctt taacataaat cttatagcaa aattatactt   420
gatattctaa atttatctat ttgctcttgt gaacctcata ttagtctaga gaaacttga    480
aatcctttca attagttgta tgtccaatac attttttacta acattttatta gtcttttaa   540
ttaagattat tgttagaaaa aaaaagattt tttaaaata aataatatgt tttagatca    600
atgtgagtta ggcttcttat attttaaaaa ataaatttat ttcatactta aaaatagttt   660
ggaatttcaa tttatttggc tgaataccat aaaatatgtc aatttgaacc ttatacccat   720
tgactatttg gtgttagaaa ccctttaaca aaaaaaaact atttggtgtt agatatcaaa   780
ataaaaaaag tttaaccatt ggtttcttat attgaattgg atattgttac atgtattaaa   840
gttttttttgg tttaattttg aaacgttgat agaaactatt aagtttaagt ttggtagtat   900
atttatttgt ggaaaattta attgccatta aatataacgt caacttttttt tggttttttt   960
tgagaagtta cgttgtgatt ttgatttcct atataaaagt tagattacgt catttttaa   1020

SEQ ID NO: 40           moltype = DNA  length = 1000
FEATURE                 Location/Qualifiers
misc_feature            1..1000
                        note = Ceres Promoter YP0097
source                  1..1000
                        mol_type = unassigned DNA
                        organism = Arabidopsis thaliana
SEQUENCE: 40
ttcatcttta tatttaagag tttaaaaact gcaactttttg ttttttcttttc actaagtctt    60
atggccacag ttaattaaaa gcagatgaaa ggtggtccaa tggaaaagga gaatgtgatt   120
gggctagttg ggagagttct gatgtctagt gttgggtaca cgtgtccgtc agttacacat   180
agcattaaat cagacggcat gtcattattc aaatctagtt cacatagtac gactaatagc   240
tgataaatta atgattatac agcatatgaa ttatgaattc aaaaaaaaaa aaaaattgaa   300
aatgttaagg agatgctata ttttacaaaa ttcatcgcaa tgctttctac taatttgcta   360
agtggtcttc tccagttagt cttgtcgatt ccaagcgata ttattaaatc ttgaagcatc   420
gctcaaagca ttatagctta agataaccaa attgttatta aaaacaccta gtgaaatttt   480
taaattaaaa caatttttgat atctttgtaa tatctaatac tactcttttct gtgtctaaaa   540
ggattaattt tcaaaaattt cacacatatt aaaaaaaaaa aaaaattact agctaaacaa   600
ttttcaataa tcataaaaca atagtaactt aataattttt tttatttttc aaaatagtcc   660
ttcaagttta caattcatttt tagtattata atcaacaaaa tttgtattaa aaagttggaa   720
aattaatctt tgtggaacaa aaaaatctag aaatcatttt ttagaattag agagagttt    780
gataaaaaaa aataaaaaaa aatagagaga ggtagtacat actaaacgat gtgatactac   840
tattgacaaa atcttaattc tcagtttagt agaataaact agaaggaatg aatgaagtaa    900
atgcgaatcc aactactaac aaaccctact tagtcatcat attttcccat atgaaatccc    960
tatataaacc catcatcatc tcccactttt ttcatatcca                         1000

SEQ ID NO: 41           moltype = DNA  length = 1004
FEATURE                 Location/Qualifiers
misc_feature            1..1004
                        note = Ceres Promoter YP0101
source                  1..1004
                        mol_type = unassigned DNA
                        organism = Arabidopsis thaliana
SEQUENCE: 41
ttctcgttct ctagaatatt gctggaccgg attaggtcaa tattattggg ccagattaga    60
tattgaattg tcgacgttgc ttacgttacg ttatatcttg tttaagaatt aaacctatcg   120
acttagtctt aattaagaaa acattgcctt aaattctctg gtctgcgacc gttttttgta   180
ccgttaaccc ctaattaaag aaacaaaata attatagaag agcactgaaa atgtgattat   240
tttaacagta ctcttatgag aaaattcgta ctttttagtt ttttttttgt acaaatctct   300
aagaaaaaca ctactactaa ttaagaaacg tttcaaacaa ttttatttttc gttggctcat   360
aatctttctt tctcggtccg ggactaaccg ttggcaaaaa aaaaaaaaaa gttgacaata   420
attattaaag cgtaaatcat acctctcaaa taaaaacttg aatttggaaa caaagacaac   480
taaaaactc gaatttaaga gaattcctaa aatcaagtga agtatcatca cttggtaaaa   540
tttcataacc gttggcttct atttctatgt gtgccttggt ttgcaggaga taatatttca   600
tttccaacca atgatattcg tacacatagt caaacaaatg tttgtctttg ttattatatt   660
gagaaagaaa caagaaagag agagagagat agataagacg aaggaagtga agcttccaag   720
cgcccaccgt taaaatctc gtgtgcaagt ttcaaataca agtggccggt ggtctccata   780
atttgatcgt catccaatta aaaggaaga aaaagcgtgt tttatacaag aaaactcatt   840
aaaatagcaa gtctagaaat atctcaacac taatctacca cgtctattac acacacacac   900
acacacactt gatcttaatt tattttcaag attcaagaaa atacccattc cattaccaca   960
acttgaccac acgcctatat aaaacata aaagcccttt cccc                   1004

SEQ ID NO: 42           moltype = DNA  length = 1000
FEATURE                 Location/Qualifiers
misc_feature            1..1000
                        note = Ceres Promoter YP0102
source                  1..1000
```

```
                        mol_type = unassigned DNA
                        organism = Arabidopsis thaliana
SEQUENCE: 42
atttggttga taacgttttc actcgactaa ttatatactt cagaaggata gtaatagaat    60
accaaaataa ttaaatgatt ggttagtgcc ttagtggaga cttttttaacc gattctaata  120
gactaatgat gtagctaagc atttatttgg gatcatcact gtttgaaaac gtgaaatgtg   180
ataaaagtta tgaaacgatt aaaatataaa ataaccgtac aaaacattat gtaccgtttt   240
tttctctgtt cttttggcga tttggtttag ttcgttacac tctaaatgtt attgcagata   300
tatatataat gatgcatttg catctgagga acatatattc ccggttaaca cttccaaatc   360
ttatatccgt ctaggtaggg atttttataaa tcatttgtgt catcatgcgt tatgcttgtc   420
ggctttgacc ataacgcaga gatatagaac tagcttttac ttaacttttta gatttattat   480
ttgatctaga gttaagtgga gatatatagt gttttttgtta gattattggt ggatgtgaga   540
gttttgtcttt agtttcaagt tgagaatata aggcaagagg agactctgag gcaatcagag   600
gttttgattg gcaaaatatc caaaaggccc aaaccaagtc gaagcccatc tcgtacaaaa   660
aaagaaagag atctgtaaga aaaaatattc tttgatattc ttacaaaaat aagtgtaaaa   720
ctttttattag tcaaaatctt caatctttaa aaactctcat cactcctacg aaagcgcgtg   780
agagttatga gacattcctt aatagcatta ctcacaagtc acaagttcaa aacgtctgac   840
tgaaacagaa acaagccttt gttgaagtct tgaagaagga acattagtac tcgtcgtata   900
gccataaaag gtaatatacg aaatttcttc gctaatctct tcaccttcct ctacgcgttt   960
cactttcact ttataaatcc aaatctccct tcgaaaacat                         1000

SEQ ID NO: 43          moltype = DNA   length = 1004
FEATURE                Location/Qualifiers
misc_feature           1..1004
                        note = Ceres Promoter YP0103
source                  1..1004
                        mol_type = unassigned DNA
                        organism = Arabidopsis thaliana
SEQUENCE: 43
gttttgaaga acaatctgga tcgaaatcta acataaggtc atcgtattca agttacgcag     60
tcaaggactt gacatcatcc tactctggtc tgaggttacc acttccaaag atggggatttt   120
tcgactcggt atgcttccta agaaattcgt tttattgaac ctagcaaata tcttgtaatg    180
taagattcct gagatgatga agaaaaaaca aactttttgtt acagcaggag aacggagaga    240
aagaaaacag agaaccaaat gctcttgaag caaacagagg aagaagacaa aaatccaaac   300
ttgagacttc ttctacacca gaaaaccgca gcattctggg acaacgcaaa acacgaaagt   360
gaaacgggca atgatatata tgtcttgggt gcgttacaag gcatcgtttg caactgttga   420
gttggataag tcaactgtct tctttttcctt tggttgtagt agctgccttt ttttttcctttt   480
gttgctttaa gaaatagccc gaaaaaaaga atgttctaca tttcggagca gaaaactaac   540
cgaatgagtt tttggtcgga tcatcggatc gatcagatat attttgagtt acgaactgtt   600
ataaaaaaag ccataatttt tgtgttgagtt tgcaaaatac cttataactt gttatttgag   660
attgcacctc catatatatt aattcgtaag agtatttatt aagtaagctt tagtataaat   720
ccttttttcc tttaaagtaa gttaatgttc tactaaataa tagtaaagtt gaagaaccgc   780
tccgttttta caccatgcac gtgttatcta acaaagaaat tagtgtacac ctaatggcta   840
atgcaaagga caacacaatg aaactaactt gactctgtgt tatagaaacc catagacatc   900
tgcatacatc ctagtatttg tataaattgg actcaaattc ctgaggacaa tcatagcaaa   960
caatcacatc atcgcaatat acataaacaa aagaggaaga aaaa                    1004

SEQ ID NO: 44          moltype = DNA   length = 1003
FEATURE                Location/Qualifiers
misc_feature           1..1003
                        note = Ceres Promoter YP0107
source                  1..1003
                        mol_type = unassigned DNA
                        organism = Arabidopsis thaliana
SEQUENCE: 44
taacaatcct tgggaacatt gcatccatag atatccggtt aagatcgatc tttgaactca     60
taaaaactag tagattggtt ggttggtttc catgtaccag aaggcttacc ctattagttg   120
aaagttgaaa ctttgttccc tactcaattc ctagttgtgt aaatgtatgt atatgtaatg   180
tgtataaaac gtagtactta aatgactagg agtggttctt gagaccgatg agagatggga   240
gcagaactaa agatgatgac ataattaaga acgaatttga aaggctctta ggtttgaatc   300
ctattcgaga atgttttttgt caaagatagt ggcgattttg aaccaaagaa acatttaaa   360
aaatcagtat ccggttacgt tcatgcaaat agaaagtggt ctaggatctg attgtaattt   420
tagacttaaa gagtctctta agattcaatc ctggctgtgt acaaaaactac aaataatcta   480
ttttagacta tttgggcctt aactaaactt ccactccatt atttactgag gttagagaat   540
agacttgcga ataaacacat tccccgagaa atactcatga tcccataatt agtcggaggg   600
tatgccaatc agatctaaga acacacattc cctcaaattt taatgcacat gtaatcatag   660
tttagcacaa ttcaaaaata atgtagtatt aaagacagaa atttgtagac ttttttttgg   720
cgttaaaaga agactaagtt tatacgtaca tttattttta agtagaaaac cgaaatttc    780
catcgaaata tatgaagttc gtatatatat ttctgcaatg tactatttg ctatttttgc   840
aactttcagt ggactactac tttattacaa tgtgtatgga tgcatgagtt tgagtataca   900
catgtctaaa tgcatgcttt gtaaaacgta acgaccaca aaagaggatc catacaaata   960
catctcatag cttcctccat tattttccga cacaaacaga gca                    1003

SEQ ID NO: 45          moltype = DNA   length = 1024
FEATURE                Location/Qualifiers
misc_feature           1..1024
                        note = Ceres Promoter YP0110
source                  1..1024
                        mol_type = unassigned DNA
```

-continued

```
                        organism = Arabidopsis thaliana
SEQUENCE: 45
gggatgcggt tccgcttcct cttgatcttg gacgagtcgg aggacattgt tggatcccag    60
tgcaatggta atataaaaca agaaaacaag agattttata ggacaatcac taaatgacat   120
ttaattgatt aaacatttat tcattaataa ttgtatgtta ctaacttcaa catttaataa   180
ttttgtttaa gatacgttta catcagagac tattaatatt tttacaggtt gtaactttaa   240
actttgtctt gaatcgaaca tgactataga ttttgggcaa acttaaagat aacaacattt   300
ccgtttttt tcaaattatt acaaatcaaa ctgatatatt agacacaaca cgattacacg   360
taatgaaaaa agaaaaagat aaaaagataa aagaaggagt cgattctgtt tggtctggtt   420
tagtgagatt caaagttaag ctcttccttt caagacatgc cttcttaaac cgggaatgtg   480
aacgtttgta atgtagtccg tccagttaat gcttccaaca tcaaatccaa attctctctt   540
ctcgtcctct gacatattct ccattaatct ctggggtatt gctgttatca aatctgtaaa   600
agaaaccaaa aaaaaagat gaaactttg cgggtaccgg ttttgtctgc tctaagaatt   660
agaatgttaa tgagttctgt cttaccttcc accatagaaa gtgtatggct cataaatagt   720
agcaaggtgt ttggcttgtt caacagattt cttgcatata aacttagct tctgcatcat   780
cttactatcc actgaactca taccactcat caacccactc cgttcttgag catctctcca   840
caaatgatcc gagaaatcat caacggaatt gaaaagtttc atcaaacgca ccataatagg   900
atcacccttta gagtccatgc atggagatgt tttgtagtgg ttataaagaa gctccgctaa   960
gtcttcgaaa accagcgggt ttatcgccga agaagcgatc tgatacacgt ttatttcagg  1020
ttcc                                                                1024

SEQ ID NO: 46          moltype = DNA  length = 1024
FEATURE                Location/Qualifiers
misc_feature           1..1024
                       note = Ceres Promoter YP0111
source                 1..1024
                       mol_type = unassigned DNA
                       organism = Arabidopsis thaliana
SEQUENCE: 46
cgattggatt tagtctatac attatagggc gcaagtttgt ggatttaaga attatataaa    60
aacttgaaat atatagtttt tatgcattct cctcttgtgt aatacataaa ccaaatatga   120
gataggttaa tctgtatttc agataatatt aaattccaaa caatattttt acttgttata   180
agaaggcaat taatatctct ctgttaatgg caagtggtac caagtagtat taaactatta   240
atgcaatgga agagtactgt tggaaattat aatcctctat cacacattca aacagatctc   300
ctgaaatctt ctcttccaaa cttgtacttc tctgatccaa atgtaggctc caaaatatag   360
acatttacca tttactaagt ccacaactcc tttcttgtct ccttcaaaaa tgactcttgt   420
gtaaccacca tatgactccg acagttcggc attgccatga tgagagctta aaaattcacc   480
ttcctgagca tttcaagtct tcactccctt agcttgacct gaaccaagat aaaatgcctt   540
tgtcgtcccg taatatccat cctgctttgg acggcatcat agttacattc gatccatcct   600
atttacaatg ttattttagt attaaaaaca tgacaataaa tttgttgtta aacatattca   660
aatacaatat gattggattt ataagtaatt gtaaatgaa atgtccttag taatatgtta   720
aaaaatacat agatacacac acgtactaaa agaggcaacg cgggagatgt cattagagga   780
agaactagga agcagagcgt tcatgcaaaa tgctaccaaa aacgttaatg caatatctca   840
actaatcagc acagtccatt tcatactgag aatgtaaaaa ccaatcagca tcgtccattt   900
tttcatctaa ttatttgtta actcttaatt ggccacaact tccaaccaca tgacgctctt   960
tctattccct ttatatattc ccatctcaaa tgttcttgga gacacaaaat atcataaaca  1020
tata                                                                1024

SEQ ID NO: 47          moltype = DNA  length = 996
FEATURE                Location/Qualifiers
misc_feature           1..996
                       note = Ceres Promoter YP0115
source                 1..996
                       mol_type = unassigned DNA
                       organism = Arabidopsis thaliana
SEQUENCE: 47
gtcgattgga tgatgaacat tctacatata taattattat gtttaagcac ttagacagca    60
taaattcttt ctaattatat aaatctaacc ttgttacatt gtacatctat aaattacttg   120
aagaaataac gagttctatt tcttttttaaa aattaaaaat actataccat atctcagtga   180
ttaagttgaa ccaaaaggta cggaggagaa acaagcattt gattcttcct tatttttattt   240
tattcatctc tcactaatga tggtggaaaa aaaagaaaa tacctaacaa acaaatatat   300
attgtcatac aaaaatattt ctatattttt agtaattag tttatattcc tcacttttca   360
gggcttatat aagaaagtga gcaaacacaa atcaaaatgc agcagcaaat actatcatca   420
cccatctcct tagttctatt ttataattcc tcttctttt gttcatgct ttgtaattat   480
agtcttattt ctctttaagg ctcaataaga ggaggtacta ttactacact tctctctact   540
tttacttgta tttagcatt aaaatcctaa aatccgtttt aaattcaaaa ataaacttag   600
agatgttaa tctcgattcg gttttcggc tttaggagaa taattatatg aaattagtat   660
ggatatcttt actagtttcc attcaaatga ttctgatttc aatctaatac tctcactctt   720
taattaaact atatgtagtg taatttcaca ctgttaaatt tctaccatgt catgtatatt   780
agagttgcat agaaaattgt aaaacatcca tttgaattcg aatgaaacaa aatgttttaa   840
aataaaattt tggttttaa aagaaaaatc taaaactgaa ttatatcgtt taaccaagtt   900
gtaaaagtca taaaacgtag tatccttgtaa atcgctcttc cacggtccaa atagacttct   960
agtaataaac aagtaaaact aattttggtt tcttac                             996

SEQ ID NO: 48          moltype = DNA  length = 1024
FEATURE                Location/Qualifiers
misc_feature           1..1024
                       note = Ceres Promoter YP0117
source                 1..1024
```

```
                        mol_type = unassigned DNA
                        organism = Arabidopsis thaliana
SEQUENCE: 48
gtcagtgagt cgattggatc acagtccttt atgataaaac aaactcataa ttattccacc    60
gacaacatgc gttttaaatt atttttttct aaattatatt atattatatt gatatcaacc   120
tagctaaaat aattcggatg gcgaaatcgg acaatttttta atagaaaaaa tgggtatgaa   180
gatagtctat gattccgttc ttagcgacta gagggacctg ctcaaatctc ccgggtgata   240
cgcgatgtca agctcaatag aaccccacaa ccgacgagac cgagaaatcc ttgatttggg   300
ctagaagatt ttgaaataaa tttaatatat tctaagtaac ttgcttaaat ttttttttcaa   360
actctaaaga cataactaac ataaagtaaa aaaaaaaaag ttaatacatg ggaagaaaaa   420
aattaaacta atgattagct ctctaacgtg tttaatctcg tatcaagttt ttttttaaaa   480
attatattgc tattaaaaca ttgtactatt gtttctatt tgtttagcta ttattcttgt    540
gaaatgaaaa gttgtgttta ttcaattact aaatggcaat atttatcttg gaaaactata   600
cctctaattg gattaggccc tagacatcct ctttagctta ttgacgttaa aattattccc   660
aaaactatta aagtttagta gtttgaaaga tgcatcaaga cctactcaga taggtaaaag   720
tagaaaacta cagtttagtgt gattatattt taaaatatat aaaacaatct tattaaacta   780
aatattcaag atatatactc aaatggaaga taaaaacatt tagtctgtta ccactaccag   840
cctagcagt cactaaatagt cactttggaa ctgagtagat atttgcatct tgagttacca    900
tggactcaaa agtccaaaaa gagaccccga gtgaaaatgc taccaactta ataacaaaga   960
agcatttaca gcggtcaaaa agtatctata aatgtttaca caacagtagt cataagcacc  1020
attg                                                               1024

SEQ ID NO: 49         moltype = DNA  length = 1000
FEATURE               Location/Qualifiers
misc_feature          1..1000
                      note = Ceres Promoter YP0119
source                1..1000
                      mol_type = unassigned DNA
                      organism = Arabidopsis thaliana
SEQUENCE: 49
taccaaaaat aaggagtttc caaaagatgg ttctgatgag aaacagagcc catccctctc    60
ctttccccct tccatgaaa gaaatcggat ggtcctcctt caatgtcctc cacctactct   120
tctcttcttt ctttttttct ttcttattat taaccattta attaatttcc ccttcaattt   180
cagtttctag ttctgtaaaa agaaaataca catctcactt atagatatcc atatctattt   240
atatgcatgt atagagaata aaaaagtgtg agtttctagg tatgttgagt atgtgctgtt   300
tggacaattg ttagatgatc tgtccatttt tttcttttt cttctgtgta taaatatatt    360
tgagcacaaa gaaaaactaa taaccttctg ttttcagcaa gtagggtctt ataaccttca   420
aagaaatatt ccttcaattg aaaacccata aaccaaaagt gatattacaa aaggaaagag   480
agatattttc aagaacaaca taattagaaa agcagaagca gcagttaagt ggtactgaga   540
taaatgatat agtttctctt caagaacagt ttctcattac ccaccttctc ctttttgctg   600
atctatcgta atcttgagaa ctcaggtaag gttgtgaata ttatgcacca ttcattaacc   660
ctaaaaataa gagatttaaa ataaatgttt cttctttctc tgattcttgt gtaaccaatt   720
catgggtttg atatgttcct tggttattgc ttatcaacaa agagatttga tcattataaa   780
gtagattaat aactcttaaa cacacaaagt ttctttattt tttagttaca tccctaattc   840
tagaccagaa catggatttg atctatttct tggttatgta ttcttgatca ggaaaaggga   900
tttgatcatc aagattagcc ttctctctct ctctctagat atctttcttg aatttagaaa   960
tctttatta atatttggt gatgtcatat ataggatcaa                         1000

SEQ ID NO: 50         moltype = DNA  length = 999
FEATURE               Location/Qualifiers
misc_feature          1..999
                      note = Ceres Promoter YP0120
source                1..999
                      mol_type = unassigned DNA
                      organism = Arabidopsis thaliana
SEQUENCE: 50
tagtttttga tttaatctac gtttttctta atcataaatg ggtaattatt agttttttgca    60
aaatcaaaat ccaaaaattg ttctaaacac tgcaaccatt taaggcctat atcactcaga   120
aaatttctgg tgggagaact aatcgtttgt ccttttctaaa tctcacatat tagaatttag   180
aattagtgtg ctacataaga atattagttc agctcggaac aactatttt tggtaaaaca    240
gagaacttaa acaaatgcat tattttatca acatgcattt tgaattgaat ataaaatttc   300
ataattgtaa agacataaat tacataaaat tttacatgaa aaaatagata tagaaagaaa   360
atgaaactaa ctgatgatat gctctctaaa tttttttaatc tcataacaag aattcaaatt   420
aattagttca tattttggt taatataaca tttacctgtc taagttggaa cttcatttgg    480
tttctgtttt gtttagtcag tattcttaat gtgaaacgga agttgaatt tattcaaact    540
taaattcaat agcattaatt aaaggcgaaa gctattatct ctacatgtgg ttcaaactag   600
acatccaatt taattagctt attgacgttg aaatgttttc caaaactact atagtttggc   660
aatttgaaag atgcatcaga actactcaga caggtaaaag tagaacctct agctgtgtga   720
attgtatgtt agtccataaa gaacatccttg taaacttcat acttaagata tatattacaa   780
tatatacttg aatggtagat aaaaacgatt agtctgattcg ctagcatact cacaactatt   840
tggaaatgag taagatattg gcattctaga gttactacta tggagacaaa agtcgaataa   900
aagagacctc acgtgaaaat gttacgagct agtaaaaaaa gcatttacac taacggtaaa   960
aaaagtatct ataaatgttt acacaaggta gtagtcatt                          999

SEQ ID NO: 51         moltype = DNA  length = 999
FEATURE               Location/Qualifiers
misc_feature          1..999
                      note = Ceres Promoter YP0121
source                1..999
```

```
                      mol_type = unassigned DNA
                      organism = Arabidopsis thaliana
SEQUENCE: 51
ttggatttt ttttgttga gtcagcagac catctaatct ctcttttcc accacagcct    60
gctttctatg aagcatttgg gcttacggtt gtggaatcaa tgacttgtgc actcccaacg  120
tttgctacct gtcatggtgg acccgcagag attatcgaaa acggagtttc tgggttccac  180
attgacccat atcatccaga ccaggttgca gctaccttgg tcagcttctt tgagaccgt   240
aacaccaatc caaatcattg ggttaaaatc tctgaaggag ggctcaagcg aatctatgaa  300
aggttggccc attctccttg acaggcttaa caatacaact tgtatcgctt caacaagatg  360
atggcttaat aaggattttt gcatgtatag gtacacatgg aagaagtact cagagagact  420
gcttaccctg gctggagtct atgcattctg gaaacatgtg tctaagctcg aaaggagaga  480
aacacgacgt tacctagaga tgttttactc attgaaattt cgtgatttgg ttagtgtaac  540
ccactgttat tcttttgatg tctacatcta ctttacttac attattcttt tcttcggttt  600
gcaggccaat tcaatcccgc tggcaacaga tgagaactga tcatgcagg gtaggatttt  660
attccctgca ctttctttag atcttttgtt tgtgttatct tgaataaaaa ttgttgggtt  720
ttgtttcctt cagtggtttg attttggact tatttgtgtt aatgttgttt tggctgttct  780
cttaatatca ataacaaata aatttactgg ttggtatcta agatctaaca atagttacta  840
ttttagagg taaagacacc aaccttgtta tattggtcag agagctaaaa ccttgacttg   900
ttgggaaaac aaaactctaa tgacagaaaa tctgacatga tgccttataa ttcacagcct  960
catgttctac ataaatccta acaatagcac tttgtttct                         999

SEQ ID NO: 52         moltype = DNA   length = 1004
FEATURE               Location/Qualifiers
misc_feature          1..1004
                      note = Ceres Promoter YP0128
source                1..1004
                      mol_type = unassigned DNA
                      organism = Arabidopsis thaliana
SEQUENCE: 52
gataaactga taatggaaaa gaacaaagaa accagttttt aactatttgc atatgtaatt   60
tatttgttgc aaattatatt tagttaaaat gtttcctcta tttatatata tatatatcag  120
tcaagcacta tgtataagaa atgtcaattt ataattttt acatgtcctt aacagaaag    180
aaaatgaatt tttacatgtc attcatagag agtcactcgt ttatttctta tatagagaat  240
aacacactca catgcatatg catgcaatat gatcattttt atgacaaaga taatcaacgg  300
aaacggtcaa gacataattg gataaacaac ttgcacgatg cacagatctg atcaaatata  360
taactctttta acatatccaa aatattcaaa agaaaaact cgatccaaac tagcaacatc   420
acgctcacgc ggtaggctaa aaatttatta atctccaaaa gtctttctta tgaacactgc  480
aaacacaaca acttgaaaag tcatataggt ttagatgatg acgcgtattg gctatcgctt  540
accggagtgg ctcataaata caataaacaa tacgtaaaag tcaaagtcaa atatatttag  600
tcaactataa ccattaatcg ggcaaaacct ttagctgtca aaacaacgtg aaaacgatat  660
ttgtatatat catcaagaat cagtagataa gagaatgatt taatcccctg actattacaa  720
ttttggtgta ataaacagtc tctattggtt tttattcttt gttttaattt ctcatgacct  780
atagagagaa ttaggtagtt tcgaaaattg gctaatcaac ttttgaaaac tactgtctgct 840
tttgcttaaa ttctctacac ttagtttcgg ataagataat tgtcggacta atagttaatc  900
ccttgacaat ctttgatatt ataaaaggtt tagttaatct cttctctata taaatattca  960
tacaccagct ttcaaaaata tataatccaa acaccaaaaa caaa                  1004

SEQ ID NO: 53         moltype = DNA   length = 1001
FEATURE               Location/Qualifiers
misc_feature          1..1001
                      note = Ceres Promoter YP0137
source                1..1001
                      mol_type = unassigned DNA
                      organism = Arabidopsis thaliana
SEQUENCE: 53
gtggcacatg ctgaaacccc gagcatctct ccggaagaca cgcgtcgttc gctccaaaga   60
aaacagtcac agctgccgga gaatctccgc cgtcttcttc tgccaccgga aaaactctct  120
ccaccacttt cagtgcccac ctcgtgttat atccactgta tcctcgtagc accatatcag  180
cctaataaaa tttatgtat caaattttaa gacatagccg aaactacact atactagaca   240
ataataatat gatttgtttc ctgaaaaatt atggtttcat gagaaacatt aatcatctat  300
aaaacaaatt agctatggca tcgaagagtt atcaatcaaa actgatgaat ctttacttaa  360
tatatacaac atatctttac cttgcggcgg agaagatcgg cgagagaagc accccagcca  420
ccgtcactaa aggattcttc agtgatggaa tcaccaaaga gaaaaaacctt ccgtctcatc  480
atcttccaca caatcttctt gagaaaatct gagagataag aaggtgtag tggttttgct   540
gaagtgatcg tgtttgattt agtaaagaaa tgctttattt attggttggg gaaacataaa  600
taaataaagt aaaagtggat gcactaaatg ctttcaccca ctaatcaccg accttttcatg 660
gttattgtg aaatacactc atagatagac atacaatacc ttatgtacgt aaataacatt   720
ttatttgtcg acacttattg aagtaacgca tagattattt tctatgtgat tgccactctc  780
agactctcag tttcaaccaa taataacaat aactacaaca acattaatca taacatatg   840
ctctggttta caattaaagc ttagattaag aaactgtaac aacgttacag aaaaaaaatg  900
ttatttacgt tttgtaagat tagtctctag aatcatcacc gttttttata tattaatgat  960
tctttcttat atataaaacc tttctcgaaa tacccatgaa a                     1001

SEQ ID NO: 54         moltype = DNA   length = 1001
FEATURE               Location/Qualifiers
misc_feature          1..1001
                      note = Ceres Promoter YP0143
source                1..1001
                      mol_type = unassigned DNA
```

```
                        organism = Arabidopsis thaliana
SEQUENCE: 54
atacaacaga tggcagatat cgagttaaat acgtgaatca gccgttacga tattttaaaa       60
ctagaaaatt atttaaaaat attgcaaaat accatttaat ttcattgttc ataaaaaaaa      120
gaaattcaaa aacttaaaaa ctgattcaaa aatttgcatt aattctcatt aacagtcttc      180
aacactacaa caacatgttt ctaatttatt ttatatttta ataattaaac aatatatacg      240
tctgcacatt gttgctccga cataatctag tataaaaata gttgcagcat atgtgaaaag      300
caagcagcat ttatcactca atacttttaa ttttatctgt tgtatgtatt aaggttttgt      360
agcttttaaga aaacgcttat aatataaaat aacttctaaa agatatttca tgcgtataca      420
ataaatattt gtgaaaaaac atttcgaaaa cgtgtacaat atataaacta ttgtgttatc      480
ttttgacatt caaacaaatg ttgacaatgt aattttatcc atgatatgat tggccaatta      540
gctgcgaggt aaaaatccgt atacgagtaa aagtaagata aaatttcgca agaagatttt      600
tagcaggaaa tctaagacaa gtgtcatgaa cgtgtcaatc aacaaacgaa aaggagaatt      660
atagaatcca gattcgacgt accacattaa taaatatcaa aacatttttat gttatttat       720
ttttgctctg gcagttacac tctttttcat tgctccaata aaaaaatcac tcgcatgcat      780
gcatatatat acaccatagt aaactccgcc tcttcttcat tttaaagta tcagtttaca       840
ctgacacaat ccttaactat tttcctttgt tcttcttcat ctttattaca catttttttc      900
aaggtaacaa ataatctttt taagtcactt ttatactcct taaatcttag attgatatat      960
gaatgcatgt taatatttca agatttatag gtctaccaaa c                         1001

SEQ ID NO: 55           moltype = DNA   length = 1003
FEATURE                 Location/Qualifiers
misc_feature            1..1003
                        note = Ceres Promoter YP0144
source                  1..1003
                        mol_type = unassigned DNA
                        organism = Arabidopsis thaliana
SEQUENCE: 55
aaacgttgca agattattga ttgtgagaaa gagtgctcaa ggtagtactg atttctgtaa       60
agctcacggt ggtgggaaac gatgttcttg gggagatggg aaatgtgaga aaatttgcta      120
gaggaaagaa gcggtttatg cgctgcgcat aacactatta tgtctcggga gaacaaagat      180
ggaagcaaga gcggtttgat tggaccggga ctctttagtg gccttgtttt tggctctact      240
tctgatcatt ctcagtctgg agctagcgct gtctctgatt gtactgattc tgttgaacga      300
atacagtttg agaataggca gaagaacaag aagtgactga taccgatgca ggttctagta      360
ccttcatcaa tgaaatctcc aagtaattca catgaaggag aaacaaacat ctatgacttc      420
atggttccgg aggagagagt tcacggcggt gggctagtaa tgtctttact tggtggctcc      480
attgatcgaa actgaaagcc atttatggta aaagtgtcac attctcagca aaaacctgtg      540
taaagctgta aaatgtgtgg aatctccga atctgtttgt agccggttac gttatgctgg       600
atcaaaaact caagatttgt tggatattgt tatgctggat cggtggtgaa accacttccc      660
ggttgctaaa taaataaacg ttttttgtttt ataatcttttt tcactaaacg gcagtatggg    720
cctttagtgg gcttccttta agcgaccaat acaatcgtcg caccggaatc tactaccatt      780
tataggttta ttcatgtaaa acctcggaaa atttgagagc cacaacggtc aagagacaaa      840
aacaacttga agataaaggg ataaggaagg cttcctaact gatggacaac atttctttcc      900
acacaaattc tcataataaa aatcttataa tacaaatact tacgtcataa tcattcaatc      960
tagtcccccat gttttaaggt cctgtttctt gtctgataca aat                      1003

SEQ ID NO: 56           moltype = DNA   length = 1004
FEATURE                 Location/Qualifiers
misc_feature            1..1004
                        note = Ceres Promoter YP0156
source                  1..1004
                        mol_type = unassigned DNA
                        organism = Arabidopsis thaliana
SEQUENCE: 56
ttggtttgca ttgtgaagat ttgtattaac tatagaacat tgaattgatg gtgtgttaagtt    60
cttacacaag cgtgcttctc ggtttgaact gtttcttttg tatgttgaat cagagcttag     120
tttataggaa ccagagtatc tacttagtca ttctctgatg ctaagtgcta aggttctacc     180
tagttgccct ctaggccctt atgttattga taacttatga agctatttga acacttgatt     240
cttaggagac ctaagttggt acagccagat agagtgtaga ttcttgttct ctatgtgaca     300
ggatcaagct gccacacata gttcaagggt atgctctgtg tgggttttgct cagattgagg    360
acaaatctat acaaggaagt agagtctttg acatttgat gttgtatgat aagaagaaga      420
aaggagagta ataagaaag agaaaaggga aacagaaaca cgtgggagaa catcccaaag      480
aggaagcaca cgcggatctt catgcaaagc tccccgattc tcccatgtgg tccctttctc     540
cctttgtccc cctcctcttt cttcttttct cattttactc cttttttac cattatacaa      600
cgaatctttt ttatcataat ttttttggttt tggtttattt tccaataaca ctttcttggt    660
tacttcccat tctcactttt tcatataaga aactcacttt gggaaactta tgtttgagaa     720
tgacaagtct ttttagagaa agtgatgtaa caaatctaaa gtgattatat aataaccttg     780
cacaatgttt ttgatttttt gtaagattcg aatattaggt ttattattcg tagggaataa     840
acttactttc aaaagcgttc ataagttaat actttcatat atgatcataa gtacggacac     900
tattgttttt tgtttgtttg tgtttattct aaaagaaagt agcttttaat tgaaatgtcc     960
tcggaggcac agtttaaagt tcgagtgtaa cagtttctaa ggca                     1004

SEQ ID NO: 57           moltype = DNA   length = 1000
FEATURE                 Location/Qualifiers
misc_feature            1..1000
                        note = Ceres Promoter YP0158
source                  1..1000
                        mol_type = unassigned DNA
                        organism = Arabidopsis thaliana
```

```
SEQUENCE: 57
ttattagatt aatagattgc attgcattgc ttgtgctttc aatttacaaa ttgtctccca    60
actccatcga cacatctctt tttgtgtata taagattcag acttgttata ttttttttat   120
aaaatatgtta ttagcatctt aagttaaatt gattttttat atctgcatta aggattacac  180
gactatattt gcgattgtgt gttggttaaa atataatttg ggatgtctt taactacatt   240
taggattata tgactatatt tggttaaata taaaatctag ctgtgattat tagtattcaa  300
aaataagtag cctaaccaat taaaacaacg gctattgggg caaattagaa cattttagtg  360
tgtccaaaat ataatggtca ttaggtcata ttcctcctag cttcatcgca gcataattga  420
atgattgcct tatttagaag agcttttcca cttcccaaa atctaggtgg gatcttttg   480
ttttgaccttt cattttctt gtttaccatt tttagctaaa ttatttacga ttacaaaaga  540
tatcaaaagt tggatcataa tacaatttat agacttactg tagaaaattc gtatgtacaa  600
gtacaacaaa ttcttcataa taaatttga aattctatt acaaatgttg taagaaatag  660
aatttgaaat atatataaac taaggagaaa aaaaaagaga acatgcattg ctctagtcag  720
agtggaccaa catcaacgag ataagataac ataaaaacca actcaccata actaaaaaca  780
tcccaagaga tccaacgatt catatcaaac acaaaaacat cgaacgatca gatttaaacc  840
atctctggta tctccaaaac acaaacactt ttttttttct tttgtctgaa tggaacaaaa  900
gcatgcgaca tctctgtgtc tttatcttct ctctcctctt cttgaaaaac tgaacccttta 960
attcttttctt cacatctcct ttagctttct gaagctgcta                      1000

SEQ ID NO: 58           moltype = DNA   length = 1005
FEATURE                 Location/Qualifiers
misc_feature            1..1005
                        note = Ceres Promoter YP0188
source                  1..1005
                        mol_type = unassigned DNA
                        organism = Arabidopsis thaliana
SEQUENCE: 58
gattggtatg aaatttcgga gaccaacaaa aaaaacttta ttgagcttgg agtgaagcta    60
tatatatggg gcaagatcat aatatgttta tatcggcctt ttcgttaact gaaaataata  120
gttttgagaa atatatcaaa tggtaaacag acatcatctt tgaaaaatac catcaatgaa  180
gttaatattg ttattggcat atggtttacc catcttaatt ttaatgcaac caaacaaaca  240
agaaacaaaa actgtataag atacaaggtg ttttacgatt ttccgtctta aaaccgaaat  300
attttttgttc ctacgacttt aaacggactt tgcttaagtt gtgtgcatgt aagctcgtcg  360
tccctcgatt gtcatcaaca ttcaccaata tcagcctcta tcacacgagt gaaggtggtg  420
attcggctta atgaaaacag agaaatattt caatatgatt cctattaaat tttaaatctt  480
tttctcaat ctctagattt tcattaaaag catcatgatt ttttttccact atgttcatat  540
atctctatca cagttttagg tacattgtag aaattggata agatacgtca tacgtctaac  600
atgaatttgg tctagcaagg aaggtttgag ataaaagtg aaaagaaaac acaagataat  660
aaattataat ttataaatgc tttatgtat tgaaaaataa gatgatttt ttttttttta   720
ataccggatt ggctgatcca cttatgatga ctcaaatgtt attaagtttc aagcaaattt  780
atgatgacac aaatcacaat gagtcaatag tagccacgaa gccagaaaaa aaaaatgtac  840
tacaaaaaga taatgatagt acaaaatgat acgtcgtact gccacatgta cgacacaact  900
cgattaccaa aaagcagagc catccaacca taaaactcaa aacacacaga ttccactggc  960
gtgtgctctc ctcacttcac tcgtccttga aacttgaggt actga               1005

SEQ ID NO: 59           moltype = DNA   length = 1002
FEATURE                 Location/Qualifiers
misc_feature            1..1002
                        note = Ceres Promoter YP0190
source                  1..1002
                        mol_type = unassigned DNA
                        organism = Arabidopsis thaliana
SEQUENCE: 59
taaatagtga cattggtaag aagaaaaaaa acactattaa atagtgaaaa aatggtttat    60
aactctctta attaacatta cttattattg ctagcaccta aaatctccca caaaatattt   120
gttgtaaaac acaaatttac aaaatgattt tgttttaaa ttagtaacac atgttcatat  180
atacgttaat aagaacatac cctatatgat tttatataaa aaaatttctt tgagacgtct  240
tattcttttt tctttaataa tatgcaattg tgagagtttg gatttgaatg gtagcattag  300
aagcaaactt gaaccaaaca tatttcatga agtcaaactt aaccaatgt gatcactaat  360
cacagtgttc gcagtgtaag gcatcagaaa ataagaagaag ggacatagct atgaatcata  420
taatcttgac acatgtttta taggtttag gtgtgtatgc taacaaaaaa tgagacagct  480
ttcttctaat agacttaata tttgggctaa atgtaccaca gttgtgaatt tcttacaaaa  540
atgggccgag ctacaaaaaa ctacaggcccc actctcaact cttatcaaac gacagcgttt  600
tactttttta aaagcacaca cttttttgttt ggtgtcggtg acggtgagtt tcgtcgcgtc  660
ttcctttaaa ttgaagcaac ggttttgatc cgatcaaatc caacggtgct gattacacaa  720
agcccgagac gaaacgttg actattaagt taggtttaa tctcagccgt taatctacaa  780
atcaacggtt ccctgtaaaa cgaatcttcc ttccttcttc acttccgcgt cttctctctc  840
aatcacctca aaaaaatcga tttcatcaaa atattcaccc gcccgaattt gactctccga  900
tcatcgtctc cgaatctaga tcgacgagat caaaccccta gaaatctaaa tcggaatgag  960
aaattgattt tgatacgaat tagggatctg tgtgttgagg ac                    1002

SEQ ID NO: 60           moltype = DNA   length = 995
FEATURE                 Location/Qualifiers
misc_feature            1..995
                        note = Ceres Promoter YP0212
source                  1..995
                        mol_type = unassigned DNA
                        organism = Arabidopsis thaliana
SEQUENCE: 60
```

```
agtcgattgg tacactctta atttaattag agtaagagat caacaaaaat atagaatttt    60
ctttatatcg aagtgctacg acctatata tatagaaaaa aaagcatagg tgaatctcta   120
aattgagatt gtgctgtagt aaacatatta agtttttagt tttttttaaga aatgaatctt   180
tttgttgatt aattcaaact agtagtcatt aagattccgg agattccaat ttagaaaagt   240
caaagattca aagaacaagt ccaggtccac atgttgaatc cgattcatca tccactcatc   300
cttcatatct tcctccaccg tctccgccca aaaaatcaat aacaataaaa aatcctaaaa   360
aaacatattt gattttgaaa aaactttatc atatattata ttaattaaat agttatccga   420
tgactcatcc tatggtcagg gccttgctgt ctctgacgtc cttaattatc attattttta   480
aatttgtctc tctcagaaaa ttacgccaca atcttcctct ttcccttttc cgaaaacagc   540
taatatttgt ggacctaaac taaataacgt agcctctaga ttttatataa ttactaatac   600
tatatgctac tacttgttat tatttactcc aatcatatat gataccaatc aagaatcact   660
acataagtag aaaactttgc aatgagtcca ttaattaaaa ttaagaataa acttaaaatt   720
ttatggtatt ttaagattcc ctttggattg taatgacaag aaatcagcaa attagtcgta   780
actcgtaaga ataaacaaga tcaattttta ctttctttac aaagattccg ttgtaattt   840
agaaattttt ttttgtcact gttttttttat agattaattt atctgcatca atccgattaa   900
gaagtgtaca catgggcatc tatatatatc taacaggtaa aacgtgtatg tacatgcata   960
aggttttacg tgcttctata aatatatgtg gcagt                              995

SEQ ID NO: 61            moltype = DNA  length = 1024
FEATURE                  Location/Qualifiers
misc_feature             1..1024
                         note = Ceres Promoter YP0214
source                   1..1024
                         mol_type = unassigned DNA
                         organism = Arabidopsis thaliana
SEQUENCE: 61
ccagtcgatt ggcgcctcgc atgcctatca tatttaaccg tcaataatgg atttggcggt    60
tttggtaggc cgggtcaacc ggattaaaag aaaacggttt ggagtccttc cttgcaattg   120
aattttcaca cattcgggtt ttgtgatttc tctgtcataa tgggcccggc acatatggtt   180
cataacccat gtgggcctat ggtataattt ttccaattaa aactattgtt aggtcgataa   240
aacaaaaaac aataaaaacg agtggaaatac acataccaaa aagaatgtga tgaacattag   300
taatttttatt ttgatggtta atgaaaaaca aaataaatgc atcttggcat cttccgttgg   360
aaagcgcaaa tagggcagat tttcagacag atatcactat gatgggggt gagagaaaga   420
aaacgaggcg tacctaatgt aacactactt aattagtcgt tagttatagg acttttttt   480
tgtttgggcc tagttatagg atcataaggt aaaaatgaag aatgaatatt agattagtag   540
gagctaatga tggagttaag tatgcacgtg taagaactgg gaagtgaaac ctcctgtatg   600
gtgaagaaac tatacaacaa agccctttgt tggtgtatac gtattaattt ttattcttt    660
atcacaagcg atacgtatct aagacataa taaatatata tcttactcat aataaatatc   720
ttaagatata tatacagtat acacctgtat atatataata ataggcata tagtagaaat   780
taatatgagt tgttgttgtt gcaaatatat aaatcaatca aaagatttaa acccaccat    840
tcaatcttgg taagtaacga aaaaaaggg aagcaagaag aaccacagaa aaggggcta    900
acaactagac acgtagatct tcatctgccc gtccatctaa cctaccacac tctcatcttc   960
ttttttcccgt gtcagtttgt tatataagct ctcactctcc ggtatatttc cccattgcac 1020
tgga                                                              1024

SEQ ID NO: 62            moltype = DNA  length = 911
FEATURE                  Location/Qualifiers
misc_feature             1..911
                         note = Ceres Promoter YP0263
source                   1..911
                         mol_type = unassigned DNA
                         organism = Arabidopsis thaliana
SEQUENCE: 62
atctagctgt ggattccacc aaaattctgg cagggccatg atctaaaaac tgagactgcg    60
cgtgttgttt tgcagtgatt tgtatttcat atttgcacta tcctacacag tccacttggt   120
atcgtaacca aacataagga gaacctaatt acattattgt tttaatttcg tcaaactggt   180
ttttacctttt tagttacata gttgattctt catttgtttt agtagttatg gagcacaata   240
atgtgcaaca aagaaagatc atagtggatt aatatgttga gaggtcagaa attcttggtt   300
aacaaaaaaa agttacaagg actgagattt tgggtgggaa aaagccatag cttttaaac    360
atgattgaac ttaaaagtga tgttatggtt tgaggggaaa aaggttgatg tcaactaaga   420
tagttgaagt aatgtcttaa actaaagtaa accaccggtc caaccgtggt ccggaagcat   480
ctctggtatg atttatccta aaaatcaaaa tagtagaaac atactttaaa tatatacatt   540
gatcggacga aaattgtaaa ctagtatagt ttcaaaaact agttgaacag ttatgtacc    600
ttaaacattt atttcaaact taaacactaa agaacatata tgaatagaag ttttataaa    660
ttactatata tctaccataa atctcttata attatgatgt cacgatgagg aagtgttgaa   720
acgttaaaat gccaaaatat aagcatgcga cggaattttg gcagaagatt gtagagttgt   780
aatctgtcgc aatcattact cgtgctagca tttttcattt tcccttcatt tgtggataac   840
gcacgatata acattctaca caccaacaag attctataaa aacgcaaagg ttgtctccat   900
agaatatcgt c                                                       911

SEQ ID NO: 63            moltype = DNA  length = 999
FEATURE                  Location/Qualifiers
misc_feature             1..999
                         note = Ceres Promoter YP0275
source                   1..999
                         mol_type = unassigned DNA
                         organism = Arabidopsis thaliana
SEQUENCE: 63
aaacattaat atgtagtaac tatgggcgta tgctttactt tttaaaatgg gcctatgcta    60
```

```
taattgaatg acaaggatta aacaactaat aaaattgtag atgggttaag atgacttatt      120
tttttactta ccaatttata aatgggcttc gatgtactga aatatatcgc gcctattaac      180
gaggccattc aacgaatgtt ttaagggccc tatttcgaca ttttaaagaa cacctaggtc      240
atcattccag aaatggatat tataggattt agataatttc ccacgtttgg tttatttatc      300
tattttttga cgttgaccaa cataatcgtg cccaaccgtt tcacgcaacg aatttatata      360
cgaaatatat atattttcca aattaagata ccacaatcaa aacagctgtt gattaacaaa      420
gagatttttt ttttttggtt ttgagttaca ataacgttag aggataaggt ttcttgcaac      480
gattaggaaa tcgtataaaa taaaatatgt tataattaag tgttttattt tataatgagt      540
attaatataa ataaaacctg caaaaggata gggatattga ataataaaga gaaacgaaag      600
agcaattta cttctttata attgaaatta tgtgaatgtt atgtttacaa tgaatgattc      660
atcgttctat atattgaagt aaagaatgag tttattgtgc ttgcataatg acgttaactt      720
cacatatcaa cttattacat aacatttatc acatgtgcgt cttttttttt ttttactttg      780
taaaatttcc tcactttta gacttttata acaattacta gtaaaataaa gttgcttggg      840
gctacaccct ttctccctcc aacaactcta tttatagata acattatc aaaatcaaaa      900
catagtccct ttcttcctata aaggttttt cacaaccaaa tttccattat aaatcaaaaa      960
ataaaaactt aattagtttt tacagaagaa aagaaaaca                            999

SEQ ID NO: 64              moltype = DNA  length = 981
FEATURE                    Location/Qualifiers
misc_feature               1..981
                           note = Ceres Promoter YP0285
source                     1..981
                           mol_type = unassigned DNA
                           organism = Arabidopsis thaliana
SEQUENCE: 64
gggattatat atgatagacg attgtatttg cgggacattg agatgtttcc gaaaatagtc       60
atcaaatatc aaaccagaat ttgatgtgaa acactaatt aaaacatata attgacaact      120
agactatatc atttgttaag ttgagcgttg aaagaaaatg aaagagtgta gactgtagta      180
cgtatgagtt tcccaaaaga tggtgcttga atattattgg gaagagactt tggttggttc      240
ggttgaatga agatttttac ctgccatgtt gatagagaaa ggcaaataaa tgtaggggtc      300
gatgtctaac gtaaagactg gatcaaccaa gagtcctcct cctcgtcttc accaaaaaaa      360
aagagtcctc ctcgtgggaaa cttatttctt ctccagccaa gatctcatct catctcttca      420
ctctatgaaa tataaaggaa tcttatggtt tttctaaaaa ctatagtacg tctatatacc      480
aaaggaaaca atataaaaatc agttaatctg ataaattttg agtaaataat aaagttaact      540
ttgtacttac ctatatcaaa ctaattcaca aaataaagta ataataacaa agaattttta      600
gtagatccac aatatacaca cacactatga gaaatcataa tagagaattt taatgatttt      660
gtctaactca tagcaacaag tcgctttggc cgagtggtta aggcgtgtgc ctgcaagta      720
catgggctct gcccgcgaga gttcgaatct tcaggcgac gtttctttg ttttcggcca      780
taaaggaaaa agcccaatta acacgtctcg ctttataagc cataaagcaa acaatgggct      840
gtctctgtct cactcacaca cgcgttttcc tactttttga ctatttttat aaccggcggg      900
tctgacttaa ttaggttttt ctttaataat cagacactct ctcactcgtt tcgtcaacat      960
tgaacacaga caaaaccgcg t                                                981

SEQ ID NO: 65              moltype = DNA  length = 996
FEATURE                    Location/Qualifiers
misc_feature               1..996
                           note = Ceres Promoter YP0286
source                     1..996
                           mol_type = unassigned DNA
                           organism = Arabidopsis thaliana
SEQUENCE: 65
gaaaacaatc ataggttacg ctattatcat cgaaaggtat gtgatgcata ttcccattga       60
accagatttc catatatttt atttgtaaag tgataatgaa tcacaagatg attcaatatt      120
aaaaatgggt aactcacttt gacgtgtagt acgtggaaga atagttagct atcacgcata      180
catatatcta tgaataagtg tgtatgcat aagaaactaa aatatttacc taaagtccag      240
ttactcatac tgatttcatg catatatgta ttatttattt attttttaata aagaagcgat      300
tggtgttttc atagaaatca tgatagattg ataggtattt cagttccaca aatctagatc      360
tgtgtgctat acatgcatgt attaatttt tccccttaaa tcatttcagt tgataatatt      420
gctcttttgt ccaactttag aaaaggtatg aaccaactga acgattaaca agtaaacatt      480
aattaatctt tatatgagat aaaaccgagg atatatatga ttgtgttgct gtctattgat      540
gatgtgtcga tattatgctt gttgtaccaa tgctcgagcc gagcgtgatc gatgccttga      600
caaactatat atgtttccg aattaattaa gttttgtatc ttaattagaa taacatttt      660
atacaatgta atttctcaag cagacaagat atgtatccta tattaattac tatatatgaa      720
ttgccgggca cctaccagga tgtttcaaat acgagagcgt attagtttcc acgtaaaatca      780
caatgacgcg acaaaatcta gaatcgtgtc aaaactctat caatacaata atatatattt      840
caagggcaat ttcgacttct cctcaactca atgattcaac gccatgaatc tctatataaa      900
ggctacaaca ccacaaagga tcatcagtca tcacaaccac attaactctt caccactatc      960
tctcaatctc tcgtttcatt tcttgacgcg tgaaaa                                996

SEQ ID NO: 66              moltype = DNA  length = 1000
FEATURE                    Location/Qualifiers
misc_feature               1..1000
                           note = Ceres Promoter YP0337
source                     1..1000
                           mol_type = unassigned DNA
                           organism = Arabidopsis thaliana
SEQUENCE: 66
taattttttt attttttggaa ctaacactta ttagtttagg tttccatcac ctatttaatt       60
cgtaattctt atacatgcat ataatagaga tacatatata caaatttatg atcattttg       120
```

```
cacaacatgt gatctcattc attagtatgc attatgcgaa aacctcgacg cgcaaaagac    180
acgtaatagc taataatgtt actcatttat aatgattgaa gcaagacgaa acaacaaca    240
tatatatcaa attgtaaact agatatttct taaaagtgaa aaaaaacaaa gaaatataaa    300
ggacaatttt gagtcagtct cttaatatta aaacatatat acataaataa gcacaaacgt    360
ggttacctgt cttcatgcaa tgtggacttt agtttatcta atcaaaatca aataaaaagg    420
tgtaatagtt ctcgtcattt ttcaaatttt aaaaatcaga accaagtgat tttttgtttga   480
gtattgatcc attgttttaaa caatttaaca cagtatatac gtctcttgag atgttgacat   540
gatgataaaa tacgagatcg tctcttggtt ttcgaatttt gaactttaat agttttcttt    600
tttagggaaa cttaatagt tgttatcat aagattagtc acctaatggt tacgttgcag      660
taccgaacca attttttacc ctttttttcta aatgtggtcg tggcataatt tccaaaagag    720
atccaaaacc cggtttgctc aactgataag ccggtcggtt ctggtttgaa aaacaagaaa    780
taatctgaaa gtgtgaaaca gcaacgtgtc tcggtgtttc atgagccacc tgccacctca    840
ttcacgtcgg tcattttgtc gtttcacggt tcacgctcta gacacgtgct ctgtcccac     900
catgactttc gctgccgact cgcttcgctt tgcaaactca aacatgtgtg tatatgtaag    960
tttcatccta ataagcatct cttaccacat taattaaaaa                           1000

SEQ ID NO: 67         moltype = DNA length = 1000
FEATURE               Location/Qualifiers
misc_feature          1..1000
                      note = Ceres Promoter YP0356
source                1..1000
                      mol_type = unassigned DNA
                      organism = Arabidopsis thaliana
SEQUENCE: 67
ttagttcatt gaaacgtcaa cttttttactt gcaaccactt tgtaggacca ttaactgcaa    60
aataagaatt ctctaagctt cacaagggt tcgtttggtg ctataaaaac attgtgtttaa   120
gaactggttt actggttcta taatcctata aatccaaata tgaagtatgg caataataat   180
aacatgttag cacaaaaaat actcattaaa ttcctaccca aaaaaaatct ttatatgaaa   240
ctaaaactta tatacacaat aatagtgata caaagtaggt cttgatattc aactattcgg   300
gattttctgg tttcgagtaa ttcgtataaa aggtttaagt tctattatgt tcactgaaat   360
cttaactttg ttttgtttcc agttttaact agtagaaatt gaattttta aaaattgtta    420
cttacaataa aatttgaatc aatatcctta atcaaaggat cttaagacta gcacaattaa    480
aacatataac gtagaatatc tgaaataact cgaaaatatc tgaactaagt tagtagtttt    540
aaaatataat cccggtttgg accgggcagt atgtacttca atacttgtgg gttttgacga    600
ttttggatcg gattgggcgg gccagccaga ttgatctatt acaaatttca cctgtcaacg    660
ctaactccga acttaatcaa agattttgag ctaaggaaaa ctaatcagtg atcacccaaa    720
gaaaacattc gtgaataatt gtttgctttc catggcagca aaacaaatag gacccaaata    780
ggaatgtcaa aaaaagaaa gacacgaaac gaagtagtat aacgtaacac acaaaaataa    840
actagagata ttaaaaacac atgtccacac atggatacaa tgcatttaa ggagcagaag     900
gcacgtagtg gttagaaggt atgtgatata attaatcggc ccaaatagat tggtaagtag    960
tagccgtcta tatcatccat actcatcata acttcaacct                         1000

SEQ ID NO: 68         moltype = DNA length = 1000
FEATURE               Location/Qualifiers
misc_feature          1..1000
                      note = Ceres Promoter YP0374
source                1..1000
                      mol_type = unassigned DNA
                      organism = Arabidopsis thaliana
SEQUENCE: 68
aagacacccg taaatgttgt catgtagaag aaactagaaa cgttaaacgc atcaaatcaa    60
gaaattaaat tgaaggtaat ttttaacgcc gcctttcaaa tattcttcct aggagaggct   120
acaagacgcg tatttctttc gaattctcca aaccattacc attttgatat ataataccga   180
catgccgttg ataagtttg tatgcaaatc gttcattggg tatgagcaaa tgccatccat    240
tggttcttgt aattaaatgg tccaaaaata gtttgttccc tactactagtt actaatttgt   300
atcactctgc aaaataatca tgatataaac gtatgtgcta tttctaatta aaactcaaaa   360
gtaatcaatg tacaatgcag agatgaccat aaaagaacat taaaaacacta cttccactaa    420
atctatgggg tgccttggca aggcaattga ataaggagaa tgcatcaaga tgatatagaa    480
aatgctattc agtttataac attaatgttt tggcggaaaa ttttctatat attagacctt    540
tctgtaaaaa aaaaaaatg atgtagaaaa tgctattatg tttcaaaaat ttcgcactag    600
tataatacgg aacattgtag tttacactgc tcattaccat gaaaaccaag gcagtatata    660
ccaacattaa taaactaaat cgcgatttct agcaccccca ttaattaatt ttactattat    720
acattctctt tgcttctcga aatttaataac ttctctatat cattctacat aataaataag   780
aaagaaatcg acaagatcta aatttagatc tattcagctt tttcgcctga gaagccaaaa    840
ttgtgaataag aagaaagcag tcgtcatctt cccacgtttg gacgaaataa aacataacaa    900
taataaaata ataaatcaaa tatataaatc cctaatttgt ctttattact ccacaatttt    960
ctatgtgtat atatataccc acctctctct tgtgtatttg                          1000

SEQ ID NO: 69         moltype = DNA length = 998
FEATURE               Location/Qualifiers
misc_feature          1..998
                      note = Ceres Promoter YP0377
source                1..998
                      mol_type = unassigned DNA
                      organism = Arabidopsis thaliana
SEQUENCE: 69
tataaaccat tcctataaca ccatatttaa acataacaat gaattgcttg gatttcaaac    60
tttattaaat ttggatttta aattttaatt tgattgaatt ataccccctt aattggataa   120
attcaaatat gtcaactttt ттттттgtaag attттттттаt ggaaaaaaaa attgattatt   180
```

```
cactaaaaag atgacaggtt acttataatt taatatatgt aaaccctaaa aagaagaaaa    240
tagtttctgt tttcacttta ggtcttatta tctaaacttc tttaagaaaa tcgcaataaa    300
ttggtttgag ttctaacttt aaacacatta atatttgtgt gctatttaaa aaataaattta  360
caaaaaaaaa aacaaattga cagaaaatat caggttttgt aataagatat ttcctgataa   420
atatttaggg aatataacat atcaaaagat tcaaattctg aaaatcaaga atggtagaca   480
tgtgaaagtt gtcatcaata tggtccactt ttctttgctc tataacccaa aattgaccct   540
gacagtcaac ttgtacacgc ggccaaacct ttttataatc atgctattta tttccttcat   600
ttttattcta tttgctatct aactgatttt tcattaacat gataccagaa atgaatttag   660
atggattaat tcttttccat ccacgacatc tggaaacact tatctcctaa ttaaccttac   720
ttttttttta gtttgtgtgc tccttcataa aatctatatt gtttaaaaca aaggtcaata   780
aatataaata tggataagta taataaatct ttattggata tttctttttt taaaaaagaa   840
ataaatcttt tttggatatt ttcgtggcag catcataatg agagactacg tcgaaaccgc   900
tggcaaccac ttttgccgcg tttaatttct ttctgaggct tatataaata gatcaaaggg   960
gaaagtgaga tataatacag acaaaacaag agaaaaga                            998

SEQ ID NO: 70          moltype = DNA   length = 999
FEATURE                Location/Qualifiers
misc_feature           1..999
                       note = Ceres Promoter YP0380
source                 1..999
                       mol_type = unassigned DNA
                       organism = Arabidopsis thaliana
SEQUENCE: 70
acaagtaccca ttcacttttt tactttttcaa tgtatacaat catcatgtga taaaaaaaaa   60
aatgtaacca atcaacacac tgagatacgg ccaaaaaatg gtaatacata aatgtttgta  120
ggttttgtaa tttaaatact ttagttaagt tatgattttta ttattttttgc ttatcactta  180
tacgaaatca tcaatctatt ggtatctctt aatcccgctt tttaatttcc accgcacacg   240
caaatcagca aatggttcca gccacgtgca tgtgaccaca tattgtggtc acagtactcg   300
tccttttttt ttcttttgta atcaataaat ttcaatccta aaacttcaca cattgagcac   360
gtcggcaacg ttagctccta aatcataacg agcaaaaaag ttcaaattag ggtatatgat   420
caattgatca tcactacatg tctacataat taatatgtat tcaaccggtc ggtttgttga   480
tactcatagt taagtatata tgtgctaatt agaattagga tgaatcagtt cttgcaaaca   540
actacggttt catataatat gggagtgtta tgtacaaaat gaaagaggat ggatcattct   600
gagatgttat gggctcccag tcaatcatgt tttgctcgca tatgctatct tttgagtgtc   660
ttcctaaact catagaataa gcacgttggt tttttccacc gtcctcctcg tgaacaaaag   720
tacaattaca ttttagcaaa ttgaaaataa ccacgtggat ggaccatatt atatgtgatc   780
atattgcttg tcgtcttcgt tttcttttaa atgtttacac cactacttcc tgacacgtgt   840
ccctattcac atcatccttg ttatatcgtt ttacttataa aggatcacga acaccaaaac   900
atcaatgtgt acgtctttttg cataagaaga aacagagagc attatcaatt attaacaatt   960
acacaagaca gcgagattgt aaaagagtaa gagagagag                            999

SEQ ID NO: 71          moltype = DNA   length = 1000
FEATURE                Location/Qualifiers
misc_feature           1..1000
                       note = Ceres Promoter YP0381
source                 1..1000
                       mol_type = unassigned DNA
                       organism = Arabidopsis thaliana
SEQUENCE: 71
cacggtcaaa gtattgctaa catggtcatt acattgaaaa agaaaattaa ttgtctttac    60
tcatgtttat tctatacaaa taaaaatatt aaccaaccat cgcactaaca aaatagaaat   120
cttattctaa tcacttaatt gttgacaatt aaatcattga aaaatacact taaatgtcaa   180
atattcgttt tgcatacttt tcaatttaaa tacatttaaa gttcgacaag ttgcgtttac   240
tatcatagaa aactaaatct cctaccaaag cgaaatgaaa ctactaaagc gacaggcagg   300
ttacataacc taacaaatct ccacgtgtca attaccaaga gaaaaaaaga gaagataagc   360
ggaacacgtg gtagcacaaa aaagataatg tgatttaaat taaaaaacaa aaacaaagac   420
acgtgacgac ctgacgctgc aacatcccac cttacaacgt aataaccact gaacataaga   480
cacgtgtacg atcttgtctt tgttttctcg atgaaaacca cgtgggtgct caaagtcctt   540
gggtcagagt cttccatgat tccacgtgtc gttaatgcac caaacaaggg tactttcggt   600
attttggctt ccgcaaatta gacaaaacag ctttttgttt gattgatttt tctcttctct   660
ttttccatct aaattctctt tgggctctta atttctttttt gagtgttcgt tcgagatttg   720
tcggagattt tttcggtaaa tgttgaaatt ttgtgggatt tttttttatt tctttattaa   780
acttttttttt attgaattta taaaaaggga aggtcgtcat taatcgaaga aatggaatct   840
tccaaaattt gatattttgc tgtttttcttg ggatttgaat tgtctcttat catcaagaat   900
ctgttaaaat ttcaatccta aaatctaagt tgagaaaaag agagatctct aatttaaccg   960
gaattaatat tctccgaccg aagttattat gttgcaggct                         1000

SEQ ID NO: 72          moltype = DNA   length = 999
FEATURE                Location/Qualifiers
misc_feature           1..999
                       note = Ceres Promoter YP0384
source                 1..999
                       mol_type = unassigned DNA
                       organism = Arabidopsis thaliana
SEQUENCE: 72
tttaaaaaat tggataaaac accgataaaa attcacattt gcaaatttta ttcagtcgga    60
atatatattt gaaacaagtt ttgaaatcca ttggacgatt aaaattcatt gttgagagga   120
taaatatgga tttgttcatc tgaaccatgt cgttgattag tgattgacta ccatgaaaaa   180
tatgttatga aaagtataac aacttttgat aaatcacatt tattaacaat aaatcaagac   240
```

```
aaaatatgtc aacaataata gtagtagaag atattaattc aaattcatcc gtaacaacaa  300
aaaatcatac cacaattaag tgtacagaaa aaccttttgg atatatttat tgtcgctttt  360
caatgatttt cgtgaaaagg atatatttgt gtaaaataag aaggatcctg acgggtgtaa  420
aaacatgcac aattcttaat ttagaccaat cagaagacaa cacgaacact tctttattat  480
aagctattaa acaaaatctt gcctattttg cttagaataa tatgaagagt gactcatcag  540
ggagtggaaa atatctcagg attttgctttt agctctaaca tgtcaaacta tctagatgcc  600
aacaacacaa agtgcaaatt cttttaatat gaaaacaaca ataatatttc taatagaaaa  660
ttaaaaaggg aaataaaata tttttttaaa atatacaaaa gaagaaggaa tccatcatca  720
aagtttata aaattgtaat ataatacaaa cttgtttgct tccttgtctc tccctctgtc  780
tctctcatct ctcctatctt tccatatat acttcatctt cacacccaaa actccacaca  840
aaatatctct ccctctatct gcaaatttc caaagttgca tcctttcaat ttccactcct  900
ctctaatata attcacatttt tcccactatt gctgattcat ttttttttgt gaattatttc  960
aaacccacat aaaaaaatct tgtttaaat ttaaaacca                          999

SEQ ID NO: 73        moltype = DNA  length = 998
FEATURE              Location/Qualifiers
misc_feature         1..998
                     note = Ceres Promoter YP0385
source               1..998
                     mol_type = unassigned DNA
                     organism = Arabidopsis thaliana
SEQUENCE: 73
actcaacaat aggacaagcc aaaaaaattc caattattgt gttactctat tcttctaaat   60
ttgaacacta atagactatg acatatgagt atataatgtg aagtcttaag atattttcat  120
gtgggagatg aataggccaa gttggagtct gcaaacaaga agctcttgag ccacgacata  180
agccaagttg atgaccgtaa ttaatgaaac taaatgttgt tggttatata ttagggaccc  240
atggccatat acacaatttt tgtttctgtc gatagcatgc gtttatatat atttctaaaa  300
aaactaacat atttactgga tttgagttcg aatattgaca ctaatataaa ctacgtacca  360
aactacatat gtttatctat atttgattga tcgaagaatt ctgaactgtt ttagaaaatt  420
tcaatacact taacttcatc ttacaacggt aaaagaaatc accactagac aaacaatgcc  480
tcataatgtc tcgaaccctc aaactcaaga gtatacatttt tactagatta gagaatttga  540
tatcctcaag ttgccaaaga attggaagct tttgttacca aacttagaaa cagaagaagc  600
cacaaaaaaa gacaaaggga gttaaagatt gaagtgatgc atttgtctaa gtgtgaaagg  660
tctcaagtct caacttttgaa ccataataac attactcaca ctcccttttt ttttcttttt  720
ttttcccaaa gtaccttttt taattccctc tataacccac tcactccatt ccctcttttct  780
gtcactgatt caacacgtgg ccacactgat gggatccacc tttccttctta cccacctccc  840
ggtttatata aaccctcac aacacttcat cgctctcaaa ccaactctct cttctctctt  900
ctctcctctc ttcacaaga agaaaaaaaa cagagccttt acacatctca aaatcgaact  960
tactttaacc accaaatact gattgaacac acttgaaa                          998

SEQ ID NO: 74        moltype = DNA  length = 1000
FEATURE              Location/Qualifiers
misc_feature         1..1000
                     note = Ceres Promoter YP0396
source               1..1000
                     mol_type = unassigned DNA
                     organism = Arabidopsis thaliana
SEQUENCE: 74
catagtaaaa gtgaatttaa tcatactaag taaaataaga taaaacatgt tatttgaatt   60
tgaatatcgt gggatgcgta tttcggtatt tgattaaagg tctggaaacc ggagctccta  120
taacccgaat aaaaatgcat aacatgttct tccccaacga ggcgagcggg tcagggcact  180
agggtcattg caggcagctc ataaagtcat gatcatctag gagatcaaat tgtatgtcgg  240
ccttctcaaa attacctcta agaatctcaa acccaatcat agaacctcta aaagacaaa  300
gtcgtcgctt tagaatgggt tcggtttttg gaaccatatt tcacgtcaat ttaatgttta  360
gtataatttc tgaacaacag aattttggat ttatttgcac gtatacaaat atctaattaa  420
taaggacgac tcgtgactat ccttacatta agtttcactg tcgaaataac atagtacaat  480
acttgtcgtt aatttccacg tctcaagtct ataccgtcat ttacggagaa agaacatctc  540
tgttttttcat ccaaactact attctcactt tgtctatata tttaaaatta agtaaaaaag  600
actcaatagt ccaataaaat gatgaccaaa tgagaagatg gttttgtgcc agattttagg  660
aaaagtgagt caaggtttca catctcaaat ttgactgcat aatcttcgcc attaacaacg  720
gcattatata tgtcaagcca atttttccatg ttgcgtactt tctattgag gtgaaaatat  780
gggtttgttg attaatcaaa gagtttgcct aactaatata actacgactt tttcagtgac  840
cattccatgt aaactctgct tagtgtttca tttgtcaaca atattgtcgt tactcattaa  900
atcaaggaaa aatatacaat tgtataattt tcttatattt taaaattaat tttgatgtat  960
taccccttta taaataggct atcgctacaa caccaataac                        1000

SEQ ID NO: 75        moltype = DNA  length = 1514
FEATURE              Location/Qualifiers
misc_feature         1..1514
                     note = Ceres Promoter p13879
source               1..1514
                     mol_type = unassigned DNA
                     organism = Arabidopsis thaliana
SEQUENCE: 75
tttcgatcct cttctttttt aggtttcttg atttgatgat cgccgccagt agagccgtcg   60
tcggaagttt cagagattaa aaccatcacc gtgtgagttg gtagcgaatt aacgaaaagt  120
ctaagtcaag attttttaaa aagaaattta tgtgtgaaaa gaagccgttg tgtatattta  180
tataatttag aaaatgtttc atcatttttaa ttaaaaaatt aataatttgt agaagaaaga  240
agcatttttt atacataaat catttacctt ctttactgtg ttttcttca cttacttcat  300
```

```
ttttactttt ttacaaaaaa gtgaaaagta aattacgtaa ttggtaacat aaattcactt    360
taaatttgca tatgttttgt tttcttcgga aactatatcg aaaagcaaac ggaaagaact    420
tcacaaaaaa ccctagctaa ctaaagacgc atgtgttctt cttattcttc atatatcctc    480
tgtttcttgt gttctgtttt gagtcttaca ttttcaatat ctgactctga ttactatatc    540
taaaagggaa catgaagaac ttgagaccat gttaaactgt acaatgcctt caaacatggc    600
taactaaaga tacattagat ggctttacag tgtgtaatgc ttattatctt taggttttt    660
aaatcccttg tattaagtta tttaccaaat tatgttcttg tactgcttat tggcttggtt    720
gttgtgtgct ttgtaaacaa caccttggc tttatttcat cctttgtaaa cctactggtc      780
tttgttcagc tcctcttgga agtgagtttg tatgcctgga acgggttta atggagtgtt      840
tatcgacaaa aaaaaatgt agcttttgaa atcacgagga gtagttttat attcaaatta    900
catgcatgca actaagtagc aacaaagtta atatggccga gttggtctaa ggcgccagat    960
taaggttctg gtccgaaagg gcgtgggttc aaatcccact gtcaacattc tcttttctc    1020
aaattaatat ttttctgcct caatggttca ggcccaatta tactagacta ctatcgcgac   1080
taaaataggg actagccgaa ttgatccggc ccagtatcag ttgtgtatca ccacgttatt   1140
tcaaatttca aactaaggga taaagatgtc atttgacata tgagatattt ttttgctcca   1200
ctgagatatt tttctttgtc caagataaaa atatcttttc tcgcatcgtc gtcttttccat   1260
ttgcgcatta aaccaaaaag tgtcacgtga tatgtcccca accactacga attttaacta   1320
cagatttaac catggttaaa ccagaattca cgtaaaccga ctctaaacct agaaaatatc   1380
taaaccttgg ttaatatctc agcccccctta taaataacga gacttcgtct acatcgttct   1440
acacatctca ctgctcacta ctctcactgt aatcccttag atcttctttt caaatttcac   1500
cattgcactg gatg                                                     1514

SEQ ID NO: 76          moltype = DNA  length = 1954
FEATURE                Location/Qualifiers
misc_feature           1..1954
                       note = Ceres Promoter p326
source                 1..1954
                       mol_type = unassigned DNA
                       organism = Arabidopsis thaliana
SEQUENCE: 76
gtgggtaaaa gtatccttct ttgtgcattt ggtattttta agcatgtaat aagaaaaacc      60
aaaatagacg gctggtattt aataaaagga gactaatgta tgtatagtat atgatttgtg    120
tggaatataa taaagttgta aaatatagat gtgaagcgag tatctatctt ttgactttca    180
aaggtgatcg atcgtgttct ttgtgatagt ttttggtcgtc ggtctacaag tcaacaacca    240
ccttgaagtt ttcgcgtctc ggtttcctct tcgcatctgg tatccaatag catacatata    300
ccagtgcgga aaatggcgaa gactagtggg cttgaaccat aaggtttggc cccaatacgg    360
attccaaaca acaagcctag cgcagtcttt tgggatgcat aagactaaac tgtcgcagtg    420
atagacgtaa gatatatcga cttgattgga atcgtctaag ctaataagtt taccttgacc    480
gtttatagtt gcgtcaacgt ccttatggag attgatgccc atcaaataaa cctgaaaatc    540
catcaccatg accaccataa actcccttgc tgccgctgct ttggcttgag caaggtgttt    600
ccttgtaaag ctccgatctt tggataaagt gttccacttt tgcaagtag ctctgacccc       660
tctcagagat gtcaccggaa tcttagacag aacctcctct gccaaatcac ttggaagatc    720
ggacaatgtc atcatttttg caggtaattt ctccttcgtt gctgctttgg cttgagcacg    780
gtgcttcttt gtaaagctcc gatctttgga taagagcgga tcggaatcct ctaggagtg     840
ccagtccctt gacctattaa tttatagaag gtttagtgt attttgttcc aatttcttct      900
ctaacttaac aaataacaac tgcctcatag tcatgggctt caaattttat cgcttggtgt    960
atttcgttat ttgcaaggcc ttggcccatt tgagcccaaa taactaaatc tagccttttc   1020
agaccggaca tgaacttcgc atattggcgt aactgtgcag ttttaccttt ttcggatcag   1080
acaagatcag atttagacca cccaacaata gtcagtcata tttgacaacc taagctagcc   1140
gacactacta aaaagcaaac aaaagaagaa ttctatgttg tcattttacc ggtggcaagt   1200
ggaccctctct ataaaagagt aaagagacag cctgtgtgta tataatctct aattatgttc   1260
accgacacaa tcacacaaac ccttctctaa tcacacaact tcttcatgat ttacgacatt   1320
aattatcatt aactctttaa attcacttta catgctcaaa aatatctaat ttgcagcatt   1380
aatttgagta ccgataacta ttattataat cgtcgtgatt cgcaatcttc ttcattagat   1440
gctgtcaagt tgtactcgca cgcggtggtc cagtgaagca aatccaacgg tttaaaacct   1500
tcttacattt ctagatctaa tctgaaccgt cagatatcta gatctcattg tctgaacaca   1560
gttagatgaa actgggaatg aatctggacg aaattacgat cttacaccaa cccctcgac    1620
gagctcgtat atataaagct tatacgctcc tccttcacct tcgtactact actaccacca   1680
catttcttta gctcaacctt cattactaat ctccttttaa ggtatgttca cttttcttcg   1740
attcatactt tctccaagatt cctgcatttc tgtagaattt gaaccaagtg tcgattttt   1800
tttgagagaa gtgttgattt atagatctgg ttattgaatc tagattccaa ttttttaattg   1860
attcgagttt gttatgtgtg tttatactac ttctcattga tcttgtttga tttctctgct   1920
ctgtattagg tttctttcgt gaatcagatc ggaa                                1954

SEQ ID NO: 77          moltype = DNA  length = 2016
FEATURE                Location/Qualifiers
misc_feature           1..2016
                       note = Ceres Promoter p32449
source                 1..2016
                       mol_type = unassigned DNA
                       organism = Arabidopsis thaliana
SEQUENCE: 77
gatcggcctt cttcaggtct tctctgtagc tctgttactt ctatcacagt tatcgggtat      60
ttgagaaaaa agagttagct aaaatgaatt tctccatata atcatgatgt actacaggtt    120
tacttgattc gcgttagctt tatctgcatc caaagttttt tccatgatgt tatgtcatat    180
gtgataccgt tactatgttt ataactttat acagtctggt tcactggagt ttctgtgatt    240
atgttgagta catactcatt catccttgg taactctcaa gtttaggttg tttgaattgc     300
ctctgttgtg atacttattg tctattgcat caatcttcta atgcaccacc ctagactatt    360
tgaacaaaga gctgtttcat tcttaaacct ctgtgtctct ttgctaaatg gtcatgcttt    420
```

```
aatgtcttca cctgtctttc tcttctatag atatgtagtc ttgctagata gttagttcta    480
cagctctctt ttgtagtctt gttagagagt tagttgagat attacctctt aaaagtatcc    540
ttgaacgctt tccggttatg accaatttgt tgtagctcct tgtaagtaga acttactggg    600
accagcgaga cagtttatgt gaatgttcat gcttaagtgt cgaacgtatc tatctctact    660
atagctctgt agtcttgtta gacagttagt tttatatctc catttttttg tagtcttgct    720
agttgagata ttacctcttc tcttcaaagt atccttgaac gctcaccggt tatgaaatct    780
ctacactata gctctgtagt cttgctagat agttagttct ttagctctct ttttgtagcc    840
tagttctttta gctctccttt tgtagccttg ctacagagta agatgggata ttacctcctt    900
gaacgctctc cggttatgac caatttgttt tagctccttg taagtagaac ttaggataga    960
gtgagtcaac tttaagaaag aacctagtat gtggcataac cagattgcag gctctgtctc   1020
ggctacagta acgtaactct atagctcttt gttttgttca gaaagaacca gtgattggat   1080
gattcgtcct tagaaactgg acctaacaac agtcattggc tttgaaatca agccacaaca   1140
atgcctatat gaaccgtcca tttcatttat ccgtttcaaa ccagcccatt acatttcgtc   1200
ccattgataa ccaaaagcgg ttcaatcaga ttatgttttta attttaccaa attctttatg   1260
aagtttaaat tatactcaca ttaaaaggat tattggataa tgtaaaaatt ctgaacaatt   1320
actgattttg gaaaattaac aaatattctt tgaaatagaa gaaaaagcct ttttcctttt   1380
gacaacaaca tataaaatca tactcccatt aaaaagattt taatgtaaaa ttctgaatat   1440
aagatatttt ttacaacaac aaccaaaaat attttattttt ttcctttttt acagcaacaa   1500
gaaggaaaaa ctttttttttt tgtcaagaaa aggggagatt atgtaaacag ataaaacagg   1560
gaaaataact aaccgaactc tcttaattaa catcttcaaa taaggaaaat tatgatccgc   1620
atatttagga agatcaatgc attaaaacaa cttgcacgtg gaaagagaga ctatacgctc   1680
cacacaagtt gcactaatgg tacctctcac aaaccaatca aaatactgaa taatgccaac   1740
gtgtacaaat taggtgttttta cctcacaacc atcgaacatt ctcgaaacat tttaaacagc   1800
ctggcgccat agatctaaac tctcatcgac caatttttga ccgtccgatg gaaactctag   1860
cctcaaccca aaactctata taagaaatc ttttccttcg ttattgctta ccaaatacaa   1920
accctagccg ccttattcgt cttcttcgtt ctctagtttt ttcctcagtc tctgttctta   1980
gatcccttgt agtttccaaa tcttccgata aggcct                              2016

SEQ ID NO: 78            moltype = DNA   length = 857
FEATURE                  Location/Qualifiers
misc_feature             1..857
                         note = Ceres Promoter PD1367
unsure                   116
                         note = n is a, c, t, g, unknown, or other
unsure                   136
                         note = n is a, c, t, g, unknown, or other
unsure                   154
                         note = n is a, c, t, g, unknown, or other
unsure                   159
                         note = n is a, c, t, g, unknown, or other
unsure                   168
                         note = n is a, c, t, g, unknown, or other
unsure                   172
                         note = n is a, c, t, g, unknown, or other
unsure                   175
                         note = n is a, c, t, g, unknown, or other
unsure                   679
                         note = n is a, c, t, g, unknown, or other
unsure                   680
                         note = n is a, c, t, g, unknown, or other
unsure                   686
                         note = n is a, c, t, g, unknown, or other
unsure                   724
                         note = n is a, c, t, g, unknown, or other
unsure                   737
                         note = n is a, c, t, g, unknown, or other
source                   1..857
                         mol_type = unassigned DNA
                         organism = Arabidopsis thaliana
SEQUENCE: 78
ttggaattaa ttctgcggcc atggggctgc aggaattcga tggcccgatc ggccacagtt     60
ttcttttctc atcttacaac aagtttccag gaggatagag acataaacga agctcngat    120
tgtatcgttc tttttnagct tttattcaca tccngaaang tcctgtangt tntangattc    180
tgttatcttg cggttttgag ttaatcagaa acagagtaat caatgtaatg ttgcaggcta    240
gatctttcat ctttgaaat ttgtttttt ctcatgcaat ttcttttagct tgaccatgag    300
tgactaaaag atcaatcagt agcaatgatt tgatttggct aagagacatt tgtccacttg    360
gcatcttgat ttggatggtt acaacttgca agacccaatt ggatacttgc tatgacaact    420
ccaactcaag agtgtcgtgt aactaagaac cttgactaat ttgtaatttc aatcccaagt    480
catgttacta tatgttttt tgtttgtatt atttttctctc ctacaattaa gctctttaga    540
gtacgtaatc tccggaacca actcctatat ccaccattta ctccacgttg tctccaatta    600
ttggacgttg aaacttgaca caacgtaaac gtatctacgt ggttgattgt atgtacatat    660
gtacaaacgt acaccctttnn ctcctncttt cacttcatca cttggcttgt gaattcatta    720
attncctgcg aaggccntgc agggccatca ccactgcagt ggaacaatga agactaatct    780
ttttctcttt ctcatctttt cacttctcct atcattatcc tcggccgaat tcagtaaagg    840
agaagaactt ttcactg                                                   857

SEQ ID NO: 79            moltype = DNA   length = 1032
FEATURE                  Location/Qualifiers
misc_feature             1..1032
```

|  |  |  |
|---|---|---|
|  | note = Ceres CLONE ID no. 8686 |  |
| misc_feature | 1..1032 |  |
|  | note = Ceres Seed Line ID no. ME03807 |  |
| misc_feature | 1..1032 |  |
|  | note = Encodes the peptide given in SEQ ID NO: 80 |  |
| source | 1..1032 |  |
|  | mol_type = unassigned DNA |  |
|  | organism = Arabidopsis thaliana |  |

SEQUENCE: 79
```
aaaaaaacac tagtatcaaa aattgaaccc gttaaccggc gacccgaaac aatgacccgg     60
tccgtcagtt tccctctctt cctcttcgcc gttgtactct ccctctcttc ttctctcctc    120
gccgacgatc ccaaaccaat ccgccgtgag gtctacgaag gaggtaagat atacgacatc    180
agccatcgtt acacgccgga gattccagct tgggaatctt cggaaggatt gggaaagacg    240
ttcctgcgat tagccgcgag tatgaagaat ggatcctcg ctaacgtatc ggagatgaaa     300
ctatctgttc actctggaac tcacgtggat gctccaggtc acttttggga taattattac    360
gatgctggtt ttgatactga ttcgcttgat ctccaagtcc taaatggtcc tgctttgttg    420
gttgatgttc cgagagataa gaacattact gctgaggtaa tggaatcact tcatatacaa    480
agaggagttc gtcgtgtgct ctttagaaca tccaacaccg acaagcggct tatgtttaag    540
aaagagtttg attcaagctt tgctgggttc atgaccgatg gggctaaatg gttggttgag    600
aatacagaca tcaaacttat tgggcttgat tatctttcat ttgctgcttt tgaggaatca    660
cctgcaacac acagggttat acttaaagga cgggatataa tcccagtgga agcgctgaag    720
ctggatggtg tggaggtagg aacatactcg cttcattgct taccgctgga attagtttga    780
gcggaaggag caccgacaag atgcattctc atcaagtgat tcagttcttc ttcttcttct    840
tcttcttctg tgtaagttgt tcagtatacc aaactgataa tgaataatat gcttcttact    900
ttacaagatc tcagaaccca tgaagcagat gtgatgattc agttgtaaaa ggaagcatac    960
ctttataaac gtgtgaatgt attatgtatg acagtatatt tgtaattctg aaggacatga   1020
taataaacct ag                                                       1032
```

|  |  |  |
|---|---|---|
| SEQ ID NO: 80 | moltype = AA  length = 255 |  |
| FEATURE | Location/Qualifiers |  |
| REGION | 1..255 |  |
|  | note = Ceres CLONE ID no. 8686 |  |
| REGION | 1..255 |  |
|  | note = Ceres Seed Line ID no. ME03807 |  |
| REGION | 40..241 |  |
|  | note = Pfam Name: Cyclase Pfam Description: Putative cyclase |  |
| source | 1..255 |  |
|  | mol_type = protein |  |
|  | organism = Arabidopsis thaliana |  |

SEQUENCE: 80
```
MTRSVSFPLF LFAVVLSLSS SLLADDPKPI RREVYEGGKI YDISHRYTPE IPAWESSEGL     60
GKTFLRLAAS MKNGSFANVS EMKLSVHSGT HVDAPGHFWD NYYDAGFDTD SLDLQVLNGP    120
ALLVDVPRDK NITAEVMESL HIQRGVRRVL FRTSNTDKRL MFKKEFDSSF AGFMTDGAKW    180
LVENTDIKLI GLDYLSFAAF EESPATHRVI LKGRDIIPVE ALKLDGVEVG TYSLHCLPLR    240
LVGAEGAPTR CILIK                                                    255
```

|  |  |  |
|---|---|---|
| SEQ ID NO: 81 | moltype = AA  length = 204 |  |
| FEATURE | Location/Qualifiers |  |
| REGION | 1..204 |  |
|  | note = Ceres CLONE ID no. 1096546 |  |
| REGION | 1..185 |  |
|  | note = Pfam Name: Cyclase Pfam Description: Putative cyclase |  |
| REGION | 1..204 |  |
|  | note = Functional Homolog of Ceres CLONE ID no. 8686 at SEQ ID NO. 80 with e-value of 8.19E-91 and BLAST sequence identity of 87.2 |  |
| VARIANT | 88 |  |
|  | note = Xaa is any aa, unknown or other |  |
| VARIANT | 99 |  |
|  | note = Xaa is any aa, unknown or other |  |
| VARIANT | 134 |  |
|  | note = Xaa is any aa, unknown or other |  |
| VARIANT | 152 |  |
|  | note = Xaa is any aa, unknown or other |  |
| VARIANT | 171 |  |
|  | note = Xaa is any aa, unknown or other |  |
| VARIANT | 194 |  |
|  | note = Xaa is any aa, unknown or other |  |
| VARIANT | 196 |  |
|  | note = Xaa is any aa, unknown or other |  |
| VARIANT | 200 |  |
|  | note = Xaa is any aa, unknown or other |  |
| source | 1..204 |  |
|  | mol_type = protein |  |
|  | organism = Brassica napus |  |

SEQUENCE: 81
```
MPAWESKEGL SNHLRLIASM KNGSFANVSE MKLSVHSGTH VDAPGHFIDE YYDAGFDCDS     60
LDLQTLNGPA LLVDVPRDKN ITAEVMEXLH IPRGVRRVXF RTSNTDKRLM FKKEFDSSFS    120
GFMTDGAKWL VENXDIKLVG LDYLSFAAFD EXPATHKVIL RGRDIIPVEA XKLDGVEAGM    180
```

```
YSLHCLPLRL VGAXGXPTRX ILIK                                       204

SEQ ID NO: 82           moltype = AA  length = 157
FEATURE                 Location/Qualifiers
REGION                  1..157
                        note = Ceres CLONE ID no. 1311812
REGION                  1..157
                        note = Functional Homolog of Ceres CLONE ID no. 8686 at SEQ
                          ID NO. 80 with e-value of 2.60E-64 and BLAST sequence
                          identity of 86.7
REGION                  13..141
                        note = Pfam Name: Cyclase Pfam Description: Putative cyclase
VARIANT                 37
                        note = Xaa is any aa, unknown or other
VARIANT                 58
                        note = Xaa is any aa, unknown or other
source                  1..157
                        mol_type = protein
                        organism = Brassica napus
SEQUENCE: 82
MDKVLTNAGF DSDSLDLQVL HGPALLVDVP RDKNITXVMK SLHIPKGVRR VLFRTLNXDR   60
RLMFKKEEFDS SFAGFMMDGA KWLVENTDIK LIGLDYLSFA AYEEAPETHK FILGERDIIP 120
VEALKLDGVE VGVYSLHCLP LRLPGAEGAP TRCILIK                          157

SEQ ID NO: 83           moltype = AA  length = 204
FEATURE                 Location/Qualifiers
REGION                  1..204
                        note = Ceres CLONE ID no. 952461
REGION                  1..204
                        note = Functional Homolog of Ceres CLONE ID no. 8686 at SEQ
                          ID NO. 80 with e-value of 1.79E-88 and BLAST sequence
                          identity of 85.7
REGION                  1..182
                        note = Pfam Name: Cyclase Pfam Description: Putative cyclase
VARIANT                 76
                        note = Xaa is any aa, unknown or other
VARIANT                 77
                        note = Xaa is any aa, unknown or other
VARIANT                 78
                        note = Xaa is any aa, unknown or other
VARIANT                 88
                        note = Xaa is any aa, unknown or other
VARIANT                 99
                        note = Xaa is any aa, unknown or other
VARIANT                 134
                        note = Xaa is any aa, unknown or other
VARIANT                 152
                        note = Xaa is any aa, unknown or other
VARIANT                 171
                        note = Xaa is any aa, unknown or other
VARIANT                 194
                        note = Xaa is any aa, unknown or other
VARIANT                 196
                        note = Xaa is any aa, unknown or other
VARIANT                 200
                        note = Xaa is any aa, unknown or other
source                  1..204
                        mol_type = protein
                        organism = Brassica napus
SEQUENCE: 83
MPAWESKEGL SNHLRLIASM KNGSFANVSE MKLSVHSGTH VDAPGHFIDE YYDAGFDCDS   60
LDLQTLNGPA LLVDVXXXKN ITAEVMEXLH IPRGVRRVXF RTSNTDKRLM FKKEFDSSFS  120
GFMTDGAKWL VENXDIKLVG LDYLSFAAFD EXPATHKVIL RGRDIIPVEA XKLDGVEAGM  180
YSLHCLPLRL VGAXGXPTRX ILIK                                        204

SEQ ID NO: 84           moltype = AA  length = 233
FEATURE                 Location/Qualifiers
REGION                  1..233
                        note = Ceres CLONE ID no. 954851
REGION                  1..233
                        note = Functional Homolog of Ceres CLONE ID no. 8686 at SEQ
                          ID NO. 80 with e-value of 4.70E-95 and BLAST sequence
                          identity of 80.4
REGION                  20..216
                        note = Pfam Name: Cyclase Pfam Description: Putative cyclase
VARIANT                 112
                        note = Xaa is any aa, unknown or other
VARIANT                 113
                        note = Xaa is any aa, unknown or other
```

```
VARIANT                 134
                        note = Xaa is any aa, unknown or other
source                  1..233
                        mol_type = protein
                        organism = Brassica napus
SEQUENCE: 84
MTSSDDLKPI RQEVYGERKI FDITHRYTQD MPVWESTEGV KPFLRLTTSM KNQSLSNTSE   60
MKLSVHTGTH LDAPGHFHDK YYDAGFDSDS LDLQVLHGPA LLVDVPRDKN IXXVMKSLHI  120
PKGVRRVLFR TLNXDRRLMF KKEFDSSFAG FMMDGAKWLV ENTDIKLIGL DYLSFAAYEE  180
APETHKFILG ERDIIPVEAL KLDGVEVGVY SLHCLPLRLP GAEGAPTRCI LIK         233

SEQ ID NO: 85           moltype = AA  length = 271
FEATURE                 Location/Qualifiers
REGION                  1..271
                        note = Ceres CLONE ID no. 1064137
REGION                  1..271
                        note = Functional Homolog of Ceres CLONE ID no. 8686 at SEQ
                         ID NO. 80 with e-value of 1.00E-90 and BLAST sequence
                         identity of 75.2
REGION                  57..257
                        note = Pfam Name: Cyclase Pfam Description: Putative cyclase
source                  1..271
                        mol_type = protein
                        organism = Zea mays
SEQUENCE: 85
MAVPPLLLLT LLSLPSLLIH AAISDAYPTI PGTAPIDGGF SDELKPIRRE VYGEGKIFDI   60
SHRYTPEMPA WESKEGIGRF LWLAASMKNG SLANNSEMKI PTHTGTHVDS PGHVYDEYYD  120
AGFDVDSLDL QVLNGPALLV DVPRNKNITA EVMKSLNIPR GVRRVLFRTL NTDRRLMFKK  180
EFDTSYVGFM KDGAQWLVDN TDIKLVGVDY LSVAAYDDLI PSHLVFLKGR ETILVEGLKL  240
DDVKAGVYSV HCLPLRLVGA EGSPIRCILI S                                271

SEQ ID NO: 86           moltype = AA  length = 121
FEATURE                 Location/Qualifiers
REGION                  1..121
                        note = Ceres CLONE ID no. 368629
REGION                  1..121
                        note = Functional Homolog of Ceres CLONE ID no. 8686 at SEQ
                         ID NO. 80 with e-value of 9.09E-37 and BLAST sequence
                         identity of 72.8
REGION                  1..103
                        note = Pfam Name: Cyclase Pfam Description: Putative cyclase
source                  1..121
                        mol_type = protein
                        organism = Zea mays
SEQUENCE: 86
MPEWESSEGS GEFLQLARSM RNGSDIANFS ELRLTAHSGT HVDAPGHVFE HYYDTGFDVD   60
TLDLAVLNGP ALLVDVPRDK NITADVMASL NMPKGVRRVL FRTLNTDRMV HNGWLIIQTS  120
N                                                                 121

SEQ ID NO: 87           moltype = AA  length = 205
FEATURE                 Location/Qualifiers
REGION                  1..205
                        note = Ceres CLONE ID no. 473732
REGION                  1..205
                        note = Functional Homolog of Ceres CLONE ID no. 8686 at SEQ
                         ID NO. 80 with e-value of 3.60E-74 and BLAST sequence
                         identity of 71.2
REGION                  1..191
                        note = Pfam Name: Cyclase Pfam Description: Putative cyclase
source                  1..205
                        mol_type = protein
                        organism = Glycine max
SEQUENCE: 87
MPVWDSTEGL GQHFLWLEKS MKNGSRANNS NMKLGVHTGT HVDAPGHFYD NYYDAGFDVD   60
SLDLTLLNGL ALLVDVPRDK NITAEVMKSL NIPRGVSRVL FRTLNTDRQL MFKKEFDTSY  120
VGFKEDGAKW LAENTDIKLV GVDYLSVAAY DHSIPSHLVF LESKEIILVE GKLDDVPAG  180
IYSLNCLPLR LVHSEASPIR CILIK                                       205

SEQ ID NO: 88           moltype = DNA  length = 831
FEATURE                 Location/Qualifiers
misc_feature            1..831
                        note = Ceres ANNOT ID no. 1441150
misc_feature            1..831
                        note = Encodes the peptide given in SEQ ID NO. 89
source                  1..831
                        mol_type = unassigned DNA
                        note = Populus balsamifera subsp. trichocarpa
                        organism = Populus balsamifera
SEQUENCE: 88
```

```
atggcatccc tcctcttgtt actgctcctg tctcccctct ccaccaccgc agcctccagc    60
ggcgcttacc ccaccatccc tggcagcata gacacctctt tccccgcttc acaagacagc   120
aaacttatcc caatcaggcg tgaggtgtat ggtgatggga gaatatttga cataacccac   180
aggtacacaa gcgacatgcc gtccatggga tcagaaaatg ggctgggtca gttcctgagg   240
ctccctgaaa gcatgaagaa tgggtccttc gccaacatat cggagatgaa gttgatcact   300
catactggca cacacgtcga tgcacctgga cattactatg atcattactt cgatgctggg   360
tttgatgtgg acactcttga ccttgaagta cttaatggtc ctggactatt aattgatgtt   420
ccaaggggga cgaacataac tgctgaagtt atgaagtcct tacatattcc caaaggagct   480
cgacgtgttc ttttcaggac agaaaatacc gacaggcgac ttatgttcaa aaatcagatc   540
gatacaagct ttgtgggatt tacaacggat ggagcaaaat ggttggtaga caacactgac   600
attaagcttg ttggaattga ttacttagct gttgctgctt ggagtgattt ggttccagct   660
catcttgtcc ttttggaaag cagggtgaga ctaatgcagt gtaaagaaat catcattgtg   720
gaaggcctaa aactcgatga catccaacct ggtgtgtatt ctatccattg tttgcctata   780
agattgctcg gtgctgaagg atcaccaacg cgatgcattc tcatcaaatg a            831
```

| SEQ ID NO: 89 | moltype = AA length = 211 |
|---|---|
| FEATURE | Location/Qualifiers |
| REGION | 1..211 |
| | note = Ceres ANNOT ID no. 1441150 |
| REGION | 1..211 |
| | note = Functional Homolog of Ceres CLONE ID no. 8686 at SEQ ID NO. 80 with e-value of 2.30E-72 and BLAST sequence identity of 68.6 |
| REGION | 13..197 |
| | note = Pfam Name: Cyclase Pfam Description: Putative cyclase |
| source | 1..211 |
| | mol_type = protein |
| | note = Populus balsamifera subsp. trichocarpa |
| | organism = Populus balsamifera |

SEQUENCE: 89
```
MPSMGSENGL GQFLRLPESM KNGSFANISE MKLITHTGTH VDAPGHYYDH YFDAGFDVDT    60
LDLEVLNGPG LLIDVPRGTN ITAEVMKSLH IPKGARRVLF RTENTDRRLM FKNQIDTSFV   120
GFTTDGAKWL VDNTDIKLVG IDYLAVAAWS DLVPAHLVLL ESRVRLMQCK EIIIVEGLKL   180
DDIQPGVYSI HCLPIRLLGA EGSPTRCILI K                                  211
```

| SEQ ID NO: 90 | moltype = AA length = 251 |
|---|---|
| FEATURE | Location/Qualifiers |
| REGION | 1..251 |
| | note = Ceres CLONE ID no. 554272 |
| REGION | 1..251 |
| | note = Functional Homolog of Ceres CLONE ID no. 8686 at SEQ ID NO. 80 with e-value of 1.90E-75 and BLAST sequence identity of 68.0 |
| REGION | 37..237 |
| | note = Pfam Name: Cyclase Pfam Description: Putative cyclase |
| source | 1..251 |
| | mol_type = protein |
| | organism = Glycine max |

SEQUENCE: 90
```
MNCYWWHALI MSGCVLGLCV GIGGCVCVVE NENGRIIIDI SHRYHPDMPA WESKDSLGQF    60
LWLTRSMANG SLANFSQFKL PAHSGTHVDA PGHVFDHYFH SGFDVDSLDL LLLNGPALLV   120
DVPRDTNISA GVMKSLNIPR GVRRVLFRTL NTYRRLMYQK EFDTSYVGFT EDGANWLVEN   180
TDIKLVGIDY LSVAAYDHLI PAHLVFLKGR EIILVEGLKL DDVAAGIYTV HCLPLRLAGA   240
EGSPIRCILI K                                                        251
```

| SEQ ID NO: 91 | moltype = AA length = 255 |
|---|---|
| FEATURE | Location/Qualifiers |
| REGION | 1..255 |
| | note = Ceres CLONE ID no. 511015 |
| REGION | 1..255 |
| | note = Functional Homolog of Ceres CLONE ID no. 8686 at SEQ ID NO. 80 with e-value of 1.40E-81 and BLAST sequence identity of 66.3 |
| REGION | 40..240 |
| | note = Pfam Name: Cyclase Pfam Description: Putative cyclase |
| source | 1..255 |
| | mol_type = protein |
| | organism = Glycine max |

SEQUENCE: 91
```
MKRGALLSVL ACAFAAVIWA ANGDDNLVPP RREVYGNGRI FDISHRYQPE MPEWESNDGI    60
GQFLWLPKSM KNGSLANNSE MKFPTHTGTH VDAPGHVFDH YFHAGFDVDT LDLDILNGPA   120
MLVDVPRDSN ITAQVMKSLN IPRGVIRVLF RTLNTDRRLM FQKEWDSSYV GFTADGAKWL   180
VENTDIKLVG IDYLSVASYD YLIPSHLVFL KDREIILVEG LKLDDVPAGL YSVHCLPLRL   240
AGAEGSPIRC ILIKN                                                    255
```

| SEQ ID NO: 92 | moltype = AA length = 265 |
|---|---|
| FEATURE | Location/Qualifiers |
| REGION | 1..265 |
| | note = Ceres CLONE ID no. 881632 |

| | | |
|---|---|---|
| REGION | 1..265 | |
| | note = Functional Homolog of Ceres CLONE ID no. 8686 at SEQ ID NO. 80 with e-value of 2.10E-78 and BLAST sequence identity of 66.3 | |
| REGION | 51..251 | |
| | note = Pfam Name: Cyclase Pfam Description: Putative cyclase | |
| source | 1..265 | |
| | mol_type = protein | |
| | organism = Triticum aestivum | |

SEQUENCE: 92
```
MAPPLLLLLL VPLVAATAPC AHPAHPSQPA SCAAEPVLAP ERREAHGGGR ILDITHYYRE    60
DMPSWESGAG VGQFLWLPAS MRNGSLANNS EMRMPTHTGT HIDASGHVFQ HYFDAGFDVD   120
TLDLDVLNGP ALLVDVPRDE NITAKTMESL HIPKGVQRVL FRTLNTDRNL MWKKEFDTSY   180
VGFMKDGAQW LVDNTDIKLV GIDYLSVAAF DDLIPSHLVL LENRDIILVE GLKLENVIPG   240
IYSLHCLPLR LRGAEGSPIR CILIK                                         265
```

| | | |
|---|---|---|
| SEQ ID NO: 93 | moltype = AA length = 269 | |
| FEATURE | Location/Qualifiers | |
| REGION | 1..269 | |
| | note = Functional Homolog of Ceres CLONE ID no. 8686 at SEQ ID NO. 80 with e-value of 1.40E-79 and BLAST sequence identity of 66.2 | |
| REGION | 55..255 | |
| | note = Pfam Name: Cyclase Pfam Description: Putative cyclase | |
| source | 1..269 | |
| | mol_type = protein | |
| | note = Oryza sativa subsp. japonica | |
| | organism = Oryza sativa | |

SEQUENCE: 93
```
MAHLAPLFLL LLLLLLPLHA AATPSAHPAY PNEPPSCAAA VPVPERREAH GGGRILDITH    60
YYREDMPSWE SDGGVGQFLW LPASMRNGSR ANNSEMRLPT HTGTHVDAPG HVFQHYFDAG   120
FDVDSLDLEV LNGLALLVDV PRDDNITAKM MESLHIPKGI QRVLFRTLNT DRQLMWKKEF   180
DTSYVGFMED GAQWLVDNTD IKLVGIDYLS VAAFDDLIPS HLVLLKNRDI ILVEGLKLEN   240
IMPGIYSLHC LPLRLRGAEG SPIRCILIK                                     269
```

| | | |
|---|---|---|
| SEQ ID NO: 94 | moltype = DNA length = 825 | |
| FEATURE | Location/Qualifiers | |
| misc_feature | 1..825 | |
| | note = Ceres ANNOT ID no. 1494052 | |
| misc_feature | 1..825 | |
| | note = Encodes the peptide given in SEQ ID NO. 95 | |
| source | 1..825 | |
| | mol_type = unassigned DNA | |
| | note = Populus balsamifera subsp. trichocarpa | |
| | organism = Populus balsamifera | |

SEQUENCE: 94
```
atgtccacca ccaaaaccat gatccctctc ctcctcctcc tcctcctctc tccctctcc    60
accaccgctt ctaccgccgc ctaccccaca atcccgggca ccatagacac ctcagtctcc   120
tcctcccaac ccgacaacct gattccaatc cgcaacgaaa tctacggcaa tggtaaaatc   180
tttgacataa gtcacagata cataaacgat atgccggttt gggactctaa agacgggttg   240
ggaaagttcc tgtcttttac cagcaagcatg aaaaatggct ctctcgctaa caactcagaa   300
atgaagttac ctactcatac tggcacgcat gttgactcac ctggacatgt ttttgatcat   360
tactttgatt ctgggttcga tgttgatact cttgatcttg aagtccttaa tggtcctgct   420
ttgctagtgg atgttccaag gcattccaat ataactgctg aagttatgaa gtccttacac   480
attccaaagg gagtgcgtcg cgtgcttttc agaacactaa acactgacag gcggcttatg   540
ttcaaaaggg agtttgatag aagttatgtg gggttcacaa aggatggtgc aaaatggttg   600
gtagacaaca ctgacatcaa gcttgttgga attgattacc tatctgttgc tgcctcagagt   660
gatttgattc catctcatct tgtctttcta gaaggcaggg aaatcatcct tgtggaggct   720
ttaaaactgg atgacatcca acctggagta tattctgtcc attgtttacc cctgaggttg   780
tttggcgccg agggatctcc aataagatgc gttctcatca aatga               825
```

| | | |
|---|---|---|
| SEQ ID NO: 95 | moltype = AA length = 274 | |
| FEATURE | Location/Qualifiers | |
| REGION | 1..274 | |
| | note = Ceres ANNOT ID no. 1494052 | |
| REGION | 1..274 | |
| | note = Functional Homolog of Ceres CLONE ID no. 8686 at SEQ ID NO. 80 with e-value of 4.30E-85 and BLAST sequence identity of 65.6 | |
| REGION | 60..260 | |
| | note = Pfam Name: Cyclase Pfam Description: Putative cyclase | |
| source | 1..274 | |
| | mol_type = protein | |
| | note = Populus balsamifera subsp. trichocarpa | |
| | organism = Populus balsamifera | |

SEQUENCE: 95
```
MSTTKTMIPL LLLLLLSPLS TTASTAAYPT IPGTIDTSVS SSQPDNLIPI RNEIYGNGKI    60
FDISHRYIND MPVWDSKDGL GKFLSLPASM KNGSLANNSE MKLPTHTGTH VDSPGHVFDH   120
YFDSGFDVDT LDLEVLNGPA LLVDVPRHSN ITAEVMKSLH IPKGVRRVLF RTLNTDRRLM   180
```

```
FKREFDRSYV GFTKDGAKWL VDNTDIKLVG IDYLSVAAWS DLIPSHLVFL EGREIILVEA    240
LKLDDIQPGV YSVHCLPLRL FGAEGSPIRC VLIK                              274

SEQ ID NO: 96           moltype = DNA  length = 1005
FEATURE                 Location/Qualifiers
misc_feature            1..1005
                        note = Ceres ANNOT ID no. 1441151
misc_feature            1..1005
                        note = Encodes the peptide given in SEQ ID NO. 97
source                  1..1005
                        mol_type = unassigned DNA
                        note = Populus balsamifera subsp. trichocarpa
                        organism = Populus balsamifera
SEQUENCE: 96
atgtccacca ccaaaaccat gatccctctc ctcctcctcc tcctcctctc tccctctcc    60
accaccgctt ctaccgccgc taccccaca atcccgggca ccatagacac ctcagtctcc   120
tcctcccaac ccgacaacct gattccaatc cgcaacgaaa tctacggcaa tggtaaaatc   180
tttgacataa gtcacagata cataaacgat atgccggttt gggactctaa agacgggttg   240
ggaaagttcc tgtctttacc agcaagcatg aaaaatgggt ctctcgctaa caactcagaa   300
atgaagttac ctactcatac tggcacgcat gttgactcac ctggacatgt ttttgatcat   360
tactttgatt ctgggttcga tgttgatact cttgatcttg aagtccttaa tggtcctgct   420
ttgctagtgg atgttccaag gcattccaat ataactgctg aagttatgaa gtccttacac   480
attccaaagg gagtgcgtcg cgtgcttttc agaacactaa acactgacag gcggcttatg   540
ttcaaaaggg agtttgatag aagttatgtg gggttcacaa aggatggtgc aaaatggttg   600
gtagacaaca ctgacatcaa gcttgttgga attgattacc tatctgttgc tgcctggagt   660
gatttgattc catctcatct tgtctttcta gaaggcaggg aaatcatcct tgtggagct    720
ttaaaactgg atgacatcca acctggagta tattctgtcc attgtttacc cctgaggatc   780
ctttattcac acttgttcaa tgctgctacc agctcacatg ccacaccatg gcacaacagg   840
caagatacaa tctaccacaa caaaagccta ctgtttatcc cacgtgaatt gtctggtcag   900
aaaggatcac aaacagaggc cagtgactca aatttaggcg ggcgcttcat tgactggcaa   960
gtggcaacag aaaccttcca cgacccagga tcagtgcttg tatag                 1005

SEQ ID NO: 97           moltype = AA  length = 334
FEATURE                 Location/Qualifiers
REGION                  1..334
                        note = Ceres ANNOT ID no. 1441151
REGION                  1..334
                        note = Functional Homolog of Ceres CLONE ID no. 8686 at SEQ
                         ID NO. 80 with e-value of 6.10E-79 and BLAST sequence
                         identity of 64.5
REGION                  60..260
                        note = Pfam Name: Cyclase Pfam Description: Putative cyclase
source                  1..334
                        mol_type = protein
                        note = Populus balsamifera subsp. trichocarpa
                        organism = Populus balsamifera
SEQUENCE: 97
MSTTKTMIPL LLLLLLSPLS TTASTAAYPT IPGTIDTSVS SSQPDNLIPI RNEIYGNGKI    60
FDISHRYIND MPVWDSKDGL GKFLSLPASM KNGSLANNSE MKLPTHTGTH VDSPGHVFDH   120
YFDSGFDVDT LDLEVLNGPA LLVDVPRHSN ITAEVMKSLH IPKGVRRVLF RTLNTDRRLM   180
FKREFDRSYV GFTKDGAKWL VDNTDIKLVG IDYLSVAAWS DLIPSHLVFL EGREIILVEA   240
LKLDDIQPGV YSVHCLPLRI LYSHLFNAAT SSHATPWHNR QDTIYHNKSL LFIPRELSGQ   300
KGSQTEASDS NLGGRFIDWQ VATETFHDPG SVLV                              334

SEQ ID NO: 98           moltype = DNA  length = 1888
FEATURE                 Location/Qualifiers
misc_feature            1..1888
                        note = Synthesized Sequence
misc_feature            1..1888
                        note = Ceres CDNA ID no. 23799376
misc_feature            1..1888
                        note = Ceres Clone ID no. 375578
misc_feature            1..1888
                        note = Ceres Seed Line ID no. ME02064
misc_feature            1..1888
                        note = Encodes the peptide given in SEQ ID NO. 99
misc_feature            1..1888
                        note = Encodes the peptide given in SEQ ID NO. 180
source                  1..1888
                        mol_type = other DNA
                        organism = synthetic construct
SEQUENCE: 98
cccggtttat ttttcttcg tcctggatgc gtcggtcgcg tgtttgatct gactaagccg     60
cggaggaggg tgctagatgt ccgtgcggtg ggcggtggct ccgaggggcg accggagtta   120
ggtccttgcc gccttcagtg cggtggggaa gcgagacatt gaaggcgcag aacccaaaga   180
atgggtaaga gaggaaagtg gtttagtgcg gtgaagaaag tcttcagctc ctccgatcca   240
gatgaaaggg aagccaaggc ccagaaggca gacaaatcga aatccaagag agatggcca    300
tttgaaagt ccaagcactc ggagccttcc atatcgacgg tgccaggcac tgctccagca   360
gtagctccgt tgccatcacc accagcaact cagccccact ctctggagat caaagatgtc   420
```

```
aatccagttg aaacagacag tgagcagaac aagcatgcct actccgttgc gcttgcgtct    480
gctgtcgctg ctgaagctgc agcagttgct gcccaggctg ctgcggaagt tgtccgcctc    540
acagcagtta ccacggctgc accaaagatg cctgttagtt cgagggaata acttgccgcc    600
accaagattc agactgcctt cagggggttat ctggcaagga gagcattgcg tgcactaaga    660
gggctagtta gattgaagtc gcttgttgat ggaaatgctg tcaaacgcca aaccgctcac    720
accttgcaat gcacacaagc aatgacaaga gttcaaactc aaatctactc tagaagggtg    780
aagttggagg aggagaaaca ggctcttcaa agacaactcc aattgaaaca tcaaagggaa    840
cttgagaaaa tgaagattga tgaagattgg gatcacagcc atcaatccaa agagcaaatt    900
gaggccaacc taatgatgaa acaggaagct gcactgaggc gagagagagc acttgcatat    960
gcattttctc accagtggag gaattctggt cgaactataa cccctacttt tacggaacct   1020
gggaaccccca actggggctg gagctggatg gagcgctgga tgacagcaag accatgggag   1080
agtcggttgg cggcggcatc ggacaaggac cctaaagaac gtgctgtgac aaagaatgcg   1140
agcaccagtg ctgttcgagt acctgtatcc cgtgccatct cgattcagag accagcaaca   1200
ccaaacaagt cgagccgccc accaagccgg cagtcacttt caaccccgcc atcgaagacc   1260
ccgtcagcct caggaaaggc caggccggca agtccaagga acagttggct gtacaaggag   1320
gatgacctga ggagcatcac gagcatccgc tccgagcgcc caaggaggca gagcacgggt   1380
ggaggctcgg tccgggacga taccagcctg accagcacac cacctctccc cagctacatg   1440
cagtcgaccg agtctgcacg ggccaagtct cggtaccgca gtctactact gactgagaag   1500
cttgaggttc ctgagagagc gcctctggcc cactccgttg tcaagaagcg cctgtcgttc   1560
cccgtcgtcg agaagccaag cgttgtgccg acagagaagc ccagggaaag agtgaggcgc   1620
cattccgacc ctccgaaggt cgatcctgcg acgctcaagg atgcccctgc tgcctgacca   1680
gtgaccaggc cttatgtgat tgttaggttt cgtgctcttt taacaccgtg atgtattatc   1740
tgagttaggt tgctttgttc gtgtcatcgt atgatctgtc cgggttgatt ttgagacagt   1800
tctaactgtg tttacagaca atgcgtgatg ctaaatgtat gtgtggttgg ttggctttaa   1860
atgtactgat atgatagtat ttgatttc                                       1888

SEQ ID NO: 99            moltype = AA  length = 311
FEATURE                  Location/Qualifiers
REGION                   1..311
                         note = Synthesized Sequence
REGION                   1..311
                         note = Ceres CDNA ID no. 23799376
REGION                   1..311
                         note = Ceres Clone ID no. 375578
REGION                   1..311
                         note = Ceres Seed Line ID no. ME02064
source                   1..311
                         mol_type = protein
                         organism = synthetic construct
SEQUENCE: 99
MTRVQTQIYS RRVKLEEEKQ ALQRQLQLKH QRELEKMKID EDWDHSHQSK EQIEANLMMK     60
QEAALRRERA LAYAFSHQWR NSGRTITPTF TEPGNPNWGW SWMERWMTAR PWESRLAAAS    120
DKDPKERAVT KNASTSAVRV PVSRAISIQR PATPNKSSRP PSRQSLSTPP SKTPSASGKA    180
RPASPRNSWL YKEDDLRSIT SIRSERPRRQ STGGGSVRDD TSLTSTPPLP SYMQSTESAR    240
AKSRYRSLLL TEKLEVPERA PLAHSVVKKR LSFPVVEKPS VVPTEKPRER VRRHSDPPKV    300
DPATLKDAPA A                                                         311

SEQ ID NO: 100           moltype = AA  length = 500
FEATURE                  Location/Qualifiers
REGION                   1..500
                         note = Functional Homolog of Ceres Clone ID no. 375578 at
                         SEQ ID NO. 252 with e-value of 2.59E-135 and BLAST
                         sequence identity of 83.4
REGION                   142..162
                         note = Pfam Name: IQ Pfam Description: IQ
                         calmodulin-binding motif
source                   1..500
                         mol_type = protein
                         note = Oryza sativa subsp. japonica
                         organism = Oryza sativa
SEQUENCE: 100
MGKKGNWFSA VKKVFSSSDP DGREAKIEKA DKSRSRRKWP FGKSKKSDPW TSTVAVPTST     60
APPPQPPPPP PTHPIQPQPE EIKDVKAVET DSEQNKHAYS VALASAVAAE AAAVAAQAAA    120
EVVRLTTATT AVPKSPVSSK DELAAIKIQT AFRGYLARRA LRALRGLVRL KSLVDGNAVK    180
RQTAHTLHCT QTMRVQTQI YSRRVKMEEE KQALQRQLQL KHQRELEKMK IDEDWDHSHQ    240
SKEQVETSLM MKQEAALRRE RALAYAFSHQ WKNSGRTITP TFTDQGNPNW GWSWMERWMT    300
SRPWESRVIS DKDPKDHYST KNPSTSASRT YVPRAISIQR PATPNKSSRP PSRQSPSTPP    360
SRVPSVTGKI RPASPRDSWL YKEDDLRSIT SIRSERPRRQ STGGASVRDD ASLTSTPALP    420
SYMQSTESAR AKSRYRSLLT DRFEVPERVP LVHSSIKKRL SFPVADKPNG EHADKLMERG    480
RRHSDPPKVD PASLKDVPVS                                                500

SEQ ID NO: 101           moltype = DNA  length = 1470
FEATURE                  Location/Qualifiers
misc_feature             1..1470
                         note = Ceres ANNOT ID no. 1465047
misc_feature             1..1470
                         note = Encodes the peptide given in SEQ ID NO. 102
source                   1..1470
                         mol_type = unassigned DNA
```

```
                        note = Populus balsamifera subsp. trichocarpa
                        organism = Populus balsamifera
SEQUENCE: 101
atggggaaaa    gagggagttg    gttctctgct    ttgaagaaag    ccctcggttc    ctctaagaaa    60
tccaaatcaa    agaagaaatg    gtcagaaaaa    gagaagaacc    gggatctagg    tgtttcttca    120
catgaagaaa    ccgttgcacc    ctctctttct    cctcctcgta    caccacctcc    tcctacagca    180
gaagatgtga    aattaactga    agctgagaac    gagcagagca    agcatgctta    ttccgtggcg    240
cttgccactg    ctgtggcagc    tgaggcagct    gttgcagccg    cccaggctgc    cgctgaggtt    300
gttcggctta    ctacagtggc    acattactct    ggaaaatcga    aggaggaaat    agctgcaatc    360
aggattcaaa    cagcatttag    aggatacctg    gcgaggaggg    cattacgtgc    tttgagaggg    420
ctggtgagat    tgaagtcatt    gatacaaggg    caatctgtca    aacggcaagc    aactgccaca    480
ttacgagcca    tgcagactct    tgctcgtgtg    cagtctcaga    ttcgtgcaag    aaggatcaga    540
atgtccgagg    aaaatgaggc    cctccaacgg    cagctccagc    agaaacatga    caaagaactt    600
gagaagttga    gaacttctat    tggagaacaa    tgggatgata    gcccacaatc    aaaggaagaa    660
gttgaagcca    gcctactaca    aaagcaagaa    gctgccatga    agagagaaag    ggcactggct    720
tatgcatact    cgcatcagca    aatgtggaag    caatcttcaa    aatcagcaaa    tgctacattc    780
atggatccaa    acaatcctcg    ttgggatgga    agttggttag    agaggtggat    ggcagcccga    840
ccttgggaga    gccgaagcac    aatagataac    aatgatcggg    cctctgttaa    gagtacaaca    900
agccgtacca    tgtctcttgg    agaaatcagc    agagcttatt    ctcgtcgtga    tcttaaccat    960
gacaataaag    cttctcctgg    tgcgcaaaaa    tcaagtcggc    ctcccagtcg    gcaatcacct    1020
tctactcccc    cctctaaggc    accatctaca    tcttcagtaa    cagggaaagc    aaagccacca    1080
agccctagag    ggagtgcttg    ggaggagac    gaggactcca    gcacacattc    cagtgtccag    1140
tctgagcgct    atcggagaca    tagcatagca    gggtcatcaa    taagagatga    tgagagtctt    1200
gcaagttcgc    cttcagttcc    aagttacatg    gcacccacac    ggtcacagtc    agcaaaggca    1260
aaatcccgct    tgtcaagccc    gttaggcata    gataataatg    gacaccaga    taaggcatca    1320
gtgggttatg    taaagaagcg    gctttccttc    tctgcttcac    cagctggagc    aaggagacac    1380
tctggtcctc    ctagggtgga    tgccagtgct    gttaaagaca    ttcaaatgca    cagagaagag    1440
aaaatgagca    atggagcaag    cagcaagtag                                              1470

SEQ ID NO: 102          moltype = AA  length = 489
FEATURE                 Location/Qualifiers
REGION                  1..489
                        note = Ceres ANNOT ID no. 1465047
REGION                  1..489
                        note = Functional Homolog of Ceres Clone ID no. 375578 at
                           SEQ ID NO. 252 with e-value of 3.29E-71 and BLAST sequence
                           identity of 56.8
REGION                  116..136
                        note = Pfam Name: IQ Pfam Description: IQ
                           calmodulin-binding motif
source                  1..489
                        mol_type = protein
                        note = Populus balsamifera subsp. trichocarpa
                        organism = Populus balsamifera
SEQUENCE: 102
MGKRGSWFSA    LKKALGSSKK    SKSKKKWSEK    EKNRDLGVSS    HEETVAPSLS    PPRTPPPPTA    60
EDVKLTEAEN    EQSKHAYSVA    LATAVAAEAA    VAAAQAAAEV    VRLTTVAHYS    GKSKEEIAAI    120
RIQTAFRGYL    ARRALRALRG    LVRLKSLIQQ    QSVKRQATAT    LRAMQTLARV    QSQIRARRIR    180
MSEENEALQR    QLQQKHDKEL    EKLRTSIGEQ    WDDSPQSKEE    VEASLLQKQE    AAMRRERALA    240
YAYSHQQMWK    QSSKSANATF    MDPNNPRWGW    SWLERWMAAR    PWESRSTIDN    NDRASVKSTT    300
SRTMSLGEIS    RAYSRRDLNH    DNKASPGAQK    SSRPPSRQSP    STPPSKAPST    SSVTGKAKPP    360
SPRGSAWGGD    EDSRSTFSVQ    SERYRRHSIA    GSSIRDDESL    ASSPSVPSYM    APTRSQAKA     420
KSRLSSPLGI    DNNGTPDKAS    VGYVKKRLSF    SASPAGARRH    SGPPRVDASA    VKDIQMHREE    480
KMSNGASSK                                                                         489

SEQ ID NO: 103          moltype = AA  length = 367
FEATURE                 Location/Qualifiers
REGION                  1..367
                        note = Ceres CLONE ID no. 474985
REGION                  1..367
                        note = Functional Homolog of Ceres Clone ID no. 375578 at
                           SEQ ID NO. 252 with e-value of 1.39E-63 and BLAST sequence
                           identity of 52.4
REGION                  11..31
                        note = Pfam Name: IQ Pfam Description: IQ
                           calmodulin-binding motif
source                  1..367
                        mol_type = protein
                        organism = Glycine max
SEQUENCE: 103
MPHYTGRTKE    EIAAIKVQTA    FRGYMARRAL    RALRGLVRLK    TLVQGQSVKR    QAASTLRSMQ    60
TLARLQSQIR    ERRIRMSEEN    QALQRQLHQK    HEKELEKLRA    AVGEEWDDSS    QSKEQIEAKL    120
LHRQEAALRR    ERALAYSFSH    QQTWKGSSKS    LNPTFMDPNN    PQWGWSWLER    WMATRPWDGH    180
STVVDHNDHA    SVKSAASRAV    SVGQITKLYS    LQDKKPSPFG    SKARRPAPQS    SHSKAPSTNG    240
KARPSSSTKG    SSVWGGDEDS    RSMFSVQSER    YRRHSIAGSS    VRDDDSRAST    PAIPSYMAAT    300
SSAKARSKII    RHSPEKKGGG    GSVSARKRLS    FSPSSAANSR    RHSDPPKVEM    VYNKDAAAT     360
VSNGRGR                                                                           367

SEQ ID NO: 104          moltype = AA  length = 378
```

| | | |
|---|---|---|
| FEATURE | Location/Qualifiers | |
| REGION | 1..378 | |
| | note = Ceres CLONE ID no. 826796 | |
| REGION | 1..378 | |
| | note = Functional Homolog of Ceres Clone ID no. 375578 at SEQ ID NO. 252 with e-value of 5.20E-57 and BLAST sequence identity of 50.3 | |
| REGION | 4..24 | |
| | note = Pfam Name: IQ Pfam Description: IQ calmodulin-binding motif | |
| source | 1..378 | |
| | mol_type = protein | |
| | organism = Triticum aestivum | |
| SEQUENCE: 104 | | |

```
MSRELAATKI QTAFRGHLAR RALRALKGLV RLKSLVQGHS VKRQATSTLR CMQTLSRVQS   60
KIRTRRIKMA EENQALQRQL LLNQELETLR MGDQWNTSLQ SKEQIEASLV SRQEAAARRE  120
RALAYAFSHQ WKSTSRSANP MFVDPSNPHW GWSWLERWMA SRPFDGRNGA SEKEGSSVDR  180
TSVHSTSLSM NLGEGETVTK ADNQVVDSLK PNDDKPPPLS TPKPSGPAPR QSPSTPSPAL  240
ARKKSATPKS GDCDGDDARS VVSTVRSERP RRHSIGASSV RDDAGSSPSV PSYMAATKSA  300
SARAKSRVQS PTLTEGAAQA ETLEKGWSSV GSAKKRLSFP AGTPPPVPAA AARRHSGPPK  360
VRQAGVEGGT EERDSSLA                                               378
```

| | | |
|---|---|---|
| SEQ ID NO: 105 | moltype = DNA length = 1366 | |
| FEATURE | Location/Qualifiers | |
| misc_feature | 1..1366 | |
| | note = Ceres CDNA ID no. 23363195 | |
| misc_feature | 1..1366 | |
| | note = Ceres Clone ID no. 105319 | |
| misc_feature | 1..1366 | |
| | note = Ceres Seed Line ID no. ME04074 | |
| misc_feature | 1..1366 | |
| | note = Encodes the peptide given in SEQ ID NO. 106 | |
| source | 1..1366 | |
| | mol_type = unassigned DNA | |
| | organism = Arabidopsis thaliana | |
| SEQUENCE: 105 | | |

```
aaattgttgt cttttaggtt ttgacagtag caaagaaaag ctgaatctag ttagaaattg    60
cttttgcagg gtttttgaat agtttgtgta ttgaagattg tctgaaatgg aagcagctat   120
tactcagagg attcagtacc catcatgggt tgattgtaga aaagttgagt gtaagccgca   180
gcgtggttca ttgcggtatt ctcagcaggt taaggtagat agaaggttta gaggtctttc   240
tttggctcgc ttgcaacctg aaagaagaat tgatcaacga agagcagttt ctccagcggt   300
ttcctgttct gataacaatt cctcagcgtt gttggagact ggaagtgttt atccatttga   360
tgaagatatt ctcaagagaa aagcagaaga ggttaaaccg tatttgaatg gacgatctat   420
gtaccttgtc ggaatgatgg gttctgggaa aacaactgtg ggaaagttaa tgtccaaagt   480
gctcggttat acgttctttg actgcgacac tttgattgaa caggcgatga atggaacttc   540
tgttgcagag atatttgttc atcacggaga gaattttttt agaggaaagg agaccgatgc   600
gcttaagaag ctctccttcga ggtatcaagt tgttgtttcc acaggtggga ggtcagttat   660
aagacccatt aactgaagt atatgcataa aggaatcagc atttggctag atgtgcctct   720
agaagcatta gcccatagaa tcgctgctgt tggaactgat tcacgaccac tgctacacga   780
tgaatcagga gatgcatact cagtggcttt caaacgtctc tcggctattt gggacgagcg   840
cggtgaagca tacacaaacg caaatgccag agtctcctta gaaaatattg cagcaaagcg   900
tggctataaa aatgtctcag atctcacacc aactgaaatt gtatcgagg ccttcgagca   960
agttctgagc tttctagaga agaaagaaac tatggagatc ccagacggcg acctctaatt  1020
tcccagcctt ctgttctccg tctcttcatt tatctgtttt atcaactaaa cgaagcaatc  1080
actcatcacc aggccattga gcaagttcag agacaaagaa gacctctagt tactggttcc  1140
gggtcattgg agcttacacg agcctaaattt tgactggaac tatggtttat tgaaagaaga  1200
ttcaatacat gtatatataa aatatatact ttttttttttg tttcagtatc atccttcttc  1260
tcttttcctt acaataagaa ttaaggaaaa gtagccgtgt ttgttaacat gggccaagaa  1320
caagcaaagt gatcattcaa atataaagt agctttctca tggaat                  1366
```

| | | |
|---|---|---|
| SEQ ID NO: 106 | moltype = AA length = 303 | |
| FEATURE | Location/Qualifiers | |
| REGION | 1..303 | |
| | note = Ceres CDNA ID no. 23363195 | |
| REGION | 1..303 | |
| | note = Ceres Clone ID no. 105319 | |
| REGION | 1..303 | |
| | note = Ceres Seed Line ID no. ME04074 | |
| REGION | 111..287 | |
| | note = Pfam Name: SKI Pfam Description: Shikimate kinase | |
| source | 1..303 | |
| | mol_type = protein | |
| | organism = Arabidopsis thaliana | |
| SEQUENCE: 106 | | |

```
MEAAITQRIQ YPSWVDCRKV ECKPQRGSLR YSQQVKVDRR FRGLSLARLQ PERRIDQRRA   60
VSPAVSCSDN NSSALLETGS VYPFDEDILK RKAEEVKPYL NGRSMYLVGM MGSGKTTVGK  120
LMSKVLGYTF FDCDTLIEQA MNGTSVAEIF VHHGENFFRG KETDALKKLS SRYQVVVSTG  180
GGAVIRPINW KYMHKGISIW LDVPLEALAH RIAAVGTDSR PLLHDESGDA YSVAFKRLSA  240
IWDERGEAYT NANARVSLEN IAAKRGYKNV SDLTPTEICI EAFEQVLSFL EKEETMEIPD  300
```

```
GDL                                                                                  303

SEQ ID NO: 107          moltype = AA  length = 249
FEATURE                 Location/Qualifiers
REGION                  1..249
                        note = Ceres CLONE ID no. 463638
REGION                  1..249
                        note = Functional Homolog of Ceres CLONE ID no. 105319 at
                        SEQ ID NO. 106 with e-value of 2.29E-79 and BLAST sequence
                        identity of 66.6
REGION                  60..236
                        note = Pfam Name: SKI Pfam Description: Shikimate kinase
source                  1..249
                        mol_type = protein
                        organism = Glycine max
SEQUENCE: 107
MMRRRTTALE VSCSYGNISA SILESGSVRA PLDEELILKN RSQEIQPYLN GRCIYLVGMM      60
GSGKTTVGKI MSQVLGYSFC DSDALVEEEV GGNSVADIFK QHGETFFRNK ETEVLHKLSL     120
MHQLVISTGG GAVTRPINWK YMHKGVSVWL DVPVEALAQR IAAVGTNSRP LLHYEAGDPY     180
TRAFMRLSAL FEERGEAYAN ANARVSLKNI AIKLGKRDVS ELSPTDIAIE ALEQIDNFLK     240
GEGGRYAEC                                                             249

SEQ ID NO: 108          moltype = DNA  length = 570
FEATURE                 Location/Qualifiers
misc_feature            1..570
                        note = Ceres ANNOT ID no. 1504048
misc_feature            1..570
                        note = Encodes the peptide given in SEQ ID NO. 109
source                  1..570
                        mol_type = unassigned DNA
                        note = Populus balsamifera subsp. trichocarpa
                        organism = Populus balsamifera
SEQUENCE: 108
atgatgggct ctggaaaaac aacagtggga aagattctct cgcaagcaat tcattattca     60
ttctgtgaca gtgacacatt ggtggagaag gatgttggtg tgacttctgt agctgaaata    120
tttcaaatat atggagagga tttcttcaga gataaagaga ctgaggcatt agaaaagcta    180
tcactagagc accgatatgt cgtttctact ggtggaggtg ctgtgataca ggatgaaaac    240
tggacgtaca tgaggaaggg gattagtgtc tggttagatg tgcctttgga agaattggca    300
cagaggattg cggctgtagg aaccaagact cgccccccttt tggatagaga accaggagat    360
gcatacacca aggcgttcag gcgtctgtct gctctgtttg aacagagata taagctcat     420
gaaaatgcta atgcaagggt ttctctggaa aatattgcag ccaaattagg atataaagat    480
gtatccaata tcacaccacc tatgattgcg attgagaaca tggcttgggt gatgcattac    540
gcagcaggtt tccgtctatt accagtgtaa                                     570

SEQ ID NO: 109          moltype = AA  length = 188
FEATURE                 Location/Qualifiers
REGION                  1..188
                        note = Ceres ANNOT ID no. 1504048
REGION                  1..188
                        note = Functional Homolog of Ceres CLONE ID no. 105319 at
                        SEQ ID NO. 106 with e-value of 5.40E-55 and BLAST sequence
                        identity of 64.2
REGION                  1..177
                        note = Pfam Name: SKI Pfam Description: Shikimate kinase
source                  1..188
                        mol_type = protein
                        note = Populus balsamifera subsp. trichocarpa
                        organism = Populus balsamifera
SEQUENCE: 109
MGSGKTTVGK ILSQAIHYSF CDSDTLVEKD VGVTSVAEIF QIYGEDFFRD KETEALEKLS     60
LEHRYVVSTG GGAVIQDENW TYMRKGISVW LDVPLEELAQ RIAAVGTKTR PLLDREPGDA    120
YTKAFRRLSA LFEQRYKAYE NANARVSLEN IAAKLGYKDV SNITPPMIAI ENMAWVMHYA    180
AGFRLLPV                                                              188

SEQ ID NO: 110          moltype = AA  length = 189
FEATURE                 Location/Qualifiers
REGION                  1..189
                        note = Ceres CLONE ID no. 1565097
REGION                  1..189
                        note = Functional Homolog of Ceres CLONE ID no. 105319 at
                        SEQ ID NO. 106 with e-value of 3.00E-29 and BLAST sequence
                        identity of 64.0
REGION                  100..173
                        note = Pfam Name: SKI Pfam Description: Shikimate kinase
source                  1..189
                        mol_type = protein
                        organism = Zea mays
SEQUENCE: 110
MEAGGVGLAL QTRAAAFGSG QRRGGLQSPI GRLRVAEPAG AAVAVRARGS KPVVPLRAKK     60
```

```
SSGGHENLHN SVDEALLLKR KSEEVLFYLN GRCIYLVGMM GSGKSTVGKI MSEVLGYSFF   120
DSDKLVEQAV GMPSVAQIFK VHSEAFFRDN ESSVLRDLSS MRRLVVATGG GAVIPTVNWY   180
LEFTPFLSF                                                           189

SEQ ID NO: 111           moltype = AA   length = 307
FEATURE                  Location/Qualifiers
REGION                   1..307
                         note = Ceres CLONE ID no. 486613
REGION                   1..307
                         note = Functional Homolog of Ceres CLONE ID no. 105319 at
                           SEQ ID NO. 106 with e-value of 1.09E-63 and BLAST sequence
                           identity of 63.0
REGION                   104..280
                         note = Pfam Name: SKI Pfam Description: Shikimate kinase
source                   1..307
                         mol_type = protein
                         organism = Zea mays
SEQUENCE: 111
MEAGGIGLAL QARAAGFGSG SGRRRGGLQA PTGSLRVADP AGPAVAVRAR GSKPVAPLRL    60
RAKKSSGGHE NSHNSVDEAL LLKRKSEEVL FYLNGRCIYL VGMMGSGKST VGKIMSEVLG   120
YSFFDSDKLV EQAVGMPSVA QIFKVHSEAF FRDNESSVLR DLSSMRRLVV ATGGGAVIRP   180
INWRYMKKGL SVWLDVPLDA LARRIAKVGT ASRPLLDQPS GDPYAMAFSK LSMLAQQRGD   240
AYANADVRVS LEEIACKQGH DDVSKLTPTD IAIESLHKIE SFVIEHTADS SASDAQTESQ   300
IQRIQTL                                                             307

SEQ ID NO: 112           moltype = AA   length = 295
FEATURE                  Location/Qualifiers
REGION                   1..295
                         note = Ceres CLONE ID no. 749796
REGION                   1..295
                         note = Functional Homolog of Ceres CLONE ID no. 105319 at
                           SEQ ID NO. 106 with e-value of 7.79E-67 and BLAST sequence
                           identity of 62.5
REGION                   108..284
                         note = Pfam Name: SKI Pfam Description: Shikimate kinase
source                   1..295
                         mol_type = protein
                         organism = Triticum aestivum
SEQUENCE: 112
MDAGVGLRPR PRAAWAGRRK PQGFPPATVP AVRLDQNPAR RPLVLRSDAG SRSTDPIRGA    60
SLKGLCCHKS AGTEKVHYSA DEALVLKQKA EDVLPYLNDR CVYLVGMMGS GKTTVGKIIA   120
EVLGYSFFDS DKLVEQSVGI PSVAEIFQVH SEAFFRDNES EVLRDLSSMH RLIVATGGGA   180
VIRPINWSYM KKGLTIWLDV PLDALARRIA AVGTASRPLL HQESGDPYAK AYAKLTALFE   240
QRMDSYANAD ARVSLENIAL KQGHNDVNVL TPSTIAIEAL LKMESFLTEK AMVRN        295

SEQ ID NO: 113           moltype = AA   length = 308
FEATURE                  Location/Qualifiers
REGION                   1..308
                         note = Functional Homolog of Ceres CLONE ID no. 105319 at
                           SEQ ID NO. 106 with e-value of 5.09E-66 and BLAST sequence
                           identity of 62.1
REGION                   105..281
                         note = Pfam Name: SKI Pfam Description: Shikimate kinase
source                   1..308
                         mol_type = protein
                         note = Oryza sativa subsp. japonica
                         organism = Oryza sativa
SEQUENCE: 113
MEAGVGLALQ SRAAGFGGSD RRRSALYGGE GRARIGSLRV AEPAVAKAAV WARGSKPVAP    60
LRAKKSSGGH ETLHNSVDEA LLLKRKSEEV LFYLNGRCIY LVGMMGSGKS TVGKIMSEVL   120
GYSFFDSDKL VEQAVGMPSV AQIFKVHSEA FFRDNESSVL RDLSSMKRLV VATGGGAVIR   180
PVNWKYMKKG LSVWLDVPLD ALARRIAKVG TASRPLLDQP SGDPYTMAFS KLSMLAEQRG   240
DAYANADVRV SLEEIASKQG HDDVSKLTPT DIAIESFHKI ENFVIEHTVD NPVGDSQADS   300
RAQRIQTL                                                            308

SEQ ID NO: 114           moltype = AA   length = 189
FEATURE                  Location/Qualifiers
REGION                   1..189
                         note = Ceres CLONE ID no. 294723
REGION                   1..189
                         note = Functional Homolog of Ceres CLONE ID no. 105319 at
                           SEQ ID NO. 106 with e-value of 4.69E-56 and BLAST sequence
                           identity of 61.2
REGION                   2..178
                         note = Pfam Name: SKI Pfam Description: Shikimate kinase
source                   1..189
                         mol_type = protein
                         organism = Zea mays
SEQUENCE: 114
```

```
MMGSGKTTVG KILSEVLGYS FFDSDKLVEK AVGISSVAEI FQLHSETFFR DNESEVLTDL    60
SSMHRLVVAT GGGAVIRPIN WSYMKKGLTV WLDVPLDALA RRIAAVGTAS RPLLHQESGD   120
PYAKAYAKLT SLFEQRMDSY ANADARVSLE HIALKQGHND VTILTPSTIA IEALLKMESF   180
LTEKTMVRN                                                           189

SEQ ID NO: 115          moltype = AA  length = 302
FEATURE                 Location/Qualifiers
REGION                  1..302
                        note = Functional Homolog of Ceres CLONE ID no. 105319 at
                         SEQ ID NO. 106 with e-value of 3.70E-79 and BLAST sequence
                         identity of 61.0
REGION                  114..290
                        note = Pfam Name: SKI Pfam Description: Shikimate kinase
source                  1..302
                        mol_type = protein
                        organism = Fagus sylvatica
SEQUENCE: 115
MDGKVANGLV VSPRIGSERF ARRTCGSVRV SRRFREQDRL PVLVSAQLQD KTRNSNWHKT    60
ASLEVSCSYK NFPASVLESG GIHAPFDDAL ILKNKSQEIE PYLSGRCIYL VGMMGSGKTT   120
VGKVLSQVLS YAFFDSDTLV EQDVDANSVA EIFNLYGEGF FRDKETEVLR KLSLMHRLVV   180
STGGGAVVRP INWKYMQKGI SVWLDVPLEA LARRIAAVGT GSRPLLHHDS GDAYTKTFMR   240
LTSLMEERSE AYANANARVS LEDVAAKLGH RDVSNLTPTA IAIEALEQIE GFLKEENGDF   300
AL                                                                  302

SEQ ID NO: 116          moltype = AA  length = 189
FEATURE                 Location/Qualifiers
REGION                  1..189
                        note = Ceres CLONE ID no. 1374869
REGION                  1..189
                        note = Functional Homolog of Ceres CLONE ID no. 105319 at
                         SEQ ID NO. 106 with e-value of 4.69E-56 and BLAST sequence
                         identity of 60.7
REGION                  2..178
                        note = Pfam Name: SKI Pfam Description: Shikimate kinase
source                  1..189
                        mol_type = protein
                        organism = Zea mays
SEQUENCE: 116
MMGSGRTTVG KILSEVLGYS FFDSDKLVEK AVGISSVAEI FQLHSETFFR DNESEVLRDL    60
SSMHRLVVAT GGGAVIRPIN WSYMKKGLTV WLDVPLDALA RRIAAVGTAS RPLLHQESGD   120
PYAKAYAKLT SLFEQRMDSY ANADARVSLE HIALKQGHND VTILTPSTIA IEALLKMESF   180
LTEKTMVRN                                                           189

SEQ ID NO: 117          moltype = AA  length = 307
FEATURE                 Location/Qualifiers
REGION                  1..307
                        note = Functional Homolog of Ceres CLONE ID no. 105319 at
                         SEQ ID NO. 106 with e-value of 4.59E-65 and BLAST sequence
                         identity of 60.6
REGION                  103..279
                        note = Pfam Name: SKI Pfam Description: Shikimate kinase
source                  1..307
                        mol_type = protein
                        note = Oryza sativa subsp. japonica
                        organism = Oryza sativa
SEQUENCE: 117
MEARAGLAMQ SRAAVGVGAG PGVGRRGRAV IRVGKRPTAA SLRVGGPAGP AAAKPLAPLY    60
CLKASRGHDS LHNSVDEALL LKRKSEEVLF YLNGRCIYLV GMMGSGKSTV AKILAEVLGY   120
SFFDSDKLVE QAVGMPSVAQ IFKEHSEAFF RDNESSVLRD LSSMRRLVVA TGGGAVIRPV   180
NWKYMKKGLS VWLDVPLDAL ARRIAQVGTA SRPLLDQPSS DPYTAAFSKL SMLAEQRGDA   240
YANADARVSL EEIAAKQGHD DVSKLTPTDI AIEALLKIEN FVTEHSTSSG PVGDLIVDSQ   300
NRRTKAL                                                             307

SEQ ID NO: 118          moltype = AA  length = 205
FEATURE                 Location/Qualifiers
REGION                  1..205
                        note = Ceres CLONE ID no. 276706
REGION                  1..205
                        note = Functional Homolog of Ceres CLONE ID no. 105319 at
                         SEQ ID NO. 106 with e-value of 2.60E-55 and BLAST sequence
                         identity of 59.3
REGION                  2..178
                        note = Pfam Name: SKI Pfam Description: Shikimate kinase
source                  1..205
                        mol_type = protein
                        organism = Zea mays
SEQUENCE: 118
MMGSGKSTVG KIMSEVLGYS FFDSDKLVEQ AVGMPSVAQI FKVHSEAFFR DNESSVLRDL    60
SSMRRLVVAT GGGAVIRPVN WKYMKKGLSV WLDVPLDALA RRIAKVGTAS RPLLDQPSGD   120
```

```
PYTMAFSKLS MLAEQRGDAY ANADVRVSLE EIASKQGHGD VSKLMPTDIA IESLHKIESF    180
VIEHAADNPA SDSQAESQIQ RIQTL                                          205
```

| | | |
|---|---|---|
| SEQ ID NO: 119 | moltype = AA  length = 305 | |
| FEATURE | Location/Qualifiers | |
| REGION | 1..305 | |
| | note = Ceres CLONE ID no. 840744 | |
| REGION | 1..305 | |
| | note = Functional Homolog of Ceres CLONE ID no. 105319 at SEQ ID NO. 106 with e-value of 2.99E-61 and BLAST sequence identity of 59.3 | |
| REGION | 105..281 | |
| | note = Pfam Name: SKI Pfam Description: Shikimate kinase | |
| source | 1..305 | |
| | mol_type = protein | |
| | organism = Triticum aestivum | |

```
SEQUENCE: 119
MEAGVGLALQ SRAAGFGSGR RRSSMYGGES GARVVSLRVS DLVGSPAAVR ARGAKPVVPL    60
RAKKSSGGGH ENLHNSVDDA LLLKRKSEEV LFQLNGRCIY LVGMMGSGKS TVGKILAEVL   120
GYSFFDSDKL VEQAVGMPSV AQIFKVHSEA FFRDNESSVL RDLSSMRRLV VATGGGAVIR   180
PVNWKNMKKG LSVWLDVPLE ALARRIAKVG TASRPLLDQP SGDPYTMAFS KLSTLAEQRG   240
DAYANADVRV SLEEIASKLG HDDVSKLTPI DIALESLHKI ESFVVEDTAV ADSQTESQAQ   300
RIHTL                                                              305
```

| | | |
|---|---|---|
| SEQ ID NO: 120 | moltype = DNA  length = 936 | |
| FEATURE | Location/Qualifiers | |
| misc_feature | 1..936 | |
| | note = Ceres ANNOT ID no. 1456544 | |
| misc_feature | 1..936 | |
| | note = Encodes the peptide given in SEQ ID NO. 121 | |
| source | 1..936 | |
| | mol_type = unassigned DNA | |
| | note = Populus balsamifera subsp. trichocarpa | |
| | organism = Populus balsamifera | |

```
SEQUENCE: 120
atggaggcaa atcttgcaca aagaatgcaa atttcgacaa catggattga ttcatacaag    60
tttccaagaa aaccaactag ttccctgcgg ttttcgggga gatttaagga acagaagaga   120
ctccaagtgt ttgtttctgc tcagtttcgg cctgtaagag atgaaaatcg acatagacag   180
gcttcttttg aggtttcttg ttcttgtaac aattctcaag ttcaacgttg gaatctgaa    240
agtctccagg atttgtttgg cgaggaagct ttgattttga agaataagtc acaagagatt   300
gagccatatt taaatggacg ctgtatatat cttgttggga tgatgggctc tggaaaaact   360
acagtgggaa agattctctc acgatcaatt cgttattcat tctgtgactg tgacaaactg   420
gtggagcagg atgttggtgt gccttctgta gctgaaatat ttgaaatata tggagaggat   480
ttcttcagag ataaagagac tgaggcatta gaaaagctat caatagaaca ccggtttgtt   540
gtttccactg gtggcggtgc tgtgatacgg gatgaaaact ggatatacat gaggaagggg   600
attagtgtct ggttagatgt gccttttgaa gaattggcac agaggatcgc ggctgtagga   660
accaagtctc gccccctttt ggataatgaa tcaggagatg catacaacac tgcattcaga   720
cgcctttcta ctctgtttga aagagacat aaagcttatg aaaatgccaa ggcgagggtt   780
tctctggaaa atattgcagc caaactagga tataaagatg tatccagtat cacacctgct   840
atgattgcga ttgagcagaa catggcttgt gtgatgcatg atgtggaagg tttccattta   900
ttaccagcag gatttgggat gcgaaagatg tgttag                             936
```

| | | |
|---|---|---|
| SEQ ID NO: 121 | moltype = AA  length = 303 | |
| FEATURE | Location/Qualifiers | |
| REGION | 1..303 | |
| | note = Ceres ANNOT ID no. 1456544 | |
| REGION | 1..303 | |
| | note = Functional Homolog of Ceres CLONE ID no. 105319 at SEQ ID NO. 106 with e-value of 4.50E-74 and BLAST sequence identity of 59.3 | |
| REGION | 107..283 | |
| | note = Pfam Name: SKI Pfam Description: Shikimate kinase | |
| source | 1..303 | |
| | mol_type = protein | |
| | note = Populus balsamifera subsp. trichocarpa | |
| | organism = Populus balsamifera | |

```
SEQUENCE: 121
MQISTTWIDS YKFPRKPTSS LRFSGRFKEQ KRLQVFVSAQ FRPVRDENRH RQASFEVSCS    60
CNNSQVSTLE SESLQDLFGE EALILKNKSQ EIEPYLNGRC IYLVGMMGSG KTTVGKILSR   120
SIRYSFCDCD KLVEQDVGVP SVAEIFEIYG EDFFRDKETE ALEKLSIEHR FVVSTGGGAV   180
IRDENWIYMR KGISVWLDVP LEELAQRIAA VGTKSRPLLD NESGDAYNTA FRRLSTLFEK   240
RHKAYENAKA RVSLENIAAK LGYKDVSSIT PAMIAIEQNM ACVMHDVEGF HLLPAGFGMR   300
KMC                                                                303
```

| | | |
|---|---|---|
| SEQ ID NO: 122 | moltype = DNA  length = 655 | |
| FEATURE | Location/Qualifiers | |
| misc_feature | 1..655 | |
| | note = Ceres CLONE ID no. 29658 | |
| misc_feature | 1..655 | |

|  |  |  |
|---|---|---|
| misc_feature | 1..655<br>note = Predicted sequence | |
| source | 1..655<br>mol_type = unassigned DNA<br>organism = Arabidopsis thaliana | |

SEQUENCE: 122
```
attcatctcc aaactttcaa aaaaaaacct aaaacaaaaa aaatctctttt ccttcttctt   60
tctccatcaa tggcgtcaac aaaacccacc gatcaaatca aacaactcaa agatatcttc  120
gctcgcttcg acatggacaa ggacggaagc ttaacgcagc tagaactcgc cgctcttctg  180
cgttctctcg gaatcaaacc tcgcggcgat caaatctctc ttctgtaaaa ccaaatcgac  240
cgtaacggta acgdatccgt agagttcgac gagctcgtcg tggcgatatt gccggatata  300
aacgaagagg tgttgataaa tcaagaacag ttgatggagg ttttccgttc gtttgatcgt  360
gacggtaacg gttcaataac ggcggcggaa cttgctggta aatgggacat              420
ccgttgactt accgtgaatt aacgaaaatg atgacggaag ctgattcaaa cggtgacggt  480
gttattagtt ttaatgagtt ttctcatatt atggctaaat cggctgctga tttttcttgga 540
ttaaccgctt cttgatctgt tttgttttaa ttactctctt tttttcttct cctgtcaatg  600
caacttgtgc aattaacaat gtgctaatct tcgtttggt gtgacgtaaa aattt         655
```

| | | |
|---|---|---|
| SEQ ID NO: 123 | moltype = AA  length = 161 | |
| FEATURE | Location/Qualifiers | |
| REGION | 1..161<br>note = Ceres CLONE ID no. 29658 | |
| REGION | 1..161<br>note = Ceres ANNOT ID no. 842118 | |
| REGION | 1..161<br>note = Phenotype: ROSETTE LEAVES Useful for making<br>  ornamental plants with modified leaves | |
| REGION | 48..76<br>note = Pfam Name: efhand Pfam Description: EF hand | |
| REGION | 1..161<br>note = Full Length Peptide Sequence for Ceres CLONE ID no.<br>  29658 | |
| source | 1..161<br>mol_type = protein<br>organism = Arabidopsis thaliana | |

SEQUENCE: 123
```
MASTKPTDQI KQLKDIFARF DMDKDGSLTQ LELAALLRSL GIKPRSDQIS LLLNQIDRNG   60
NGSVEFDELV VAILPDINEE VLINQEQLME VFRSFDRDGN GSITAAELAG SMAKMGHPLT  120
YRELTEMMTE ADSNGDGVIS FNEFSHIMAK SAADFLGLTA S                      161
```

| | | |
|---|---|---|
| SEQ ID NO: 124 | moltype = DNA  length = 483 | |
| FEATURE | Location/Qualifiers | |
| misc_feature | 1..483<br>note = Ceres ANNOT ID no. 1464081 | |
| misc_feature | 1..483<br>note = Encodes the peptide sequence given in SEQ ID NO. 125 | |
| source | 1..483<br>mol_type = unassigned DNA<br>note = Populus balsamifera subsp. trichocarpa<br>organism = Populus balsamifera | |

SEQUENCE: 124
```
atggcaaccc ttcagaccga tcagctcaag cagctcaagg acatcttcat tcgcttcgac   60
atggattccg atggcagcct cacgcagctg gagctcgctg cgcttctacg ttctcttggc  120
ctcaaaccta caggtgatca acttcatgtt ctgttatcaa acatggatgc taatggaaat  180
ggttatgttg agtttgatga gctggtcagt gctatattgc ctgatatgaa tgaagaagta  240
ttgatcaacc aggagcagtt gttggaggtt tttcgatcat ttgacaggga tggcaatgga  300
ttcattactg ctgctgagct tgcaggatca atggctaaaa tgggacaccc tttgacgtat  360
cgtgagctat cagatatgat gagagaggct gacaccaatg gagatggtgt tttgagtttt  420
aatgagtttg caaacgtcat ggcaaaatct gctgctgatt tccttggcat caaagttcca  480
tag                                                                483
```

| | | |
|---|---|---|
| SEQ ID NO: 125 | moltype = AA  length = 140 | |
| FEATURE | Location/Qualifiers | |
| REGION | 1..140<br>note = Ceres ANNOT ID no. 1464081 | |
| REGION | 1..140<br>note = Functional Homolog of Ceres CLONE ID no. 29658 at<br>  SEQ ID NO. 123 with e-value of 4.20E-55 and BLAST sequence<br>  identity of 81.7 | |
| REGION | 27..55<br>note = Pfam Name: efhand Pfam Description: EF hand | |
| source | 1..140<br>mol_type = protein<br>note = Populus balsamifera subsp. trichocarpa<br>organism = Populus balsamifera | |

SEQUENCE: 125
```
MDSDGSLTQL ELAALLRSLG LKPTGDQLHV LLSNMDANGN GYVEFDELVS AILPDMNEEV   60
LINQEQLLEV FRSFDRDGNG FITAAELAGS MAKMGHPLTY RELSDMMREA DTNGDGVLSF  120
```

```
NEFANVMAKS AADFLGIKVP                                                  140

SEQ ID NO: 126          moltype = AA  length = 158
FEATURE                 Location/Qualifiers
REGION                  1..158
                        note = Ceres CLONE ID no. 651548
REGION                  1..158
                        note = Functional Homolog of Ceres CLONE ID no. 29658 at
                         SEQ ID NO. 123 with e-value of 2.80E-58 and BLAST sequence
                         identity of 78.9
REGION                  120..148
                        note = Pfam Name: efhand Pfam Description: EF hand
source                  1..158
                        mol_type = protein
                        organism = Glycine max
SEQUENCE: 126
MLETDQIKQL NDIFKRFDMD QDGSLTHLEL AALLRSLGIK PTGDEIYALL SNMDENGNGY    60
IEFDELVHAI MPDLTESVLI NQEQLLEVFR SFDRDGNGYI TASELAGSMA KMGQPLTYRE   120
LASMMAEADS NGDGVISFNE FAALMAKSAA EFLGVKVA                           158

SEQ ID NO: 127          moltype = AA  length = 173
FEATURE                 Location/Qualifiers
REGION                  1..173
                        note = Functional Homolog of Ceres CLONE ID no. 29658 at
                         SEQ ID NO. 123 with e-value of 4.80E-47 and BLAST sequence
                         identity of 65.3
REGION                  61..89
                        note = Pfam Name: efhand Pfam Description: EF hand
source                  1..173
                        mol_type = protein
                        note = Oryza sativa subsp. japonica
                        organism = Oryza sativa
SEQUENCE: 127
MTTMAARRSE AAPAPQQLRG SQLKQLRELF RRFDMNGDGS LTQLELAALL RSLGLRPTGD    60
EVHALLAGMD ANGNGSVEFD ELAAAIAPVL TTQTHLVDQA QLLEVFRAFD RDGNGFISAA   120
ELARSMARLG QPLTFEELTR MMRDADTDGD GVISFKEFAA VMAKSALDFL GVA          173

SEQ ID NO: 128          moltype = AA  length = 172
FEATURE                 Location/Qualifiers
REGION                  1..172
                        note = Ceres CLONE ID no. 287120
REGION                  1..172
                        note = Functional Homolog of Ceres CLONE ID no. 29658 at
                         SEQ ID NO. 123 with e-value of 1.49E-45 and BLAST sequence
                         identity of 64.0
REGION                  60..88
                        note = Pfam Name: efhand Pfam Description: EF hand
source                  1..172
                        mol_type = protein
                        organism = Zea mays
SEQUENCE: 128
MTRSAPPASP PAPKPVLRGS QLEQLREIFR RFDMDGDGSL TQLELGALLR SLGLRPTGEE    60
ARALLAAMDS NGNGAVEFGE LAAAIAPLLT TQTHLVDQAQ LLEVFRAFDR DGNGYISAAE   120
LARSMARIGQ PLTFEELTRM MRDADADGDG VISFNEFAAV MAKSALDFLG VA           172

SEQ ID NO: 129          moltype = AA  length = 177
FEATURE                 Location/Qualifiers
REGION                  1..177
                        note = Ceres CLONE ID no. 759217
REGION                  1..177
                        note = Functional Homolog of Ceres CLONE ID no. 29658 at
                         SEQ ID NO. 123 with e-value of 1.29E-44 and BLAST sequence
                         identity of 63.3
REGION                  62..90
                        note = Pfam Name: efhand Pfam Description: EF hand
source                  1..177
                        mol_type = protein
                        organism = Triticum aestivum
SEQUENCE: 129
MTKPSPSPSP APAKGAGSLR GSQLKQLRSL FDRFDMDGDG SLTQLELAAL LRSLGLRPTG    60
DESRALLLAI DADGSGTVEF DELARAIAPV LTAHAPRLVD QAQLLEVFRA FDRDGNGYIS   120
AAELARSMAK LGQPLTFEEL RTMMRDADAD GDGVISFGEF AAVMARSALD FLGVPAA      177

SEQ ID NO: 130          moltype = AA  length = 149
FEATURE                 Location/Qualifiers
REGION                  1..149
                        note = Functional Homolog of Ceres CLONE ID no. 29658 at
                         SEQ ID NO. 123 with e-value of 2.29E-24 and BLAST sequence
                         identity of 43.3
```

| | |
|---|---|
| REGION | 12..40 |
| | note = Pfam Name: efhand Pfam Description: EF hand |
| source | 1..149 |
| | mol_type = protein |
| | note = Malus x domestica |
| | organism = unidentified |

SEQUENCE: 130

```
MADQLTDDQI SEFKEAFSLF DKDGDGCITT KELGTVMRSL GQNPTEAELQ DMINEVDADG   60
NGTIDFPEPL NLMARKMKDT DSEEELKEAF RVFDKDQNGF ISAAELRHVM TNLGEKLTDE  120
EVDEMIREAD VDGDGQINYE EFVKVMMAK                                   149
```

| | |
|---|---|
| SEQ ID NO: 131 | moltype = DNA  length = 679 |
| FEATURE | Location/Qualifiers |
| misc_feature | 1..679 |
| | note = Ceres CLONE ID no. 2767 |
| misc_feature | 1..679 |
| | note = Ceres Seed Line ID no. ME00774 |
| misc_feature | 1..679 |
| | note = Encodes the peptide given in SEQ ID NO. 132 |
| source | 1..679 |
| | mol_type = unassigned DNA |
| | organism = Arabidopsis thaliana |

SEQUENCE: 131

```
agaagctaga agaagaaagg agaagaagaa acaaagagag aagatgaaga atgttatgct   60
gattattgac gagagcaacg caagttatga tttactcatt tgggcacttg aaaaccaaaa  120
agataccatt gagagctcca aagtttatat ctttgcaaaa cagccacaaa attcctttac  180
tcctcctacc gtactttctt catcagtcgg ctttgctcaa atttctatc cattttcacc  240
taattcagaa ctcataagat tggctcaaga aaagaatatg aaaattgctt tgggtatatt  300
agagaaagcc aagaagatat gtttaaatca tgggatcaag gcagagacat ttactaatgt  360
tggagaccct aaagatctaa tccgcaagat aattcaagaa cgaaatatca atttaatagt  420
tacgagcgat caacaaagtc tcaaaaagtg tacacaaaat acagattgtt ctcttcttgt  480
cgtgaagaaa agacttcgca aagattaaag attaaggaag ttacaaaatt caccaatata  540
tataattttc tatgtggtta attgagattg tgtaatgatt tggggttgta gtttcaggtg  600
ttgatttggg gttgtagttt gaactttataa ttgtgttatg tgtataaata tttgtgttta  660
tatatatcaa gttagtatg                                               679
```

| | |
|---|---|
| SEQ ID NO: 132 | moltype = AA  length = 154 |
| FEATURE | Location/Qualifiers |
| REGION | 1..154 |
| | note = Ceres CLONE ID no. 2767 |
| REGION | 1..154 |
| | note = Ceres Seed Line ID no. ME00774 |
| REGION | 1..148 |
| | note = Pfam Name: Usp Pfam Description: Universal stress protein family |
| source | 1..154 |
| | mol_type = protein |
| | organism = Arabidopsis thaliana |

SEQUENCE: 132

```
MKNVMLIIDE SNASYDLLIW ALENQKDTIE SSKVYIFAKQ PQNSFTPPTV LSSSVGFAQI   60
FYPFSPNSEL IRLAQEKNMK IALGILEKAK KICLNHGIKA ETFTNVGDPK DLIRKIIQER  120
NINLIVTSDQ QSLKKCTQNT DCSLLVVKKR LRKD                              154
```

| | |
|---|---|
| SEQ ID NO: 133 | moltype = DNA  length = 597 |
| FEATURE | Location/Qualifiers |
| misc_feature | 1..597 |
| | note = Ceres ANNOT ID no. 1486744 |
| misc_feature | 1..597 |
| | note = Encodes the peptide given in SEQ ID NO. 134 |
| source | 1..597 |
| | mol_type = unassigned DNA |
| | note = Populus balsamifera subsp. trichocarpa |
| | organism = Populus balsamifera |

SEQUENCE: 133

```
atggagaaac aaatagaagg gtctaagaag agggtgatgg tgatcataga tgagagcgag   60
tacagttatc attccttcat gtgggtagtt gacaatctca agaatttat cactgagtcg  120
ccgcttgtca tccttgctgc acttcctgct cctaactgta aatttttta tggggcacag  180
tttggcaccg ctgccctctg ttgtccagtc tctcccaccc tagatttgat ctgtgccatt  240
caagaaaaaa acaagaagat cttattaggt atccttggaga agctgtgaa tatctgtgat  300
agtcgagggg tgaaagcaga acaattttta gaagccgggg agccttatga actcacatgc  360
aatgctgttc agaagaacaa tattaatctc ctcgtgattg gtaacacatc cattaatgga  420
actctcaaaa ggttaggaaa tttctttgta acttcaaaaa tcatttcgac agctctcgaa  480
agtcgcataa attgtatgaa cctgattcaa aatgagttat ttcaagaact tgaacatgct  540
ggcatggttg tcaacccta ttaactcttgc aacaagctcc actaccagaa gcactga    597
```

| | |
|---|---|
| SEQ ID NO: 134 | moltype = AA  length = 186 |
| FEATURE | Location/Qualifiers |
| REGION | 1..186 |
| | note = Ceres ANNOT ID no. 1486744 |

```
REGION                  1..186
                        note = Functional Homolog of Ceres CLONE ID no. 2767 at SEQ
                           ID NO. 132 with e-value of 1.90E-18 and BLAST sequence
                           identity of 43.4
source                  1..186
                        mol_type = protein
                        note = Populus balsamifera subsp. trichocarpa
                        organism = Populus balsamifera
SEQUENCE: 134
MVIIDESEYS YHSFMWVVDN LKEFITESPL VILAALPAPN CKFFYGAQFG TAALCCPVSP    60
TLDLICAIQE KNKKILLGIL EKAVNICASR GVKAETILEA GEPYELTCNA VQKNNINLLV   120
IGNTSINGTL KRLGNFFVTS KIISTALESR INCMNLIQNE LFQELEHAGM VVNPINSCNK   180
LHYQKH                                                              186

SEQ ID NO: 135          moltype = DNA  length = 540
FEATURE                 Location/Qualifiers
misc_feature            1..540
                        note = Ceres ANNOT ID no. 1463968
misc_feature            1..540
                        note = Encodes the peptide given in SEQ ID NO. 136
source                  1..540
                        mol_type = unassigned DNA
                        note = Populus balsamifera subsp. trichocarpa
                        organism = Populus balsamifera
SEQUENCE: 135
atggagaaac aaatagaagg gtctaatcag aaggtgatgg tgatcataga tgagagtgag    60
tgcagttatc atgcactcat gtgggtgctt gaaaatctca aaggattcat tactgactca   120
ccgcttgtca tgtttgctgc actacctact cctaactgta actttgcata tggggcacaa   180
cttggcacca ctgcgttgta ttgtacagtc tcacccaccc taggtttgat tgttccatg    240
caagaaaaaa gcaagaaaat cttattgggt gtcttgagaa agctgtgga tatctgtgat    300
agtcgagggg tgaaagcaga gacaatcaca gaagctgggg agccttatga gctcataagc   360
agtgctgttc aaaagaacaa gattaatcta ctagtgatcg gtgacacact cgttaatgga   420
acccttaaaa gtcacatgtc tcttgatact ggaatggtta cagtgacgtt aacctgttac   480
ccaaaacctc atcctactca aaatatagat tatcattcag atgggtacca atacaaatga   540

SEQ ID NO: 136          moltype = AA  length = 167
FEATURE                 Location/Qualifiers
REGION                  1..167
                        note = Ceres ANNOT ID no. 1463968
REGION                  1..167
                        note = Functional Homolog of Ceres CLONE ID no. 2767 at SEQ
                           ID NO. 132 with e-value of 7.09E-19 and BLAST sequence
                           identity of 43.0
source                  1..167
                        mol_type = protein
                        note = Populus balsamifera subsp. trichocarpa
                        organism = Populus balsamifera
SEQUENCE: 136
MVIIDESECS YHALMWVLEN LKGFITDSPL VMFAALPTPN CNFAYGAQLG TTALYCTVSP    60
TLGLICSMQE KSKKILLGVL EKAVDICDSR GVKAETITEA GEPYELISSA VQKNKINLLV   120
IGDTLVNGTL KSHMSLDTGM VTVTLTCYPK PHPTQNIDYH SDGYQYK                 167

SEQ ID NO: 137          moltype = DNA  length = 447
FEATURE                 Location/Qualifiers
misc_feature            1..447
                        note = Ceres ANNOT ID no. 1517263
misc_feature            1..447
                        note = Encodes the peptide given in SEQ ID NO. 138
source                  1..447
                        mol_type = unassigned DNA
                        note = Populus balsamifera subsp. trichocarpa
                        organism = Populus balsamifera
SEQUENCE: 137
atggagaaac aaatagaagg gtctaatcag aaggtgatgg tgatcataga tgagagtgag    60
tgcagttatc atgcactcat gtgggtgctt gaaaatctca aaggattcat tactgactca   120
ccgcttgtca tgtttgctgc actacctact cctaactgta actttgcata tggggcacaa   180
cttggcacca ctgcgttgta ttgtacagtc tcacccaccc taggtttgat tgttccatg    240
caagaaaaaa gcaagaaaat cttattgggt gtcttggaga aagctgtgga tatctgtgat   300
agtcgagggg tgaaagcaga gacaatcaca gaagctgggg agccttatga gctcataagc   360
agtgctgttc aaaagaacaa gattaatcta ctagtgatcg gtgacacact cgttaatgga   420
acccttaaaa gttcccgacc ccactag                                       447

SEQ ID NO: 138          moltype = AA  length = 136
FEATURE                 Location/Qualifiers
REGION                  1..136
                        note = Ceres ANNOT ID no. 1517263
REGION                  1..136
                        note = Functional Homolog of Ceres CLONE ID no. 2767 at SEQ
                           ID NO. 132 with e-value of 7.09E-19 and BLAST sequence
```

```
                          identity of 43.0
source                    1..136
                          mol_type = protein
                          note = Populus balsamifera subsp. trichocarpa
                          organism = Populus balsamifera
SEQUENCE: 138
MVIIDESECS YHALMWVLEN LKGFITDSPL VMFAALPTPN CNFAYGAQLG TTALYCTVSP    60
TLGLICSMQE KSKKILLGVL EKAVDICDSR GVKAETITEA GEPYELISSA VQKNKINLLV   120
IGDTLVNGTL KSSRPH                                                  136

SEQ ID NO: 139            moltype = AA  length = 162
FEATURE                   Location/Qualifiers
REGION                    1..162
                          note = Ceres CLONE ID no. 684584
REGION                    1..162
                          note = Functional Homolog of Ceres CLONE ID no. 2767 at SEQ
                           ID NO. 132 with e-value of 2.29E-13 and BLAST sequence
                           identity of 37.6
REGION                    11..159
                          note = Pfam Name: Usp Pfam Description: Universal stress
                           protein family
source                    1..162
                          mol_type = protein
                          organism = Triticum aestivum
SEQUENCE: 139
MAAQAPPPPP PEQKMMVAID ESECSHYALE WALRNLAPRR LILFTVQPFS PLSYLPVGSP    60
LGPSVASPEL IRSVTEHQRQ LAQALVDKAK AICAEHGVDA ETVIEVGDPK ETICEAAEKL   120
NVDLLILGSH SRGPVQRFFL GSVSNYCSHH AKCPVLVVKK KE                      162

SEQ ID NO: 140            moltype = DNA  length = 468
FEATURE                   Location/Qualifiers
misc_feature              1..468
                          note = Ceres ANNOT ID no. 1463969
misc_feature              1..468
                          note = Encodes the peptide given in SEQ ID NO. 141
source                    1..468
                          mol_type = unassigned DNA
                          note = Populus balsamifera subsp. trichocarpa
                          organism = Populus balsamifera
SEQUENCE: 140
atggcggagc acgtgacgga aaatggaggg gtaccacttg agaggaaagt gatggttgcc    60
gttgatgatg gtgagtatag ccactatgct ctcatgtggg tacttgacaa tcttgaggaa   120
tctatcacta aatcacctct agttatcttc accgcacagc ctcctcccag caataaccat   180
tcttttactg ccgctgctct cagttctgct cgcatgtact gctcggtttc agccaatccg   240
gagtatactt acactatcca agaccagaat aagaagatcg cgtttgcttt gctggagaaa   300
gctaaagaaa tttgtgctgg tcgaggagtt gatgctgaga cattaacaga ggtgggtgat   360
cctcaaacag ccatatgcga tgcagttcaa aggctcaata ttagcctgct tgttttaggg   420
gagcgcggca ttggcaaaat caaaaggtgg gatgatggcg caagttaa                468

SEQ ID NO: 141            moltype = AA  length = 138
FEATURE                   Location/Qualifiers
REGION                    1..138
                          note = Ceres ANNOT ID no. 1463969
REGION                    1..138
                          note = Functional Homolog of Ceres CLONE ID no. 2767 at SEQ
                           ID NO. 132 with e-value of 1.19E-16 and BLAST sequence
                           identity of 36.0
REGION                    1..136
                          note = Pfam Name: Usp Pfam Description: Universal stress
                           protein family
source                    1..138
                          mol_type = protein
                          note = Populus balsamifera subsp. trichocarpa
                          organism = Populus balsamifera
SEQUENCE: 141
MVAVDDGEYS HYALMWVLDN LEESITKSPL VIFTAQPPPS NNHSFTAAAL SSARMYCSVS    60
ANPEYTYTIQ DQNKKIAFAL LEKAKEICAG RGVDAETLTE VGDPQTAICD AVQRLNISLL   120
VLGERGIGKI KRWDDGAS                                                 138

SEQ ID NO: 142            moltype = AA  length = 148
FEATURE                   Location/Qualifiers
REGION                    1..148
                          note = Ceres CLONE ID no. 1059727
REGION                    1..148
                          note = Functional Homolog of Ceres CLONE ID no. 2767 at SEQ
                           ID NO. 132 with e-value of 1.90E-9 and BLAST sequence
                           identity of 31.6
REGION                    1..145
                          note = Pfam Name: Usp Pfam Description: Universal stress
```

```
                               protein family
source                  1..148
                        mol_type = protein
                        organism = Glycine max
SEQUENCE: 142
MVAIDDSDCS KHALRWTLSY LKDSLADSDI ILFTAQPQLD LSSVYASSYG AAPIELINSM   60
QQNYKNAALN RIEEGTKICA ESGVTPKKVM EFGNPKEAIC DAVEKLGVDL LIVGSHGKGA  120
LERTFLGSVS NYCVNKAKCP VLVVRTKA                                    148

SEQ ID NO: 143          moltype = AA   length = 165
FEATURE                 Location/Qualifiers
REGION                  1..165
                        note = Ceres CLONE ID no. 1272732
REGION                  1..165
                        note = Functional Homolog of Ceres CLONE ID no. 2767 at SEQ
                         ID NO. 132 with e-value of 2.29E-6 and BLAST sequence
                         identity of 27.7
REGION                  12..161
                        note = Pfam Name: Usp Pfam Description: Universal stress
                         protein family
source                  1..165
                        mol_type = protein
                        organism = Zea mays
SEQUENCE: 143
METAAVAASS AGRRIMVAVD EGEESLHALN WCLANVVSPA GGDTLVLVHA RRPRPVYAAM   60
DSAGYMMTSD VLASVERHAN AVSAAAVDKA KRVCADHPHV KVETTVESGD PRDVICDAAN  120
KMAADLLVMG SHGYGFIQRA FLGSVSNHCA QNCKCPVLIV KRPKE                 165

SEQ ID NO: 144          moltype = AA   length = 145
FEATURE                 Location/Qualifiers
REGION                  1..145
                        note = Ceres CLONE ID no. 283925
REGION                  1..145
                        note = Functional Homolog of Ceres CLONE ID no. 2767 at SEQ
                         ID NO. 132 with e-value of 2.29E-6 and BLAST sequence
                         identity of 27.6
REGION                  1..141
                        note = Pfam Name: Usp Pfam Description: Universal stress
                         protein family
source                  1..145
                        mol_type = protein
                        organism = Zea mays
SEQUENCE: 144
MVAVDEGEES LHALNWCLAN VVSPAGGDTL VLVHARRPRP VYAAMDSAGY MMTSDVLASV   60
ERHANAVSAA AVDKAKRVCA DHPHVKVETM VESGDPRDVI CDAANKMAVG SHGYGFIQRA  120
FLGSVSNHCA QNCKCPVLIV KRPKE                                       145

SEQ ID NO: 145          moltype = DNA   length = 901
FEATURE                 Location/Qualifiers
misc_feature            1..901
                        note = Ceres CLONE ID no. 16403
misc_feature            1..901
                        note = Ceres Seed Line ID no. ME01468
misc_feature            1..901
                        note = Encodes the peptide given in SEQ ID NO. 146
source                  1..901
                        mol_type = unassigned DNA
                        organism = Arabidopsis thaliana
SEQUENCE: 145
gtcttgtgaa ttgtagccac tatggcagtc tcctcactct caatccgctg tggtggtttc   60
tcaccaacaa tctcccacaa gacagaaatt ctctgtccaa atccatcact caaagcttgt  120
tgtttacttt catccggtgg taaggccgac tcctcggaga gtacttacca aaaaggcagc  180
ggaaacaatt ggaagagaag gcaagctctt gtgggagtag aactttagt ggcaacttca   240
attccagcaa ctttgcttct tgctgaagag ataccaaaaa gctactcgcc ttttgtggat  300
cgagaagacg ggtattctta ctattaccca tcagactgga gggaatttga cttcaggca   360
catgattcag ccttcaaaga tagatacttg caactgcaga atgtgcgggt caggttcata  420
ccaacgagaa aaacgacat ccatgaagta ggtcctatgg aagaggtggt ttatgatcta   480
gtgaagcata agtttgcagc accaaaccaa gtagctacca tctacgatat gaaagagagg  540
gtggaagatg gaaagaacta ttacacgttt gagtatggac taagaactcc tatctatgca  600
accacttcct ttgcaacagt ggcagttgga acaacagat actacactct catagttgga  660
gcaaatgaga gaaggtggag gaaagtgaaa aagcagcttc aagttgtggc cgactctttg  720
aagatccttc agatttgaca aacacaagaa acatcttact cctatatatc tttctctctc  780
tgtggttaca aaactgtctg tagataacaa tttgatattt tcatattctc tataactcca  840
acgatggttt tggcattgtg agttagaatc tgagttggtt cagtaattca atcaaacttg  900
c                                                                  901

SEQ ID NO: 146          moltype = AA   length = 238
FEATURE                 Location/Qualifiers
REGION                  1..238
```

```
                              note = Ceres CLONE ID no. 16403
REGION                        1..238
                              note = Ceres Seed Line ID no. ME01468
REGION                        1..238
                              note = Phenotype: Cold Germination Useful for making plants
                                with increased tolerance to cold stress
REGION                        1..238
                              note = Phenotype: Cold Growth Useful for making plants with
                                increased tolerance to cold stress
REGION                        54..236
                              note = Pfam Name: PsbP Pfam Description: PsbP
source                        1..238
                              mol_type = protein
                              organism = Arabidopsis thaliana
SEQUENCE: 146
MAVSSLSIRC GGFSPTISHK TEILCPNPSL KACCLLSSGG KADSSESTYQ KGSGNNWKRR    60
QALVGVGTLV ATSIPATLLL AEEIPKSYSP FVDREDGYSY YYPSDWREFD FRAHDSAFKD   120
RYLQLQNVRV RFIPTEKNDI HEVGPMEEVV YDLVKHKFAA PNQVATIYDM KERVEDGKNY   180
YTFEYGLRTP IYATTSFATV AVGNNRYYTL IVGANERRWR KVKKQLQVVA DSLKILQI    238

SEQ ID NO: 147               moltype = AA   length = 234
FEATURE                      Location/Qualifiers
REGION                        1..234
                              note = Ceres CLONE ID no. 611156
REGION                        1..234
                              note = Functional Homolog of Ceres CLONE ID no. 16403 at
                                SEQ ID NO. 146 with e-value of 7.29E-67 and BLAST sequence
                                identity of 58.9
REGION                        63..232
                              note = Pfam Name: PsbP Pfam Description: PsbP
source                        1..234
                              mol_type = protein
                              organism = Glycine max
SEQUENCE: 147
MVVSSCSLSW ISPCLSHKLN LPHTNCLPRN IATSSSNTVF CELDTTPSGE SHCRRRPLLL    60
GIGALTANLQ PTNLVFAQEK PDRYRAFVDY EDGYSYVYPI DWKEFDFRAH DSAFKDRYLQ   120
LQNVRVRFIP TEKKDIRDLG PMEEVIYDLV KHRYAAPNQR PTINDMQEKT IDGKHYYTFE   180
YILTSPNYSS ASFATIAIGN GRYYTLIVGA NERRWKRFRD QLKVVADSFR LLDI        234

SEQ ID NO: 148               moltype = DNA   length = 699
FEATURE                      Location/Qualifiers
misc_feature                  1..699
                              note = Ceres ANNOT ID no. 1464944
misc_feature                  1..699
                              note = Encodes the peptide given in SEQ ID NO. 149
source                        1..699
                              mol_type = unassigned DNA
                              note = Populus balsamifera subsp. trichocarpa
                              organism = Populus balsamifera
SEQUENCE: 148
atggcaatat cttcactctc attgagttgg gcttccacta ccttatccca aaagttaagt    60
gtccctggtt caaatgaaat attgcctaga gtagcagcat tttctggcaa taactctgta   120
acatgcacgg cagaggcaac cttcaatgaa gaaagcaatt gcaagagacg tctgctactg   180
ctaggagttg gagcactaac gacaagttta gtcccagcaa atttcctttt tgctgaagag   240
ataccaaaga actacacatc tttttgtgga ctttgaagatg ggtattcata ttattacccc   300
tcagactgga ttgattttga cttcaggaga catgattctg catttaagga cagaacgaag   360
caattgcaga atgttagggt gagatttata ccaaccgaga aaaagacat tcatgaattg   420
ggtccaatgg aagagtatga cagtcacatg cagcaagaaa ttatgaacgt gaaacttttca   480
aattttcttg aaaaccagaa aaccgtagag ggaaaaaact actacacctt cgatgacgaa   540
cttacatctc caaactactc aagtgtttca tttgcaacca tagttattgc caatgggaga   600
ttttacactc tgatagttgg cgcaaatgaa agacggtgga gaagatatcg cagtcagcta   660
aaagtggtag cagactcttt caaggtgctt gacatctaa                         699

SEQ ID NO: 149               moltype = AA   length = 232
FEATURE                      Location/Qualifiers
REGION                        1..232
                              note = Ceres ANNOT ID no. 1464944
REGION                        1..232
                              note = Functional Homolog of Ceres CLONE ID no. 16403 at
                                SEQ ID NO. 146 with e-value of 4.39E-60 and BLAST sequence
                                identity of 56.2
REGION                        53..230
                              note = Pfam Name: PsbP Pfam Description: PsbP
source                        1..232
                              mol_type = protein
                              note = Populus balsamifera subsp. trichocarpa
                              organism = Populus balsamifera
SEQUENCE: 149
MAISSLSLSW ASTTLSQKLS VPGSNEILPR VAAFSGNNSV TCTAEATFNE ESNCKRRLLL    60
```

```
LGVGALTTSL VPANFLFAEE IPKNYTSFVD FEDGYSYYYP SDWIDFDFRG HDSAFKDRTK     120
QLQNVRVRFI PTEKKDIHEL GPMEEYDSHM QQEIMNVKLS NFLENQKTVE GKNYYTFEYE     180
LTSPNYSSVS FATIVIANGR FYTLIVGANE RRWRRYRSQL KVVADSFKVL DI             232

SEQ ID NO: 150          moltype = AA   length = 178
FEATURE                 Location/Qualifiers
REGION                  1..178
                        note = Functional Homolog of Ceres CLONE ID no. 16403 at
                         SEQ ID NO. 146 with e-value of 4.20E-32 and BLAST sequence
                         identity of 39.8
REGION                  20..175
                        note = Pfam Name: PsbP Pfam Description: PsbP
source                  1..178
                        mol_type = protein
                        note = Oryza sativa subsp. japonica
                        organism = Oryza sativa
SEQUENCE: 150
MLLAAGAAVF LSWPNLAANA AEAKKGFLPV TDKKDGYSFL YPFGWQEVVV QGQDKVYKDV      60
IEPLESVSVN TIPTSKQDIR ELGPPDQVAE ALIRKVLAAP TQKTKLIEAK ENDVDGRTYY     120
TFEFTAQAPN FTRHALGAIA IANGKFYTLT TGANERRWEK IKDRLHTVVD SFKIEARV       178

SEQ ID NO: 151          moltype = AA   length = 257
FEATURE                 Location/Qualifiers
REGION                  1..257
                        note = Functional Homolog of Ceres CLONE ID no. 16403 at
                         SEQ ID NO. 146 with e-value of 4.69E-33 and BLAST sequence
                         identity of 39.5
REGION                  86..241
                        note = Pfam Name: PsbP Pfam Description: PsbP
source                  1..257
                        mol_type = protein
                        note = Oryza sativa subsp. japonica
                        organism = Oryza sativa
SEQUENCE: 151
MATHSTSAPA APAFSAFPLA AAVRFPCASA TSNTCAFSLA EHLTREGMFF DLQSIKREAE      60
ERSRRRMLLA AGAAMFLSWP NPAAYAAEAK KGFLPVTDKK DGYSFLYPFG WQEVVVQGQD     120
KVYKDVIEPL ESVSVNTIPT SKQDIRELGP PDQVAEALIR KVLAAPTQKT KLIEAKENDV     180
DGRTYYTFEF TAQAPNFTRH ALGAIAIANG KFYTLTTGAN ERRWEKIKDR LHTVVDSFKI     240
EAREVRFNGK CREHGSY                                                   257

SEQ ID NO: 152          moltype = AA   length = 242
FEATURE                 Location/Qualifiers
REGION                  1..242
                        note = Ceres CLONE ID no. 1551032
REGION                  1..242
                        note = Functional Homolog of Ceres CLONE ID no. 16403 at
                         SEQ ID NO. 146 with e-value of 2.39E-32 and BLAST sequence
                         identity of 39.2
REGION                  59..239
                        note = Pfam Name: PsbP Pfam Description: PsbP
source                  1..242
                        mol_type = protein
                        organism = Zea mays
SEQUENCE: 152
MATAVPAACL RAPCSSPAAV ARRLGAGGPS LRKRHCAVAP VAAACGPAPP RLLDNEEAVC      60
SVRRRVLVAG AAAFLSRPNP AAFAAEAKKG FLPVVDKKAG YSFLYPFGWE EVAVQGQDKV     120
YKDVIEPLES VSVNSIPTSK EDIRDLGPPD KVAEALIKKV LAPSTQKTKL IEAKENDVDG     180
RAYYTFEFTA QAPNYTRHAL GAIVIANGKF YTLTTGANER RWEKMKDRLH TVVDSFKIEN     240
RI                                                                   242

SEQ ID NO: 153          moltype = DNA   length = 1172
FEATURE                 Location/Qualifiers
misc_feature            1..1172
                        note = Ceres CLONE ID no. 3964
misc_feature            1..1172
                        note = Ceres Seed Line ID no. ME00199
misc_feature            1..1172
                        note = Encodes the peptide given in SEQ ID NO. 154
source                  1..1172
                        mol_type = unassigned DNA
                        organism = Arabidopsis thaliana
SEQUENCE: 153
aaagcatcaa ataagtaaat aaaaactctt ttatgttcac cttttttcact atcctctctt     60
tgtgtttcaa atcgtgggaa caaattatca caatggaggc ttctaaagaa gctcatcacc    120
ttccaaacta catgaaagac gacaacgtta gtcaagaaac caagaacttg atcacttctc    180
taccttcaga caaagatttc atgggttatg gtctctacaa ctacaaaggt tgttggtact    240
atccaaacac actccaagcc gttcttgacg tccaaaaaca cttcaagcca cgagatactg    300
atataatcct cgcttctttg cccaaaggtg gaacccacttg gctcaaatcc ctaattttcg    360
ctgttgtaca tagagaaaag taccgcggaa ccccctcaaac acatcctttg ctcttacaaa    420
```

```
accctcatga ccttgtccca tttcttgagg ttgagttata cgctaatagc caaattccgg    480
atctcgcaaa gtattcttct cctatgatct tttctacaca catgcactta caagcattgc    540
gtgaagccac cacaaaagct tgcaaaaccg tatatgtgtg tagaggtatc aaagatacgt    600
ttgtctccgg ctggcattat agaaacatgt tgcatcgcac caagatggat caagccactt    660
ttgagctcat gtttgatgct tattgtagag gagttctctt atatgaccct tattgggaac    720
atgtattgag ctattggaaa gggagcttga agcaaagga gaatgttctt ttcatgaagt    780
acgaagagat aattgaggag cctcgtgttc aagtcaagag actcgccgag ttcttggaat    840
gtccattcac caaggaagaa gaagaaagtg gatcggtgga ggagatcttg aagttgtgta    900
gtttacgaaa tttaagcaat ttggaggtta ataagaatgg gacaacgaga attggtgtag    960
attctcaggt gttctttagg aaaggtgaag ttggtgattg gaagaatcat cttacgccac   1020
aaatggcgaa aacctttgat gagattattg actatagact aggagactcc ggttttgatat   1080
ttcaataagg ttgtgttgtg ttttttttct tttgtcatcc gaaataaat taggactcaa   1140
acgagtcatt cttgaaaaaa aaaaaaaaaa aa                                 1172

SEQ ID NO: 154          moltype = AA  length = 351
FEATURE                 Location/Qualifiers
REGION                  1..351
                        note = Ceres CLONE ID no. 3964
REGION                  1..351
                        note = Ceres Seed Line ID no. ME00199
REGION                  1..351
                        note = Phenotype: Dark Green Useful for increasing
                          chlorophyll and photosynthetic capacity
REGION                  1..351
                        note = Phenotype: WHOLE PLANT Useful for making bigger
                          plants
REGION                  1..351
                        note = Phenotype: Curled 3 Useful for making plants with
                          altered leaf shape eg curled leaves
REGION                  1..351
                        note = Phenotype: Standing Rosette Shaped Useful for making
                          plants with increased biomass and foliage
REGION                  88..347
                        note = Pfam Name: Sulfotransfer_1 Pfam Description:
                          Sulfotransferase domain
source                  1..351
                        mol_type = protein
                        organism = Arabidopsis thaliana
SEQUENCE: 154
MFTFFTILSL CFKSWEQIIT MEASKEAHHL PNYMKDDNVS QETKNLITSL PSDKDFMGYG    60
LYNYKGCWYY PNTLQAVLDV QKHFKPRDTD IILASLPKGG TTWLKSLIFA VVHREKYRGT   120
PQTHPLLLQN PHDLVPFLEV ELYANSQIPD LAKYSSPMIF STHMHLQALR EATTKACKTV   180
YVCRGIKDTF VSGWHYRNML HRTKMDQATF ELMFDAYCRG VLLYGPYWEH VLSYWKGSLE   240
AKENVLFMKY EEIIEEPRVQ VKRLAEFLEC PFTKEEEESG SVEEILKLCS LRNLSNLEVN   300
KNGTTRIGVD SQVFFRKGEV GDWKNHLTPQ MAKTFDEIID YRLGDSGLIF Q            351

SEQ ID NO: 155          moltype = AA  length = 337
FEATURE                 Location/Qualifiers
REGION                  1..337
                        note = Functional Homolog of Ceres CLONE ID no. 3964 at SEQ
                          ID NO. 154 with e-value of 1.49E-61 and BLAST sequence
                          identity of 48.6
REGION                  73..324
                        note = Pfam Name: Sulfotransfer_1 Pfam Description:
                          Sulfotransferase domain
source                  1..337
                        mol_type = protein
                        note = Oryza sativa subsp. japonica
                        organism = Oryza sativa
SEQUENCE: 155
MAPSFRLSSA PESADEATAH KEIYDQLRRV AETFPSAPSL IGLPCSRHPD GWYTFTNGVV    60
SSMVIKEHLT ARATDIFLTT FPKSGTTWLK VLLYSTLHRG TDELVAHSPH QLVPFLESQV   120
FVNDRIPDLS SLSSPRLFMT HIPSQSLPNS VATSGCKVVY LCRDPKDCFV SLWHFWNRFM   180
PWDIDEAHRQ FCDGVSQFGP FWEHILGYWR WHVEKPNQVL FLTYEELAAD TLGQLRRLAE   240
FVGCPFTTEE QKHGVDRNIV EACALENMSG LEVNRSGTIT IVDSTVPNNT FFRRGVVGDW   300
RNHLTPEMAR RIDEITKSKF KGSGLLLHPQ FLQVKRE                            337

SEQ ID NO: 156          moltype = DNA  length = 1119
FEATURE                 Location/Qualifiers
misc_feature            1..1119
                        note = Ceres ANNOT ID no. 1448303
misc_feature            1..1119
                        note = Encodes the peptide given in SEQ ID NO. 157
source                  1..1119
                        mol_type = unassigned DNA
                        note = Populus balsamifera subsp. trichocarpa
                        organism = Populus balsamifera
SEQUENCE: 156
atgcctgcct ctactacaac ttccatggtt ctcaaccatt tcacaaagaa tcaagcaaat    60
```

```
gacaatggag aggatttaga gagattaacc aatgagtgca aggaattgct gctttcactc    120
ccaagagaga agggttggag aactgcatgc ctctataaat acaaagggtt ttggtgccaa    180
ccaaaagaaa tccaagcgat aatctctttt caaaaacact ttgaaccaag agacactgat    240
gttatcctag catcaatacc taaatcagga actacctggc tcaaagccct atcttttgcc    300
atcttgaatc gcaagaaatt tgcaatctct agtaatgacc acccttttgc cgtctctaat    360
cctcacgatc ttgcaccttt ctttgagtac aagcttatg cagacaagca agttcctgac    420
ctctcgaaac tccctgatcc tagactttt gccacccaca ttccatttgc ttcacttcaa    480
gactccatca agaagtctaa ttgccggatt atttatatct gtagaaaccc ttttgacact    540
tttatttcct catggacttt cagcaacaag ctgagatcga aaactgttcc tccactgtta    600
ctagaggaaa ccttcaaaat gtattgcgaa ggggttgtgt ggttcggtcc cttctgggac    660
catatgttgg gatactggaa ggaaagcttg gagagacaag acaaggtgtt gttcttgaag    720
tatgaggaca tgaaagcaga tgttacgttt tacttgaaga agattgccaa atttcttggc    780
tgccctttt caatggaaga agaaaaggaa ggtgtagtgg aaaagatagc cagcctttgt    840
agctttgaga agatgaagaa tttagaagtt aacaaatctg gaaggtctat tacgaacttc    900
gaaaataagc acttgtttag gaaagctgaa gtcggagatt gggtgaatta tctgtctcct    960
tcaatggtga agcaattatc tcaattaata gaggaaaagt tgggtggatc tggaggtgtc   1020
caagctgctg ctgctgctgc ttcttcttct tcttctgtta aaagaagaa attcgagcta   1080
cagagatatg gagagaataa gaatacaaat gtcaattga                           1119

SEQ ID NO: 157          moltype = AA   length = 364
FEATURE                 Location/Qualifiers
REGION                  1..364
                        note = Ceres ANNOT ID no. 1448303
REGION                  1..364
                        note = Functional Homolog of Ceres CLONE ID no. 3964 at SEQ
                        ID NO. 154 with e-value of 2.89E-72 and BLAST sequence
                        identity of 47.4
REGION                  70..330
                        note = Pfam Name: Sulfotransfer_1 Pfam Description:
                        Sulfotransferase domain
source                  1..364
                        mol_type = protein
                        note = Populus balsamifera subsp. trichocarpa
                        organism = Populus balsamifera
SEQUENCE: 157
MVLNHFTKNQ ANDNGEDLER LTNECKELLL SLPREKGWRT ACLYKYKGFW CQPKEIQAII    60
SFQKHFEPRD TDVILASIPK SGTTWLKALS FAILNRKKFA ISSNDHPLLV SNPHDLAPFF   120
EYKLYADKQV PDLSKLPDPR LFATHIPFAS LQDSIKKSNC RIIYICRNPF DTFISSWTFS   180
NKLRSETVPP LLLEETFKMY CEGVVGFGPF WDHMLGYWKE SLERQDKVLF LKYEDMKADV   240
TFYLKKIAKF LGCPFSMEEE KEGVVEKIAS LCSFEKMKNL EVNKSGRSIT NFENKHLFRK   300
AEVGDWVNYL SPSMVKQLSQ LIEEKLGGSG GVQAAAAAAS SSSSVIKKKF ELQRYGENKN   360
TNVN                                                                364

SEQ ID NO: 158          moltype = DNA   length = 1233
FEATURE                 Location/Qualifiers
misc_feature            1..1233
                        note = Ceres ANNOT ID no. 1501305
misc_feature            1..1233
                        note = Encodes the peptide given in SEQ ID NO. 159
source                  1..1233
                        mol_type = unassigned DNA
                        note = Populus balsamifera subsp. trichocarpa
                        organism = Populus balsamifera
SEQUENCE: 158
atgcctgcct ctactacaac ttccatggtt ctcaaccatt tcacaaagaa tcaagcaaat     60
gacaatggag aggatttaga gagattaacc aatgagtgca aggaattgct gctttcactc    120
ccaagagaga agggttggag aactgcatgc ctctataaat acaaagggtt ttggtgccaa    180
ccaaaagaaa tccaagcgat aatctctttt caaaaacact ttgaaccaag agacactgat    240
gttatcctag catcaatacc taaatcagga actacctggc tcaaagccct atcttttgcc    300
atcttgaatc gcaagaaatt tgcaatctct agtaatgacc acccttttgc cgtctctaat    360
cctcacgatc ttgcaccttt ctttgagtac aagcttatg cagacaagca agttcctgac    420
ctctcgaaac tccctgatcc tagactttt gccacccaca ttccatttgc ttcacttcaa    480
gactccatca agaagtctaa ttgccggatt atttatatct gtagaaaccc ttttgacact    540
tttatttcct catggacttt cagcaacaag ctgagatcga aaactgttcc tccactgtta    600
ctagaggaaa ccttcaaaat gtattgcgaa ggggttgtgt ggttcggtcc cttctgggac    660
catatgttgg gatactggaa ggaaagcttg gagagacaag acaaggtgtt gttcttgaag    720
tatgaggaca tgaaagcaga tgttacgttt tacttgaaga agattgccaa atttcttggc    780
tgccctttt caatggaaga agaaaaggaa ggtgtagtgg aaaagatagc cagcctttgt    840
agctttgaga agatgaagaa tttagaagtt aacaaatctg gaaggtctat tacgaacttc    900
gaaaataagc acttgtttag gaaagctgaa gtcggagatt gggtgaatta tctgtctcct    960
tcaatggtga agcaattatc tcaattaata gaggaaaagt tgggtggatc tggtattgaa   1020
ttcaaagtgt ttcctatac tagcactact ccgtctacat ctccaaggct tttcgctgct   1080
cacattccct attcatcatt gcccgaatcc atcaagaagt ctaattgtcg tgaagtttac   1140
atttatcgta acccttttaa cgtggtggca tcctggtttc atttttccaa tgttgaaggt   1200
gaaccagaga agctggatga ggagtatttt tga                                1233

SEQ ID NO: 159          moltype = AA   length = 410
FEATURE                 Location/Qualifiers
REGION                  1..410
```

```
                        note = Ceres ANNOT ID no. 1501305
REGION                  1..410
                        note = Functional Homolog of Ceres CLONE ID no. 3964 at SEQ
                           ID NO. 154 with e-value of 6.70E-73 and BLAST sequence
                           identity of 47.0
REGION                  353..397
                        note = Pfam Name: Sulfotransfer_1 Pfam Description:
                           Sulfotransferase domain
source                  1..410
                        mol_type = protein
                        note = Populus balsamifera subsp. trichocarpa
                        organism = Populus balsamifera
SEQUENCE: 159
MPASTTTSMV  LNHFTKNQAN  DNGEDLERLT  NECKELLLSL  PREKGWRTAC  LYKYKGFWCQ    60
PKEIQAIISF  QKHFEPRDTD  VILASIPKSG  TTWLKALSFA  ILNRKKFAIS  SNDHPLLVSN   120
PHDLAPFFEY  KLYADKQVPD  LSKLPDPRLF  ATHIPFASLQ  DSIKKSNCRI  IYICRNPFDT   180
FISSWTFSNK  LRSETVPPLL  LEETFKMYCE  GVVGFGPFWD  HMLGYWKESL  ERQDKVLFLK   240
YEDMKADVTF  YLKKIAKFLG  CPFSMEEEKE  GVVEKIASLC  SFEKMKNLEV  NKSGRSITNF   300
ENKHLFRKAE  VGDWVNYLSP  SMVKQLSQLI  EEKLGGSGIE  FKVFPYTSTT  PSTSPRLFAA   360
HIPYSSLPES  IKKSNCREVY  IYRNPFNVVA  SWFHFSNVEG  EPEKLDEEYF               410

SEQ ID NO: 160          moltype = AA  length = 312
FEATURE                 Location/Qualifiers
REGION                  1..312
                        note = Functional Homolog of Ceres CLONE ID no. 3964 at SEQ
                           ID NO. 154 with e-value of 6.40E-61 and BLAST sequence
                           identity of 46.6
REGION                  49..308
                        note = Pfam Name: Sulfotransfer_1 Pfam Description:
                           Sulfotransferase domain
source                  1..312
                        mol_type = protein
                        organism = Flaveria chloraefolia
SEQUENCE: 160
MEDIIKTLPQ  HTCSFLKHRF  TLYKYKDAWN  HQEFLEGRIL  SEQKFKAHPN  DVFLASYPKS    60
GTTWLKALAF  AIITREKFDD  STSPLLTTMP  HDCIPLLEKD  LEKIQENQRN  SLYTPISTHF   120
HYKSLPESAR  TSNCKIVYIY  RNMKDVIVSY  YHFLRQIVKL  SVEEAPFEEA  FDEFCQGISS   180
CGPYWEHIKG  YWKASLEKPE  IFLFLKYEDM  KKDVPSVKK   LADFIGHPFT  PKEEEAGVIE   240
DIVKLCSFEK  LSSLEVNKSG  MHRPEEAHSI  ENRLYFRKGK  DGDWKNYFTD  EMTQKIDKLI   300
DEKLGATGLV  LK                                                           312

SEQ ID NO: 161          moltype = AA  length = 343
FEATURE                 Location/Qualifiers
REGION                  1..343
                        note = Ceres CLONE ID no. 703785
REGION                  1..343
                        note = Functional Homolog of Ceres CLONE ID no. 3964 at SEQ
                           ID NO. 154 with e-value of 1.30E-60 and BLAST sequence
                           identity of 46.2
REGION                  74..332
                        note = Pfam Name: Sulfotransfer_1 Pfam Description:
                           Sulfotransferase domain
source                  1..343
                        mol_type = protein
                        organism = Triticum aestivum
SEQUENCE: 161
MASSPQSSSS  APKADDKAAS  HKEIYDQLLE  VVSTYPTAPS  GIGRPYTHHP  DGWYAFTPAV    60
VNAMVIKRHL  KACDTDVFLS  TFPKSGTTWL  KALLFATLRR  TADGPAIAAL  AAHSPHQLIP   120
FLEVQVFSNG  RIPDLSSLPA  PRLLMTHIPS  RSLPESVAAS  GCKVVYLCRD  PKDCFVSLWH   180
FWNRFAPSPW  DLGEALQQFC  DGVSLFGPFW  EHVLGYWRWH  VERPEQVLFL  TYEELAADTL   240
GQLKRLAAFL  GRPFTSEERE  ARVDREIVEA  CAMESLAGLE  VNRSGKTDMT  ESSVANNIFF   300
RRGVVGDWKN  HLTPEMARRI  DEITDSKFRG  SGLALTPATA  DQN                      343

SEQ ID NO: 162          moltype = AA  length = 325
FEATURE                 Location/Qualifiers
REGION                  1..325
                        note = Functional Homolog of Ceres CLONE ID no. 3964 at SEQ
                           ID NO. 154 with e-value of 4.99E-61 and BLAST sequence
                           identity of 45.8
REGION                  65..320
                        note = Pfam Name: Sulfotransfer_1 Pfam Description:
                           Sulfotransferase domain
source                  1..325
                        mol_type = protein
                        organism = Brassica napus
SEQUENCE: 162
MSSSSSVPDY  LRDEKLTQET  RDLISSLPSE  KGWLVSQIYQ  FQGRWHTEAL  LQGILTCQKH    60
FKAKDSDIIL  VTNPKSGTTW  LKSLVFALIN  RHKFPVSSGD  HPLLVTNPHL  LVPFMEGVYY   120
ESPDFDFSLL  PFPRLMNTHI  SHLSLPESVK  SSSCQIVYCC  RNPKDMFVSL  WHFGKKLAPQ   180
```

```
ETADYPLEKA VEAFCQGKFI AGPFWDHVLE YWYASLENPN KVLFVTYEEL KKQTEVEVKR   240
IAEFIGCGFT AEEEVSEIVK LCSFESLSRL EVNRQGKLPN GIETNAFFRK GEIGGWRDTL   300
SESLADAIDR TTEEKFGGSG LKFSC                                        325

SEQ ID NO: 163            moltype = AA   length = 312
FEATURE                   Location/Qualifiers
REGION                    1..312
                          note = Functional Homolog of Ceres CLONE ID no. 3964 at SEQ
                           ID NO. 154 with e-value of 2.70E-60 and BLAST sequence
                           identity of 45.8
REGION                    49..308
                          note = Pfam Name: Sulfotransfer_1 Pfam Description:
                           Sulfotransferase domain
source                    1..312
                          mol_type = protein
                          organism = Flaveria bidentis
SEQUENCE: 163
MEDIIKTLPQ HTCSFLKQRF TLYKYQDVWN HQEFLEGRML SEQTFKAHPN DVFLASYPKS    60
GTTWLKALAF AIITREKFDD STSPLLTTMP HDCIPLLEKD LEKIQENQRN SLYTPISTHF   120
HYKSLPESAR TSNCKIVYIY RNMKDVIVSY YHFLRQIVKL SVEEAPFEEA VDEFCQGISS   180
CGPYWEHILG YWKASLEKPE IFLFLKYEDM KKDPVPSVKK LADFIGHPFT PKEEEAGVIE   240
NIIKLCSFEK LSSLEVNKSG MHRPEEAHSI ENRLYFRKGK DGDWKNYFTD EMIEKIDKLI   300
DEKLGATGLV LK                                                      312

SEQ ID NO: 164            moltype = AA   length = 323
FEATURE                   Location/Qualifiers
REGION                    1..323
                          note = Functional Homolog of Ceres CLONE ID no. 3964 at SEQ
                           ID NO. 154 with e-value of 1.30E-60 and BLAST sequence
                           identity of 44.4
REGION                    64..318
                          note = Pfam Name: Sulfotransfer_1 Pfam Description:
                           Sulfotransferase domain
source                    1..323
                          mol_type = protein
                          organism = Brassica napus
SEQUENCE: 164
MESSSVPVYL KDENLTQETR DLLSSLPSEK GWLVSQMYQF EGIWQTQALV QGIVNCQKHF    60
EANDSDVILA TLAKSGTTWL KALLFALIHR HKFPVSGKHP LLVTNPHSLV PYLEGDYCSS   120
PEVNFAELPS PRLMQTHLTH HSLPVSIKSS SCKIIYCCRN PKDMFVSIWH FGRKLAPEKT   180
AEYPIETAVA AFCKGKFIGG PFWDHVLEYW YESLKNPNKV LFVTYEELKK QTEVEVKRIA   240
EFIGCGFTAE EEVSEIVKLC SFESLSSLEV NRQGKLPNGI ESNAFFRKGE TGGWRDTLSE   300
SLADVIDRTT EQKFGGSGLK FSS                                          323

SEQ ID NO: 165            moltype = AA   length = 323
FEATURE                   Location/Qualifiers
REGION                    1..323
                          note = Functional Homolog of Ceres CLONE ID no. 3964 at SEQ
                           ID NO. 154 with e-value of 2.20E-58 and BLAST sequence
                           identity of 44.4
REGION                    63..318
                          note = Pfam Name: Sulfotransfer_1 Pfam Description:
                           Sulfotransferase domain
source                    1..323
                          mol_type = protein
                          organism = Brassica napus
SEQUENCE: 165
MSSSSSSYLR DEDLTQETRD LISSLPSEKG WLVSQMYQFQ GRWHTQALLQ GLLQYQKHFE    60
AKDSDIILVT NPKSGTTWLK ALVFSLINRH KFPVSSGDHP LLVTNPHLLI PPFLEGVYYES  120
PNFDFTELPS PRLMNTHISL LSLPESVKSS SCKIVYCCRN PKDMFVSLWH FGKKLASQET   180
ADYPIEKAVE AFCQGKFIGG PFWDHVLEYW YASLENPNKV LFVTYEELKK QTGDTIKRIA   240
EFLGCGFIEE EEVGGIVKLC SFESLSSLEA NREGKLPNGV ETKAFFRKGE VGGWRDTLSE   300
SLAEEIDRTM EEKFQGSGLK FSC                                          323

SEQ ID NO: 166            moltype = AA   length = 324
FEATURE                   Location/Qualifiers
REGION                    1..324
                          note = Functional Homolog of Ceres CLONE ID no. 3964 at SEQ
                           ID NO. 154 with e-value of 9.20E-53 and BLAST sequence
                           identity of 44.1
REGION                    65..319
                          note = Pfam Name: Sulfotransfer_1 Pfam Description:
                           Sulfotransferase domain
source                    1..324
                          mol_type = protein
                          organism = Brassica napus
SEQUENCE: 166
MSSSSSVPDY LRDENLTQKT KDLISSLPSE KGWLVCQMYQ FQGRWHTQAL LQGILTCQKH    60
FEAKDSDIIL VTNPKSGTTW LKALVFALIN RHKFPVYSVI ILSCYQSALL VPFLGRSLLR   120
```

```
SPDFDFSQLS SPRLMNTHIS HLSLPESVKS SSCKIVYCCR NPKDMFVSLW HFGKKLAPEE    180
TADYPIEKAV EAFCQGKFIG GPFWDHVLEY WYASLENPNK VLFVSYEEPK KKTGETIKRI    240
AEFLGCGLVG EEEVRAIVKL CSFESLSSLE VNREGKLPSG METRAFFRKG EVGGWRDTLT    300
ESLAEVIDRT IEEKFQGSGL KFSC                                          324

SEQ ID NO: 167          moltype = AA  length = 290
FEATURE                 Location/Qualifiers
REGION                  1..290
                        note = Functional Homolog of Ceres CLONE ID no. 3964 at SEQ
                         ID NO. 154 with e-value of 3.59E-42 and BLAST sequence
                         identity of 44.1
REGION                  182..290
                        note = Pfam Name: Sulfotransfer_1 Pfam Description:
                         Sulfotransferase domain
source                  1..290
                        mol_type = protein
                        note = Oryza sativa subsp. japonica
                        organism = Oryza sativa
SEQUENCE: 167
MAPSFPLSFA PQSADEAAAH KEIYDQLRQT VETFPTAPNS SNSFTYSRHP DGWYTFPEGV     60
VSAMVIKSHL TARTTDIFMV TFPKSGTTWL KTLLHSALHR GANDLAAHSP HQLVPFLETQ    120
VPFIKDRIPDL SSLPAPRLLM THIPSQSLPD SVADSGCKVV YLCRDPNRKF RPWDINEAHR   180
HFCDGVSLFG PYWEHVLGYW RWHTKRPSQV LFLTYEELTT DTLGQLRHLA EFVGCPFMVE    240
EQELGVDRKI VEACAMESLS RLEVNQSGTT DMVDKTYVNN IFFRRGVVGD               290

SEQ ID NO: 168          moltype = AA  length = 345
FEATURE                 Location/Qualifiers
REGION                  1..345
                        note = Ceres CLONE ID no. 1064128
REGION                  1..345
                        note = Functional Homolog of Ceres CLONE ID no. 3964 at SEQ
                         ID NO. 154 with e-value of 1.19E-59 and BLAST sequence
                         identity of 43.8
REGION                  74..332
                        note = Pfam Name: Sulfotransfer_1 Pfam Description:
                         Sulfotransferase domain
source                  1..345
                        mol_type = protein
                        organism = Zea mays
SEQUENCE: 168
MATVFPRDAG VSTPEADEAK KIYDEARRVV STYETVPSPS GTLQDYCRHP SGWCITLPIM     60
VSSMVAEQHF EARGTDVLLV TMPKSGTTWI KALLYAAAHR TDDTSSSILR QLASHNSHQL    120
VPFLEAQVYT KDQIPDLSSL PAPRLFATHI PAESLPPSVV ASGCKVVYLC RDPKDCFVSL    180
WHFMNKFTPW DIDEAHGRFC EGVSLYGPFW EHVLSYWRWH VDRPGQVLFL TYEELSADPL    240
GQLRRLAEFI GRPFTPGEQE AGVDREIAEA CAMKSMVNQE VNQSRTTEIV EMPIPNGIFF    300
RRGVVGDWTN YLTPEMAGRI DEITKSKFEG SGLMLPKTIS EISKI                   345

SEQ ID NO: 169          moltype = AA  length = 279
FEATURE                 Location/Qualifiers
REGION                  1..279
                        note = Functional Homolog of Ceres CLONE ID no. 3964 at SEQ
                         ID NO. 154 with e-value of 1.90E-54 and BLAST sequence
                         identity of 43.0
REGION                  11..262
                        note = Pfam Name: Sulfotransfer_1 Pfam Description:
                         Sulfotransferase domain
source                  1..279
                        mol_type = protein
                        note = Oryza sativa subsp. japonica
                        organism = Oryza sativa
SEQUENCE: 169
MVVKSHLTAR ATDIFLVTFP KSGTTWIKAL PYSALHRRAD ELLAHSPHQL ISFLESQVFV     60
KDRIPDLSSL PEPWLLMTHI PSQSLPDSVA ASGCKVVYLC RDPKDCFVSL WHFWNRFMPW    120
NIDDAHRQFC NGVSLFGLYW EHVLSYWNWH VERPSEVLFL TYEELAADTL GHLRRLAEFV    180
GRPFTTEEQD ARVDRKIVEI CAMESLSGLE VNRSGMTNFT KKDVPNNISF RRGVVGDWRN    240
HLTPEMARRI DEITEVKFKG SGLLLHPPFL QVKRELNEL                          279

SEQ ID NO: 170          moltype = AA  length = 250
FEATURE                 Location/Qualifiers
REGION                  1..250
                        note = Functional Homolog of Ceres CLONE ID no. 3964 at SEQ
                         ID NO. 154 with e-value of 6.29E-38 and BLAST sequence
                         identity of 39.0
REGION                  55..248
                        note = Pfam Name: Sulfotransfer_1 Pfam Description:
                         Sulfotransferase domain
source                  1..250
                        mol_type = protein
                        organism = Triticum monococcum
```

```
SEQUENCE: 170
MNKRLLDSRH  CLANANCGLA  LPLVLFNVCC  YEGLWVHYFH  VAGAVALQLR  LAPLQDDVIV     60
ASFPKSGTTW  LNALTFATMA  RRTNPAAGAG  HPLLRLNPHQ  CIPFLDKLFQ  SCTEAKLEAL    120
PSPRLMNTHM  PIDMIMPGGG  GCKVVYICRE  PKDMVISQWH  FLRRLQPDLP  LADLLESVCS    180
GAMPYGPVWD  HILGYWRAST  ARPDGVLFLR  YEELLRNPAE  KVRELARFVG  LPFSDAEEEA    240
GVVHDIVKLE                                                                250

SEQ ID NO: 171            moltype = DNA   length = 865
FEATURE                   Location/Qualifiers
misc_feature              1..865
                          note = Ceres CLONE ID no. 965405
misc_feature              1..865
                          note = Ceres Seed Line ID no. ME09814
misc_feature              1..865
                          note = Encodes the peptide given in SEQ ID NO. 172
source                    1..865
                          mol_type = unassigned DNA
                          organism = Brassica napus
SEQUENCE: 171
agtcgtcgtc ttctgtgtaa gaaatatctt atcttaggtg tgcagaccga agtctagagt     60
atcttcaagc ttcaacttct tagctatgtc ggccgatgat tcttcaaatg ctacagatgt    120
tgacgggaag ctcggctccg atttaaacgt taactcagat ggtgaagatg ggcggataa    180
tgattcctca aagacattga ctattcctgc tcccgccgtt tgtcttgtcc ggttcgccgg    240
agatgcagct ggtggtgccg tcatgggctc tatctttgga tatggttcag gattgttcaa    300
gaagaaaggc tttaaaggat catttgcaga tgcaggacag tctgcaaaga cttttgctgt    360
tttgtccgga gtacacagtt tggttgtttg ccttctgaaa caactcagag gaaagatga    420
tgccattaat gttggagttg ctgggtgctg caccggtctt gctcttagtt tccctggtgc    480
tccacaggct cttctacaga gttgcctcac ttttgggggt ttctctttta tccttgaggg    540
actaaacaaa agacaaacag ccttggctca ctctgtctcc ttaagacacc aaaccggaaa    600
ctttggagat catcaacaac gtcctttaca actctccctg gctctcccaa tccatgaaga    660
aatcaaagga ttctcttctt tctgcaagtc cttaactaaa cccaagaaga tctaatttcg    720
ccatgattat cctttcttg ttccttatgt tctctctgta gattcttaat gattccctgc    780
ttttgctgta ctttgtgaga gaatatttta tgaaagatct tttgatataa attttgcacc    840
gtttgctcta aaaaaaaaaa aaaaa                                           865

SEQ ID NO: 172            moltype = AA   length = 209
FEATURE                   Location/Qualifiers
REGION                    1..209
                          note = Ceres CLONE ID no. 965405
REGION                    1..209
                          note = Ceres Seed Line ID no. ME09814
REGION                    39..157
                          note = Pfam Name: Tim17 Pfam Description: Tim17/Tim22/Tim23
                            family
source                    1..209
                          mol_type = protein
                          organism = Brassica napus
SEQUENCE: 172
MSADDSSNAT  DVDGKLGSDL  NVNSDGEDAA  DNDSSKTLTI  PAPAVCLVRF  AGDAAGGAVM     60
GSIFGYGSGL  FKKKGFKGSF  ADAGQSAKTF  AVLSGVHSLV  VCLLKQLRGK  DDAINVGVAG    120
CCTGLALSFP  GAPQALLQSC  LTFGAFSFIL  EGLNKRQTAL  AHSVSLRHQT  GNFGDHQQRP    180
LQLSLALPIH  EEIKGFSSFC  KSLTKPKKI                                         209

SEQ ID NO: 173            moltype = AA   length = 210
FEATURE                   Location/Qualifiers
REGION                    1..210
                          note = Ceres CLONE ID no. 5367
REGION                    1..210
                          note = Functional Homolog of Ceres CLONE ID no. 965405 at
                            SEQ ID NO. 172 with e-value of 6.89E-87 and BLAST sequence
                            identity of 85.5
REGION                    40..158
                          note = Pfam Name: Tim17 Pfam Description: Tim17/Tim22/Tim23
                            family
source                    1..210
                          mol_type = protein
                          organism = Arabidopsis thaliana
SEQUENCE: 173
MAANDSSNAI  DIDGNLDSDS  NLNTDGDEAT  DNDSSKALVT  IPAPAVCLFR  FAGDAAGGAV     60
MGSIFGYGSG  LFKKKGFKGS  FADAGQSAKT  FAVLSGVHSL  VVCLLKQIRG  KDDAINVGVA    120
GCCTGLALSF  PGAPQALLQS  CLTFGAFSFI  LEGLNKRQTA  LAHSVSLRHQ  TGLFQDHHRA    180
LPLSLALPIP  EEIKGAFSSF  CKSLAKPRKF                                        210

SEQ ID NO: 174            moltype = AA   length = 214
FEATURE                   Location/Qualifiers
REGION                    1..214
                          note = Functional Homolog of Ceres CLONE ID no. 965405 at
                            SEQ ID NO. 172 with e-value of 4.30E-78 and BLAST sequence
                            identity of 79.6
```

```
REGION              40..158
                    note = Pfam Name: Tim17 Pfam Description: Tim17/Tim22/Tim23
                       family
source              1..214
                    mol_type = protein
                    organism = Arabidopsis thaliana
SEQUENCE: 174
MAAENSSNAI NVDTSLDSDS KPNRDANDMT DHDSSSKALV IPAPAVCLVR FAGDAASGAF     60
MGSVFGYGSG LFKKKGFKGS FVDAGQSAKT FAVLSGVHSL VVCLLKQIRG KDDAINVGVA    120
GCCTGLALSF PGAPQAMLQS CLTFGAFSFI LEGLNKRQTA LAHSVSFRQQ TRSPQHDLPL    180
LSLAIPIHDE IKGAFSSFCN SLTKPKKLKF PHAR                                214

SEQ ID NO: 175      moltype = AA  length = 212
FEATURE             Location/Qualifiers
REGION              1..212
                    note = Functional Homolog of Ceres CLONE ID no. 965405 at
                       SEQ ID NO. 172 with e-value of 7.30E-76 and BLAST sequence
                       identity of 79.4
REGION              40..156
                    note = Pfam Name: Tim17 Pfam Description: Tim17/Tim22/Tim23
                       family
source              1..212
                    mol_type = protein
                    organism = Arabidopsis thaliana
SEQUENCE: 175
MAAENSSNAI NVDTSLDSDS KPNRDANDMT DHDSSSKALV IPAPAVCLVR FAGDAASGAF     60
MGSVFGYGLF KKKGFKGSFV DAGQSAKTFA VLSGVHSLVV CLLKQIRGKD DAINVGVAGC    120
CTGLALSFPG APQAMLQSCL TFGAFSFILE GLNKRQTALA HSVSFRQQTR SPQHDLPLLS    180
LAIPIHDEIK GAFSSFCNSL TKPKKLKFPH AR                                  212

SEQ ID NO: 176      moltype = AA  length = 213
FEATURE             Location/Qualifiers
REGION              1..213
                    note = Ceres CLONE ID no. 1060894
REGION              1..213
                    note = Functional Homolog of Ceres CLONE ID no. 965405 at
                       SEQ ID NO. 172 with e-value of 3.50E-76 and BLAST sequence
                       identity of 77.5
REGION              39..157
                    note = Pfam Name: Tim17 Pfam Description: Tim17/Tim22/Tim23
                       family
source              1..213
                    mol_type = protein
                    organism = Zea mays
SEQUENCE: 176
MAAENPSNGV DVDTSLASDS NDNRKASDLT NHDSSMALTV PSTAVCLGRF AGDAAGGAVM     60
GSIFGYGSGL FKKKGFKGSF ADAGQSAKNF AILSGVHSLV VCLLKKLRGK DDAINVGIAG    120
CCTGLALSYP GAPQAMLQSC VTFGAFSFIL EGLNKRQTAL AHSVSSRHDQ TRSLKDDLPL    180
SLALPIHEEI KGAFSSFCKS LTKPKKLAFP SSR                                 213

SEQ ID NO: 177      moltype = AA  length = 203
FEATURE             Location/Qualifiers
REGION              1..203
                    note = Ceres CLONE ID no. 639280
                    1..203
                    note = Functional Homolog of Ceres CLONE ID no. 965405 at
                       SEQ ID NO. 172 with e-value of 6.40E-45 and BLAST sequence
                       identity of 68.0
REGION              29..147
                    note = Pfam Name: Tim17 Pfam Description: Tim17/Tim22/Tim23
                       family
source              1..203
                    mol_type = protein
                    organism = Triticum aestivum
SEQUENCE: 177
MAARSENESD GDVGTNPAEG GSSLSLPPLA AGPAVCVLRS AGDFAGGAFV GSIFGYGQGL     60
LSKKGLKGSL GNAGSSAKSF AVLSGVQSLV LCLLRKLRGK DDIINSGIAG CCTGLALSFP    120
GTPQALLQNC ATFAAFSCIM EGLNKQQTAM AHTLTGNALT FAHDNGAGVL PPSLSPQSSM    180
LPMLSPHAAR PWSPSLRSTR QQH                                            203

SEQ ID NO: 178      moltype = DNA  length = 645
FEATURE             Location/Qualifiers
misc_feature        1..645
                    note = Ceres ANNOT ID no. 1494390
misc_feature        1..645
                    note = Encodes the peptide given in SEQ ID NO. 179
source              1..645
                    mol_type = unassigned DNA
                    note = Populus balsamifera subsp. trichocarpa
```

```
                          organism = Populus balsamifera
SEQUENCE: 178
atggcgacgg cgaattctcc aaacaccagc aacaactctg attccgatgt cgaagaccct   60
aaccctaatc cttcaagtaa taataacaat gcatcaatta ttccttctgc tgagtccagt  120
accccttccg tctgcctcat ccgcttcgct ggtgactccg ctgcaggcgc ctttatgggc  180
tccatcttcg gctacggttc gggattgatt aagaagaaag gcttcaaagg atcctttggg  240
gaagcaggat cttgtgccaa gacttttgca gttctatctg gagtacacag tttggttgtc  300
tgctttctga gaggctgcg agggaaggat gatgtcatca atgctggagt agctggatgt  360
tgtactggtc ttgctctgag ttttccaggt gcacctcagg cacttctgca gagttgcctt  420
acttttggag cattctcatt catcatcgaa gggctgaaca agaagcaagc agcactggct  480
cactctattt cttcaaggaa taaatgtgac tatcacagca aaccttgtcc gctagcactc  540
cctctttcag tccctcttcc agatgaacta aagggcct tctccttttt ctgcaagtcc  600
ttaaggaaac ccaagagtgc caattttccc gccgccgccc cctga              645

SEQ ID NO: 179             moltype = AA  length = 214
FEATURE                    Location/Qualifiers
REGION                     1..214
                           note = Ceres ANNOT ID no. 1494390
REGION                     1..214
                           note = Functional Homolog of Ceres CLONE ID no. 965405 at
                             SEQ ID NO. 172 with e-value of 8.10E-61 and BLAST sequence
                             identity of 67.1
REGION                     38..156
                           note = Pfam Name: Tim17 Pfam Description: Tim17/Tim22/Tim23
                             family
source                     1..214
                           mol_type = protein
                           note = Populus balsamifera subsp. trichocarpa
                           organism = Populus balsamifera
SEQUENCE: 179
MATANSPNTS NNSDSDVEDP NPNPSSNNNN ASIIPSAESS TPSVCLIRFA GDSAAGAFMG   60
SIFGYGSGLI KKKGPKGSFG EAGSCAKTFA VLSGVHSLVV CFLKRLRGKD DVINAGVAGC  120
CTGLALSFPG APQALLQSCL TFGAFSFIIE GLNKKQAALA HSISSRNKCD YHSKPCPLAL  180
PLSVPLPDEL KGAFSFFCKS LRKPKSANFP AAAP                             214

SEQ ID NO: 180             moltype = AA  length = 136
FEATURE                    Location/Qualifiers
REGION                     1..136
                           note = Synthesized Sequence
REGION                     1..136
                           note = Ceres CDNA ID no. 23799376
REGION                     1..136
                           note = Ceres Clone ID no. 375578
REGION                     1..136
                           note = Ceres Seed Line ID no. ME02064
source                     1..136
                           mol_type = protein
                           organism = synthetic construct
SEQUENCE: 180
MGKRGKWFSA VKKVFSSSDP DGKEAKAQKA DKSKSKRRWP FGKSKHSEPS ISTVPGTAPA   60
VAPLPSPPAT QPHSLEIKDV NPVETDSEQN KHAYSVALAS AVAAEAAAVA AQAAAEVVRL  120
TAVTTAAPKM PVSSRE                                                136

SEQ ID NO: 181             moltype = DNA  length = 1020
FEATURE                    Location/Qualifiers
misc_feature               1..1020
                           note = Ceres CLONE ID no.19199
misc_feature               1..1020
                           note = Encodes the peptide given in SEQ ID NO. 182
source                     1..1020
                           mol_type = unassigned DNA
                           organism = Arabidopsis thaliana
SEQUENCE: 181
acccactaga accgttgtaa cctacgaccc ataataatgt accatctcct tatcattatc   60
actacactct ccttctcttc aattaacata accttcgccg tcgatgaagc tttcccttca  120
attcccacta ccttcagcgt cgcaacgaaa caacactacg acgtaaaacc aatccaccat  180
gaagtttatg acgagaaag gaagatatac gacatcagcc accagtacac gccggagttg  240
ccggtttggg agtcttcaga aggactaggg aactttctta gacttgccgt gagtatgaag  300
aatggatccg atgctaatat ctcgaagatg gaactatctg ttcactctgg aactcatgtt  360
gatgcaccag gccatttcca tgaccattat tatgagtctg gttttgatac tgattcactt  420
gatcttcaaa tccttaatgg tcctgcttta ttggttgatg ttccaagaga taagaacatt  480
tcagctgagg ttatgaaatc actacatatt ccaagaggga tccgtcgtgt tctctttaaa  540
acattgaaca ctgataggag gcttatgttt aagaaagaat ttgattcaag ctttgtcggg  600
tttatggtcg atggggcgaa atggttggtt gaaaatacaa acatcaaact tgttgggctt  660
gattatcttt catttgctgc ttatgatgaa gcacctgcga cgcataggtt tatacttgaa  720
cgacgggata taatccctgt cgaagcgctc aagctggatg acgtggaggt aggaatgtac  780
acgcttcatt gcttaccgtt aagattggtt ggagcggaag gagcaccaac gagatgcatt  840
ctcatcaagt gattcagttc atcttttttct atctaagttg tatatgaatt actgataata  900
aacaataggc ttttggctt cttgcttcca agatctcata accatatcga agatgttaac  960
```

```
                        atatgggatg attttgttgt aaaagaagcg tctaatctta ttatataaag tatggttttc    1020

SEQ ID NO: 182          moltype = AA  length = 271
FEATURE                 Location/Qualifiers
REGION                  1..271
                        note = Ceres CLONE ID no. 19199
REGION                  57..257
                        note = Pfam Name: Cyclase Pfam Description: Putative cyclase
REGION                  1..271
                        note = Functional Homolog of Ceres CLONE ID no. 8686 at SEQ
                          ID NO. 80 with e-value of 2.60E-100 and BLAST sequence
                          identity of 83.4
source                  1..271
                        mol_type = protein
                        organism = Arabidopsis thaliana
SEQUENCE: 182
MYHLLIIITT LSFSSINITF AVDEAFPSIP TTFSVATKQH YDVKPIHHEV YDGERKIYDI    60
SHQYTPELPV WESSEGLGNF LRLAVSMKNG SDANISKMEL SVHSGTHVDA PGHFHDHYYE   120
SGFDTDSLDL QILNGPALLV DVPRDKNISA EVMKSLHIPR GIRRVLFKTL NTDRRLMFKK   180
EFDSSFVGFM VDGAKWLVEN TDIKLVGLDY LSFAAYDEAP ATHRFILERR DIIPVEALKL   240
DDVEVGMYTL HCLPLRLVGA EGAPTRCILI K                                 271

SEQ ID NO: 183          moltype = DNA  length = 1291
FEATURE                 Location/Qualifiers
misc_feature            1..1291
                        note = Ceres CLONE ID no.1940431
misc_feature            1..1291
                        note = Encodes the peptide given in SEQ ID NO. 184
source                  1..1291
                        mol_type = unassigned DNA
                        organism = Gossypium hirsutum
SEQUENCE: 183
agggtatcac gatcccttaa aagcggcaca gcaagccaat gagtggagcg cagattttaa    60
acgcaaaaaa ccaacttcac ttcccatttc ctagtcttcc acgatgactc ccctccactt   120
cttcctcctc ctcctccttt cgtcagctgc tttaatctcc gcggccgccg ccaccgccac   180
caccgcatat ccttccatcc cgggcaccga ttccacaact gattgtggcc tatccggagg   240
ggacgagaat ccagttccca tccgtcgcga agtctacggt aacggcaaga tattcgacat   300
cagccatagg tacaccgtcg acatgccgtc ttgggaatcc aaggacggcg tgggacagtt   360
cctatggttg cctaaaagca tgaagaacgg ttccctcgct aataattcgg agatgaaact   420
cccaactcac accggcaccc accttgacgc tccggacacg gtcatcgatc ggtacttcga   480
tgccggcttc gatgtcgata ccctagattt ggaagtactt aatggtcctg ccctgttgat   540
agatgttcca agggataaaa acattactgc cgaggttatg gagtctttga aaataccaaa   600
gggagtacgt agagttcttt tcagaacatt aaatactgac aggcgactaa tgtttaagaa   660
agagtttgat acaagctacg ttggatttat gaaggatgga gcagagtggt tggttaaaca   720
cactgacata aaacttattg gaattgatta cttatctgtt gctgcctttg atgatttgat   780
tccatctcat atagttttcc tagaagaccg ggatatcatt cttgtggaag gtttaaaact   840
cgataacgtt caacctggaa tatattcagt ccattgctta ccattaagat tgcttggtgc   900
tgaaggatca ccaacaagat gcattctcat caaatgatgt tgttgtcctt gttactataa   960
aagacttgag ataagtgggt acgttttcaa ggcaatgatg atgctaatgg cacaccgtca  1020
tcttacaccg tcgtcttatt aggcatgttg tttggaaaga ggaaatgggc gggtgacatt  1080
aagggtgtg tttgattgga acaaggcaaa taacgggttt atgagttaga acttgacgct  1140
gttaggaatc ctagaaggga gcttcagtat agaaatttgg ttgcagtgaa ctacacttt   1200
cgtgtaatat atcattatga tatttctttt aagttccctt ttatttcata ataataata   1260
cacttacgcc atatttttgg ttggttggag t                                1291

SEQ ID NO: 184          moltype = AA  length = 277
FEATURE                 Location/Qualifiers
REGION                  1..277
                        note = Ceres CLONE ID no. 1940431
REGION                  63..263
                        note = Pfam Name: Cyclase Pfam Description: Putative cyclase
REGION                  1..277
                        note = Functional Homolog of Ceres CLONE ID no. 8686 at SEQ
                          ID NO. 80 with e-value of 1.49E-86 and BLAST sequence
                          identity of 72.1
source                  1..277
                        mol_type = protein
                        organism = Gossypium hirsutum
SEQUENCE: 184
MTPLHFFLLL LLSSAALISA AAATATTAYP SIPGTDSTTD CGLSGGDENP VPIRREVYGN    60
GKIFDISHRY TVDMPSWESK DGVGQFLWLP KSMKNGSLAN NSEMKLPTHT GTHLDAPGHV   120
IDRYFDAGFD VDTLDLEVLN GPALLIDVPR DKNITAEVME SLKIPKGVRR VLFRTLNTDR   180
RLMFKKEFDT SYVGFMKDGA EWLVKHTDIK LIGIDYLSVA AFDDLIPSHI VFLEDRDIIL   240
VEGLKLDNVQ PGIYSVHCLP LRLLGAEGSP TRCILIK                            277

SEQ ID NO: 185          moltype = DNA  length = 1349
FEATURE                 Location/Qualifiers
misc_feature            1..1349
                        note = Ceres CLONE ID no.1646125
```

```
misc_feature          1..1349
                      note = Encodes the peptide given in SEQ ID NO. 186
source                1..1349
                      mol_type = unassigned DNA
                      organism = Glycine max
SEQUENCE: 185
aatatgtcgc cgcctcaatt tttcagacca aaatgatttt ttaaaatttt tttgtcattg   60
ttgtaaaaat aacaaataat aaataaaaaa attaaaaaat aacattctgt caagagatgg  120
atgtgtttca ttcatctttg tgtttcattc atctttctca gtcaaccatg aactctcgat  180
cactctttgc cttcctcttc gcaatttgcg cgcactccgt cgccgttgcc gacacctcct  240
ccgcgtatcc ttccatcccc ggcacggaaa ccggtgagtg ctccctccgc ggcgtggggcg  300
tgggcgacgg tgttctggtt cctccacggc gagaagtata cgaggagggg cgaatcttcg  360
acatcactca cagatatgtc cccgagatgc cggtgtggga ctcgacggag gggctcgggc  420
aacacttcct gtggctcgat aagagcatga agaatggctc gctcgctaac agctctaaca  480
tgaagctcgg tgttcacacc ggcacccatg tcgacgcgcc cggtcacttt tacgacaatt  540
actacgacgc tggcttcgac gttgactcac tcgacctaac gctcctcaat ggccttgcac  600
ttctggttga tgttccgcgg gataaaaaca ttactgctga ggttatgagg tccctgaata  660
tccctagagg tgtaagccgt gtgcttttca gaactttaaa cactgacagg cgactcatgt  720
ttaagaaaga atttgacaca agctatgtgg gattcaagga ggatggtgca aaatggctgg  780
cagagaacac tgacatcaaa cttgtaggag ttgattactt atctgttgct gcttatgatc  840
actccattcc atctcatctt gttttctgg aaagcaagga aatcattctt gtggaaggcc  900
taaagcttga tgatgtccca gcaggaatat attcattgaa ttgcttgcct cttaggttgg  960
ttcactctga ggcatcacca attcgatgta ttctgatcag atgatccatg atggggtcaa 1020
acctggtttt caattgcacg gatgaacctg ccattagaag caacgtagcc ccgaatacaa 1080
ttagtggtgt ccataagaag cagtttgatg caaattgcaa gctaagctga tagtagtacg 1140
ttgaaattac tcgtatttta cgtccttggg ttgtaaacta ccgagttatt gtgattaaac 1200
ttcagttgcg gactaggggt ccacctgtat taactatgt ttttaatatt tacctaggca 1260
agtacttgcg caattctgaa tacgcatgct tgtacgcctc aataattata tctatttctc 1320
tatgaaaaat aaaaaaaaaa aaaaaaaaa                                  1349

SEQ ID NO: 186        moltype = AA  length = 278
FEATURE               Location/Qualifiers
REGION                1..278
                      note = Ceres CLONE ID no. 1646125
REGION                63..264
                      note = Pfam Name: Cyclase Pfam Description: Putative cyclase
REGION                1..278
                      note = Functional Homolog of Ceres CLONE ID no. 8686 at SEQ
                       ID NO. 80 with e-value of 5.39E-84 and BLAST sequence
                       identity of 71.3
source                1..278
                      mol_type = protein
                      organism = Glycine max
SEQUENCE: 186
MNSRSLFAFL FAICAHSVAV ADTSSAYPSI PGTETGECSL RGVGVGDGVL VPPRREVYEE   60
GRIFDITHRY VPEMPVWDST EGLGQHFLWL DKSMKNGSLA NSSNMKLGVH TGTHVDAPGH  120
FYDNYYDAGF DVDSLDLTLL NGLALLVDVP RDKNITAEVM RSLNIPRGVS RVLFRTLNTD  180
RRLMFKKEFD TSYVGFKEDG AKWLAENTDI KLVGVDYLSV AAYDHSIPSH LVFLESKEII  240
LVEGLKLDDV PAGIYSLNCL PLRLVHSEAS PIRCILIR                         278

SEQ ID NO: 187        moltype = DNA  length = 953
FEATURE               Location/Qualifiers
misc_feature          1..953
                      note = Ceres CLONE ID no.1759790
misc_feature          1..953
                      note = Encodes the peptide given in SEQ ID NO. 188
source                1..953
                      mol_type = unassigned DNA
                      organism = Panicum virgatum
SEQUENCE: 187
acgtgtcaac tgcacttcca gaaaggcaaa tccattccat ggagctcgcg ccgctgctcc   60
tgctccccc gctgctgctg ctccggcgg cggccgtcgc ctccggcggt gagccgccgc  120
tggcgcaccc ggcctatgcg cgcggcgccg aggaggcatg cggcgtggcg gcgctgccag  180
cgccggagcg gcgcgaggag ttcgacgcg ggcggatccg gacatcagc cactactacg  240
gcgcggacat gccggcgtgg gagtcggcgg agggctccgg cgagttcctg cggctggcgc  300
ggtccatgcg caacgctcc gacatcgcca acttctcgga gctccgcctc accgcgcact  360
ccggcaccca cgtcgacgcg ccggggcacg tcttcgagca ctactacgac accggcttcg  420
acgtcgacac gctcgacctc gccgtcctca acgggccagc gctgttggtt gacgttcccc  480
gagataagaa cataacaggt gttcgacgtg tactcttccg aacctaaat actgacagaa  540
agcttatgtg gaagaaagag tttgatacta gttatgttgg cttcatgaag gatggtgcac  600
aatggctggt cgacaatact gacatcaaac tagttgaagt tgattacttg tctgtgggtg  660
catttgcgca atgcattcca gctcatctag tatttcttga aaaagggag gtaatccttg  720
tggaagcctt aaatctggag catgctaccc tggaatata tgccttgcat tgcttgccac  780
taagattgcg tgttgctgaa ggttctcctg caaaatgcat ccttatcaag tgacacatgg  840
ttacaaccat ctagaaaacc tttgtactat cttatggcac gtatgataat gaaataagaa  900
aaggtcaacg catatgactt cttctcttgc atcaaaaaaa aaaaaaaaaa aaa         953

SEQ ID NO: 188        moltype = AA  length = 264
FEATURE               Location/Qualifiers
```

```
REGION                  1..264
                        note = Ceres CLONE ID no. 1759790
REGION                  60..250
                        note = Pfam Name: Cyclase Pfam Description: Putative cyclase
REGION                  1..264
                        note = Functional Homolog of Ceres CLONE ID no. 8686 at SEQ
                           ID NO. 80 with e-value of 8.09E-74 and BLAST sequence
                           identity of 68.2
source                  1..264
                        mol_type = protein
                        organism = Panicum virgatum
SEQUENCE: 188
MELAPLLLLP PLLLLPAAAV ASGGEPPLAH PAYARGAEEA CGVAALPAPE RREEFDGGRI    60
VDISHYYRAD MPAWESAEGS GEFLRLARSM RNGSDIANFS ELRLTAHSGT HVDAPGHVFE   120
HYYDTGFDVD TLDLAVLNGP ALLVDVPRDK NITGVRRVLF RTLNTDRKLM WKKEFDTSYV   180
GFMKDGAQWL VDNTDIKLVG VDYLSVGAFD ECIPAHLVFL EKREVILVEA LNLEHATPGI   240
YALHCLPLRL RGAEGSPAKC ILIK                                         264

SEQ ID NO: 189          moltype = DNA  length = 1029
FEATURE                 Location/Qualifiers
misc_feature            1..1029
                        note = Ceres CLONE ID no.741003
misc_feature            1..1029
                        note = Encodes the peptide given in SEQ ID NO. 190
source                  1..1029
                        mol_type = unassigned DNA
                        organism = Triticum aestivum
SEQUENCE: 189
agcaccacct actagcccac acatatccgc gacgccgatg ccccaaatgg cgtctcctct    60
cctcctcctc cctctcgccg ccgcccaccgc accgtgcgcc catccggcct acccgagcca   120
gccggcgtcg tgcgccgcgg agcccgcgct ggcgccggag cgccgggaga cgcacggcgg   180
gggccgcatc ctggacatca cccactacta ccgggaggac atgccctcgt gggagtccag   240
cgccggggtg ggccagttcc tgtggctgcc cgcctccatg cgcaacggct ccctcgccaa   300
caactccgag atgcggatgc cacccacac cggcaccgcc ccggccacgt                360
cttccagcac tacttcgacg ctggcttcga cgtcgacacc ctcgacctcg acgtcctcaa   420
cggtcctgca ctgctggttg atgttccaag ggatcaaaat attactgcta aaacgatgga   480
atctttgcat attcctaaag gagttcaacg ggtactttc agaacattaa acactgcagg     540
gaacctaatg tggaagaaag agtttgacac aagctatgta ggttttatga agatggtgc    600
ccaatggttg gtagacaaca cggatattaa gcttgtcgga atagctatt tgtccgttgc     660
agctttcgat gacctgatcc cttcacattt agttttctc gaaaaccggg atgtcattct     720
tgtggagggc ctcaaactgg agaatgtcaa acctgggata tactcgttgc attgcctgcc   780
acttcggttg cgtggagcgg aaggttcgcc gatcagatgc atccttataa agtgaagaca   840
cttgtatccc gctgcgattt agttttatac cgcaagcact cttataaact agactagaa    900
tgtgtacaaa accccatctt tgatagcgga cgagtattgt aaatgtctcc acaaacatgg   960
tggcactttg acgcttagta aggagcgaca aacgactagg ggtgcaaatg tgtaaaaaaa  1020
aaaaaaaaa                                                           1029

SEQ ID NO: 190          moltype = AA  length = 265
FEATURE                 Location/Qualifiers
REGION                  1..265
                        note = Ceres CLONE ID no. 741003
REGION                  51..251
                        note = Pfam Name: Cyclase Pfam Description: Putative cyclase
REGION                  1..265
                        note = Functional Homolog of Ceres CLONE ID no. 8686 at SEQ
                           ID NO. 80 with e-value of 9.39E-80 and BLAST sequence
                           identity of 67.2
source                  1..265
                        mol_type = protein
                        organism = Triticum aestivum
SEQUENCE: 190
MPQMASPLLL LPLAAATAPC AHPAYPSQPA SCAAEPALAP ERRETHGGGR ILDITHYYRE    60
DMPTSWESSAG VGQFLWLPAS MRNGSLANNS EMRRMPTHTGT HVDAPGHVFQ HYFDAGFDVD  120
TLDLDVLNGP ALLVDVPRDQ NITAKTMESL HIPKGVQRVL FRTLNTDRNL MWKKEFDTSY   180
VGFMKDGAQW LVDNTDIKLV GIDYLSVAAF DDLIPSHLVF LENRDVILVE GLKLENVKPG   240
IYSLHCLPLR LRGAEGSPIR CILIK                                         265

SEQ ID NO: 191          moltype = AA  length = 269
FEATURE                 Location/Qualifiers
REGION                  1..269
                        note = Public GI ID no. 35215089
REGION                  55..255
                        note = Pfam Name: Cyclase Pfam Description: Putative cyclase
REGION                  1..269
                        note = Functional Homolog of Ceres CLONE ID no. 8686 at SEQ
                           ID NO. 80 with e-value of 1.90E-79 and BLAST sequence
                           identity of 66.2
source                  1..269
                        mol_type = protein
```

```
                        note = Oryza sativa subsp. japonica
                        organism = Oryza sativa
SEQUENCE: 191
MAHLAPLFLL LLLLLLPLHA AATPSAHPAY PNEPPSCAAA VPVPERREAH GGGRILDITH   60
YYREDMPSWE SDGGVGQFLW LPASMRNGSR ANNSEMRLPT HTGTHVDAPG HVFQHYFDAG  120
FDVDSLDLEV LNGLALLVDV PRDDNITAKM MESLHIPKGI QRVLFRTLNT DRQLMWKKEF  180
DTSYVGFMED GAQWLVDNTD IKLVGIDYLS VAAFDDLIPS HLVLLKNRDI ILVEGLKLEN  240
IMPGIYSLHC LPLRLRGAEG SPIRCILIK                                   269

SEQ ID NO: 192          moltype = AA  length = 270
FEATURE                 Location/Qualifiers
REGION                  1..270
                        note = Public GI ID no. 115475854
REGION                  56..256
                        note = Pfam Name: Cyclase Pfam Description: Putative cyclase
REGION                  1..270
                        note = Functional Homolog of Ceres CLONE ID no. 8686 at SEQ
                        ID NO. 80 with e-value of 1.90E-79 and BLAST sequence
                        identity of 66.2
source                  1..270
                        mol_type = protein
                        note = Oryza sativa subsp. japonica
                        organism = Oryza sativa
SEQUENCE: 192
MMAHLAPLFL LLLLLLLPLH AAATPSAHPA YPNEPPSCAA AVPVPERREA HGGGRILDIT   60
HYYREDMPSW ESDGGVGQFL WLPASMRNGS RANNSEMRLP THTGTHVDAP GHVFQHYFDA  120
GFDVDSLDLE VLNGLALLVD VPRDDNITAK MMESLHIPKG IQRVLFRTLN TDRQLMWKKE  180
FDTSYVGFME DGAQWLVDNT DIKLVGIDYL SVAAFDDLIP SHLVLLKNRD IILVEGLKLE  240
NIMPGIYSLH CLPLRLRGAE GSPIRCILIK                                  270

SEQ ID NO: 193          moltype = DNA  length = 909
FEATURE                 Location/Qualifiers
misc_feature            1..909
                        note = Ceres ANNOT ID no.1450986
misc_feature            1..909
                        note = Encodes the peptide given in SEQ ID NO. 194
source                  1..909
                        mol_type = unassigned DNA
                        note = Populus balsamifera subsp. trichocarpa
                        organism = Populus balsamifera
SEQUENCE: 193
atggaggaa attttgcaca aagaatgcaa atttcgacaa catggattga tacaggcaat    60
cttgcaagaa aaccaactgg ttttctacgg ttttcgggga gattaaagga acagaagaga  120
ctccaagtgt ttgttctgc tcagtttcga cctgtaagag atgaaaatcg acatagattg   180
gcttcttttg aggtttctcg ctcttataac aattctcgag tttcgacgtt ggaatctgag  240
agtctccagg atttgcttga cgatgaagct ttgattttga agaataagtc gcaggagatt  300
gagccctatt taaacggacg ctgtatatat ctttgttgga tgtgggctc tggaaaaaca  360
acagtgggaa agattctctc gcaagcaatt cattattcat tctgtgacag tgacacattg  420
gtggagaagg atgttggtgt gacttctgta gctgaaatat ttcaaatata tggagaggat  480
ttcttcagag ataaagagac tgaggcatta gaaaagctat cactagagca ccgatatgtc  540
gtttctactg gtgtgaggtgc tgtgatacag gatgaaaact gacgtacat gaggaaggtg  600
attagtgtct ggttagatgt gcctttggaa gaattggcac agaggattgc ggctgtagga  660
accaagactc gcccccttt ggatagaaa ccaggagatg catacaccaa ggcgttcagg    720
cgtctgtctg ctctgtttga acagatat aaagcttatg aaaatgctaa tgcaagggtt    780
tctctggaaa atattgcagc caaattagga tataaagatg tatccaatat cacaccacct  840
atgattgcga ttgagaacat ggcttgggtg atgcattacg cagcaggttt ccgtctatta  900
ccagtgtaa                                                         909

SEQ ID NO: 194          moltype = AA  length = 302
FEATURE                 Location/Qualifiers
REGION                  1..302
                        note = Ceres ANNOT ID no. 1450986
REGION                  115..291
                        note = Pfam Name: SKI Pfam Description: Shikimate kinase
REGION                  1..302
                        note = Functional Homolog of Ceres CDNA ID no. 23363195 at
                        SEQ ID NO. 106 with e-value of 2.09E-73 and BLAST sequence
                        identity of 55.9
source                  1..302
                        mol_type = protein
                        note = Populus balsamifera subsp. trichocarpa
                        organism = Populus balsamifera
SEQUENCE: 194
MEGNFAQRMQ ISTTWIDTGN LARKPTGFLR FSGRLKEQKR LQVFVSAQFR PVRDENRHRL   60
ASFEVSRSYN NSRVSTLESE SLQDLLDDEA LILKNKSQEI EPYLNGRCIY LVGMMGSGKT  120
TVGKILSQAI HYSFCDSDTL VEKDVGVTSV AEIFQIYGED FFRDKETEAL EKLSLEHRYV  180
VSTGGGAVIQ DENWTYMRKG ISVWLDVPLE ELAQRIAAVG TKTRPLLDRE PGDAYTKAFR  240
RLSALFEQRY KAYENANARV SLENIAAKLG YKDVSNITPP MIAIENMAWV MHYAAGFRLL  300
PV                                                                302
```

```
SEQ ID NO: 195           moltype = DNA  length = 1392
FEATURE                  Location/Qualifiers
misc_feature             1..1392
                         note = Ceres CLONE ID no.1973421
misc_feature             1..1392
                         note = Encodes the peptide given in SEQ ID NO. 196
source                   1..1392
                         mol_type = unassigned DNA
                         organism = Gossypium hirsutum
SEQUENCE: 195
ctctccgtta tttggatctg atgttgattt tatgttttaa agtgctttgt tttcagtttt   60
ttttttttggt gaagtagagc ataatttc agcattgcat gcaacttcaa tctgaattta   120
gggttttat tatgaaccga acccgttttg caaagattta aaactatggg atctgcaagt   180
tatctgaaat agtcttcatt tctcttggag tcagagagca aagcccttca caaaattcat   240
tttctcttta ttaattatcc aagggctga aatggaggc tggagttgca tgcaagttga    300
attatccgac atgattgag tcagaaaggt ttgggaggaa ctcgactggt actttgcggt    360
tcagtcggat agcaaagcaa gaacacaagg cccggctggt tgtttcggcg cactttccgg   420
ttctgacatc ttctaatcgg tttagatcgg tctctttcga ggtttcctgc tcttcctcta   480
agaacttttc agcttcaaca attgaaactg gtagcgttca tgcacccttat gatgaagctt   540
tagtgttaaa gaataagtca ctagaggttg agccatattt aaatgggcac agtatatatc   600
ttgttggatt gatgggttct ggaaaaacta cagtgggaaa aattctgtct aacgtactca   660
gttattcatt ttgtgacagt gacgtgttaa tagagcagga ggtgaatgga atgtctgtag   720
ccgaagtatt taagcttcat ggtgagagat tcttcagaaa gaaggagact gaggtattgc   780
agaggctctc ttcaaagaaa cagcttgttg tttctactgg cggaggtgca gttgtatggg   840
atgtgaactg ggattatatg caaaagaagg gggttgttgt ctggttagat gtacctttgg   900
aagccttggc acagaggatt gctgcagtag gtactcattc tcgtccctt ttgcattatg    960
aacatggcga tccctataca aaggctttaa acggctgtc ttaccttttg gaactgaggg   1020
gtaaaaatta tgctaaagca aatgcccggg tttcattgaa agaaattgca ggcaaactag   1080
gttatagaga tgtatcagat cttactccaa cagagattgc aatcgaggca ttgcaacaaa   1140
ttgaagggta tctaaaggag gaaggtggca tggtcattgc tggattatag ttttgaaaaa   1200
gctatagata tggtgattga atttcgtttt atttgtggca tagcatgtca aaattgacca   1260
gttttttttt ccatctctgc accggtgtag tttgtttcca caactaagtt gtgtaactca   1320
caatgtattg tcactaaata tcatgaacat gatgcacttg tatatgtttg cctaattcat   1380
ttttgtttta gt                                                       1392

SEQ ID NO: 196           moltype = AA  length = 305
FEATURE                  Location/Qualifiers
REGION                   1..305
                         note = Ceres CLONE ID no. 1973421
REGION                   114..291
                         note = Pfam Name: SKI Pfam Description: Shikimate kinase
REGION                   1..305
                         note = Functional Homolog of Ceres CDNA ID no. 23363195 at
                           SEQ ID NO. 106 with e-value of 2.90E-78 and BLAST sequence
                           identity of 55.8
source                   1..305
                         mol_type = protein
                         organism = Gossypium hirsutum
SEQUENCE: 196
MEAGVACKLN YPTWIESERF GRNSTGTLRF SRIAKQEHKA RLVVSAHFPV LTSSNRFRSV    60
SFEVSCSSSK NFSASTIETG SVHAPYDEAL VLKNKSLEVE PYLNGHSIYL VGLMGSGKTT   120
VGKILSNVLS YSFCDSDVLI EQEVNGMSVA EVFKLHGERF FRKKETEVLQ RLSSKQLVV   180
STGGGAVVWD VNWDYMQKKG VVVWLDVPLE ALAQRIAAVG THSRPLLHYE HGDPYTKALK   240
RLSYLLELRG KNYAKANARV SLKEIAGKLG YRDVSDLTPT EIAIEALQQI EGYLKEEGGM   300
VIAGL                                                               305

SEQ ID NO: 197           moltype = AA  length = 287
FEATURE                  Location/Qualifiers
REGION                   1..287
                         note = Public GI ID no. 38344899
REGION                   100..276
                         note = Pfam Name: SKI Pfam Description: Shikimate kinase
REGION                   1..287
                         note = Functional Homolog of Ceres CDNA ID no. 23363195 at
                           SEQ ID NO. 106 with e-value of 3.39E-66 and BLAST sequence
                           identity of 55.5
source                   1..287
                         mol_type = protein
                         note = Oryza sativa subsp. japonica
                         organism = Oryza sativa
SEQUENCE: 197
MDAGVGLRAK PGAWAGLGNP RRSSTARVPV RFAVEKFAQP LVLGSDRRSC GAKLKVSCSR    60
KPAGIDKTYY SADEALVLKQ KAEDVVPYLN DRCIYLVGMM GSGKTTVGKI LAEVLGYSFF   120
DSDKLVEKAV GISSVAEIFQ LHSEAFFRDN ESEVLRDLSS MHRLVVATGG GAVIRPINWS   180
YMKKGSTIWL DVPLDALARR IAAVGTASRP LLHQESGDPY AKAYAKLTAL FEQRMDSYAN   240
ADARVSLEHI AVKQGHSNVT TLTPSAIAIE ALLKMESFLT EKAMIRN                287

SEQ ID NO: 198           moltype = AA  length = 300
```

| FEATURE | Location/Qualifiers |
|---|---|
| REGION | 1..300 |
| | note = Public GI ID no. 114200 |
| REGION | 113..288 |
| | note = Pfam Name: SKI Pfam Description: Shikimate kinase |
| REGION | 1..300 |
| | note = Functional Homolog of Ceres CDNA ID no. 23363195 at SEQ ID NO. 106 with e-value of 6.80E-77 and BLAST sequence identity of 54.7 |
| source | 1..300 |
| | mol_type = protein |
| | organism = Lycopersicon esculentum |

SEQUENCE: 198

```
MEARVSQSLQ LSSWINSDKV VRKPSGLLRF SEKWNEKPRH RVVVSCHLQP RKAAHSDRRV   60
QLKVSCSPQN VQASVLESGC FSASIDEIET LKNKAEEVEE YLDGRCVYLV GMMGCGKTTV  120
GRILAETLGY SFFDCDRLIE QAVGGITVAE IFELRGESFF RDNETEVLHK LSLMHRLVVS  180
TGGGAVVRPI NWRHMHKGIS VWLDVPLEAL AKRITTEGTK SRPLLHEESG DVYDTTLKRL  240
TTLMETRGEN YANASARVSL ENIALKREKD VCHITPAEIT LEVLIQIENF LKTQKSVVVL  300
```

| SEQ ID NO: 199 | moltype = DNA length = 1248 |
|---|---|
| FEATURE | Location/Qualifiers |
| misc_feature | 1..1248 |
| | note = Ceres CLONE ID no.1769327 |
| misc_feature | 1..1248 |
| | note = Encodes the peptide given in SEQ ID NO. 200 |
| source | 1..1248 |
| | mol_type = unassigned DNA |
| | organism = Panicum virgatum |

SEQUENCE: 199

```
ctccttcaat tccctctcat ctcgcgtctc cgcacggaga gccgccctcc tcgtccgccg   60
ccgcctgccg ccggcgagct cttcattacc ccggcgatgg ccggcctatc caaaaccacc  120
atcaccaatc acgtctagca catctcgccc gagcggctga gccacacgtc acagcaacac  180
atcaagccgc gcggatcgac aggaagatgg aggcgagcgt gggcatccgg gcgcggcccg  240
gtgcgtgggc cgggctcgag aagccgcgcg gcgcttgctc tgcaagagtc ccggcggcgg  300
ggctcacggc ggagaagctg ccggcgaggc tggctctggg aaccgatccg gcgaggagca  360
cggatcctgt gctccgtgcc gcaaagatga agcttcgtg ttgcaagaaa tcgacaggta  420
ctgaaaaggt ccactactct gccgatgaag ctctcatact acagcaaaaa gcccaggatg  480
ttctcccgtta cttggatggc cgatgcattt atctagtcgg aatgatgggt tcaggcaaaa  540
ctacagttga gaagtatta gctgaagtac taggttattc tttcttcgac agtgataagt  600
tggtagagaa ggctgtcggt atatcatctg ttgctgagat ttttcagctc cacagtgaag  660
cattcttcag agataatgag agtgaggtcc taagggattt gtcatcaatg catccggttag  720
ttgttgcaac tggaggtggt gccgtgatcc gaccaatcaa ttggagttac atgaagaaag  780
ggctgactgt gtggttagat gttccactgg atgcacttgc aagaaggatt gctgccgtgg  840
gaactgcatc tcggccctc ttgcatcagg aatctggtga cccatatgca aaggcttatg  900
caaaacttac atcacttttt gagaaagaa tggactcgta tgctaatgcg gatgccagag  960
tttcacttga acatattgca ttaaaacaag ggcataatga tgtcactata cttacaccta 1020
gtaccattgc cattgaggca ttattaaaga tggaaagttt ccttactgag aaggccatgg 1080
tcagaaactg accgcttgtt gctggggaaa agggcaccaa cagcatatgg ccctgtttg 1140
tttaattgtg cttgtacata tgcctttgca tgagctcttt acagtactgt tagattgttg 1200
ttcatgcaac atgaaagatg attattcgaa aaaaaaaaaa aaaaaaaa                1248
```

| SEQ ID NO: 200 | moltype = AA length = 294 |
|---|---|
| FEATURE | Location/Qualifiers |
| REGION | 1..294 |
| | note = Ceres CLONE ID no. 1769327 |
| REGION | 107..282 |
| | note = Pfam Name: SKI Pfam Description: Shikimate kinase |
| REGION | 1..294 |
| | note = Functional Homolog of Ceres CDNA ID no. 23363195 at SEQ ID NO. 106 with e-value of 2.79E-64 and BLAST sequence identity of 53.0 |
| source | 1..294 |
| | mol_type = protein |
| | organism = Panicum virgatum |

SEQUENCE: 200

```
MEASVGIRAR PGAWAGLEKP RGACSARVPA AGLTAEKLPA RLALGTDPRR STDPVLRAAK   60
MKASCCKKST GTEKVHYSAD EALILQQKAQ DVLPYLDGRC IYLVGMMGSG KTTVEKILAE  120
VLGYSFFDSD KLVEKAVGIS SVAEIFQLHS EAPFRDNESE VLRDLSSMHR LVVATGGGAV  180
IRPINWSYMK KGLTVWLDVP LDALARRIAA VGTASRPLLH QESGDPYAKA YAKLTSLFEK  240
RMDSYANADA RVSLEHIALK QGHNDVTILT PSTIAIEALL KMESFLTEKA MVRN         294
```

| SEQ ID NO: 201 | moltype = DNA length = 745 |
|---|---|
| FEATURE | Location/Qualifiers |
| misc_feature | 1..745 |
| | note = Ceres CLONE ID no.1728680 |
| misc_feature | 1..745 |
| | note = Encodes the peptide given in SEQ ID NO. 202 |
| source | 1..745 |
| | mol_type = unassigned DNA |

```
                          organism = Musa acuminata
SEQUENCE: 201
gctctcgtcg ctaccgcaat ggcagcatca catggttggc tcacttctct gcccaaccaa    60
ttggctgtcg caagctctgt cgtcaaccat cgatccgctg cggctgcttc gttcgtcgtc   120
agggcgagct cgacggggat gc atcacttacg gagaaggatt gtttaaggag aaggcaggtt   180
ttagttggac tcagttcctt gaccgctgct ttgtcccggg caaattttgc aagtgctgaa   240
gatataccgg agaattttcg agctttcgtg gattttacag atggatatgc atactattat   300
ccttccgatt ggagagattt tgattacatg ggccatgatt cagcatttaa agatcgattt   360
gcagcattgc aacatgtcag agtcagtttc attcctaccg aaaagaaaga tattcgtgat   420
ttgggatcca tggaggaggt catttttcaac ttggtaaaaa atatttatgc tgcaccaaat   480
cagattccga gcatatatga gatgcaggag cgaactgtcg atggaaagaa ctattggaca   540
ttcgaatacg aacttgaatc cccaagcttt tcccgtactg cctttgcgac aatagctatt   600
ggcaatgggc ggtactacac attagttgtt ggtgcaaatg agaggcggtg gactagactt   660
cggaacaagc tcaaggtggt agcagactct ttcaagattc ttgacatatg aaactagaag   720
tgcttgcctg ccgaaccatg agtcc                                         745

SEQ ID NO: 202          moltype = AA  length = 230
FEATURE                 Location/Qualifiers
REGION                  1..230
                        note = Ceres CLONE ID no. 1728680
REGION                  48..228
                        note = Pfam Name: PsbP Pfam Description: PsbP
REGION                  1..230
                        note = Functional Homolog of Ceres CLONE ID no. 16403 at
                          SEQ ID NO. 146 with e-value of 1.10E-58 and BLAST sequence
                          identity of 60.2
source                  1..230
                        mol_type = protein
                        organism = Musa acuminata
SEQUENCE: 202
MAASHGWLTS LPNQLAVASS VVNHRSAAAA SFVVRASSTD ASLTEKDCLR RRQVLVGLSS    60
LTAALSRANF ASAEDIPENF RAFVDFTDGY AYYYPSDWRD FDYMGHDSAF KDRFAALQHV   120
RVSFIPTEKK DIRDLGSMEE VIFNLVKNIY AAPNQIPSIY EMQERTVDGK NYWTFEYELE   180
SPSFSRTAFA TIAIGNGRYY TLVVGANERR WTRLRNKLKV VADSFKILDI              230

SEQ ID NO: 203          moltype = DNA  length = 842
FEATURE                 Location/Qualifiers
misc_feature            1..842
                        note = Ceres CLONE ID no.1807796
misc_feature            1..842
                        note = Encodes the peptide given in SEQ ID NO. 204
source                  1..842
                        mol_type = unassigned DNA
                        organism = Gossypium hirsutum
SEQUENCE: 203
atggcagtgg caatggcgat gaattcagtt tcattgaact gggttccacc ttcctttaca    60
aagaaggcaa attatgtgac aaactccact gagctagccc caccttctgc tttttcttcg   120
caaaactcac tcacgtacac caaagaaacc atttccaatg aagaaaacaa ttgcaagaga   180
agactgttgc tcttgggtgt tggagttatt acagctaatt tactccctgc aaattcccct   240
ctagcagaag agataccaca aaactatcga gcttttgttg acattccaga tgggtattct   300
tattactacc catcagattg gagggaattt gattttagag gacatgattc agcattcaaa   360
gacaggtttc ttcaactgca aaatgtaagg gtgagattca taccaactga taagcaagac   420
atccatgagt tggggccaat agaagaggtt gtttacaatt tggtgaatca tgtttatgct   480
gcaccaaatc aaatggtcaa tatacttgat atgcaagaga gaacaagtga tgggaaaaac   540
tattatacct ttgaatatga actcacctct ccaaactatg ctagtgcttc ctttgcaaca   600
atagctattg gaaatgggag atattacaca ctggttgttg gagcacttga agacggttga   660
agaaggcttc gaaacaagct gaaagtggtg gccgactcct tcaaggtgct tgacatctga   720
tgaccccccca acttatcttt tcattgtata taaaccccga aacataccat tggttttgtt   780
tagttgagcg tcatcgtcaa ctttaactat ttctccttct caaaaaaaaa aaaaaaaaa    840
aa                                                                  842

SEQ ID NO: 204          moltype = AA  length = 235
FEATURE                 Location/Qualifiers
REGION                  1..235
                        note = Ceres CLONE ID no. 1807796
REGION                  51..233
                        note = Pfam Name: PsbP Pfam Description: PsbP
REGION                  1..235
                        note = Functional Homolog of Ceres CLONE ID no. 16403 at
                          SEQ ID NO. 146 with e-value of 5.30E-70 and BLAST sequence
                          identity of 59.1
source                  1..235
                        mol_type = protein
                        organism = Gossypium hirsutum
SEQUENCE: 204
MAMNSVSLNW VPPSFTKKAN YVTNSTELAP PSAFSSQNSL TYTKETISNE ENNCKRRLLL    60
LGVGVITANL LPANSLLAEE IPQNYRAFVD IPDGYSYYYP SDWREFDFRG HDSAFKDRFL   120
QLQNVRVRFI PTDKQDIHEL GPIEEVVYNL VNHVYAAPNQ MVNILDMQER TSDGKNYYTF   180
EYELTSPNYA SASFATIAIG NGRYYTLVVG ALERRWRRLR NKLKVVADSF KVLDI        235
```

```
SEQ ID NO: 205            moltype = DNA  length = 883
FEATURE                   Location/Qualifiers
misc_feature              1..883
                          note = Ceres CLONE ID no.1771837
misc_feature              1..883
                          note = Encodes the peptide given in SEQ ID NO. 206
source                    1..883
                          mol_type = unassigned DNA
                          organism = Panicum virgatum
SEQUENCE: 205
ataactgatg ctgggataca agcgtcagag aacacttcct cgagctcagt gctatcctaa    60
actactgaag aaatggcaag cctgcagaat ctgatttgct ccgtatctaa acaactggtt   120
gcgccaaatt ttgcggtgac tgccaaactg aatgggggct ctcactctgt tgtcccagca   180
agctcaagcg gagcatcttc gcatgaaaag aatgtcacga aaaggcagtt agctttgctt   240
ggtgctggag cattagccac cggcctactg aagacaagct ccgcatttgc tgaagaagta   300
cctaagaatt acaagtctta cgtggatgca aaagatggat attcgtatct ttatccagcc   360
gagtggaggg atttcgactt cttgggtcat gattcagcat tcaaagatcg taatctgact   420
cttcagtgtg tccgtgtggg gtttattcct actgataaaa cagatattcg cgacctagga   480
ccaatgcgatg aggccatctt caatttggta acaacgtttt acgctgcccc aaatcaaaaa   540
ccgtcgatct atgacatgca agagcgcacg gtggacggca gaactactg acgttcgag    600
tacgatctgg aggctccggg ctacggcgta tccgcgttcg cagcagtcgc cattggaaac   660
ggtcggtact acacgctgat cgtgaccgcg aacgaacgcc ggtggagcag gctccggaac   720
aggctcaaag tcgtcgcgga ctcttttcaag atctccgacc tgaccgcgtg accgccagcg   780
ttctcgttaa ctgtaatgga cggtctcatt cagtcatggt atatatactt acgcgcgcca   840
taatcgtgcg tgtttcattt gctaaaaaaa aaaaaaaaaa aaa                    883

SEQ ID NO: 206            moltype = AA  length = 232
FEATURE                   Location/Qualifiers
REGION                    1..232
                          note = Ceres CLONE ID no. 1771837
REGION                    73..228
                          note = Pfam Name: PsbP Pfam Description: PsbP
REGION                    1..232
                          note = Functional Homolog of Ceres CLONE ID no. 16403 at
                            SEQ ID NO. 146 with e-value of 6.49E-56 and BLAST sequence
                            identity of 52.3
source                    1..232
                          mol_type = protein
                          organism = Panicum virgatum
SEQUENCE: 206
MASLQNLICS VSKQLVAPNF AVTAKLNGAS HSVVPASSSG ASSHEKNVTK RQLALLGAGA    60
LATGLLKTSS AFAEEVPKNY KSYVDAKDGY SYLYPAEWRD FDFLGHDSAF KDRNLALQCV   120
RVGFIPTDKT DIRDLGPMDE AIFNLVNNVY AAPNQKPSIY DMQERTVDGK NYWTFEYDLE   180
APGYGVSAFA TVAIGNGRYY TLIVTANERR WSRLRNRLKV VADSFKISDL TA           232

SEQ ID NO: 207            moltype = DNA  length = 841
FEATURE                   Location/Qualifiers
misc_feature              1..841
                          note = Ceres CLONE ID no.1853106
misc_feature              1..841
                          note = Encodes the peptide given in SEQ ID NO. 208
source                    1..841
                          mol_type = unassigned DNA
                          organism = Gossypium hirsutum
SEQUENCE: 207
aagcacggat tcaaagtgat aaaaaaaaaa tccttcattt tgcaggaaaa aaatggctg     60
atttggattc ttcaagctct tcctctgaag atattgaaac aaactctgat cctaattcgt   120
caaaagctat aatccccaat cctctcaatt ccaattctaa ttcacctgcc gtatgcctcc   180
tccaattcgc aggagactcc accgctggtg ccttcatggg ctccatcttc ggctacggtt   240
cgggattgat taaaagaag gttttaaag gatccttgtg gaggctgga tcttatgcca    300
agacatttgc agttttgtcg ggtgtacaca gttgtggtct tgcttcttg aagaggttgc   360
ggggaaaaga tgatgttatt aatgctgggg tagctggatg ttgcactggg cttgctctaa   420
gtttcccagg tgcaccccag gcacttatac agagctgtct cacatttggg gcattctcat   480
ttatcgttga agggcttaac aagcagcagc cagcattggc acattcattt tctgtgagaa   540
acaagagcgg gcactatgag gggcctcatc ctatagcgct ccctctttca ctccctattc   600
cagatgagct gaaggagct ttttcttctt tctgcaggtc cttaagtaaa ccaaatgaag     660
gcaagttttc tactggtaac tgatgggaag gggccattca tcagtgttaa tcgtctgtta   720
tatgtagatt gttgattgtt gcgagtgttg ggagttacaa tgtaagaatg tagaatcaaa   780
attatctgag agctaggaaa tgggaaattg tttttttgtcc taaaaaaaaa aaaaaaaaaa   840
a                                                                   841

SEQ ID NO: 208            moltype = AA  length = 209
FEATURE                   Location/Qualifiers
REGION                    1..209
                          note = Ceres CLONE ID no. 1853106
REGION                    34..152
                          note = Pfam Name: Tim17 Pfam Description: Tim17/Tim22/Tim23
                            family
```

| | | |
|---|---|---|
| REGION | 1..209 | |
| | note = Functional Homolog of Ceres CLONE ID no. 965405 at SEQ ID NO. 172 with e-value of 5.20E-63 and BLAST sequence identity of 71.4 | |
| source | 1..209 | |
| | mol_type = protein | |
| | organism = Gossypium hirsutum | |

SEQUENCE: 208

```
MADLDSSSSS SEDIETNSDP NSSKAIIPNP LNSNSNSPAV CLLQFAGDST AGAFMGSIFG    60
YGSGLIKKKG FKGSFVEAGS YAKTFAVLSG VHSLVVCFLK RLRGKDDVIN AGVAGCCTGL   120
ALSFPGAPQA LIQSCLTFGA FSFIVEGLNK QQPALAHSFS VRNKSGHYEG PHPIALPLSL   180
PIPDELKGAF SSFCRSLSKP NEGKFSTGN                                    209
```

| | | |
|---|---|---|
| SEQ ID NO: 209 | moltype = DNA   length = 867 | |
| FEATURE | Location/Qualifiers | |
| misc_feature | 1..867 | |
| | note = Ceres CLONE ID no.1899181 | |
| misc_feature | 1..867 | |
| | note = Encodes the peptide given in SEQ ID NO. 210 | |
| source | 1..867 | |
| | mol_type = unassigned DNA | |
| | organism = Gossypium hirsutum | |

SEQUENCE: 209

```
aggcacgtcg agaaaggggg aaaaggaact catagtagtt tttggacaaa aatggctact    60
tcggattctc caaacacttc agctggatct gatattgaaa caaaccctaa tcctaattct   120
tcaaaagcca taatcctaac accatccaat tccaattccc ctgccgtatg cctcttccaa   180
ttcgcaggag actccgccgc cggtgccttc atgggctcca tctttggcta cgggtcagga   240
ttgattaaaa agaaaggctt taaggatcc tttgtggagg caggatctta cgccaagaca   300
tttgcagttt tgtccggcgt tcacagtttg gttgtttgct ttttgaagag gcttcgggga   360
aaagatgatg ttattaatgc cggtgtagcc ggatgctgca ctggacttgc tctaagtttc   420
ccaggtgcac ctcaggcact tctacagagc tgtctcacct tggggcatt ctcatttatc    480
atcgaagggc ttaacaagca gcagccagca ttggcacatt catttctgc gagaaacaag   540
agtgcacacc acaagggacc tcgtccttta gcactacccc tttctatccc tattccggat   600
gagctgaaag gagctttttc ttcgttctgc aagtcctctgg taaaaccaaa taaaggtagg   660
tttcctacag gtaactaagt agtaggtgga ccattttcct ttttttcctgt tgtttgtaga   720
attttgcaag tgttgagaat gtagactgaa agttttgtct gagatttgaa gcttttttaca   780
agcagaaaga tgaaattgct tcttttcttg tgttgattca attatattat ctgtctggtt   840
cagtagtaaa aaaaaaaaaa aaaaaaa                                      867
```

| | | |
|---|---|---|
| SEQ ID NO: 210 | moltype = AA   length = 208 | |
| FEATURE | Location/Qualifiers | |
| REGION | 1..208 | |
| | note = Ceres CLONE ID no. 1899181 | |
| REGION | 33..151 | |
| | note = Pfam Name: Tim17 Pfam Description: Tim17/Tim22/Tim23 family | |
| REGION | 1..208 | |
| | note = Functional Homolog of Ceres CLONE ID no. 965405 at SEQ ID NO. 172 with e-value of 4.09E-63 and BLAST sequence identity of 71.2 | |
| source | 1..208 | |
| | mol_type = protein | |
| | organism = Gossypium hirsutum | |

SEQUENCE: 210

```
MATSDSPNTS AGSDIETNPN PNSSKAIILT PSNSNSPAVC LFQFAGDSAA GAFMGSIFGY    60
GSGLIKKKGF KGSFVEAGSY AKTFAVLSGV HSLVVCFLKR LRGKDDVINA GVAGCCTGLA   120
LSFPGAPQAL LQSCLTFGAF SFIIEGLNKQ QPALAHSFSA RNKSAHHKGP RPLALPLSIP   180
IPDELKGAFS SFCKSLVKPN KGRFPTGN                                     208
```

| | | |
|---|---|---|
| SEQ ID NO: 211 | moltype = DNA   length = 919 | |
| FEATURE | Location/Qualifiers | |
| misc_feature | 1..919 | |
| | note = Ceres CLONE ID no.1758700 | |
| misc_feature | 1..919 | |
| | note = Encodes the peptide given in SEQ ID NO. 212 | |
| source | 1..919 | |
| | mol_type = unassigned DNA | |
| | organism = Panicum virgatum | |

SEQUENCE: 211

```
ggaacacgat aacgagacgg caggtggggg aggagccgag gagggcttca ggggtttcag    60
ggcggagagg agaagatggc ggcgaagcgc gagaccgagt cggacggcga agagctcggc   120
ggcgaggcct ccaaccctgc gagcggtggc gcgactccgc cgcccctagc cgcagctccc   180
gtcgtctgcc tcctccgctc cgctgggac ttcgccggcg gcgccttcgt cggatccatc    240
gtcggaatg gacaaggcct gatcactaag aaaggtttca agggttcatt cagcaatgct    300
gggtcctctg ctaagacttt tgcagttcta tctggggtcc agagtttggt tgtgtgcttg   360
ctgagaaggc tgcgtgggaa agatgacatt gtcaatgctg gtatagctgg ttgttgcact   420
ggcattgctt tgagcttccc aggagcacca caagcgttgc ttcagagctg tgccacctt    480
gcagcgtttt cttgcatcat ggaggggctc aacaagcagc aggctgcaat ggctcacact   540
cttggcacaa ctgcattgac ggttgcgcat gataaaggag gtgtactgcc cccattcacg   600
```

```
cttccaccaa ttctggatgc atcagatgct ttagcttcat gctgccaagc cttagtaaag   660
cctaagcact agactacagg ataggggaga gagacatgct gaagaaagat agcttcagtt   720
ttcatttctt tattatgttg acctagcata tctgcatatg taaattttgc ttctggacaa   780
gctgtggaac gtgcctaaaa cctagttttg ctttgagcaa ctggacaggt tttcttgatg   840
tgttcgtgtt gcgaattccg ctggttctgg cattattaaa atcataaata cttgcctcga   900
aaaaaaaaaa aaaaaaaa                                                 919

SEQ ID NO: 212         moltype = AA  length = 198
FEATURE                Location/Qualifiers
REGION                 1..198
                       note = Ceres CLONE ID no. 1758700
REGION                 31..149
                       note = Pfam Name: Tim17 Pfam Description: Tim17/Tim22/Tim23
                         family
REGION                 1..198
                       note = Functional Homolog of Ceres CLONE ID no. 965405 at
                         SEQ ID NO. 172 with e-value of 3.10E-49 and BLAST sequence
                         identity of 62.4
source                 1..198
                       mol_type = protein
                       organism = Panicum virgatum
SEQUENCE: 212
MAAKRETESD GEELGGEASN PASGGATPPP LAAAPVVCLL RSAGDFAGGA FVGSIVGYGQ   60
GLITKKGFKG SFSNAGSSAK TFAVLSGVQS LVVCLLRRLR GKDDIVNAGI AGCCTGIALS  120
FPGAPQALLQ SCATFAAFSC IMEGLNKQQA AMAHTLGTTA LTVAHDKGGV LPPFTLPPIL  180
DASDALASCC QALVKPKH                                                198

SEQ ID NO: 213         moltype = AA  length = 203
FEATURE                Location/Qualifiers
REGION                 1..203
                       note = Public GI ID no. 108706643
REGION                 35..153
                       note = Pfam Name: Tim17 Pfam Description: Tim17/Tim22/Tim23
                         family
REGION                 1..203
                       note = Functional Homolog of Ceres CLONE ID no. 965405 at
                         SEQ ID NO. 172 with e-value of 7.40E-48 and BLAST sequence
                         identity of 59.0
source                 1..203
                       mol_type = protein
                       note = Oryza sativa subsp. japonica
                       organism = Oryza sativa
SEQUENCE: 213
MAAKRGSESD GDELGGGGAA EGTSPNDGGA SPPPLAAAPA VCFIRSAGDF AGGAFIGSIV   60
GYGQGLFTKK GFKGSFSTAG SSAKTFAVLS GVQSLVVCLL RRLRGKDDIV NAGIAGCCTG  120
LALSFPGTPQ ALLQSCATFA AFSCIMEGLN KQQAAMAQTL GGSALTVSHQ NGGVLPPFTL  180
PPLLDASDAL SSCCQPLVLK PKH                                          203

SEQ ID NO: 214         moltype = DNA  length = 1066
FEATURE                Location/Qualifiers
misc_feature           1..1066
                       note = Ceres CLONE ID no. 1096546
misc_feature           1..1066
                       note = Encodes the peptide given in SEQ ID NO. 81
source                 1..1066
                       mol_type = unassigned DNA
                       organism = Brassica napus
SEQUENCE: 214
atactctaaa tagctcgatg ccaaaaaatc agamtgattg aatagtttag ttcgatacca    60
tcaataaacc cgttgacccg atccaatgac ccgctccgtg aacttccctc tcctcggcct   120
cgccgccgca ctcctcctct cacctctcct gccgtctct ggtaaactcg ccgacgacct   180
caagccaaac cgccaggagg tttayggcgg aggkaagata ttcgacatca gccaccgtta   240
cacgccggag atgccggcgt gggagtctaa ggagggactt cgaaccacc tgagactgat   300
cgcgagtatg aagaacggat cgttcgctaa cgtgtcggga gtgaaactgt ctgttcactc   360
cggaacacac gtggatgctc caggccactt cattgatgag tattacgacg ctggtttcga   420
ttgcgattcg cttgacctcc aaactctaaa cggtcctgct ttgttggttg atgttccgag   480
agacaagaac ataactgctg aggtaatgga atcmcttcat attccaaggg gagttcgtcg   540
tgtgcctyttc agaacatcca acactgacaa gcggcttatg tttaagaaag agttcgattc   600
aagctttttct ggattcatga ctgatggggc caagtggttg gttgagaacm cggacatcaa   660
acttgttggg cttgattatc tttccttttgc tgcttttgac gagtcmccgg caactcacaa   720
ggttatactt agaggaaggg atataatccc tgtcgaagct ytgaagctgg atggtgttga   780
ggcaggaatg tactcgcttc attgcttacc gctgagattg gttggagcar aaggggcmcc   840
aaccaggkgc attctcatca agtgattcag ttcttccgty ttcttttaa gttggtcagc   900
caactgatca taaataatat gtttattact tccaagatcc cmcaatcata aagcaggtat   960
catgatgagg atgattccag ttgtaaaagt aaacaatacc tttatagacg tatgtgtatg  1020
tttgtatgtg taattytgaa agatattgat aataaagtta agactg                 1066

SEQ ID NO: 215         moltype = DNA  length = 490
FEATURE                Location/Qualifiers
```

```
misc_feature             1..490
                         note = Ceres CLONE ID no. 1311812
misc_feature             1..490
                         note = Encodes the peptide given in SEQ ID NO. 82
unsure                   263
                         note = n is a, c, t, g, unknown, or other
unsure                   332
                         note = n is a, c, t, g, unknown, or other
unsure                   362
                         note = n is a, c, t, g, unknown, or other
unsure                   405
                         note = n is a, c, t, g, unknown, or other
unsure                   429
                         note = n is a, c, t, g, unknown, or other
unsure                   448
                         note = n is a, c, t, g, unknown, or other
unsure                   454
                         note = n is a, c, t, g, unknown, or other
source                   1..490
                         mol_type = unassigned DNA
                         organism = Brassica napus
SEQUENCE: 215
aatatcagtt tgattgatca tcataaaatt gacagaccaa taaaacatta cgaacagaat    60
actatatgaa taccaaccaa ggttcatgaa tccacgttga cctacgaacc gagataatga   120
ttcctttcct caccatcgcc aggacactct tcctctcctc tgtcatcgcc gctgatgaag   180
cttttccgtc gattcccact accttccacg tagccatgac ctcctctgac gatctgaaac   240
cgatccgtca ggagggttat ggngaaagga agatattcga cataaaccca ccggtacacg   300
caggatatgc cggtctgggg aatcgacaga angaggtaaa ccggttcctg cgtctaacca   360
cngagtatga agaaaccaat cccctctcta atacccgcgg gagangaaaa ctatcttgtt   420
cacaccggnt acacacccct tggatggcnc aggnccactt ttcatggaca aggtattaac   480
gaacgctggg                                                          490

SEQ ID NO: 216           moltype = DNA   length = 1066
FEATURE                  Location/Qualifiers
misc_feature             1..1066
                         note = Ceres CLONE ID no. 952461
misc_feature             1..1066
                         note = Encodes the peptide given in SEQ ID NO. 83
source                   1..1066
                         mol_type = unassigned DNA
                         organism = Brassica napus
SEQUENCE: 216
atactctaaa tagctcgatg ccaaaaaatc agactgattg aatagtttag ttcgatacca    60
tcaataaacc cgttgacccg atccaatgac ccgtccgtg aacttccctc tcctcggcct   120
cgccgccgca ctcctcctct cacctctcct cgccgtctct ggtaaactcg ccgacgacct   180
caagccaaac cgccaggagg tttacggcgg agggaagata ttcgacatca gccaccgtta   240
cacgcggag atgccggcgt gggagtctaa ggagggactt cgaaccacc tgagactgat   300
cgcgagtatg aagaacggat cgttcgctaa cgtgtcggag atgaaactgt ctgttcactc   360
cggaacacac gtggatgctc caggccactt cattgatgag tattacgacg ctggtttcga   420
ttgcgattcg cttgacctcc aaactctaaa cggtcctgct tgttggttg atgttccgag   480
agacaagaac ataactctg aggtaatgga atcmcttcat attccaaggg gagttcgtcg   540
tgtgctyttc agaacatcca acactgacaa gcgcgttatg tttaagaaag agttcgattc   600
aagctttcct ggattcatga ctgatgggc caagtggttg gttgagaacm cggacatcaa   660
acttgttggg cttgattatc tttccttgc tgcttttgac gagtcmccgg caactcacaa   720
ggttatactt agaggaaggg atataatccc tgtcgaagct ytgaagctgg atggtgttga   780
ggcaggaatg tactcgcttc attgcttacc gctgagattg gttggagcar aagggggcmcc   840
aaccaggkgc attctcatca agtgattcag ttcttccgty ttctttttaa gttggtcagc   900
caactgatca taaataatat gtttattact tccaagatcc cmcaatcata aagcaggtat   960
catagatgag atgattccag ttgtaaaagt aaacaatacc tttatagacg tatgtgtatg  1020
tttgtatgtg taattytgaa agatattgat aataaagtta agactg                 1066

SEQ ID NO: 217           moltype = DNA   length = 1071
FEATURE                  Location/Qualifiers
misc_feature             1..1071
                         note = Ceres CLONE ID no. 954851
misc_feature             1..1071
                         note = Encodes the peptide given in SEQ ID NO. 84
source                   1..1071
                         mol_type = unassigned DNA
                         organism = Brassica napus
SEQUENCE: 217
atcagtttga ttgatcatca taaaattgac agaccaataa acattacga acagaatact    60
atatgaatac caaccaaggt tcatgaatcc acgttgacct acgaaccgag ataatgattc   120
ctttcctcac catcgccagt acactcttcc tctcctctgt catcgccgct gatgaagctt   180
ttccgtcgat tcccactacc ttccactag ccatgacctc tctgacgat ctgaaaccga   240
tccgtcagga ggtttatggc gaaaggaaga tattcgacat aacccaccgg tacacgcagg   300
atatgccggt ctgggaatcg acagaaggag ttaaaccgtt cctgcgtcta accacgagta   360
tgaagaacca atccctctct aatacctcgg agatgaaact atctgttcac accggtacac   420
accttgatgc accaggccac tttcatgaca agtattacga cgctggtttc gattcggatt   480
```

```
cgcttgacct ccaagtccta catggccctg ccctgttggt tgatgttcca agggataaga   540
atatcactgr ggttatgaaa tcacttcata ttccaaaggg agttcgtcgt gtgctcttca   600
gaacattgaa cmctgatagg cggcttatgt ttaagaaaga gttcgattcg agctttgctg   660
gattcatgat ggatggggcg aaatggttgg ttgagaatac agatatcaaa cttattgggc   720
ttgattatct ttcttttgct gcttatgagg aagcgcctga aacgcacaag tttatactag   780
gagaacggga tataatccct gtggaagcgc tgaagctgga tggtgtggag gtaggagtgt   840
actcgcttca ttgcttaccg ttgagattgc ctggagcgga aggtgcacca acgagatgta   900
ttctcatcaa gtgattcagt tcatctcctt ctctataagc tagttgttca gtatacgaaa   960
gtgattataa gaacaaaata aaggcttytt acttccaaga tytggaacaa tagagcatat  1020
gttacatatg tcaagaattt taaagttcaa gattcacttg gataccttta t           1071

SEQ ID NO: 218           moltype = DNA   length = 933
FEATURE                  Location/Qualifiers
misc_feature             1..933
                         note = Ceres CLONE ID no. 1064137
misc_feature             1..933
                         note = Encodes the peptide given in SEQ ID NO. 85
source                   1..933
                         mol_type = unassigned DNA
                         organism = Zea mays
SEQUENCE: 218
aacaatggca gttcctccac ttctcctcct cacactcctc tccctccctt ctcttctcat    60
ccacgccgcc atctccgatg cttacccac cattcccgga accgctccga tcgacggagg    120
tttctccgat gaactcaaac ccatccgccg tgaggtctac ggcgaaggca aaatcttcga   180
catcagccca cgctacacgc cggagatgcc ggcgtgggag tcaaagaag gaatcggacg    240
gtttctatgg ctagccgcga gcatgaagaa cgggtcgctc gctaacaact ccgagatgaa   300
gatcccgact cacactggga cccacgtcga ttcgcctgga cacgtgtacg atgagtatta   360
cgacgctggg ttcgatgtag actcgcttga tctccaagtc ttaaacggtc ctgcgttgtt   420
ggttgatgtt ccaaggaaca agaacataac tgccgaagtg atgaagtctc ttaacatacc   480
aagaggagtc cgtcgtgtgc ttttcagaac attgaatact gacaggcgtc tgatgttcaa   540
gaaggagttt gatacaagct atgtcggatt catgaaggac ggcgcacaat ggttggtaga   600
caacactgac atcaaacttg ttgggggttga ttatctatca gtagctgcat atgatgatct   660
gattccgtcc cacctagtat tcctaaaagg ccgagagact atactggtgg agggattgaa   720
gctggatgat gtgaaggcag gagtctactc tgttcattgc ttacctctaa gacttgttgg   780
agcagaaggg tctccaattc gctgcatcct catcagttga tttcttcctc caaaacttgg   840
agttgtctgt atgcaagtta accttttcgta tctttacttc aagatcttat gcttgacaaa   900
aaaaaaaagt aaaataaata aggaaacttg gcg                                933

SEQ ID NO: 219           moltype = DNA   length = 1179
FEATURE                  Location/Qualifiers
misc_feature             1..1179
                         note = Ceres CLONE ID no. 368629
misc_feature             1..1179
                         note = Encodes the peptide given in SEQ ID NO. 86
source                   1..1179
                         mol_type = unassigned DNA
                         organism = Zea mays
SEQUENCE: 219
aaaaactccc cagtcaaggc gcatatccat tccatggatc tcgcgcccct gctccttctc    60
tcccagctgc tgctgcttcc ggtggtggcg gttgtctccg gcgagaccgc cgcgcacccg   120
ggctacacac acgctgagga ggcatgcagc ggtgtgctag aggcagaggc ggagaaagca   180
acggtgctgg tgcctgcgcc agagcggcgc gaagagttcg acgggggcg gatcgtggac    240
atcagccact actaccgcga ggacatgccg gagtgggagt catcagaggg ctccggcgag   300
ttcctgcagc tggcgcgttc catgcgcaac ggctccgaca tcgctaactt ctcggagctc   360
cggctcactg cgcactccgg cacccacgtc gacgcgccgg gacacgtctt cgagcactac   420
tacgacaccg gcttcgacgt cgacaccctc gacctcgctg tcctcaacgg accagcgctg   480
ttggttgacg ttcccagaga taagaacatc acagctgatg ttatggcatc cctaaacatg   540
cctaaaggtt ttcgacgtgt actctttcgg accctaaata cagacaggat ggtgcacaat   600
ggttggttga taatacagac atcaaactag ttggagttga ctacttgtca gtgggcgcat   660
ttgatgaatg cattccagct catctagtat ttcttgaaaa aagggaggtc atacttgtcg   720
aagccttgaa tctggagcat gttagccctg gaatatacat cttgcattgc ttgccactaa   780
gattgcgggg tgctgaaggt tctcctgcaa gatgcatcct catcaagtga catggttata   840
accatcccaa aaagcattgt acaatcaatc ttgaaaccta cctattcagt cttttcgaag   900
tgcttataga agtatggttt tcatgcgtgt gtttataggg atggtgtgag gacccaataa   960
tatggagctg ggctagtact gatccaatcg cactaatat gagctgaaga tactacataa   1020
aacatgaaca atatggagtt ttatatactg gaccccagtc caggttttaa atccacccct  1080
gcaaggggta aattatgttt tgtgtttggg agtgtatatt tctatattgc agtttgaaaa  1140
aaactatgta tgtaataaaa taagaataca tcaattcat                         1179

SEQ ID NO: 220           moltype = DNA   length = 1195
FEATURE                  Location/Qualifiers
misc_feature             1..1195
                         note = Ceres CLONE ID no. 473732
misc_feature             1..1195
                         note = Encodes the peptide given in SEQ ID NO. 87
source                   1..1195
                         mol_type = unassigned DNA
                         organism = Glycine max
SEQUENCE: 220
```

```
aaagtaaacc atgaattctc tatcactctt caccttcctc tgcgcaattt gtgcgcactc    60
cgtcgccgtc acctccgcgg catatccttc catcccggc acggaaaccg gagagtgctc    120
cctccgcggc gtcggcgtcg gcgacggtgt tctggtccct ccgcggcgag aagtgtacga   180
ggaggggcga atcttcgaca tcacccacag gtatgtcccc gagatgccgg tgtgggactc   240
gacggagggg ctcgggcagc acttcctgtg gctcgaaaag agcatgaaga atggctcgcg   300
cgctaacaac tccaacatga agctcggtgt tcacaccggc acccatgtcg acgcgcccgg   360
tcactttac gacgccgg cttcgatgtt gactcactcg acctaacact   420
cctcaatggc cttgcacttt tggttgatgt tccacgggaa aaaaacatta ctgctgaggt   480
tatgaagtcc ttgaatatcc ctagaggtgt aagccgcgtg cttttcagaa ctttaaacac   540
tgacaggcaa ctcatgttta agaaagaatt tgacacaagc tatgtgggat tcaaggagga   600
tggtgcaaaa tggctggcag agaacaccga catcaaactt gtaggagtcg attacttatc   660
tgttgctgct tatgatcact ccattccatc tcatcttgtt ttcctggaaa gcaaggaaat   720
cattcttgtg gaaggcctaa agcttgatga tgtcccagca ggaatatatt cactgaattg   780
cttgcctctt aggttggttc actctgaggc atcaccaatt cgatgcattc tgatcaaatg   840
atcaaatgat ggggtcaaac ctggttttca attgcacgga tgaacctgcc acaagaagca   900
acgtagccac gaatacaatt agtggtgtcc ataagaagca gtttgatgca aattgcaagc   960
taagctgata gtagtatgtt gaattactct tagtttacgt ccttgggttg gaaagtactg  1020
aattattgtg attaaacttc agttgcggac taggggtcc acctgtatta acttatgctt   1080
ttaatatttt cctaggcaag tacttgtgca attctgaaga cgcatgcttg tacgtctcaa   1140
taattatatc tatttctctt tgaaaaataa tgaaatacta ctaataatct cgggc        1195

SEQ ID NO: 221          moltype = DNA  length = 1200
FEATURE                 Location/Qualifiers
misc_feature            1..1200
                        note = Ceres CLONE ID no.554272
misc_feature            1..1200
                        note = Encodes the peptide given in SEQ ID NO. 90
source                  1..1200
                        mol_type = unassigned DNA
                        organism = Glycine max
SEQUENCE: 221
atgaatgagc taagtggaaa gtgaaaacgt gcctctttac taacgaaacc aaagcatgaa     60
gatgaattgc tactggtggc atgccctgat aatgagtggt gtgtgttgg gcttgtgcgt    120
gggcatagga ggttgtgtat gtggtggtgga gaacgagaat ggaagaatca tcattgatat   180
tagtcacagg taccatcctg atatgcctgc ctgggaatcc aaggatagcc ttgggcagtt   240
tttgtggctt acaagaagca tggccaatgg ttctctggct aacttctccc aattcaagct    300
ccccgctcac agcggcaccc atgtcgatgc tcccggacat gttttcgatc actatttcca    360
ttctggctt tgatgtcgact ctctcgattt actactcctt aatggccctg cactattagt    420
tgatgttcca agagatacaa acatcagtgc tggtgtttag aagtcattga atattccgag    480
gggcgtacgt cgtgtgctct tccgaacatt aaatacttac aggcggctta tgtatcagaa    540
ggaattgac acaagctatg tgggattcac agaagatgga gcaaattggc tagtggagaa    600
cactgacatt aagcttgtgg aatagatta tctatctgtt gctgcttacg accacttgat    660
tccagctcac cttgtttttc tgaaaggcag ggaaatcatc ctcgtggaag gcctgaagct    720
tgatgatgtg gcagcaggaa tatatacggt ccattgctta cctcttaggt tggctggtgc    780
tgagggatca cccataagat gcattctcat caaataataa gtcaacagct agcagtccaa    840
atgccgacac gacatgcagc agtggtttat gcttggaaat gggtcttaat tacgagcata    900
aggttgagtt tcaatgtagt tttctttaaat acgaataagt tggaaaaata aatataaagt    960
ggtgtcccgt gtccatttgg agcaaggtat cataaatgct tagcaaagtg cataaacgct   1020
cctacaaatc atttcagaaa taaagcagta tggatattgg atgatatata aagtactatg   1080
taatatgcag tgaaggtata acaaatgtca aatagcaatt attcttgcgt actttaaat   1140
acactatatg gatggatgtt tggaattatt attttttaag aaggatgttt ggaattgttt  1200

SEQ ID NO: 222          moltype = DNA  length = 1251
FEATURE                 Location/Qualifiers
misc_feature            1..1251
                        note = Ceres CLONE ID no.511015
misc_feature            1..1251
                        note = Encodes the peptide given in SEQ ID NO. 91
source                  1..1251
                        mol_type = unassigned DNA
                        organism = Glycine max
SEQUENCE: 222
gatgcgaaaa tatctcgttc atgttaatgt tatgataacg aggaatggac tatgatgctg     60
ttctgttggt gacggtgtga ttgattgtga cgaaatctga caatgaagc tggagcattg    120
ttgtcagtgc ttgcctgcgc cttgcgggga gtgatctggg cagcgaacgg cgacgacaac    180
ctcgtcccgc ctcgccggga agtgtacggc aatgggcgaa tattcgacat cagtcatcgg    240
taccaacccg agatgccgga atgggaatcg aatgacggca tagggcagtt cctgtggctt    300
cccaagagca tgaagaacgg ttccctcgcc aacaactccg aaatgaagtt tcccacccac    360
accggcacgc acgtcgatgc ccccggtcac gtgttcgaca actacttcca cgccggcttc    420
gatgtcgaca cgctcgactt ggacatcctc aacggacctg ctatgttggt tgatgttcca    480
agagatagta atattaccgc tcaagttatg aagtcgttga atattccaag gggtgtaata    540
cgtgttctct tccgaacttt aaataccgac cggcggctga tgtttcagaa ggaatgggac    600
tcaagctatg tgggattcac agccgatgga gccaaatggc tagtggagaa cacagatatc    660
aaacttgtag gaattgatta cctatctgtt gcttcttatg attcatctcac           720
cttgtttttc taaaagacag ggagatcatt ctcgtggaag gcttgaagct tgatgatgtt    780
ccagcagggt tatattcagt ccattgctta cctcttaggt tggctggtgc tgagggatca    840
ccaatacggt gcattctgat taaaaattag ggtgtccaca tgtctgtgtt cggtgtccgc    900
gtcggtgtcg gtgcttcata ggctggaact gataaattgg catggggtg tggtgtcctt    960
atggagcaag atagtttcaa tgttgtgcaa caactttgt agcttatgtt tacacttact   1020
```

```
aaaaacatgc ataagcactt caaaaaatca ttttgaaaag gaaataatg tatatataga    1080
taatttgcac atttcattag cacttcaaga gagatgcaac gatattggca ttgcgctgaa    1140
tttggttttc ttttgtctgc taggttggaa aggaataagt tggcacaatg gtgtctttat    1200
ggagcaagat agtatcaata atgtttgtta aagaaaaaaa aaaaaaaaa a              1251

SEQ ID NO: 223          moltype = DNA   length = 1173
FEATURE                 Location/Qualifiers
misc_feature            1..1173
                        note = Ceres CLONE ID no.881632
misc_feature            1..1173
                        note = Encodes the peptide given in SEQ ID NO. 92
source                  1..1173
                        mol_type = unassigned DNA
                        organism = Triticum aestivum
SEQUENCE: 223
gaataacccg cacctatcca cgacaccgag ggagaggagc aactgatccc cgacgcccca    60
aatggcgcct ccctcctcc tcctcctcct cgtccctctc gtcgccgcca ccgcaccgtg    120
cgcccaccg gcccacccga gccagccggc gtcgtgccgc gcggagcccg tgctggcgcc    180
ggagcgccgg gaggcgcacg gcggggccg catcctggac atcacccact actaccggga    240
ggacatgccc tcgtgggagt ccggcgccgg ggtgggccag ttcctctggc tgcccgcctc    300
catgcgcaac ggctccctcg ccaacaactc cgagatgcgg atgcccaccc acaccggcac    360
ccacatcgac gcctccggcc acgtcttcca gcactacttc gacgctggct tcgacgtcga    420
caccctcgac ctcgacgtcc tcaacggtcc tgcactgctg gttgatgttc caagggatga    480
aaatattact gctaaaacga tggaatcttt gcatattcct aaaggagttc aacgggtact    540
ttttagaaca ttaaacactg acaggaacct aatgtggaag aaagagtttg acacaagcta    600
tgtgggttt atgaaagatg gtgcccaatg gttggtagac aacacggata ttaagcttgt    660
cggaatagac tatttgtccg ttgcagcttt cgatgacttg atcccttcac atttagtttt    720
acttgaaaac cgggatatca ttcttgtgga gggcctcaaa ctggagaatg tcatacctgg    780
gatatactcg ttgcattgcc tgccacttcg gttgcgtgga gctgaaggtt cgccgatcag    840
atgcatcctt ataaagtgaa agacatttgc atcccgctgc ggcggtttag tttgataccg    900
caagcactta tatataaaaa tagaatgtgt atagcagcaa aactcgtgtc tttgataccaa    960
gaggagtact gtcatgtgtc cagaaacatg gtggcacttc gatgcttagt aaggagcgac    1020
aaacggctag gatgcaaat gtgtagcctc tagggtaccc tccgaacctt tagttgggct    1080
atagaaggga tggattacaa tacaaaccgc aatgttcggt ggtaccaaaa tcccaaaaaa    1140
aaaaaaaaaa aaaaagaaa aaaaaaaaaa aaa                                 1173

SEQ ID NO: 224          moltype = DNA   length = 1347
FEATURE                 Location/Qualifiers
misc_feature            1..1347
                        note = Ceres CLONE ID no.474985
misc_feature            1..1347
                        note = Encodes the peptide given in SEQ ID NO. 103
source                  1..1347
                        mol_type = unassigned DNA
                        organism = Glycine max
SEQUENCE: 224
aggaacagag caaacatgct gcttcttttgg cttttgccac tgctgttgct gcagaggctg    60
ctgttgccgc tgctcaggct gctgccgagg ttgttcgtct cacaagtatg ccacattaca    120
ctggaaggac taaggaagaa attgcagcca tcaaggttca gactgcattc cgtggatata    180
tggcaagaag ggcattgcgt gcgttgagag gattggtgag gttgaaaaca ttagtacaag    240
ggcaatctgt taaacggcaa gctgctagca ccctacgaag catgcaaact ctagcaagat    300
tacagtctca gattcgtgaa aggagaatta gaatgtccga agagaaccaa gctcttcagc    360
gccaactaca tcagaaacat gaaaaagaac ttgagaagtt gcgtgctgct gttggagaag    420
aatgggatga tagctcgcag tcaaaggagc aaattgaagc aaaattgttg cacaggcaag    480
aagctgcttt cgagaagagag agagctttgg cctattcatt ctcacatcag caaacatgga    540
agggctcttc aaagtcatta aatccaacat ttatggatcc aaacaatccc aatgggggt     600
ggagttggct agagagatgg atggctacta ggccatggga tggccatagc actgtggtgg    660
atcacaatga ccatgcatct gtgaagagtg cagcgagccg tgccgtgtct gtagggcaaa    720
tcaccaaatt gtactctctc caagataaaa aaccttccac ttttggctca aaagcaagaa    780
gacctgcccc tcaaagttcc cattcaaagg caccatctac taatgaaaa gcaaggccat     840
caagctcaac aaagggtagt agtgtttggg gtggagatga ggactcaaga agcatgttta    900
gtgttcagtc ggagcgctac cgccgacaca gcattgcagg atcctcagtg agagatgatg    960
atagccgtgc aagcacacct gccattcaa gttacatggc agccacaagc tcagcaaagg    1020
ccaggtccaa aatcataagg cattcacctg aaaaaaaagg tggtggtgt tctgtttctg    1080
caaggaagcg actttctttc tcaccctctt ctgctgctaa ttcaagaagg cattctgatc    1140
ctcctaaggt ggaaatggtt tacaataagg atgctgctgc ggctacagta agcaatggaa    1200
ggggaaggta gtgtgctggg gatgtcattg ccacttcagc aattcttgta ggagcacaat    1260
atctatggat ctatttggat aaacttctcc ataatcactt ataaatgaag aaaaacaaaa    1320
gtaatataga aaaaaaaaaa aaaaaaa                                        1347

SEQ ID NO: 225          moltype = DNA   length = 1716
FEATURE                 Location/Qualifiers
misc_feature            1..1716
                        note = Ceres CLONE ID no.826796
misc_feature            1..1716
                        note = Encodes the peptide given in SEQ ID NO. 104
source                  1..1716
                        mol_type = unassigned DNA
                        organism = Triticum aestivum
```

```
SEQUENCE: 225
ataggacttc acagacagac tgactcaatc ctaacccaat ccctcccatg cttccatcta    60
ctctagcaga aattgcagag gaggttggcc gccgccggct ccagcgcagg cgcagcctac   120
ccgcgggatc tgacgccctc cgcctcctac ctcgaggcac gcgcctcagg ctcagctccc   180
ccgccgccc tccccccgcta ccccgacgac ttccaagagg aggagcatga aattgagcat   240
gtcgccgccg cgccagcgcc agcgccagcc acggatgcgc cgctacctgc ccctcctgcc   300
gccgcaccac cacaggttca ggctgccatt gcgccggctt cttcctcttg tgtcatgtcc   360
agggagctcg ccgccaccaa gatccagacc gccttccgag gtcacctggc aagaagggcg   420
ctgcgggcat tgaaaggcct ggtcagactc aagtcgctgg tccaaggcca ctccgtcaag   480
cgccaggcca ccagcacgct tcgctgcatg cagactctgt cccgggtcca gtccaagata   540
cggacgagga ggatcaagat ggccgaggag aaccaggccc ttcagcgcca gctcttgttg   600
aaccaggaac tagagactct caggatggga gatcagtgga ataccagcct gcagtccaag   660
gagcaaatca aggcgagcct cgtgagcagg caagaggccg cggctagaag agaacgggct   720
ctcgcatacg cattctccca ccagtggaag agcacctcaa ggtctgccaa ccgatgttc   780
gtggacccga gtaacccgca ctggggctgg agctggctgg agcggtggat ggcgtcgagg   840
ccgttcgacg gccgcaacgg ggcgtccgag aaggagggca gcagcgtcga ccgcacgtcg   900
gtgcacagca ccagcctgag catgaacctc ggagaaggtg agacggtcac aaaggcggac   960
aaccaggtgg tggactcttt gaagccgaat gatgataagc cgccgccgct ttcgactccg  1020
aagccgtccg gccctgcccc caggcagtcc ccgtcgacgg cctcgccggc gctggcgagg  1080
aagaagagcg cgacgcccaa gagtggagac tgcgacggcg acgacgcgag gagcgtggtc  1140
agcactgtcc ggtccgagcg gccccggagg cacagcatcg gcgcgtccag cgtgcgtgac  1200
gacgcgggct cttcccgtc ggtgccgagc tacatgccgc caccaagtc gggcgtcgcc  1260
agggccaagt cgcgtgtgca gagcccgacg ctgaccgagg gtgctgctca agctgagacg  1320
ctggagaaag gatggtcttc tgtgggttca gcgaagaagc ggctgtcctt ccggctgggg  1380
acgccaccgc cggtgccggc ggcggcggcg aggcggcact ccgggcctcc caaggtgcgg  1440
caggcgggcg tggaaggtgg tacggaggaa cgggactgcg cccttgcgtg acatcatggg  1500
aagcagatta tggtgtggag cagagcgag cggaatttgt tgcatttgtt gagtgaaagg  1560
aacgcagaat gtgtgttgtg tggatccatt ggatttgatt tgatttgtat gatggcagta  1620
ttcctatttg attattcatt gaataatata agtatctgta atgaagataa aaggagggga  1680
cacgaacatt atttcaaaag aaaaaaaaaa aaaaaa                            1716

SEQ ID NO: 226        moltype = DNA  length = 1381
FEATURE               Location/Qualifiers
misc_feature          1..1381
                      note = Ceres CLONE ID no.463638
misc_feature          1..1381
                      note = Encodes the peptide given in SEQ ID NO. 107
source                1..1381
                      mol_type = unassigned DNA
                      organism = Glycine max
SEQUENCE: 226
attagattct gcttccattt ttttttttct ctctacacct cttcttcttc acttcctctt    60
tactgtttgt tacttcaatt ttgtgattcg ttctttctgg attcaattga gtaaaaatct   120
gcgtggtttg agcaatggat gttaaagctg cgccgaggtt acaactttca gcggtggttc   180
aacccgaaag tattggaaga agaccaccca gcacatgtcg tttgggtgtg tctcgggaac   240
cgcagagcct tcgggtttt gttcgtcaa cgatgatgcg ccgcagaaca accgctttgg   300
aggtttcctg ttcttacggc aacatttcag cttcaatatt ggaatctgaa agtgttcgtg   360
ctcctcttga tgaagagctg attctaaaga atagatcgca agagatccag ccatatttaa   420
atggacgctg tatttatctt gttggaatga tgggctctgg gaaaacaacg gtggggaaga   480
taatgtcaca agtgcttggt tattcatttt gtgatagtga tgcattggtg gaggaggagg   540
ttggtggaaa ctctgtagct gatatattca agcaacatgg tgaaacttc ttcgtaata   600
aggagactga ggtgttgcat aagctatccc tgatgcatca acttgttatt tctactggtg   660
gaggtgctgt tacaaggccc atcaattgga aatatatgca caagggagtt agtgtttggt   720
tggatgtacc agtggaagcc ctggcacaga gaattgcagc tgtaggaact aattctcgcc   780
cccttctaca ctatgaagca ggagatcctt cacacacggg tcttatgcgt ttgtctgctc   840
tttttgaaga gagaggtgaa gcatacgcca acgccatgc cagggtctca ttaaaaaata   900
tagcaataaa actgggcaaa agagatgtgt ccgaattgtc tccaacagat attgcaattg   960
aggcgctaga acaaattgac aacttttga aggggaagg gggccgctat gcagaatgct  1020
agtacaagct ttggttacaa gcttctttt gattgttcat attttttttt atgcaattgc  1080
gattaaggtc atgctgtcga cctcgctttt ggtaaaaaaa aaaaaaaggt ggtaatgcaa  1140
catgcacttt gttatgcat aattttgtgtt ggcaaatggg caaatccaa cagccaattg  1200
caacaacatt taatttatgt tctgttattt gttgaatgtt gatgtgtgtg tgtatatata  1260
ctggagaacg aagtgttgta atcggagttg ggttgatcaa tttatgtatg ccctcctcta  1320
aagaggtttg tatgttgtaa agtgacacgc atattaaa ttcttcttta tcttatattt  1380
g                                                                  1381

SEQ ID NO: 227        moltype = DNA  length = 1542
FEATURE               Location/Qualifiers
misc_feature          1..1542
                      note = Ceres CLONE ID no.1565097
misc_feature          1..1542
                      note = Encodes the peptide given in SEQ ID NO. 110
source                1..1542
                      mol_type = unassigned DNA
                      organism = Zea mays
SEQUENCE: 227
aagtcgtagc cgactggtcg ccgcgtcccc ctttccccgc gcagcagcag agcaccatcc    60
ggtgaccgag caatggaggc gggggcgtg ggcctggcg tgcagacgcg gcggcggcc   120
ttcggctccg gccagcgccg gggcggccta cagtcgccca tcgggaggct gagagtcgct   180
```

```
gaaccggcgg gagctgcggt tgccgtgcgg gctcgcgggt ccaagcccgt cgtaccgctc    240
cgtgcgaaga aatcatccgg aggtcatgaa aacttgcata actccgttga cgaagctctc    300
ctgttgaaga gaaaatcaga agaagttctg ttctacttaa acgggaggtg tatttactta    360
gtgggaatga tgggttctgg aaaaagtact gtggggaaga tcatgtctga agtcttgggt    420
tattcgttct ttgatagtga caaattagtg gagcaagctg ttggaatgcc ttcagttgct    480
caaatattca aagttcacag tgaagccttc tttcgggata tgagagtag cgtcttgagg     540
gatctgtcct ccatgcgacg attagttgtt gccaccggag gtggtgctgt catccgacca    600
gttaactggt atctagagtt cactccattt ctttctttta aatgggtcgc tttgttttct    660
ttgaatcaac agtattgtga cctgtcgttc cattatcagg aaatatatga agaagggcct    720
atccgtttgg ttagatgtgc ccttggatgc tcttgctagg cgtattgcta aagtgggaac    780
cgcttctcgt cctcttctgg accaaccgtc cggtgatcca tacacaatgg tagctactta    840
ttctttcaat attctttcat gctcgtgaaa cggaattgtt tcttcattct atttggacaa    900
agaactgctc atagatccac ttgagccttg aagccctatc ctggattcca gtccttact    960
tgtggacttg tggtagcaaa tgctcagact tcttatgcta gttctaatat ggatcactca    1020
ctgggttcct tatttgttat aggcctttc taagctcagc atgcttgcag agcaaagggg    1080
tgatgcttat gcaaatgcgg atgtaagggt ttctctggaa gagattgcat ctaaacaagg    1140
tcatggcgat gtctctaagc tgatgccgac tgatatcgca attgaggtaa gcttaccgcg    1200
aatatcatgt ctcttttccag aaaccatcag acagcttttc aaaagataac acgcttaccg    1260
tcttcgcagt cacttcataa gatcgagagt ttcgtcatcg agcacgctgc tgataatcca    1320
gctagcgact cgcaagctga gtcacagatc caaaggatac agaccttgta atatcttaat    1380
ccttctgttt tgtaccgaag cgtacccct agagcatcgt tgggttattt gttcgttgaa    1440
gtgtcacgag ggagagaaaa aaaaaacct gaagtatttc ttgttgtaag ttgtaaagga    1500
atggaataaa ggagctaata atccgaaaaa aaaaaaaaaa aa                      1542

SEQ ID NO: 228         moltype = DNA   length = 1283
FEATURE                Location/Qualifiers
misc_feature           1..1283
                       note = Ceres CLONE ID no.486613
misc_feature           1..1283
                       note = Encodes the peptide given in SEQ ID NO. 111
source                 1..1283
                       mol_type = unassigned DNA
                       organism = Zea mays
SEQUENCE: 228
gtcactgctt tacgtcccaa caggcggcac atttccgcca ccagctacca ccgcctgcgc     60
gcagcgcggt cctctctctc ctcttcttta cacctcacct ccggatcgct cagagattga    120
gccgtagccc gactggtcgc cgcgtcccct cccccgcgc agcagcagag cacccaccgg     180
cgagcgagca atgaggcgg ggggcatcgg cctggcgctg caggcgcggg cggcgggctt    240
cggctccggc tccaggccgg gccggggcgg cctacagcg cccaccggga gcttgagagt    300
cgctgatccg gcgggacctg cggtcgcgtg gcgggctcgc gggtccaagc ccgttcgcacc   360
gctccgactc cgtgcgaaga aatcgtccgg aggtcatgaa aactcgcaca actccgttga    420
cgaagctctc ctgttgaaga gaaaatcaga agaagttctg ttctacttga acgggaggtg    480
tatttaccta gtaggaatga tgggttctgg aaaaagtact gtggggaaga ttatgtctga    540
agtcttgggt tattcgttct ttgatagtga caagttagtg gagcaagctg ttggaatgcc    600
atcagttgcc caaatattca aggtcctatg tgaagccttc tttcgggata tgagagtag    660
tgtcttgaga gatttgtcct ccatgcgacg attagttgtt gccaccggag gtggtgctgt    720
tatccgacca attaactgga gatatatgaa gaagggcta tctgtttggt tagatgtgcc    780
cttggatgct cttgctaggc gtattgctaa agtgggaact gcctctcgtc ctcttctgga    840
ccaaccatct ggtgatccgt acgcaatggc cttttctaag ctcagcatgc ttgcacagca    900
aagggggtgat gcttatgcaa atgcagatgt aagggtttct ctggaagaga ttgcatgtaa    960
acaaggtcat gatgatgtct ctaagctgac acctactgat attgcaattg agtcacttca    1020
taagatcgag agcttcgtca tcgagcacac tgctgatagt tcagctagcg acgcgcaaac    1080
tgagtcgcag atccagagga tacagacctt gtagaacctt aatcccttg tttgccacat    1140
agagcatcgt tgagttattt gttcgttgca gcgtcacgag ggagagaaaa aagagtgaaa    1200
cgtttcttga tgtgagttgt aaggaatgg aagaagggag ctaataatcc aaagtgtgcc    1260
gttggctaaa aaaaaaaaa aaa                                             1283

SEQ ID NO: 229         moltype = DNA   length = 1403
FEATURE                Location/Qualifiers
misc_feature           1..1403
                       note = Ceres CLONE ID no.749796
misc_feature           1..1403
                       note = Encodes the peptide given in SEQ ID NO. 112
source                 1..1403
                       mol_type = unassigned DNA
                       organism = Triticum aestivum
SEQUENCE: 229
gcgatctccc aaccccccct ttacctcttc tgtctcttct tccctccgcc gcggcgccgc     60
tcgccacgcc accccgcgtat ccatccacca ccgttccgc gatggccgcc ggcgtactca    120
acacccagcc ccgcctcaac taaccacgga tgatacacat agctcctgtt aacttcctgc    180
cactcgtccc gtcccccctg agggagagga gatggacgcc ggcgtgggtc tccggccaag    240
gccccgtgca gcatgggccg gacgacgaa gccgcaggga ttcccccgg cgacggtgcc    300
ggcggtgagg ctcgaccaga atccggcgcg cggccgctg gttctgcgct ccgacgcggg    360
gagccggagc accgatccga tccgtggcgc cagcctcaag ggcctgtgct gccacaaatc    420
ggcaggtacc gagaaagtcc actattctgc tgatgaggcc ctcgtactga gcaaaaagc    480
agaggatgtg ctcccttacc tgaatgaccg ctgtgtttat ctagttggaa tgatgggttc    540
tggcaaaact acagttggga agataatagc tgaagtacta ggctattcat tctttgacag    600
tgataagctg gttgagcagt ctgttggcat accgtcggtg gctgagattt tcaggtcca     660
cagtgaagca ttcttcagag ataacgagag tgaggtacta agggatttgt cgtcaatgca    720
```

-continued

```
ccgattaatt gttgcaacgg gaggtggtgc ggtgatacga ccaatcaatt ggagttatat    780
gaagaaagga ctcactattt ggttagatgt tccattggat gccctcgcaa gaaggattgc    840
tgcggtgggt actgcgtcac gacccctcct gcatcaggaa tctggtgatc cttatgcaaa    900
ggcctatgcc aaacttacag cacttttttga acaaagaatg gattcatatg ctaatgctga    960
tgcccgagtt tcccttgaaa atattgcact caaacaagga cataatgatg tgaatgtact    1020
tacaccaagt accatcgcta ttgaggcatt gctaaagatg gagagctttc ttactgagaa    1080
ggccatggtc agaaactgac cagatctcgg tggttaaaaa gaaagatgac aaccaatggt    1140
tcttggttgc cgtgatgtac ataccttttgc ataagacatt cttcttgata tagccagagc    1200
tatgacagag gataacttgg gttttttactt gagtgaacta tatgtgaata gctctaaatt    1260
aagacaatgt ttgtcttgtc tttatcttgc tgcaatttga tatatgggat ttggagtaa    1320
atattaagtg atatcccttg tacattttga agcaaccaga atttacatca atatattatt    1380
ttgagacaaa aaaaaaaaaa aaa                                             1403

SEQ ID NO: 230           moltype = DNA  length = 1347
FEATURE                  Location/Qualifiers
misc_feature             1..1347
                         note = Ceres CLONE ID no.294723
misc_feature             1..1347
                         note = Encodes the peptide given in SEQ ID NO. 114
source                   1..1347
                         mol_type = unassigned DNA
                         organism = Zea mays
SEQUENCE: 230
ctgattcctg aacacaccct cgtctccgca cggaggccgt cctctcctct cctctcctct    60
gcgtccgcca ctgccgccca ccgctcgccc acgcgcgctc cattacctcg gcgggcgatg    120
gccgacctat ccaacaccgg ctccacctaa cacgagcggc gccccgcct aggcggctgg    180
ctggtcggtc gtcgagcagc tagcggcggc agcgcccgga ggccgtctca ctctcctcgt    240
cggggcggca ggagatggag gccatcgtgg gcgtccgcgc gccgccgcgt ggccgtgcct    300
gggccggcct cgagaagccg ccgcgcgccg cttgctgcgc cagagtcccg acggcgaggc    360
tcgcggtcgc ggcggacagg ccgcggaggc tggtgctgcc gccgccgat acgcggaggg    420
ccgcggatta tcctgccctc cgttgcgccg cgcaatctgc aggaacagga aggtccact    480
actctgctga tgacgctctc atactacagc aaaaagccca ggatgttctg ccttacttgg    540
atggccgttg cgtttatctt gttggaatga tgggttcagg caaaactaca gttgggaaga    600
tactatccga agtgttaggt tattcgttct tcgacagtga taagttggta gagaaggctg    660
ttggtatttc atctgttgct gagatctttc agctccatag cgaaacattc ttcagagata    720
atgagagtga ggtcctgacg gatctgtcat caatgcatcg gttggttgtt gcaaccggag    780
gtggtgcagt gatccgacca atcaattgga gttacatgaa gaaagggctg accgtatggt    840
tagatgtccc actggatgca cttgcaagaa gaatcgctgc tgtaggaacc cgtctcgac    900
cactcttgca tcaggaatcc ggtgatcctt atgcaaaggc ttatgcaaaa cttacgtcac    960
tttttgagca aagaatggac tcgtatgcta atgctgatgc cagagtttca cttgaacata    1020
ttgcattaaa acaaggccat aatgatgtca ctatacttac acctagtacc atcgccattg    1080
aggcattgct aaagatggaa agttttctta ccgagaagac catggtcaga aactgacctc    1140
tgaatgaga gggaaaggat gctgacaaca tgtggcccct gtttgtttaa ttgtacatat    1200
accttttgcat tattgcctaa actctttcta cagtgttgtt ggattattgt ttgtgcagca    1260
tgaaagagga ccgtttgagt ttgtatttat gcaaatgaat aagtaaataa ctttcagtta    1320
aaacaatgac aattcgttat ttatcgc                                         1347

SEQ ID NO: 231           moltype = DNA  length = 1318
FEATURE                  Location/Qualifiers
misc_feature             1..1318
                         note = Ceres CLONE ID no.1374869
misc_feature             1..1318
                         note = Encodes the peptide given in SEQ ID NO. 116
source                   1..1318
                         mol_type = unassigned DNA
                         organism = Zea mays
SEQUENCE: 231
ctcctgaaca caccacccct cgtcgcacga cgatggaggc cgtcctctcc tcctctctgc    60
gtccgcact gcccaccgct cgcccgcgcg cgctccatta cctccggcggg cgatggccga    120
cctatccaac accggctcca cctaacacga cagcgcccc cgcctaggcg gcagctggct    180
ggtcggtcgt cgagcagcta gcggcggcag cgcccgagg gaggccgtct cactctcctc    240
gtcgggcgg caggagatgg aggccatcgt gggcgtccgc gcgccgccgc gtggccgtgc    300
ctgggccggc ctcgagaagc cgccgcgcgc cgcttgccgc gccagagtcc cgacggcgag    360
gctcgcggtc gcggcggaca ggccgcggag gctggtgctg ctgccgccgag atacgcggag    420
ggccgcggat cctgccctcc gttgcgccgc gcaatctgca ggaacaggaa aggtccacta    480
ctctgctgat gacgctctca tactacagca aaaagcccag gatgttctgc cttacttgga    540
tggccgttgc gtttatcttg ttggaatgat gggttcaggc agaactacag ttgggaagat    600
actatccgaa agtgttaggtt attccttctt cgacagtgat aagttggtag agaaggctgt    660
tggtatttca tctgttgctg agatctttca gctccatagc gaaacattct tcagagataa    720
tgagagtgag gtcctgaggg atctgtcatc aatgcatcgg ttggttgttg caaccggagg    780
tggtgcagtg atccgaccaa tcaattggag ttacatgaag aaagggctga ccgtatggtt    840
agatgtccca ctggatgcac ttgcaagaag aatcgctgct gtaggaaccc gtctcgacc    900
actcttgcat caggaatctg gtgatcctta tgcaaaggct tatgcaaaac ttacatcact    960
ttttgagcaa agaatggact cgtatgctaa tgctgatgcc agagttttca cttgaacata    1020
ttgcattaaa acaaggccata atgatgtcac tatacttaca cctagtacca tcgccattga    1080
ggcattgcta aagatggaaa gttttctta ccgagaagac catggtcaga actgacctct    1140
gaatgagag ggaaaggatg ctgacaacat gtggcccttg tttgtttaat tgtacatata    1200
cctttgcatt attgcctaaa ctctttctac agtgttgttg gattattgtt tgtgcagcat    1260
gaaagaggac cgtttgagtt tgtatttatg caaatgaata agtaaataat tttcagtt    1318
```

```
SEQ ID NO: 232           moltype = DNA  length = 1234
FEATURE                  Location/Qualifiers
misc_feature             1..1234
                         note = Ceres CLONE ID no.276706
misc_feature             1..1234
                         note = Encodes the peptide given in SEQ ID NO. 118
source                   1..1234
                         mol_type = unassigned DNA
                         organism = Zea mays
SEQUENCE: 232
caccggctac cacctgccgc ctgcgccctg ccctccctct gttttttctag accccccggat    60
cgctcagaga ttgagtcgta gtcgcacccg actagtcgcc gcgtcctcct ttccccgcgc    120
agcagcagag caccacccgg tgaccgagca atggaggcgg ccgtgtggg cctggcgctg    180
cagacgcggg cggcggcctt cggctccggc cagcgccggg gcggcctaca gtcgcccatc    240
gggaggctga gagtcgctga accggcggga gctgcggttg ccgtgcgggt tcgcgggtcc    300
aagcccgtcg taccgctccg tgcgaagaaa tcatccggag gtcatgaaaa cttgcataac    360
tccgttgacg aagctctcct gttgaagaga aaatcagaag aagttctgtt ctacttaaac    420
gggaggtgta tttacttagt gggaatgatg ggttctggaa aaagtactgt ggggaagatc    480
atgtctgaag tcttgggtta ttcgttcttt gatagtgaca aattagtgga gcaagctgtt    540
ggaatgcctt cagttgctca aatattcaaa gttcacagtg aagccttctt tcgggataat    600
gagagtagcg tcttgaggga tctgtcctcc atgcgacgat tagttgttgc caccggaggt    660
ggtgctgtca tccgaccagt taactggaaa tatatgaaga agggcctatc cgtttggtta    720
gatgtgccct tggatgctct tgctaggcgc attgctaaag tgggaaccgc ttctcgtcct    780
cttctggacc aaccgtccgg tgatccatac acaatggcct tttctaagct cagcatgctt    840
gcagagcaaa ggggtgatgc ttatgcaaat gcggatgtaa gggtttctct ggaagagatt    900
gcatctaaac aaggtcatgg cgatgtctct aagctgatgc cgactgatat cgcaattgag    960
tcacttcata agatcgagag tttcgtcatc gagcacgctg ctgataatcc agctagcgac   1020
tcgcaagctg agtcacagat ccaaaggata cagaccttgt aatatcttaa tccttctgtt   1080
ttgtaccgaa gcgtaccccc tagagcatcg ttggtttatt tgttcgttga agtgtcacga   1140
gggagagaaa aaaaaaaacc ctgaagtatt tcttcttgta agttgtaaag gaatggaata   1200
aaggagctaa taatccgaag tgtaccgttg gccg                               1234

SEQ ID NO: 233           moltype = DNA  length = 1254
FEATURE                  Location/Qualifiers
misc_feature             1..1254
                         note = Ceres CLONE ID no.840744
misc_feature             1..1254
                         note = Encodes the peptide given in SEQ ID NO. 119
source                   1..1254
                         mol_type = unassigned DNA
                         organism = Triticum aestivum
SEQUENCE: 233
accactcgcc gcccccagc agccaccgga cacctgccga aagcgcgaga gagccgtagc    60
cgatcgcatc gccgcgtagt ggccgccgca gagcaaccgg cgagcaatgg aggcgggcgt   120
ggggctggcg ctgcagtcga gggccgcggg gttcggctcc ggccgccgcc ggagctcgat   180
gtacggcggc gagagcgggg ctcgggtcgt gagcttgcgg gtcagtgatc tggtggggtc   240
gccggccgcc gtgcgggcgc gcggggccaa gccccgtcgtc ccgctccgcg ccaagaaatc   300
gtccggagga ggtcatgaga acttgcataa ctccgttgac gatgccctct gttgaagag    360
aaaatcagaa gaggttcttt tccagttgaa tggtcggtgc atttacctag ttggtatgat   420
gggttcgggc aaaagtacgg tggggaagat ctttggctga gtttttgggtt attcattctt   480
cgacagtgat aaaattggtcg aacaagctgt tggcatgcct tcagttgctc aaatttttcaa   540
ggttcacagt gaagccttct tcagggataa tgagagtagc gtcttgaggg atttgtcctc    600
aatgcggcga ttagttgttg caactggagg tggtgctgtt atccgaccag ttaactgaa    660
aaatatgaag aagggcctat ctgtttggtt ggatgtgcca tttgaagctc ttgcaaggcg    720
tattgctaaa gtggggactg cctcgcgtcc tcttctagat caaccatccg gcgatccata    780
cacaatggcc ttttcgaaac tcagcacccta cgcggagcaa aggggcgatg cttatgcaaa    840
tgctgatgtc agagtttccc tcgaagagat cgcatctaag ctgggccatg acgacgtctc    900
taagctgaca ccgattgata ttgctctcga gtcgctccaa aagatcgaga gcttttgtcgt    960
agaagacacc gccgtcgccg actcacaaac ggaatcgcaa gctcaaagga tacatacctt   1020
gtaggatatg aatccttttt gcaccatgta gggcgcggcg cggcccagcg cagctgagtt   1080
attcgttcgt tgtgtcgaca aggaggaagc tggagtatct ctttttctttg taagctgaa   1140
aatgcgggaa taatggagct agctaataca aagatccttg ttggttgaaa gaaccctggc   1200
ttccccccctg gcttgatgaa aacaatatgt caccttccaa aaaaaaaaaa aaaa        1254

SEQ ID NO: 234           moltype = DNA  length = 746
FEATURE                  Location/Qualifiers
misc_feature             1..746
                         note = Ceres CLONE ID no.651548
misc_feature             1..746
                         note = Encodes the peptide given in SEQ ID NO. 126
source                   1..746
                         mol_type = unassigned DNA
                         organism = Glycine max
SEQUENCE: 234
ataaccgaac aaaattaaag aaaaaaaaaa cccactattc aaaaccaaat ccaaaaacca     60
agacaccccc attaggtagc taggccttaa ttgatctcct tttctttcac caccaccaac    120
aacgatgtcc atgctcgaaa ccgaccaaat caagcaactc aacgacatat tcaagcgctt    180
cgacatggac caggacggca gcctgaccca cctggagctg gcggcgctcc tccggtccct    240
```

```
                                       -continued
gggcatcaaa cccaccggcg acgaaatcta cgccctcctc tctaacatgg acgaaaacgg    300
caacggctac atcgagttcg acgagctcgt gcatgccatc atgcctgacc tcaccgagag    360
cgtcctcatc aaccaggagc agctcctcga ggtcttccgg tctttcgacc gtgatggcaa    420
cggctacatc acagccagcg agctcgcggg ttccatggcg aagatgggcc agccactcac    480
ctaccgcgag ctcgcctcca tgatggctga ggccgatagc aacggcgacg gcgtcattag    540
cttcaacgag ttcgccgccc tcatggccaa atccgccgct gaatttctcg gcgtcaaggt    600
cgcctagatg gctagatcaa tacggggcta ataatttcgt atgtttgtgt aacccttttt    660
atttttttgt gttttcttta gggtacgtgt acgttggtgt aaaggcaagg agatcgaaca    720
aagataaata attaagggat attttg                                         746

SEQ ID NO: 235          moltype = DNA  length = 851
FEATURE                 Location/Qualifiers
misc_feature            1..851
                        note = Ceres CLONE ID no.287120
misc_feature            1..851
                        note = Encodes the peptide given in SEQ ID NO. 126
source                  1..851
                        mol_type = unassigned DNA
                        organism = Zea mays
SEQUENCE: 235
atcatccctg cagttgtgga tcagttcgtc ctccgtctct ctccacaagt ctcctctagg     60
cgccaagcaa tgacaaggtc agcaccgccg gcctctcctc cggccgcgaa gcccgtgctg    120
cgcgggagcc agctggagca gctccgcgag atcttccggc gcttcgacat ggacggcgac    180
ggcagcctga cgcagctgga gctggggcg ctgctgcgt cgctgggcct gcgcccacg       240
ggggaggagg cccgcgcgct gctggcggcc atggactcca acggcaacgg cgcggtggag    300
ttcggcgcaa tggcggccgc catcgcgccg ctgctcacca cgcagacgca cctcgctcgac 360
caggcccagc tcctggaggt gttccgcgcc ttcgaccgcg acggcaacgg ctacatctcc    420
gccgccgagc tggcgatc catggcgcgc atcggccagc cgctcacctt cgaggagctc     480
acgcgcatga tgcgcgacgc cgacgccgac ggcgacggcg tcatcagctt caacgagttc    540
gccgcgtca tggccaagtc cgcgctcgac ttcctcggcg tcgcctgatg ccctctgatg    600
gaccgatcga tcgatcggtc tcgctcaccg cccgccgccg taaccccgtg tcctgtgac    660
cctgtccctc gccgccatt gattacctgt tctctctctc tctctctctc tcttttgtta    720
ggaagatgct catccggtta atgtaggata actgacacaa gataatgtaa ctcaaaaact    780
catcgctggt ttgtaacatg gatgaactcg gaaaatgtgt acatattttg gatggatttg    840
ttcaatcttc c                                                         851

SEQ ID NO: 236          moltype = DNA  length = 848
FEATURE                 Location/Qualifiers
misc_feature            1..848
                        note = Ceres CLONE ID no.759217
misc_feature            1..848
                        note = Encodes the peptide given in SEQ ID NO. 129
source                  1..848
                        mol_type = unassigned DNA
                        organism = Triticum aestivum
SEQUENCE: 236
cggtctcacc ccaaacccat tgtgcatctc catccccacc tcctccgatc ccatccaccc     60
ccaccctcac cgccaccaag tcaaagatcc aaccttcact ccaccaccat gacgaagcca    120
tcgccatccc catcgccggc gccggccaag ggcgcgggt cgctgcgggg cagccagctg     180
aagcagctgc gctccctctt cgaccgcttc gacatggacg cgacggcag cctcacccag    240
ctcgagctgc cggccctgct ccgctccctc ggcctgcgcc ccacggggga cgagtcgcgg    300
gccctcctcc tcgccatcga cgccgacggc agcggcaccg tggagttcga cgagctggcg    360
cgggccatcg cgccggtgct caccgcccac gcgccgcggc tcgtcgacca ggcgcagctg    420
ctcgaggtct tccgcgcctt cgaccgcgac ggcaacggct acatctccgc cgccgagctc    480
gcgcgttcca tggccaagct gggccagccg ctcacgttcg aggagctgg gaccatgatg    540
cgggacgcgg acgcggatgg ggacggcgtg attagctttg gagagttcgc cgccgtcatg    600
gccaggtccg cgctcgactt cctcggcgtc ccgccgcct gagatgtgag atgatgaccg    660
gccgggctcc ggctggctct gatcggatgg actggtagta tgattcttct tctttggtag    720
aactagtcgt agtagggtgg ttcaaggccc ggactggatc aactgtgacg aactcacacg    780
gagttgcaac gttgacctgg aatgtgtata aattttggta atttggtcaa tcgatgcgtc    840
cgctgctg                                                             848

SEQ ID NO: 237          moltype = DNA  length = 766
FEATURE                 Location/Qualifiers
misc_feature            1..766
                        note = Ceres CLONE ID no.684584
misc_feature            1..766
                        note = Encodes the peptide given in SEQ ID NO. 139
source                  1..766
                        mol_type = unassigned DNA
                        organism = Triticum aestivum
SEQUENCE: 237
cgaaaagtgg acctttgta ctagtacttc agacagacag aagcagaagc aaccagccga     60
agctcgttcc tcgtagacag ttggacagtc gtctcgatcc atcgtccatc ccgtctcgcc    120
agcagccgac catggccgcg caggcgccgc cgccgccgcc gccggagcag aagatgatgg    180
tggccatcga cgagagcgag tgcagccact acgcgctcga gtgggccctg cgcaacctcg    240
cgccccgccg cctcatcctc ttcaccgtcc agccttctc ccctctcagc tacctccccg    300
tcggctcccc gcttggcccg tcgtggcgt cgccggagct catcaggtcg gtgaccgagc    360
accagcggca gctcgcccag gcgctcgtcg acaaggccaa ggccatctgc gccgagcacg    420
```

```
gggttgatgc agagaccgtc atcgaggtgg gtgatcccaa ggaaaccata tgcgaagctg   480
cggagaagtt gaatgttgat ctgctcatcg tgggaagcca cagccgtggg cctgtacaaa   540
ggttttcct tggcagtgtg agcaactact gtagccacca cgcgaagtgc ccggttcttg    600
ttgtgaagaa gaaagaatga aactccgcta tctactgtat tcatggacat cgtgtgaaga   660
accttgaga tgtgtatcta catgttgttt gtcacagcat ctagttgcat acttgcatat    720
gaataaacat actttgccaa tttgaaaaca actatatatt cagtct                  766

SEQ ID NO: 238          moltype = DNA   length = 693
FEATURE                 Location/Qualifiers
misc_feature            1..693
                        note = Ceres CLONE ID no.1059727
misc_feature            1..693
                        note = Encodes the peptide given in SEQ ID NO. 142
source                  1..693
                        mol_type = unassigned DNA
                        organism = Glycine max
SEQUENCE: 238
gatcaaactg tagtcaaact catctgacga tcgatcgatc gatcatttgg aagaaaccat   60
ggtggaagag aaaagtggga agaagcaagt gatggtggcg atcgacgaca gcgattgcag   120
caaacacgct ctccgatgga cgctctcgta tctcaaagac agcctcgccg attccgatat   180
catcctcttc accgcgcagc ctcagctcga tctcagctcc gtctacgctt cctcttatgg   240
cgccgctccg atagagctga taaactcaat gcagcagaac tacaaaaacg cagcgttgaa   300
tcggattgag gaagggacca agatttgcgc tgagagcggg gttaccccaa agaaggtgat   360
ggagtttgga aacccaaag aagcgatatg tgatgctgtt gagaagcttg gtgttgattt    420
gctaatcgtt ggtagccatg gcaaagggc tctagagagg actttccttg gaagtgttag    480
caattactgt gttaacaagg ctaagtgccc agttcttgtg gtcaggacaa aggcttgaag   540
agtttgagaa ccgcctcgct tgctgtatgt gtgttgtgta aacatattga taataatgct   600
ttgtttgtat actactactg tttggaaaaa aactttgtga atggaaataa atatattatt   660
ggtttgataa ataacgagct ttgctgtgct ctt                                693

SEQ ID NO: 239          moltype = DNA   length = 853
FEATURE                 Location/Qualifiers
misc_feature            1..853
                        note = Ceres CLONE ID no.1272732
misc_feature            1..853
                        note = Encodes the peptide given in SEQ ID NO. 143
source                  1..853
                        mol_type = unassigned DNA
                        organism = Zea mays
SEQUENCE: 239
aaagcggact gctctcctca attgtcaggc agtagcatcc atttgattgt tctatcctct   60
tctctgttct cacccccttg caagcaacaa tcgttcaccg atcgatccag tgcgtcctgc   120
atggaaactg ccgccgtcgc cgcctccagt gccgggcgcc gcatcatggt ggccgtggac   180
gagggcgagg agagcctgca cgcgctcaac tggtgcctcg ccaacgtcgt ctccccggca   240
ggaggcgaca cgctggtgct cgtccacgcc cgccgcccgc gccggtccta cgccgccatg   300
gacagcgcag ggtacatgat gacctcggac gtgctggcga cgttgagag gcacgccaac    360
gcggtctcgg cggcggcggt cgacaaggcc aagccgtct gacccgacca cccgcacgtc    420
aaggtggaga cgacggtgga gagcggggac ccgcgggacg tcatctgcga cgcagccaac   480
aagatgccg cggaccgct cgtcatgggc agccatggtt acggcttcat ccagagggcg     540
ttcttggca gcgtcagcaa ccactgcgcg cagaactgca aatgcccggt cctcattgtc    600
aagagcccca aggagtagaa ggttcctcgc atgtaacgct gcagcttagc caataatgct   660
tcatggcgac catataggca tatatgtaca cacttcacat cccattgcat ggcagtgtct   720
tccctagttc aacaactagc tttctgctgg aataaggtgt tcagagttca gacagagtat   780
gtactgtaca tactatcttc ttgcatttgg tactcttgtt tagtgaaaag cgttccgtaa   840
aaaaaaaaaa aaa                                                      853

SEQ ID NO: 240          moltype = DNA   length = 812
FEATURE                 Location/Qualifiers
misc_feature            1..812
                        note = Ceres CLONE ID no.283925
misc_feature            1..812
                        note = Encodes the peptide given in SEQ ID NO. 144
source                  1..812
                        mol_type = unassigned DNA
                        organism = Zea mays
SEQUENCE: 240
agtagcatcc aattgattgt tctatcctct tctctgttct cacccccttg caagcgccaa   60
gcaacaatcg ttcaccgatc gatccagtgc gtcctgcatg gaaactgccg ccgtcgccgc   120
ctccggtgcc gggcgccgca tcatggtggc cgtggacgag ggcgaggaga gcctgcacgc   180
gctcaactgg tgcctcgcca acgtcgtctc cccggcagga ggcgacacgc tggtgctcgt   240
ccacgcccgc cgcccgcgcc cggtctacgc cgccatggac agcgcaggt acatgatgac    300
ttcgacgtg ctggcgagcg tcgagaggca cgccaacgcg gtctcggcgg cggcggtcga    360
caaggccaag cgcgtctgcg ccgaccatcc gcacgtcaag gtgagacga tggtggagag   420
cggggacgtca tctgcgacgc agccaacaag atgcccgtgg gcagccgtgg gcagcttagc  480
ttacggcttc atccaagggg cgttcttggg cagcgtcagc aaccactgcg cgcagaactg   540
caaatgcccg gtcctcattg tcaagagcc caaggagtag aaggttcctc gcatgtaacg   600
ctgcagctta gccaataatg tttcatgggc gaccatatag gcatatatgt acacacctca   660
catcccattg catggcagtc ttcccttccc tagttcaaca actagctttc tgctggaata   720
aggtgttcag acagagtatg tactgtacat actatcttct tgcatttggt actcttgttt   780
```

```
ggagagaagc gttccgtaac cttcggttgc ct                                      812

SEQ ID NO: 241          moltype = DNA  length = 1002
FEATURE                 Location/Qualifiers
misc_feature            1..1002
                        note = Ceres CLONE ID no. 611156
misc_feature            1..1002
                        note = Encodes the peptide given in SEQ ID NO. 147
source                  1..1002
                        mol_type = unassigned DNA
                        organism = Glycine max
SEQUENCE: 241
attatccagc aaacactatc tcaatagtga agctctaaac cactgccaag tatggtagtt          60
tcttcgtgct ctttgagctg gatttcacct tgcttatccc ataagctaaa cttgccacat        120
acaaattgtt tgcctcgcaa cattgcaact tcatcttcca acactgtctt ttgtgaattg        180
gacacaaccc ccagcggaga aagtcattgc cggagaagac cgctactgtt aggcattgga        240
gcattaactg caaatttaca accaacaaat ttggtctttg ctcaagaaaa accagacaga        300
taccgagctt ttgtggacta tgaagatggg tattcttacg tatatcccat tgattggaag        360
gaatttgact tcaggggctca tgattctgca ttcaaagaca gatatctaca gttacagaat       420
gtacgggtga gatttatacc aaccgagaag aaagacatcc gagatttggg tcctatggaa        480
gaggttatat acgatttggt gaaacataga tacgcagcac caaaccaaag accaacaata       540
aatgacatgc aggagaaaac catagatgga aaacattact ataccttttga atatatactt      600
acatcaccaa attattctag tgcctccttt gcaacaattg ctataggaaa tggaaggtac       660
tacacgttaa ttgttggagc caatgaaagg cgatggaaaa gatttcgaga tcagcttaaa       720
gtggtagcag actcctttag gcttcttgac atctgaaatg tcacgggaca atgcaaaaca      780
tgttttaatt tgcctacaga tcaagtttga aatattcgta tatcagagca aaataagttt       840
ttacaagtga atgatatctt ctactatacc aatagaactc tcttttgtac atcgcatgca      900
aagtgacttt gtctgtcatt tgtggtgcaa actcaattcg ttgttcctcg tctactctta      960
cattgttcca ctgctactcc tttatggagt atttcggttg gg                         1002

SEQ ID NO: 242          moltype = DNA  length = 944
FEATURE                 Location/Qualifiers
misc_feature            1..944
                        note = Ceres CLONE ID no.1551032
misc_feature            1..944
                        note = Encodes the peptide given in SEQ ID NO. 152
source                  1..944
                        mol_type = unassigned DNA
                        organism = Zea mays
SEQUENCE: 242
agtcgcctcg attcgcttcc gcccatcct ccttcccgac gcctcacatg gcaacggccg         60
tgcccgccgc ctgcctccgc gcgccgtgct cctctccagc ggccgtcgca cgccgacttg      120
gggccgtggg cccgtcgctg cgcaagcggc attgcgccgt cggcccccgtc gctgccgcct      180
gcggccccgc gccgccgcgg ctgcttgaca acgaggaggc ggtctgctcc gtacggcggc      240
gtgtgctggt tgccggtgcc gccgcgttcc tctcccggcc taatccggcg gcattcgcag      300
cagaggctaa gaaagggttc ctgcccgtcg tcgacaagaa ggctggctac tctttcctct     360
acccgttcgg atgggaggaa gtggctgtgc aagggcaaga caaggtgtac aaagatgtga     420
tagagcctct cgagagtgtg agcgtcaact ctattccaac tagcaaggag gatatccgtg     480
atcttggtcc tccggataag gttgccgagg ctctgattaa aaaggttttg gcaccatcaa     540
cacagaagac aaagttaatt gaggcgaaag agaatgatgt tgatgggagg gcttactaca     600
cttttgagtt cacagctcag gctccaaact acaccagaca tgcactttggt gctattgtaa    660
ttgcaaatgg caaattttac acattgacca ctggagcaaa cgagaggagg tgggaaaaga    720
tgaaggatag gctgcatact gttgtggatt ccttcaaaat cgaaaataga atatgagtgc    780
ctgaattgct gtgttgtttt tccttcgttg attcgctttt tcttacataa ctgcagtgct    840
gagatttttc agtagtaaat accgggattg tggattatgc tgatcagttt catttcgaaa   900
tgtttgttac cagacttgag caaaaataaa aaaaaaaaaaa aaaa                      944

SEQ ID NO: 243          moltype = DNA  length = 1395
FEATURE                 Location/Qualifiers
misc_feature            1..1395
                        note = Ceres CLONE ID no.703785
misc_feature            1..1395
                        note = Encodes the peptide given in SEQ ID NO. 161
source                  1..1395
                        mol_type = unassigned DNA
                        organism = Triticum aestivum
SEQUENCE: 243
atctgaatgc tagaaggagg tggttggacg atgaggcatc ccaacacggt agaaggagtt       60
ccgcctatcg aagttgagag ggccaatttg aaaaaaagaa aaagttgaga gggacagaga      120
gggaaacatc tggcattct cgttgcagaa agtagagcgc tgtacaaacg ggccttcacg       180
aaccaagaga catccatcaa atttcatggc gtcctctcca caatcctcct cctctgcacc     240
caaagccgac gacaaggcag cgtcccacaa agaaatctac gaccagctac tagaggtcgt    300
gtccacctac ccgacggcgc ctagcggcat cggccgcccg tacaccacc acccagacgg    360
ctggtacgga ttcacgccgg ccgtcgtgaa cgcatgtgc atcaagcggc acctcaaggc    420
gtgcgacacc gacgtcttcc tctccacctt tcccaagtcc ggcaccacct ggctcaaggc    480
gctcctgttt gcgaccctcc gccgcaccgc ggacgggcca gcgatcgcgg cgctcgcagc   540
ccacagcccc caccagctca tccctttcct cgaggtccag gttttcagca acggccggat    600
cccagacctg agctcccctcc ctgcgccgcg gtcctgatga cgcacatcc cgtcccggtc   660
gctgccggag tccgtggccg cctccggctg caaggtggtg tacctgtgcc gggacccaa   720
```

```
ggactgcttc gtgtcgctct ggcacttctg gaaccggttc gcgccgtcgc cgtgggacct   780
cggtgaggcg ctccagcagt tctgcgacgg cgtctccctg ttcgggcctt tctgggagca   840
cgtgctgggc tactgcgct  ggcatgtgga gaggccggag caggttctat tcctgaccta   900
cgaggagctc gccgccgaca ccctcggcca gctgaagcgg ctcgctgcgt ttctcgggcc   960
cccgttcacg tcagaggagc gggaagccag ggtagacagg gagatcgtgg aggcatgcgc  1020
catggagagc ctggcgggac tggaggtgaa ccgctccggg aagacggaca tgaccgagtc  1080
ttcagtggcg aacaacatat tcttccggcg cggcgtcgtt ggcgactgga gaaccacct   1140
gacgccggag atggctagaa ggatcgatga gatcaccgat agcaagttca gaggatcggg  1200
gttggcgttg acgccggcaa ccgcagatca gaactagtgg gttcatgatg gcagatgcta  1260
tataaataag gacgacttgc gcaacatttt tataaaatat tgtactatta atgtcaggca  1320
tgataacttg atcagcaaac atgcgaaggg aaataacaga agtgttacca tacagtaata  1380
tacatgaata tcgtt                                                   1395

SEQ ID NO: 244        moltype = DNA   length = 1320
FEATURE               Location/Qualifiers
misc_feature          1..1320
                      note = Ceres CLONE ID no. 1064128
misc_feature          1..1320
                      note = Encodes the peptide given in SEQ ID NO. 168
source                1..1320
                      mol_type = unassigned DNA
                      organism = Zea mays
SEQUENCE: 244
atttacgatt agcctagcga ctcggcatgg ctactgtctt cccccgtgac gccggcgtct    60
ccacgccgga agccgacgag gctaagaaaa tctacgatga agcacggcga gtggtgtcca   120
cctacgagac tgttcccagt cccagcgaga ccctgcgagg ttactgccgc caccccagcg   180
gctggtgcat aaccctgccg atcatggtga gctccatggt cgcagagcag cactttgagg   240
cgcgtggcac cgacgtgctc cttgttacga tgcccaagtc cgggactacc tggatcaagg   300
ccctcctcta tgctgcggcc caccgcactg acgacacatc atcgtccata ctccggcagc   360
tcgcctccca caactcccac cagctcgttc ctttcctcga ggccaggtc tacaccaagg   420
accagattcc agacctgagc tcgcttcccg cgccacggct cttcgccacg cacatcccgg   480
ctgagtcgct gccacccctc cgttgtggcg tccggctgcaa ggtggtgtac ttgtgccggg   540
accccaagga ctgcttcgtg tctctctggc actttatgaa caagttcacc ccatgggaca   600
tcgacgaggc acacggccgg ttctgcgagg gtgtctcgtt gtatgggcca ttttgggagc   660
acgtgctgag ctactggcgt tggcacgtcg accgaccggg tcaggtgctc ttcctgactt   720
acgaggagct cagcgccgac ccgctcggcc aactgaggcg cctagccgag ttcattgggc   780
gcccccttcac gccgggggag caggaggcgg gagtggacag ggagattgcg gaggcatgtg   840
ccatgaaaag catggtcaac caggaggtga accagtccag gacgaccgaa atcgttgaga   900
tgccgattcc caacgggatc ttcttccggc gaggcgtgct cggagactgg accaactacc   960
tcacgccgga gatggcagga aggatcgatg agattaccaa gagcaagttt gaaggatccg  1020
gcctcatgct gccgaaaaca atctcggaaa tctcaaagat ctagcatccc tccgtcgtgt  1080
ttgatgtttg aaatcgttca ccttttttt  tctcttgttgt aaactgcacc ctgctggcac  1140
tggcttggct gaataaaaaa agcttgcatt gttcttgttg atcaaacgaa ataccagctg  1200
gcgagttgtt gatgttacgg aaaaggcctg cttagtctta ggtatttttc ttatcggttt  1260
aattgtgatc aaatgtgttt gtactctgct taattattaa taaaaatgat tgtatgcacc  1320

SEQ ID NO: 245        moltype = DNA   length = 864
FEATURE               Location/Qualifiers
misc_feature          1..864
                      note = Ceres CLONE ID no. 5367
misc_feature          1..864
                      note = Encodes the peptide given in SEQ ID NO. 173
source                1..864
                      mol_type = unassigned DNA
                      organism = Arabidopsis thaliana
SEQUENCE: 245
actatcaatt cgactggaaa aaggatattt ccagattagg tagagagaga gcaaaagtac    60
tttcattcag acttcagttt aagctatggc ggcgaacgat tcttcaaatg ctattgcat   120
cgacgggaat ctcgactccg attcgaatct taacactgac ggtgacgaag cgaccgataa   180
tgattcctcg aaggcattgg ttactatccc tgctccagcc gtttgtcttt tccggttcgc   240
cggagatgct gctggtggcg ccgttatggg ctctatcttc ggatatggtt caggattgtt   300
caagaagaaa ggcttcaaag gatcatttgc agatgcaggg cagtctgcta agactttgc   360
tgttttatct ggagtccaca gtttggttgt ttgccttctg aagcaaatcc gaggcaaaga   420
tgacgccatt aatgttggag tagcagggtg ttgcactggt cttgctctta gtttccctga   480
tgctccacag gctcttctac agagttgtct cacgtttggg gcattctctt ttattcttga   540
gggactcaac aaaagacaaa cagctttggc cacactcggtc tcgttgagac accaaaccgg   600
actgttccaa gatcatcatc gtgctttacc actctctctt gctctcccga tcctgaaga   660
aatcaaagga gccttttctt ctttctgcaa gtccttagct aaaccaagga agttctaatc   720
tcgtcttatt attctcccct tcttgtgtct taggctctct ctatgtagat gtaaaattct   780
cccgcttttg ttgtactttg tgagacatgt tttgtgaaag cttttgca agagccaatt   840
tgaagagaaa aagagttgtg tacg                                         864

SEQ ID NO: 246        moltype = DNA   length = 766
FEATURE               Location/Qualifiers
misc_feature          1..766
                      note = Ceres CLONE ID no. 1060894
misc_feature          1..766
                      note = Encodes the peptide given in SEQ ID NO. 176
source                1..766
```

```
                        mol_type = unassigned DNA
                        organism = Zea mays
SEQUENCE: 246
aggtagaaag cgaaactctc tctccagctt cagaggcttc agctatggcg gccgagaatc    60
cttcaaacgg tgtagacgtc gacacgagtc tcgcttccga ttcaaacgat aaccgcaaag   120
ccagtgattt gaccaatcat gactcttcca tggcattgac agtcccttcc accgccgttt   180
gtctcggccg tttcgccgga gatgcagcag cggcgccgt catggggtct atattcggct    240
atggttctgg attgtttaag aaaaaagggt ttaagggatc atttgcggat gcgggtcagt   300
ctgcaaagaa ttttgcgatt ttatctggag tgcacagttt ggttgtttgc cttctgaaga   360
aactgcgagg gaaagatgat gccattaacg ttggaattgc tggatgctgc actggccttg   420
ctcttagtta cccaggtgca ccacaagcaa tgctacaaag ctgtgtcact tttggtgcct   480
tttctttcat cctcgaagga ctcaacaaga ggcaaacagc tttggctcac tctgtctcct   540
cgagacatga tcaaaccaga agtctgaaag atgatttacc actctccttg gctctcccaa   600
tccatgaaga gatcaaagga gctttctcat ccttctgcaa atctttaaca aaacccaaga   660
agctcgcgtt ccctagctca cgttgatcga agttttttt gtatcctact acttccttt    720
gtagatgtta aaagaacaga tgaaaacaag aatcatgttt caaaac                 766

SEQ ID NO: 247          moltype = DNA   length = 864
FEATURE                 Location/Qualifiers
misc_feature            1..864
                        note = Ceres CLONE ID no. 639280
misc_feature            1..864
                        note = Encodes the peptide given in SEQ ID NO. 177
source                  1..864
                        mol_type = unassigned DNA
                        organism = Triticum aestivum
SEQUENCE: 247
gaaacaggaa acgataacga aactcgcaga gagggcggac atggcggcga ggagcgagaa    60
cgagtcggac ggcgacgtgg gcaccaaccc gccgagggg ggctcgtccc tgtccctgcc    120
gcctctagct gccggtccag ccgtgtgcgt cctccggtcc gccgggagct tcgccggcgg   180
cgccttcgtc ggatctatct ttggatatgt acaaggtttg ctatctaaga agggtttgaa   240
gggctcactc ggcaatgcag ggtcttctgc caaaagtttt gcagttcttt ctggcgtcca   300
gagtttggtt ttgtgcttgt tgaggaagct gcgtgggaaa gatgatatca tcaattccgg   360
cattgctggt tgttgcacag gtcttgcttt gagttttcca ggtacaccac aagcgctgct   420
tcagaactgc gccaccttcg cagcattctc atgcatcatg gaggggctca acaagcaga    480
gaccgcgatg gcgcacaccc tcactgggaa cgccttgacc tttgcacacg caatggcgc    540
gggcgtcctc cccccttcac tctcccccca atcctcgatg cttccgatgc tttcgcctca   600
tgctgccagg ccttggtcgc caagcctaag aagcactaga cagcagcatt aggagggaga   660
gagtgagata tgctcaggaa acctagctag ctcctagcgt tatgtaaatt ttgcttttgg   720
ataatgtcga aaatctagat tgtttgcttt ttcagccggg tgtttttgt cgccgcgttt    780
cgtggcgtgg gcttgctttg ttgatgatat gtcaaggata gattttgttt accgggaaga   840
taagatgtcg tggaaaattt tgcc                                          864

SEQ ID NO: 248          moltype = DNA   length = 827
FEATURE                 Location/Qualifiers
misc_feature            1..827
                        note = Synthesized Sequence
misc_feature            1..827
                        note = Ceres CLONE ID no. 29658
misc_feature            1..827
                        note = Ceres Seed Line ID no. ME02907
misc_feature            1..827
                        note = Encodes the peptide given in SEQ ID NO. 249
misc_feature            1..827
                        note = Encodes the peptide given in SEQ ID NO. 250
misc_feature            1..827
                        note = Encodes the peptide given in SEQ ID NO. 251
source                  1..827
                        mol_type = other DNA
                        organism = synthetic construct
SEQUENCE: 248
gtaagggatg acgcacaatc ccactatcct tcgcaagacc cttcctctat ataaggaagt    60
tcatttcatt tggagagaac acgggggact ctggcctgca gggccatcac cactgcagtg   120
gtacctagaa catcctaatc gaaaaattca tctccaaact ttcaaaaaaa aacctaaaac   180
aaaaaaaatc tctttccttc ttcttttctc atcaatggcg tcaacaaaac ccaccgatca   240
aatcaaacaa ctcaaagata tcttcgctcg cttgacatg gacaaggacg gaagcttaac    300
gcagctagaa ctcgccgctc ttctgcgttc tctcggaatc aaacctcgcg gcgatcaaat   360
ctctcttctg taaaaccaaa tcgaccgtaa cggtaacgga tccgtagagt tcgacgagct   420
cgtcgtggcg atattgccgg atataaacga agaggtgttg ataaatcaag acagttgat    480
ggaggttttc cgttcgtttg atcgtgacgg taacggttca ataacggcgg cggaacttgc   540
tgggtcaatg gctaaaatgg gacatccgtt gacttaccgt gaattaacgg aaatgatgac   600
ggaagctgat tcaacggtg acggtgttat tagtttaat gagttttctc atattatggc    660
taaatcggct gctgattttc ttggattaac cgcttcttga tctgttttgt tttaattact   720
ctctttttt cttctcctgt caatgcaact tgtgcaatta acaatgtgct aatctttcgt   780
ttggtgtgac gtaaaaattt ataaaaaaaa aaaaaaaaaa aaaaaa                  827

SEQ ID NO: 249          moltype = AA   length = 73
FEATURE                 Location/Qualifiers
REGION                  1..73
```

```
                          note = Synthesized Sequence
REGION                    1..73
                          note = Ceres CLONE ID no. 29658
REGION                    1..73
                          note = Ceres Seed Line ID no. ME02907
REGION                    1..73
                          note = Peptide encoded by SEQ ID NO. 248
REGION                    1..73
                          note = Phenotype: ROSETTE LEAVES Useful for making
                           ornamental plants with modified leaves
source                    1..73
                          mol_type = protein
                          organism = synthetic construct
SEQUENCE: 249
MEVFRSFDRD GNGSITAAEL AGSMAKMGHP LTYRELTEMM TEADSNGDGV ISFNEFSHIM    60
AKSAADFLGL TAS                                                      73

SEQ ID NO: 250            moltype = AA  length = 121
FEATURE                   Location/Qualifiers
REGION                    1..121
                          note = Synthesized Sequence
REGION                    1..121
                          note = Ceres CLONE ID no. 29658
REGION                    1..121
                          note = Ceres Seed Line ID no. ME02907
REGION                    1..121
                          note = Peptide encoded by SEQ ID NO. 248
REGION                    1..121
                          note = Phenotype: ROSETTE LEAVES Useful for making
                           ornamental plants with modified leaves
source                    1..121
                          mol_type = protein
                          organism = synthetic construct
SEQUENCE: 250
MTHNPTILRK TLPLYKEVHF IWREHGGLWP AGPSPLQWYL EHPNRKIHLQ TFKKKPKTKK    60
ISFLLLSPSM ASTKPTDQIK QLKDIFARFD MDKDGSLTQL ELAALLRSLG IKPRGDQISL   120
L                                                                  121

SEQ ID NO: 251            moltype = AA  length = 52
FEATURE                   Location/Qualifiers
REGION                    1..52
                          note = Synthesized Sequence
REGION                    1..52
                          note = Ceres CLONE ID no. 29658
REGION                    1..52
                          note = Ceres Seed Line ID no. ME02907
REGION                    1..52
                          note = Peptide encoded by SEQ ID NO. 248
REGION                    1..52
                          note = Phenotype: ROSETTE LEAVES Useful for making
                           ornamental plants with modified leaves
source                    1..52
                          mol_type = protein
                          organism = synthetic construct
SEQUENCE: 251
MASTKPTDQI KQLKDIFARF DMDKDGSLTQ LELAALLRSL GIKPRGDQIS LL            52

SEQ ID NO: 252            moltype = AA  length = 498
FEATURE                   Location/Qualifiers
REGION                    1..498
                          note = Ceres Clone ID no. 375578
REGION                    1..498
                          note = Full Length Peptide Sequence for Ceres CLONE ID no.
                           375578
source                    1..498
                          mol_type = protein
                          organism = Zea mays
SEQUENCE: 252
MGKRGKWFSA VKKVFSSSDP DGKEAKAQKA DKSKSKRRWP FGKSKHSEPS ISTVPGTAPA    60
VAPLPSPPAT QPHSLEIKDV NPVETDSEQN KHAYSVALAS AVAAEAAAVA AQAAAEVVRL   120
TAVTTAAPKM PVSSREELAA TKIQTAFRGY LARRALRALR GLVRLKSLVD GNAVKRQTAH   180
TLQCTQAMTR VQTQIYSRRV KLEEEKQALQ RQLQLKHQRE LEKMKIDEDW DHSHQSKEQI   240
EANLMMKQEA ALRRERALAY AFSHQWRNSG RTITPTFTEP GNPNWGWSWM ERWMTARPWE   300
SRLAAASDKD PKERAVTKNA STSAVRVPVS RAISIQRPAT PNKSSRPPSR QSLSTPPPSKT  360
PSASGKARPA SPRNSWLYKE DDLRSITSIR SERPRRQSTG GGSVRDDTSL TSTPPLPSYM   420
QSTESARAKS RYRSLLLTEK LEVPERAPLA HSVVKKRLSF PVVEKPSVVP TEKPRERVRR   480
HSDPPKVDPA TLKDAPAA                                                498

SEQ ID NO: 253            moltype = DNA  length = 1836
```

| FEATURE | Location/Qualifiers |
|---|---|
| misc_feature | 1..1836 |
| | note = Ceres Promoter p530c10 |
| source | 1..1836 |
| | mol_type = unassigned DNA |
| | organism = Oryza sativa |

SEQUENCE: 253

```
gcctctcgac cacgagttta gcacttgtgc aacatatatg cgtgcgatga acatctactg    60
atgcgccatg cgaattttag cgttcgttca tgacgcttcc aacggcacag aggctgagca   120
gcagcatgca tgcatggctc ttgtgaaaac aaaaaaggtt actgctaaat gacatgctgc   180
tgtagctagc tagcagaatg caaggcccat gcatatgcaa tgctatgcga caagtacagt   240
accagcatgt atggtagcca gctaactaat ctatcagcag aggcagcaag ctcgtgcatg   300
gtgtgatgca cttctctcca gtaatctagt ggtaattttc acccaaagcg ttgctcatat   360
ggacagtaat tagtaatatt accaaggttc acaatcccgt tacctgacca aatactactc   420
acgaatggta tctctggttt tcgttaaaac cgttggtaaa ccagcaaaaa tagacaaaat   480
ttgtcaaaat tttaaatttt agttttttt ttaacttaa gccgggaaac cttgaagttt    540
gtgctgtcga gctgtcctgg gaaggacggt tttggttggg attgtgaacc ctggttactg   600
cacttcattt ttgaacagat attagtgcaa cagacaaatg ccaacgcatt tttttctgtt   660
taccggcaag ctgaagcttt tacgatcccc atacagccgt tgctgcaaac ctgccaagaa   720
agagcagcag aaacaggtgt cattttgtgg tggaaagcca agtaaagtaa acagaagatg   780
gaagatagta aggaccaggg agtgaggcag gggacacatg gcccacgcct ccctgcacat   840
tttcgtgtat aaatacaggt ggatgcatcg ctctcccagc atccatcggt tctctgctct   900
gttcatccat agagtttcct cctcttctcc tttagtgcaa ggtagagaag agcatgctgtg   960
tgtgtgtgtg tgtgtgaact gtgaagtgca gagtgcttct gtagttctgt gttatgtcca  1020
tagtgatctt gttaggattg ttgctatgga tgcatgatgt tatggttgat ctctgaatta  1080
cagtagggac ttttctgaga tctctggatt agtgggggat gctaaatttt tttctggttg  1140
catcagcttg ggtttctggt attggtgtgg gttcttgctc tgaattttgg ttcagaatgt  1200
cgatttgttt gtgtttgttc tctgaagttg agagtagcta tgatccatcc agcacagaac  1260
tgcaggtcct gcctgccggc tgcatataca ggacatgcca ttttgcaagc ctgggctta   1320
tggttttctct tttggagttc ttcttcttgc atgatctgtg ttctctaaca aaggaagcaa  1380
gatttagcaa cttttattcag agacaagaaa aggatctggc aaccttttgt ttctgtttta  1440
tcctactcgt aaagattgtt atttaagcaa aaatttccca aaagtttaa atataatttc   1500
catgatgtgc cactctcatg tccttgaacc tggcactcat tatgggctcc tcagaagtgc  1560
tgtagctaat gtcactaatc ttttgtatct ttgttcatag tcttgtattt tatgatgctt  1620
atccctttgt gctttccatg tttgatgtcc aaatgtcatg gcaatgtttt tgacttctag  1680
taggggtttt agtaccttt tgttagataa gtacatccaa attcgtttta tttattcaaa   1740
aatcattctg tttattcact gaaaacattt gtccattcaa tggactcata aactgtctgt  1800
gtttttcagg cttgaggatc catctagaag atagca                            1836
```

| SEQ ID NO: 254 | moltype = DNA  length = 3000 |
|---|---|
| FEATURE | Location/Qualifiers |
| misc_feature | 1..3000 |
| | note = Ceres Promoter pOsFIE2-2 |
| source | 1..3000 |
| | mol_type = unassigned DNA |
| | organism = Oryza sativa |

SEQUENCE: 254

```
gcttaacaca tgaactacca aaatatactg atcactttgt tctagtcata catacccttaa   60
gtcattttat tctgcagtgt ttggattgga gggagcattc tagcatccct tgggtcgttc   120
cagcaaatgt ggttctccaa agcagagtaa gcacaacaca gtattttagg ttatgtttcc   180
cctatctcgt cacggacagc tcacaagtta atgtgattta tctcactata gatacgagtt   240
acatggagta tcctcatcc aaaggaagtg cccatgaagt tgtggagcat cgctacgatt    300
tgtgaccaaa tttgggtgca tgtgggcaat cgtattacag ccaccctgtt gttgatctat   360
atcgactatt atccgacgat atttatcatt atattatgac tagttagttt gtagattttg   420
agagggcaac ataagaagca atccagctta acctgttatg ttcttgatgg tagattctag   480
ttcatgtgtt gaatctgttc tccctgctgt agaatgtatc gagttgctgc tctctactct   540
gtacttttag aatacctttt caatcatttg gagtcagctg attgttgtac tacttatacg   600
ccacctgatt agtcatgtca acaattaaac ttgagcactg gttaagttaa gagtggcctg   660
attgtagttg ataatcacat tttattcgta gacattgtat gctggatctt tatcagccac   720
cgtcagatca tcctctgtaa taaatcttca tcagacgtgt gtgccaatcg caaggaacac   780
gaaatgcatc cgaaatgtta ctctgagtta atcaatacta taattcttgg tcaaattaat   840
tatttatatc tataaagttt aaattaaatt taggaaaatg aattcatgca aatcttgtgg   900
taagttgtca atttcataaa aaatccagct tactactccc ttttaggag tgtgttgtgg    960
ctgcacactt ctgcctttg atatatacgg ttctattca tggtgactcc tttattatta   1020
ttaaaacaat cccagttact tggtaagtgc taatcacgaa tcaaagtcaa cataacaaat  1080
catgtgcgta cagctataac tcgattacac aaacaacaaa attcatattt gaacataaat  1140
ccagttgtag catatctggt agtataaagt ttttttttg tatagaagag ttttaatttc   1200
tgtaagtttt ggaaagcatt taatcctaga aattgtagtg tagctcaact aaaaaataaa  1260
tgaacttgaa tcgaaattgg gttgtatcat aaatctttac cactcaaacg aatattatc   1320
ctaaaccaca aatgactctt tcatcaagg aatgttttgt tttcagcatt ttaaaaaaa    1380
acttttctaa tatggttttc atgtttcgtt cttttgaaat ttaacatcta tttaatttgc  1440
acggctccat aaattcaacg gatacatatt ctgaataatt actaaggagg catatatcgg  1500
ctctcttaat acaaccgctt gtttctcaaa atttattttg agttttgtct acacattctc  1560
aaggacggta caaacacact atagatgttc acaattttt tttctaaag ttgattgatg    1620
gacaaatgtt tgaacatata aacatataag cactgaatat ttgcttatgc aggaggtatt  1680
tatatcaagt tcgatacttt actaccatag tccctaggac actaaatgc cttcaatgat    1740
ctgatgaagc ctaagagaga atattgatca gtggagcgac ttgcaactac acatggcaca  1800
agtagactag acacggtata tattcatatt aacttgttaa aatttactta cttaacagtt  1860
cacttgtggt gcatccatat caattcttac ttacacaata tttgtaaaaa caacctaaca  1920
```

```
ctataggatg acctagacaa cctttatgtc aatcacactt agaagatgat cgtcttttta  1980
ataaataatg tgtactacac accatgctct ccatatagat caagatctac aaacccttcc  2040
acttataaac cttaccacca aaaactcatt aagttgcttc atttatctat gctattaaga  2100
aaaaaactta tttcgtttat gccatttcta gaaatggcta gtcacactat tcacaatatt  2160
atataataaa taaaagtttc aaatattcat ccaccaaaaa tcatcaagtc gtgggactta  2220
tatgttaatt agagaagtcc ctttgggtgc aatcgatttt ggaaaccctc aattttttct  2280
atacatagaa gagagagatg tctagttgca attgcttttg cgatgtgcca accacccttc  2340
tagctttcat ccacgtctac ttaattgcca ttcttcttct tctttttctt cactattact  2400
acctcctatc ttagcgaatc ttcttcttct tcactattac tacctcccac cttagtgaat  2460
tcatcctcat tgttcacaat gacattgcta agttaactag gtatgctaag tacacaatta  2520
gaatataacc tagagccttt gtttccatca tacttaaaag atgacatttt tatatagata  2580
aagtgtgcta ctcacaaggc ttactatata tatgtatgat acacacaaac tccacaaccc  2640
aaaactcttt caagttgtgt ggcccatcta tgctattaaa aagccattt  agcccatcca  2700
acatgagaaa ccctagggtt ttttccctat aaaagatacc taggttattg ttgcttttcc  2760
accccgcccg ccgccgctcc ctattcctat ttaatcccat ctctcttcct catcaccgct  2820
ctcctctctc caggcaagag gtacgcactt tttgttcgg  atttgaaatc tttgcttcgt  2880
tttactatca ttggtcataa gttctttttt gaagatgttt gagaataagt ttatcattga  2940
gattatcgtc acttgtgata ggaagtacgc aacctcaagc cggacaagac gtgagcaaag  3000

SEQ ID NO: 255       moltype = DNA   length = 2023
FEATURE              Location/Qualifiers
misc_feature         1..2023
                     note = Ceres Promoter pOsMEA
source               1..2023
                     mol_type = unassigned DNA
                     organism = Oryza sativa
SEQUENCE: 255
gagagcagaa catagtagcc gctgttttct gggggtgcaa tttgtgcaag atcgctatcc   60
ttatggacca tgcaagcacc aagcaatatt aagccaggtc caacagcggt cttggggaat  120
tcagaaatga gcttaaaaac ctccttgagc tggccagctc agccaaggag gtccatcatg  180
catgtgcatg ctcaatactt ggaattattg caaaatgatc ggtcattgac tggaagactt  240
tgcgccctcc ctcagccaac cttatgtggc tgcatgcata gagtaccaac aggaaggtag  300
cgtttgttgg aataaggttt gcatccagca tgtccttgta gagcttcaaa gcctcagcac  360
cttggcccat gaaggccata tccagctaat tgcattccat gagaccacat tcttgctatc  420
catactgttg aagtgaagat gctccgagct tcggaaatgc ttccacacta tgcatacatg  480
tcaatgagca ctgtcatgac ataaacattg ggcccaagt  cctcctcagc gataatccta  540
tgcagccact ttcccaggga caaagctcca agctgtgcac acgctgaaag agagctagaa  600
atgatgattg gatttggtca cacgctaagt accagtcattt gctcaaagag ggcaattgcc  660
atctccgtcc agccattcta ggcatccct  ggtattattg ctttccatga ttccgattcc  720
gtggtcttct atggcatcgc attgaaggcc ttccttgcag actccatatc atttaaccta  780
cagtacaata tggtaattgc tgtcgacact ggagaattcg cagtaaatcc agacttgaga  840
ggaccatgta agcattgatc aagcagttca ttcccaaaca gactatacgg gatcagtgcc  900
agtgctcgag tttggcttca attccaaggc catcaaccca ataaacagat taactgatga  960
accaaccatg caattcgccg agcaaacata gattaagcat tgtaggcaac caaatctgga 1020
ttctccatca agtcaaagag acgccatgca gaattccaca tccccgctgt atacaccgag 1080
atcaaccggt cagaacatgc tcatactccg ccaaccctct cttcagaaca tgctcatact 1140
ccgccaaccc tctcttcttct gcaagaggca tcctccccaa ttccccattg ttatatctgt 1200
tgctggtaag accgttgcca gcgtggttgt gtcagaccga acagactctg cactcgccat 1260
cctcacgaac gactccaggg cctccgaacc aggaagcccg gccggccatc agcgtgttcc 1320
acataacggt atccggcgac tgcacagtgt cgaacacctt gcgtgcgtgg tcacctctgg 1380
acagcatgaa gcgtacaggc tacagcttgg ccaatgcgga cgccacgaac gtgtcggcgg 1440
cgtaacccgc gcgtgcagcg cgccgcgcgc gggctgcgga gtcggttgga gacgacacgc 1500
cgccgccatg agagcaatga gcgaggtggc ggcgaaggcg aaggagaagt agtcgaggca 1560
agcggaagag aaggcggcag cggagaaagc gatcggggcg gcgaggagg  tgggtgggag 1620
ggagggacgc gtagcggagg tcggagggagg agggagctga ggtttccggg gcgggggtcg 1680
agagggtagt gtacggaggc gagggacacg gcgaggatct ggtcgaggta gcgcagtgtg 1740
aaggaaagcg cgatgaggcg gagggcgccg cgaagagcg  gcgcggcgga tagcgggagg 1800
aggcggcgcc ggcggggtct catccgattg gaaacagatt gggaagggg  aggggtagg  1860
aatacgtggc gtcggcagta ttaggtagag agagaaaccc tttccatcct ttgtctctta 1920
gccccgaagg agagagaaaa atcagaaaaa aaaaacccc  gccgtgtggg ggaagcagag 1980
ctccggacgc tggcgccgct cgcgccaccg cacccgcacc gcc                   2023

SEQ ID NO: 256       moltype = DNA   length = 2034
FEATURE              Location/Qualifiers
misc_feature         1..2034
                     note = Ceres Promoter pOsYp102
source               1..2034
                     mol_type = unassigned DNA
                     organism = Oryza sativa
SEQUENCE: 256
gaacgaccca aacgcgtaaa tgtggtact  ggtttccctg ctttgccgag taccagcagc   60
cacgaagaac gttacacaat cgagtacaaa atctataaga gcaagtttaa tagcatagcc  120
aaatactacc tctaaatcat ctatagccaa tttaatagtt catttattca ataatttactt 180
ataaacatat actacaatca ttaatatatg gtcttacttc ttatacacat aatattttgg  240
agtccgtgtt acagctggct ataaatataa gggattttgg ttggatgtgg tacatcctat  300
tataatgaat ctagacatga aacctgtcca aattcatcgt gctaggatac gccacatcta  360
accaaaatct cttatcttta gggatggaga gagtaataat taaatgaagc taggtagagt  420
ttccggtca  atacgcttgc gtgtgcttat aagagcatgg ccaacagttt cccgatactc  480
ttcccaatat cagttttgag gagttttgtt ggaaaaaatc gctccaacag tagacctaaa  540
```

```
tcacccctaa aagcttggcg tttccaaacc cgcatatttc gttctccact tgtagggaag    600
agactcggcg cccaatcctt caaccgcatg cacttcgcgc gcgctgtgtg aaaattttcc    660
taccaggttc ttctttgtgc gttcgtctac ctgtgagtca atccatcacg ccagcagcct    720
catcttcccc gcagctgtct gggaaagcag ccatggctcc cccaagcttc cccagcgtcg    780
acatttttt ctcagcggca gcgccagacc catctccaac ccaattgggc ggaccttcgt    840
cggcgctccc ccagcaccac caccgactcg aatcggccgt cgcccctatt catctccaat    900
cgtccctcga ccctaccgca tcctgcagca cagcctgtct ctcgcgtcag actggcgctg    960
cgctccccc ggtaatgtgc aggcgacaaa ggccccatgc gatgcgacca gcagccggcg   1020
acaaccggag gtgcccagtc gctggccttc atcgaatcat cgtgcacctc ggtcggagtc   1080
gatttctgat tgttgctgct gctcaaatct ggagcttgct attgctgaga actgcttggt   1140
ggtggtactg gaaatttgtt gtttgctggc tgatgaaaac tgttgttctt tgctgctaaa   1200
aactgctgct tgctagtact gaaaagtact attgcagctg ctgaaatatc ttgctgcttg   1260
ctgctgaaaa cttcaagttg ttaacaccgt tcacactaaa aaagctgaaa tttttttct    1320
gggctgaaaa ccccattgtt gatgattgca gaaccaatat ttttccatgt aaaatacagg   1380
agatcgtggt aataatcaag tgaaatatca ttttggggca aatactcaga tcgtacctga   1440
agccaatgga aacattgttc aatgcttaaa ctgtcagtta tgatgtcaaa gagattgatc   1500
actgaatgtc ctgaaaggag ccgtgaggag gatgcagcat tgcagcgtgc gcgagcgtga   1560
gtgggaggaa ggaatgacga ttctgttggt agttgtcgat gtggcctact tttttgtttt   1620
tgaggattaa atttgggaa tctcttggag ataaaaggta ttctcatacc ttaaatcctt    1680
tttagagatc taaaaaaaat gatttagggg attgaatttt gggtggctgt tggtgatgct   1740
ctaagttgca catcctgggg aaaaacctcc ctaatccatc agcaaaccga tcaaccaccc   1800
acgacaagtc gacgccaccg tttttttttt ctccctccta agtcctaacc ccacaaaaat   1860
cccgcgaact ttcgtctcac cacgcgccgc gtgcccccta caaataccaa acaacaccca   1920
ccacgtccac tcacaaacca cgcaggaaac ctcagaaaat caccgtacgc gacgcgggcc   1980
caagaaaacc ccgacagaaa ccgcgcagca gcaacaccac caccggcgtc ggag         2034

SEQ ID NO: 257          moltype = DNA  length = 1877
FEATURE                 Location/Qualifiers
misc_feature            1..1877
                        note = Ceres Promoter pOsYp285
source                  1..1877
                        mol_type = unassigned DNA
                        organism = Oryza sativa
SEQUENCE: 257
ggcccgagtt aaacgatctt ccacgtgtca gcgaatccta gtcgttcgat gaatctgaat     60
ctgacttgtg gtggttggac ggccacgtgt taaaaaggg aaacgtccgc atcacccgat    120
gctgggacat ttgcaatttc gatccagctg tagattgacc agttgttact ctcttttttt   180
taacaccata caaacgtaat actccctctg tcccaaaata taagtatttt ttttaacctc   240
ggttcagtct tcgaggtgct acttttgacca ataatattta taaaaataag atgttttaaa   300
taaagagagt tgcatatat gatagctcgt ttaatgataa acaaagtacc atcaaattta    360
catgattaat ctttttaatt tatttgctat taatagttaa aatttaaaaa gtttgacttc    420
acactgttct aaaaatactt atatttggg acggagggag tacacattag agcaggtaca    480
atagcagact agtagccagc tataaacata ttttaatgag ataaagatg agagagaaca    540
gcgggctaca gatctgtagc cagctgcagc acggactcca agacattgtg tgtgtatgac   600
aggtgggacc atatattaat agtacagtaa gtaactattg tatgaattgg ctattagatt   660
agctataggt gaattgtagc tagtagtggg ctatactatt gaacttactc ttatatctct   720
caatatctcc agaaaactag gacgatatat attgatata acaaagtcat catagatatc    780
tcgctatcga catatatatt acctatcact gaaaaaataa ttaatcataa atgcaagcac    840
atatactacg ttcaacactg aatgtaggta gattggtaga cgggttccac cgcaagaaaa    900
gcattgcacc agtgaagaaa gaaacatcgg aatttgtatg tagtttgttg tttgatgaat    960
tcttttgatt aaaaaaaact aaaatcagag ttgattcagt taatggtgtt gcctacgata   1020
tacttccata tcatgatatc actgtagact atgaatcata tctttaatta aaactaaatc   1080
aagaaattaa gtatgagacc tcaactcaat gaagaatttc tagttgaaaa acattcctag   1140
tgtgcgttcg gatggaggta gggatcttct ctccgttcat ataaaccgg atggttcatt    1200
agaacatgat taattaagca acagttaatc taaaaataaa ttaatatttt ttaagaaatt   1260
tttgtataga gatcttttga aaaaaataca ttggttagaa agcatactaa taaaagaga    1320
aaaataagaa catagtacta tagtagaaaa tgagaacttg gagtatttga gaggatggga   1380
aataagaaga ttaagaagat gcgtaaagtg aacggttaac gcatgattga ttaattaaat   1440
attaattatt ttaaatttgg aaaataaatt agtatgattt ttaagcaaca tatatatata   1500
tatatatata tatatagaaa aacatagttt tagaaaatat aagcgtgtaa aacgatatgc   1560
aggaacgaaa cgttgagcat tcaaaatttc aaattgaaca tatgaatcaa gagagaataa   1620
aaaaagaggc cttctaggct ggcatggaca attggacatg ttttcaacta gggtttcaag   1680
cttcgagcat ccacttttgt ccttgcaaac tttatacgag aaggcccgtg aatctagccc   1740
cccacaccac cccacccgcc cgccgccgcg ggcgccctcg cctcccctcc cttctcctcc   1800
tctccgcccc cgccgccagg ccgtccacct ccgccgtctc ctccccatt cgcacccaag    1860
gcgctggcgc ggaaggc                                                 1877

SEQ ID NO: 258          moltype = DNA  length = 1000
FEATURE                 Location/Qualifiers
misc_feature            1..1000
                        note = Ceres Promoter PT0565
source                  1..1000
                        mol_type = unassigned DNA
                        organism = Arabidopsis thaliana
SEQUENCE: 258
caccaaatat agtgttattt caatactaaa atggtgttat ggttggagat gccctaaaga     60
taaacatgac gagacacgag atttattaat ttccttgatca accataactt aataacttaa   120
tattaatttc acttaataat ttccaattaa gtgaatcttc acttccaccaa aagttcctaa   180
cgaactctta ttttctagca tcaatattac catgaactag catcaatact atcatgaaaa   240
```

```
attcctactt cctatccaac tcttaataac aatgctagtc ttaacaatat tcatcaaaaa    300
cttgatatag accttctaac ttagccacga ctagtatcgg tgaataccaa aattaatgta    360
ttcatgagaa cttgagattt ctctaatgta ttccttgttac taaacaagta acaacactca   420
agaaatatca tgatcaaata ttttactcat aaactccata tttcacattt tgaaaatttt    480
aaacagcaaa tcacattgaa ttttcgtggt aaaagtattt aaaattgaaa aatagcagct    540
cctgatttca atgtataaat ttatctttat atggtttatg tctccaactt attttaaaaa    600
agagagaaag agcacccaaa aggtgaccgt tgaaattcg aatttatttc cgtttgaaat     660
tcgaattcaa aaaagtaaa ccgaaccgag tctcgttact gactgtcaca cattgtttcc    720
ctaaaagcta attaacccat acgtggcgta atataacagg tcagtgatca atactaaata   780
acagacatac acctttaaaa ttcgtgcacg ctccaaaaca aaatctacac ttcaaaatca   840
acggtcacga tcattcctca aatttcaaaa aattatttaa cctcacttcc ttcgctttgt   900
ttttaaaacc tctctctctt tctctttctc tttcgccatt aaaactctgt ttcctttttc   960
agagattctc agagaagatt catttttaccc taagaaaaaa                        1000

SEQ ID NO: 259          moltype = DNA  length = 999
FEATURE                 Location/Qualifiers
misc_feature            1..999
                        note = Ceres Promoter YP0015
source                  1..999
                        mol_type = unassigned DNA
                        organism = Arabidopsis thaliana
SEQUENCE: 259
ttgagcctta ttgttgttat tgactttag ccaatagaaa gagatggaaa ttcaataatt      60
atccacaaaa ttccaaatca ttggtgtaca aaaagatcta aggctgttat attttcaaaa   120
aagaaagaaa agaaatgcaa caaatatgga ttaaactgtg gtttgtaaat tgagctttgc   180
atgaaaactt tatcactatg atttcactac tccatattta ttgactaaag tggcactaat    240
gaatttctta atcatgaaat cttgtatcaa aaagtactaa aataaacatg acattggcaa    300
ttaggaaaat tctaaattag aaattagtaa aaatgaaagg tgaaagggaa agatgatgat   360
atgaattggt tggtgaccag gagaaatgta tcccgatttt tgcagacact ttcagtgtcc    420
ccattcatat aattatggcc cacctcgtta agatttttca ttcaccacca taacaagatc    480
taagcttaga tttcatgtaa ttaaacatat aatatacttg ccaatactat ctaataaagt    540
atacttaagc aaaaattatt actctagtgt aaggcgatga aatataagtt tagttgaaaa    600
tttatgtcga tataacaaag tataatgaat taagaccttg gttttcgatt aacaaactaa    660
ttaaacacta gttttgccta caaaaaccgg gaatcgtatt caaaaccgaa cgacaaaaca    720
agggacaagt tgagagacaa aaccaaatca gcatctttct tccagaaatg tcatgaccac    780
atgacgtcat cttgacccct cttcattgtg atatctgtgg ataaagcgca cgtgtttaat    840
tcacgaacct tcgtagtaac gaaaaatcca caactttcat atttttttaat tacccactaa    900
actaaaacaa atttggaaaa acatgaaaaa cttttctttt ttttccaggt tcgtgaacct    960
cgtaccctct atataaacct cttaaccacc ttccacata                          999

SEQ ID NO: 260          moltype = DNA  length = 999
FEATURE                 Location/Qualifiers
misc_feature            1..999
                        note = Ceres Promoter YP0087
source                  1..999
                        mol_type = unassigned DNA
                        organism = Arabidopsis thaliana
SEQUENCE: 260
tgaattgagt aaaatgtgtt ttcaaacagt taggtggtag aaggtaaagg taataacatc     60
atgatcttac taaaagaatt gttgcatact aactatcaat attctcaaca acataatata    120
atgttttttt aggtaatttt ccattttaat tttttgtgat taaacaatta aacaactcga    180
atgatgatga taaaaaaaaa aaattaacaa ctcgaataag ttaaagtagc aatacacatg    240
tcgttcaatt caaccaataa agtaagactt atattttaa gaagttgact aatagcttaa     300
taagttggaa aacttgtgta gtttcttaat tcccacgtgc agtaagaaat aaaaatgaaa    360
aaaattatta tatccttccc actctgcgac ttttctttta ttttatcaaa tattaaaaag    420
attcatatca cagtttacac attgaaatca taaacgataa ttatgtattt tgtaataaaa    480
agttagttct gaagctcata ctttggatag tcgctagtcg ctaatatgct ccttgtaata    540
attaaagtca ctacgacgca cgtcaaagcc gatatttagg gcttaattga tgcgtgtttt    600
tcttttcata taatagtaat ataaattagt actaataaag tatgatggat ggttgagaca    660
gaaaagaaaa aagatgactg tatggtcatc attacaaaga agaatgtatt cttcatgttc    720
ttaagaataa taaaatgtca cttgtaaatc aagttggtaa gcatttttag aacttttgttc    780
gatgcaacgt atgatgattt atgtagacaa aagataaaac cgtatcttca actattgcca    840
agaaaagata aaacctaatc tagtcagtct ctcaacataa atacaaccca atagccaaac    900
tgtgtccaat tcgagagaaa actaaactaa aacaaaacac aaaagcccaa cataagccca    960
ataaaaaccca ttttataaac agaacattac taacactca                         999

SEQ ID NO: 261          moltype = DNA  length = 1000
FEATURE                 Location/Qualifiers
misc_feature            1..1000
                        note = Ceres Promoter YP0093
source                  1..1000
                        mol_type = unassigned DNA
                        organism = Arabidopsis thaliana
SEQUENCE: 261
atgatgaaca ttctacatat ataattatta tgtttaagca cttagacagc ataaattctt     60
tctaattata taaatctaac cttgttacat tgtacatcta taaattactt gaagaaataa    120
cgagttctat ttctttttaa aaattaaaaa tactatacca tatctcagtg attaagttga    180
accaaaaggt acgagggaga aacaagcatt tgattcttcc ttatttttat ttattcatct    240
ctcactaatg atggtggaga aaaaaagaaa atacctaaca aacaaatata tattgtcata    300
```

```
caaaaatatt tctatatttt tagttaatta gtttatattc ctcacttttc agggcttata    360
taagaaagtg agcaaacaca aatcaaaatg cagcagcaaa tactatcatc acccatctcc    420
ttagttctat tttataattc ctcttctttt tgttcatagc tttgtaatta tagtcttatt    480
tctctttaag gctcaataag aggaggtact attactacac ttctctctac ttttacttgt    540
attttagcat taaaatccta aaatccgttt taaattcaaa aataaactta gagatgttta    600
atctcgattc ggttttttcgg ctttaggaga ataattatat gaaattagta tggatatctt    660
tactagtttc cattcaaatg attctgattt caatctaata ctctcactct ttaattaaac    720
tatatgtagt gtaatttcac actgttaaat ttctaccatg tcatgtatat tagagttgca    780
tagaaaattg taaaacatcc atttgaattc gaatgaaaca aaatgttttta aaataaaatt    840
ttggtttta aaagaaaaat ctaaaactga attatatcgt ttaaccaagt tgtaaaagtc    900
ataaaacgta gtatccttgta aatcgctctt ccacggtcca aatagacttc tagtaataaa    960
caagtaaaac taattttggt ttcttactaa ttttcacaga                          1000

SEQ ID NO: 262         moltype = DNA   length = 999
FEATURE                Location/Qualifiers
misc_feature           1..999
                       note = Ceres Promoter YP0108
source                 1..999
                       mol_type = unassigned DNA
                       organism = Arabidopsis thaliana
SEQUENCE: 262
ttagctgaac caggaaattg atctctctata ccagtttccg ggtttagatt ggtttgatgg     60
cgatttgatt aaaccccccga aattttatgt cgtagttgtg catagtatta ttattctttg    120
cggacaatag acgtatcggg accaagttct gtagcaaaat tgtataagct taagtttgat    180
gaaatttaaa ggtaatcact aaaacccaaa tgggacaata aaccggtgaa gatttagagt    240
ttttaatttt gactcatgaa tctggagaaa gagccctcgt taaaaggagt gaatcaatcc    300
ataggggaaa aagttttgtc tttttaaaaa ctaaagaacc aaaccttaat agaagcagct    360
caatgtgtga caacttttcca ctggcactaa gataaagtga ctagcgatga gtgcaattat    420
tgaaatagta gatggtaaat attacataca agagtaaaaa tatctttatg tcaatgctta    480
attcagtgtt tctggttaac aagagaaact tctctaactt tcgtaattgg tgtcttataaa    540
attttatgca attatgattt tacccttta ctacttttca ttagctttca cgaatctatt    600
ttgacaagag aaatcattag aggtaaacat gcttttttggt caagggcctt aacagttcca    660
ccaatcaagc tcaaaagttg tacttaaccg acatcttctg tgaaaacata taattacatg    720
tacaaatcaa aactacctta tgaaataaat agaaatattg cagttcattt ctaattttaac    780
ctcttcaact tttaaaacta tttacatttg tttatgtcat ttctagtcat tttgatgcaa    840
attgtaccat ttatggatta tcttcacaaa tttttaagtt ggtgaaaact ttttggtggg    900
tagttaaaac ttgaaataga aatttacttt accaaaataa actaatgaaa agtaatcact    960
ccactcccta taataagatt tccaacgttc ccactaagc                            999

SEQ ID NO: 263         moltype = DNA   length = 999
FEATURE                Location/Qualifiers
misc_feature           1..999
                       note = Ceres Promoter YP0022
source                 1..999
                       mol_type = unassigned DNA
                       organism = Arabidopsis thaliana
SEQUENCE: 263
tagttccatt acaatttcca aatgattgt tacaaagcta caagattatt cgaaatagga     60
tttcatccat aagagagaat ggtgtggtcg acgctacaat gttgatttat tggttgtggt    120
ttgcatcttg gggatgtcaa atcctaagtt tcaagttctt gtaaaaacgt tttcaggttt    180
ctttaatata ttttaatatt aatgtaaaaa gaaaagatat agcttttgta caaaaaatt    240
tgtttaatca ctatgtagga ggatgcgatc aaattcatgg aatgatgtat tattagcttt    300
tctatcctca ctctaaaaac aatactatag tgagttaaat aatttgatca tttcaatgta    360
gattaaaatt ttattaaaag aagaaaaatt taaaagccta taacaaaata aaaaaggagg    420
ctcgaggtat gatgggtgta gcagaagagc tggcaacagc tatcgactga gtgattacga    480
actcagtact cagtgttctc agctcacaca ctctttttt gttctctttc ttttggacag    540
ctttcatttt ctcttttctt tttctattt tgttcaaaa ttccatccat attaaaatag    600
gcctgatcat gagaataaag gaaatactaa tgatgagttt ctcaataatg caataagatg    660
caattattat gagctattta ctattgaaaa tgagcaaata aatgtcaaaa cacaatctgg    720
ttaagttaga gcaactccat tgtataggat tcatgtagtt tctaagaaaa caaaatgtat    780
taatatttta cttttacatc caaaaaacca acttatatga gtaatagaaa cgatcctaat    840
attaggaatt ttagagattt tctctcatct gtttcttaac ttttcaatat ttttattttt    900
taaaattgta tgagttccta ctaagaaact actgctggag ttggtcttag cttcccaatg    960
cttctccacc tatatatatg catatctcct tcttaaaac                            999

SEQ ID NO: 264         moltype = DNA   length = 999
FEATURE                Location/Qualifiers
misc_feature           1..999
                       note = Ceres Promoter YP0080
source                 1..999
                       mol_type = unassigned DNA
                       organism = Arabidopsis thaliana
SEQUENCE: 264
aagcggcaat ttagtaagaa gtactcaaag tatcatttac caaaagtata tggttttggg     60
aagagttgtt agggatgtat tctttctaaa cagatgatat gacgatgttc ttgaaaacta    120
atgttaaaga cggaatctct ggcatccttca ctcgggagat atattaaacc gttgattgta    180
gttagccatg tacttagctt agtgcacaaa taatctgctg caagaaatct ttttctatta    240
taatatctct catttaaaca ttagaacata ttgtttaact tgtcttccta gaaataaaac    300
tgctaatttc ttatggtaaa ctattttcct ttagattgca caatcgaact cgaaaatcta    360
```

```
gtggagacta tgtgactatg tttatatata tgaaacctaa atcaaattat cccaataatt   420
gggagacaca aaagaaaaat tacgaaagaa aacaggaaat caaatcaaaa gataaagaga   480
aggtaaaaaa aggcaagaag cactaatgtt taatatttat agttttctcc attaaagaaa   540
aagcgatgat gtgtgttctc atcttttgtg aaagtatata tattgctttt gcttttctca   600
aaagcaaaag actcatccaa caagaacaaa aaaaaaaact aaagctcaat ccaaaagacg   660
aagaatgcat tggatactac aacttctttt tcacttttct ttcaaattta caattatgat   720
tttcacaata cagtttattc aaaaataaat aaaaaaacga ggcatgaaaa taatgattat   780
cctcttcact tattaagcca ctcactataa gcagagcaac tccagaacat agtgagcccc   840
caaaacatta aagcatgatg atgtctaatg atgatgatct cttcgttcc atttctctaa    900
atttttggga tttctgcgaa gacccttctt ctctttctct tctctgaact tcaagattcg   960
tgtcggacaa attttttgttt ttatttttct gatgttaca                         999
```

```
SEQ ID NO: 265            moltype = DNA   length = 3000
FEATURE                   Location/Qualifiers
misc_feature              1..3000
                          note = Ceres Promoter PR0924
source                    1..3000
                          mol_type = unassigned DNA
                          organism = Arabidopsis thaliana
SEQUENCE: 265
atctataacg agtaacatg ttgccagttt gaatcaagaa gcttggatga tgaatgaatg     60
gatcggtttg tggtacaatt cttaaaattg tagtagagga gacagagaaa aaacatgata   120
agactttggt atttacaact tgacggagac aagacagtaa gccaaatctg tcacaaaaac   180
actcaaactc ttttctcagt gttttgagtt taaagagaga cttattcact tccccttcg    240
taacacttat ttgtctccca accaaacagt ttctgtcctt tcccttgtcc tcccacgtgc   300
atctttatat ctcatgaact ttcgtttcta gatcttgaat aatgtcttag tggattaggt   360
ttgttgtcgg taaattaggt gaccgttttt ttcttatatt tggaagatcg cgggatgaag   420
cagatactga gtttcagggc atacacacct aatttgaaaa tcattgttag tccaatttca   480
cttttaatctt gtttacaaaa aaattgatct gaaaatgttg atgggataag taaaaatgta   540
agttttgcta gtagtcatga tataataata gcaaaaccag atcaatttg agcaaaagga    600
agaaacaaaa aacagatcga tcccacgagc aagactaagt gtaaagtggt tcccacaaga   660
gccatatgga tatggtcctt caacttttaa agcccattac ttcagtggtc gacccgacat    720
tacgccacga gtagtcacgc acgcacgact ccgttcacgt gacattcacg ttgatattc    780
cccctctact ctcttctgct tggttgatct aaaaaacatg aagagaccaa cctaatttca   840
tattaatata tgatatagac ttcatactca acagtcactt tcgtaatcca aatccatatc   900
ttacgaaatt agttctttaat aaaggttgtg gattaagtta taatattgtg ttaagagtta   960
agacacagca tataaccttg taccaacagt gctttattct taaatggaaa caaaacatat  1020
gtcaatgtca agcatacagc taaaatatca ttatctaata ttaagagtaa aacaagataa  1080
ttaaaaattg aaacaacacc atatttttat agctttactt atcgtatttt tctagtcttc  1140
atggtaattg tgttgcttta ttttgtttat aaatgaattt ggttcgacca gatagtctaa  1200
tatcagtttt taaacactgg ttttaataaa atcatatgtc ggcaattcaa cctgttacgt  1260
tgtatgattg tatcctagtc aaatagggga ggaggtacta gtcgtttcaa ttagtttacg  1320
taatcaatcc aaagaaacta taagctataa agatcctcaa tttgttggtt acaataaaaa  1380
caacagttgt caaaatttat gtttataaaa agtaataact atgttcctc ccatatagag    1440
caaagtacct caggataggc aaaccgtact taatagccct tattcataat ttgatccaac  1500
tcttccccac aaaattgcaa ctgatgaagt caatacttgt atagtgagtc aagctataaa  1560
tgtctagtga tagttttgtc tcttaaaagg ttaacaaaag ttatgacaag ctgaaaaatc  1620
agagtttgct aggagtatta cttacagtta tcagtttaag tatcacatttt atagtattgt  1680
atacaatgat tcttaaattc cacctttttcc gtgcgaaacc aaattttcta ttggaaacat  1740
agaatgtaaa caaaaatatg ggacgttgtc cgttccaaca ttaaccaaac ttgtctatta  1800
ctaatattcg tgttggtttg atgttggatg tctaaattcg ttgaatcagt tgtctctgta  1860
cgaaatatgc atcttcttat ttcttagtat agatgcactt tatcattctt ttagtacatg  1920
cttaattttt tttttttaaaa tatgttgatt gtcatattgc caaagtatg aattaaagac    1980
gcacatctaa cacaagttag cagccgtaaa tccttccata aatttatttt gcaagttttg  2040
ctcattatat aatgagcgga atttatgata taatcgtttt taataatgtt atgttttgat  2100
caaaatttga aattaaaagt aggtgagaac ttgttataca gtgtagataa ggtggatctt  2160
gaatataaaa ataaaattta taagatgtat ttaaagcaga aaagcataaa actttagata  2220
aaataatgta aaaatgtgtt agcatcaatg ttgggatatt ggccgacccg aacttaatca  2280
atgtcggaag ccattacttc tctcccaaaa gaccttttc cttcggagaa ctaggaactt   2340
cctcactacc tttcgcttaa cgtgaaagcc ataaatttca tatattcata aaaatcagaa  2400
aatctaaaac tgtttagtat cacctgtttt tggtatagac tattggtttt gtgttacttc  2460
ctaaactata tgatttcgta cttcattgga tcttatagag atgaatattc gtaaaaagat  2520
aagttatctg gtgaaacgtt acttcagtca tgttgggtct agatttacat actactatga  2580
aacattttaa gataataatt atcctagcca actatatgtt ctatatatg ggccagaagcg   2640
atatagaact aaaagttcag aatttaacga tataaattac tagtatattc taatacttga  2700
atgattactg ttttagttgt ttagaataaa tagtagcgtg ttggttaaga taccatctat  2760
ccacatctat atttgtgtgg gttacataaa atgtacataa tattatatac atatatatgt  2820
atattttga taaagccata tattactcct tgacctctgc ccccatttcc ttttactata   2880
aataggaata ctcatgatcc tctaattcag caatcaacac aacgaacac aacctttcc    2940
aaagccaata ataaagaac aaaagcttt agtttcatca aagacgaagc tgccttagaa    3000
```

```
SEQ ID NO: 266            moltype = DNA   length = 1000
FEATURE                   Location/Qualifiers
misc_feature              1..1000
                          note = Ceres Promoter YP0388
source                    1..1000
                          mol_type = unassigned DNA
                          organism = Arabidopsis thaliana
SEQUENCE: 266
```

```
agaagtattc acgcaccaag gttatatttg tagtgacata ttctacaatt atcacatttt    60
tctcttatgt ttcgtagtcg cagatggtca atttttttcta taataatttg tccttgaaca   120
caccaaactt tagaaacgat gatatatacc gtattgtcac gctcacaatg aaacaaacgc   180
gatgaatcgt catcaccagc taaaagccta aacaccatc ttagttttca ctcagataaa    240
aagattattt gtttccaacc tttctattga attgattagc agtgatgacg taattagtga   300
tagtttatag taaaacaaat ggaagtggta ataaatttac acaacaaaat atggtaagaa   360
tctataaaat aagaggttaa gagatctcat gttatattaa atgattgaaa gaaaaacaaa   420
ctattggttg atttccatat gtaatagtaa gttgtgatga agtgatgac gtaattagtt    480
gtatttatag taaaacaaat taaaatggta aggtaaattt ccacaacaaa acttggtaaa   540
aatcttaaaa aaaaaaaaag aggtttagag atcgcatgcg tgtcatcaaa ggttcttttt   600
cactttaggt ctgagtagtg ttagactttg attggtgcac gtaagtgttt cgtatcgcga   660
tttaggagaa gtacgtttta cacgtggaca caatcaacgg tcaagatttc gtcgtccaga   720
tagaggagcg atacgtcacg ccattcaaca atctcctctt cttcattcct tcattttgat   780
tttgagtttt gatctgcccg ttcaaaagtc tcggtcatct gcccgtaaat ataaagatga   840
ttatatttat ttatatcttc tggtgaaaga agctaatata aagcttccat ggctaatctt   900
gtttaagctt ctcttcttct tctctctcct gtgtctcgtt cactagtttt ttttcgggggg  960
agagtgatgg agtgtgtttg ttgaatagtt ttgacgatca                        1000

SEQ ID NO: 267          moltype = DNA   length = 283
FEATURE                 Location/Qualifiers
misc_feature            1..283
                        note = Ceres Promoter PD0901
source                  1..283
                        mol_type = unassigned DNA
                        organism = Arabidopsis thaliana
SEQUENCE: 267
caaagtatttt gacaagccat atggttttgg atcaaaaagt cggtccaaaa ttaatgtttt    60
atgtgcaaga accgacccat tgtacacacg tgttaacatc ttcaagactt tcatctctat   120
ttttcttttg gtcattaaga tacccattga tccgaatctg ttacattccc acctacttt    180
ttaattttta ctatccactc caaattaaac acaaccgatg attttaataa ttggaagctt   240
tttaaaatat ttctccacgt gcctctttgt gtttgtctat ata                    283

SEQ ID NO: 268          moltype = DNA   length = 1000
FEATURE                 Location/Qualifiers
misc_feature            1..1000
                        note = Ceres Promoter PT0623
source                  1..1000
                        mol_type = unassigned DNA
                        organism = Arabidopsis thaliana
SEQUENCE: 268
aaagttattg acattttgaa aggaccgtaa atattaccaa aaaactgacg gagttaggat    60
cggccacgta gaaagggaca aagagagaac agtcacggac tcggccagac taagtatggg   120
cctgtctgaa tccaaactca gctaagttcc aaaagcataa agagagatgt gtaatgaaat   180
gaacgtattc tagaaacgaa agcaatgtta tgctttgttt ttgagccaca tgttttttggg  240
agatggagag aatctttttt acgttttttaa cctaacccac ttggcacttg gccaaaaaag   300
tgagaagaaa ctgtggcgaa tgagtaggcc acgccatgga ctttgttcct tgtccttcaa   360
aagttaaatt tatgttatgc gtggggacaa tctaagcaag gtggttcctt taaatatcgc   420
agcttcctct tttacacttt tggagcctac gtgttttgtt ttggaccggc caaatacacg   480
agtcagtcag tttagaaata atttggatgt ccaaaaatct tggagatcca aataaaataa   540
ttagcatgtt ttagttcata agaatatgaa atgtagataa actgtctata ttaatttttc   600
catagaattg gctttttatc gaggtgatgt acttaatgac tttgttgatt actactcgta   660
taacaataaa gaatatgata ctatgtgaga cttataatga atttggtgtg tgttaattaa   720
tccagttgaa acagtttaat aacaaatcag aataaaaatt gtagtaagaa aatttgaacg   780
ctgatccttc aacctagata gtgaaccttt caaatactat atgattcacg tgtaatgttt   840
ttgaccgttg gttattttg tgtgaactat attaacttat caatatcgaa aggctaaata   900
agtaaataac taaaagaaag ttcaggaaac aactcgacct aatgacctat catttctgat   960
cacccgtcct ataaatacat acgtaagatc attcgttact                        1000

SEQ ID NO: 269          moltype = DNA   length = 873
FEATURE                 Location/Qualifiers
misc_feature            1..873
                        note = Ceres CLONE ID no.565421
misc_feature            1..873
                        note = Encodes the peptide sequence at SEQ ID NO 270
source                  1..873
                        mol_type = unassigned DNA
                        organism = Glycine max
SEQUENCE: 269
tcaacataac tgttgttccc ttcttttgcac tgcaaattcc ctgtgcatgt attagttttt    60
gattgatttt tttttctctg aggggggcac attaattgtg ctcaatactc atacattgcg   120
gttcctttat tattttgtaa ttcattacat tgatattgat taacatgtca tttgtcaaaa   180
agagtctaat ttagttggtt gatcagagtg tgtgatagtc ttcgattcca cggattaaag   240
aaaaattaac atgtcatcaa agcttcaagt tcagcagctt aatcagttaa gggagatttt   300
cggtcgattt gacatggact cagatggaag cctaacaatg ctagagctag cagcacttct   360
taggtctctg gggctgaagc cctcgggtga ccaagtccaa gcactgttag ccaacatgga   420
ctcaaacgcc aatggcaaag tggagtttga tgaattgata agagccatat tacctgacat   480
aaatgcacag gttttgctga accaagaaca gctcctaggg gtgttcaagt gcttcgatcg   540
cgacggcaac ggttacatat cggccgcaga gttggccggg gcaatggcca aaatgggcca   600
gccactcacg taccgagagc tcacggagat gatcaaagag gctgacacgg atggggatgg   660
```

```
tgttattagc ttcactgagt ttgccactat catggctcgc tctgcttctg attttctagg   720
cctctcgttc tgctgaccgt ataacatata ttcatttcat ctaagttgta caatattctt   780
gatttttttt cctttgaat gaatgaatca atcaaataat gatatttggt ttgtactggg    840
tattactaat actaattacc cacaattcct gcc                                873
```

| | |
|---|---|
| SEQ ID NO: 270 | moltype = AA   length = 161 |
| FEATURE | Location/Qualifiers |
| REGION | 1..161 |
| | note = Ceres CLONE ID no. 565421 |
| REGION | 1..161 |
| | note = Functional Homolog of Ceres Clone ID no. 29658 at SEQ ID NO. 123 |
| REGION | 87..115 |
| | note = Pfam Name: efhand Pfam Description: EF hand |
| VARIANT | 100 |
| | note = Xaa is any aa, unknown or other |
| VARIANT | 151 |
| | note = Xaa is any aa, unknown or other |
| source | 1..161 |
| | mol_type = protein |
| | organism = Glycine max |

```
SEQUENCE: 270
MSSKLQVQQL NQLREIFGRF DMDSDGSLTM LELAALLRSL GLKPSGDQVQ ALLANMDSNA   60
NGKVEFDELI RAILPDINAQ VLLNQEQLLG VFKCFDRDGX GYISAAELAG AMAKMGQPLT  120
YRELTEMIKE ADTDGDGVIS FTEFATIMAR XASDFLGLSF C                      161
```

| | |
|---|---|
| SEQ ID NO: 271 | moltype = DNA   length = 842 |
| FEATURE | Location/Qualifiers |
| misc_feature | 1..842 |
| | note = Ceres CLONE ID no.3747 |
| misc_feature | 1..842 |
| | note = Encodes the peptide sequence at SEQ ID NO 272 |
| source | 1..842 |
| | mol_type = unassigned DNA |
| | organism = Arabidopsis thaliana |

```
SEQUENCE: 271
acttttctc caatggcttc tctgaagctt tcaccttctt ctccaatctc catttctaag    60
gttggtgtga ttccttcctc taagaaagga cttcatttc ttgtaaaagc agagcaccat   120
tcctcgtctt cttcttctca tcttcaagat aaatgtcaga gacgtctgat tgtaacattt   180
ggtgttgttg ctccttggat tcattgctt agtagagctc cattatcatt tgctgcagaa   240
agcaaaaaag gattccttgc tgtctctgac aataaagatg cttatgcgtt tctctatcca   300
tttggttggc aggaagttgt gattgaaggt caagataagg tatacaaaga tgtgattgag   360
cctttagaaa gtgttagtgt gaatttggtc ccaactagca acagactat taaagaattt   420
ggccctccca agcagatagc tgaaacactg ataaagaaag ttttggcacc tccaaatcag   480
aaacaaccc ttattgatgc atcagagcat gatgtcgatg ggaagactta ttatcagtttt  540
gagttcactg ttcaagctag aaactacact cgccatgctc tgggtaccat cacggttttc   600
aacggaaact tctacacact gacgacggga gcgaatgaaa ggtggtgaa gaaatgaaa    660
gataggcttc acactgtggt agattccttc aagatcactg tttgaaaata ctgtaatcaa   720
gtttgctttg gttgtctctt gttttgccca tttcttgtat ttttgtccat tcttcttctc   780
tctttcccctt aacaatattc tttttcctgta agagagattc aataactctt gacttgcctc   840
cc                                                                 842
```

| | |
|---|---|
| SEQ ID NO: 272 | moltype = AA   length = 230 |
| FEATURE | Location/Qualifiers |
| REGION | 1..230 |
| | note = Ceres CLONE ID no. 3747 |
| REGION | 1..230 |
| | note = Functional Homolog of Ceres Clone ID no. 16403 at SEQ ID NO. 146 |
| REGION | 43..229 |
| | note = Pfam Name: PsbP Pfam Description: PsbP |
| source | 1..230 |
| | mol_type = protein |
| | organism = Arabidopsis thaliana |

```
SEQUENCE: 272
MASLKLSPSS PISISKVGVI PSSKKGLSFL VKAEHHSSSS SSHLQDKCQR RLIVTFGVVA    60
PWISLLSRAP LSFAAESKKG FLAVSDNKDA YAFLYPFGWQ EVVIEGQDKV YKDVIEPLES  120
VSVNLVPTSK QTIKEFGPPK QIAETLIKKV LAPPNQKTTL IDASEHDVDG KTYYQFEFTV  180
QARNYTRHAL GTITVFNGNF YTLTTGANER RWEKMKDRLH TVVDSFKITV            230
```

| | |
|---|---|
| SEQ ID NO: 273 | moltype = DNA   length = 1205 |
| FEATURE | Location/Qualifiers |
| misc_feature | 1..1205 |
| | note = Ceres CLONE ID no.34878 |
| misc_feature | 1..1205 |
| | note = Encodes the peptide sequence at SEQ ID NO 274 |
| source | 1..1205 |
| | mol_type = unassigned DNA |
| | organism = Arabidopsis thaliana |

```
SEQUENCE: 273
acaacactcg acacagaagc aaaaacaaaa atgggtgaga agatatatcc aaggaacttg    60
aaggaagaag aagaaaacca aagtgaagat tccaaaagtt tgatctcttc acttccttca   120
gacatagatt gctctgggac caagttgtac aagtatcaag gatgttggta cgataaagac   180
attctccaag caatcctcaa attcaacaaa atctttcagc cacaagaaac cgatataatt   240
gttgcttctt tccccaaatc aggtacgact tggctcaagg cactcacatt cgcactcgct   300
caaagatcaa aacatacttc agaaaatcat cctctgctaa ctcataatcc tcatgagcta   360
gtgccgtacc tcgagctcga tctttatctc aaaagctcga aaccggatat gtccaagtta   420
ccatcatcat ctccgagatt gttctcaacc cacatgtgct taaagtacca                480
atgaaggaga ctccttgcaa gatagtgtat gtgtgcagga acgtaaaaga cgtgttggta   540
tcactttggt gtttcgaaaa ctccattagt ggagaaaaca atttaagtct cgaggctttg   600
ttcgagtctt tatgtagcgg agttaactta tgcggtccct tgtgggaaaa tgtgttaggc   660
tattggagag gaagcttgga agatcctaag catgtgcttt tcttgaggta cgaggagttg   720
aagacggaac ctcgtgtgca aatcaagaga cttgcagagt tcttagattt tccattcaca   780
aaggaagaag aagatagtgg aggtgtagac aagatcttgg aactttgttc tctaagaaac   840
cttagccggt tggagatcaa caaaacagga agcttgtcgg aaggagtaag tttcaagagt   900
ttttttccgta aaggggaagt tggtgattgg aagagttata tgactcctga aatggaaaac   960
aaaatcgaca tgattgttga ggagaaactt caaggctctg gtttgatatt gtagagttca  1020
tatctctatg tatatgtgaa caggttttaat ctcaaaccta ataatgctgg tttgttcttt  1080
tcttgtatgc aatgtaataa aagttacttt gatgtaaggt taagagttta agattctgag  1140
cgatgtgtcg ttttttgtttc ctttgataat caataaagct agcggctttt cttcttcgcc  1200
aaggc                                                               1205

SEQ ID NO: 274           moltype = AA   length = 327
FEATURE                  Location/Qualifiers
REGION                   1..327
                         note = Ceres CLONE ID no. 34878
REGION                   1..327
                         note = Functional Homolog of Ceres Clone ID no. 3964 at SEQ
                         ID NO. 154
REGION                   66..324
                         note = Pfam Name: Sulfotransfer_1 Pfam Description:
                         Sulfotransferase domain
source                   1..327
                         mol_type = protein
                         organism = Arabidopsis thaliana
SEQUENCE: 274
MGEKDIPRNL KEEEENQSED SKSLISSLPS DIDCSGTKLY KYQGCWYDKD ILQAILKFNK    60
IFQPQETDII VASFPKSGTT WLKALTFALA QRSKHTSENH PLLTHNPHEL VPYLELDLYL   120
KSSKPDMSKL PSSSPRLFST HMSFDALKVP MKETPCKIVY VCRNVKDVLV SLWCFENSIS   180
GENNLSLEAL FESLCSGVNL CGPLWENVLG YWRGSLEDPK HVLFLRYEEL KTEPRVQIKR   240
LAEFLDFPFT KEEEDSGGVD KILELCSLRN LSGLEINKTG SLSEGVSFKS FFRKGEVGDW   300
KSYMTPEMEN KIDMIVEEKL QGSGLIL                                       327

SEQ ID NO: 275           moltype = DNA   length = 1459
FEATURE                  Location/Qualifiers
misc_feature             1..1459
                         note = Ceres CLONE ID no.295570
misc_feature             1..1459
                         note = Encodes the peptide sequence at SEQ ID NO 276
source                   1..1459
                         mol_type = unassigned DNA
                         organism = Zea mays
SEQUENCE: 275
acgcagggtg gctaggagtt gagtcgtgca gaagagacaa aggtcctcac ttggctaagc    60
tagacacgta cgagtgcagg aaacaagata agtcgcggtt tgcgacggcg agaagcgccg   120
gatgagtgtc cactgtccac aagtccagat tccaattcca gtccgatcgt gagctcagct   180
cagctccgct agtcctctcc ccgcacgcac caccaccagc agcagtccag caccatgggc   240
ggcgccctgc tcctcacgct gctcctcgcg gccgtgcccc tctccktggg cggcggcggc   300
ggcgcgcacc cgggctactc cgacgacgac gagagcgcct gcacggtgga cgggggcgg   360
gagctgctgc ggcggatsga ggagcgcggg cccgacaggg gcatcatcga catcacgcac   420
gcggtcgtgc mggacctgcc ggcgttcgcc acggggcgg tcgcgggcc catgctgcgc   480
ctcagggagt csatggcgga cgggtcgcga gtacaacctg tcggagctgc ggatggagtg   540
ccacaccggc acgcacgtcg acgcgcctgg ccacatccac cgggcccact tsgccgcctg   600
cctcgacgtc gacacgctcg acctccacgt cctcaacgga cctgcattgc tagttgatgt   660
gccaagaaac acaaatataa cagctgaagc gatggaattc ctaaacatcc cgagagggt   720
tcgccgagtt ctgttcagaa cactgaacac tgacaggaag ttgatgtgga ggaagggagg   780
tgacatgagc tacgttgggt ttacagagga tggcgcgcas tggttagtca acaacaccga   840
cataaagtca gttggagttg acggtctgtc agwggcatcc tttgatcacc tgatctctga   900
ccacgtggtc tttttttcaaa aaaccccgga tataatccct gttgagagcc tsaatctgga   960
cgacatcgag gcgggggatat acatgctgca ctgtctacct ctcaggctgg tcggagccga  1020
gggtgcaccg accagatgca tcctcatcaa gtgatcgttc ctcggccggc ctgctcttgc  1080
tgccttgctg gaggtggcga cactggacca tgyccagctg agctggtgct ccgtcgtggg  1140
tcgccgtgca aatatttggc tcgcatgcag tcgtcgatct atatgaaca gaacactgca  1200
tgcctatgta gatacgcttg tatgacaat aaaggaaccg cagtacttct gtcgawaaa   1260
tastwkkggg tgrgmcggta atstaaaaca csaggcmtac twggtaagc tgggaggccc   1320
tgsmwaggct gaggmtrgmg gctggggatg gatccagagt tttwattcga atgstatttt   1380
ttttgggyc mtatttttctt tgattgtara craataacat atatgatttt ctatatctct  1440
actaaaaaaa aaaaaaaaa                                                1459
```

```
SEQ ID NO: 276            moltype = AA  length = 271
FEATURE                   Location/Qualifiers
REGION                    1..271
                          note = Ceres CLONE ID no. 295570
REGION                    1..271
                          note = Functional Homolog of Ceres CLONE ID no. 8686 at SEQ
                          ID NO. 80
REGION                    57..257
                          note = Pfam Name: Cyclase Pfam Description: Putative cyclase
source                    1..271
                          mol_type = protein
                          organism = Zea mays
SEQUENCE: 276
MGGALLLTLL LAAVPLSLGG GGGAHPGYSD DDESACTVDA GAELLRRMEE RGPDRRIIDI    60
THAVVPDLPA FATGAVAGPM LRLRESMADG SEYNLSELRM ECHTGTHVDA PGHINQAHFA   120
ACLDVDTLDL HVLNGPALLV DVPRNTNITA EAMEFLNIPR GVRRVLFRTL NTDRKLMWRK   180
GGDMSYVGFT EDGAQWLVDN TDIKLVGVDG LSVASFDHLI SAHVVFFKTP DIIPVESLNL   240
DDIEAGIYML HCLPLRLVGA EGAPTRCILI K                                  271

SEQ ID NO: 277            moltype = DNA  length = 1212
FEATURE                   Location/Qualifiers
misc_feature              1..1212
                          note = Ceres CLONE ID no.150484
misc_feature              1..1212
                          note = Encodes the peptide sequence at SEQ ID NO 278
source                    1..1212
                          mol_type = unassigned DNA
                          organism = Arabidopsis thaliana
SEQUENCE: 277
acaacactcg acacaaaagc aaaaacaaaa atgggtgaga agatattcc aaggaacttg     60
aaggaagaag aagaagaaga agaagaaaac caaagtgaag aaaccaaaag tttgatctct   120
tcacttcctt cagacataga ttgctcaggg accaagttgt acaagtacca aggatgttgg   180
tacgacaaag atattctcca agcaatcctc aatttcaaca aaaactttca gccacaagaa   240
acggatataa ttgttgcttc tttccccaaa tcgggtacga cttggctcaa ggcactcaca   300
ttcgcactcg cgcaaagatc aaaacacact tcagacaatc atcctctgct aactcataat   360
cctcatgagc tagtgccgta cctcgagctc gatctttatc tcaaaagctc gaaaccggat   420
ttgaccaagt tgccatcatc atctccgaga ttgttctcaa cccacatgtc ctttgatgcg   480
cttaaagtac cgttgaaaga gtctccttgc aagatcgtgt acgtgtgcag gaacgtgaat   540
gacgtattga tatcactttg gtgtttcgaa aactccatga gtggagaaaa caatttaagt   600
ctcgaggctt tgttcgagtc tttatgtagc ggagttaact tatgcggtcc cttatgggaa   660
aatgtgttag gctattggag aggaagcttg gaagatccta gcatgtgct tttcttgagg   720
tacgaggagt tgaagacgga gcctcgtgtg caaatcgaga gacttgcaga gttcttagat   780
tgtccattca caaaggaaga agaagatagt ggaggtgtag acaagatctt ggaactttgt   840
tctctaagaa accttagcgg tttggagatc aacaaaacag gaagcttgtc ggaaggagta   900
agtttcaaga gttttttccg taaaggggaa gttggtgatt ggaagagtta tatgactcct   960
gaaatgaaca acaaaatcga catgattgtt gaggagaaac ttcaaggctc tggttttgaaa  1020
ttgtagagtt catatctcta tgtatatgtg tgggaacagg tttaatctca aacctaataa   1080
tgctggtttg ttcttttctt gtatgcaatg taataaaagt tacttgatg taaggttaag   1140
agtttaagat tcttagtgat gtgttgttgt ttttgtttcg tttgataacg aataaagcta   1200
gcggcttttc tc                                                      1212

SEQ ID NO: 278            moltype = AA  length = 331
FEATURE                   Location/Qualifiers
REGION                    1..331
                          note = Ceres CLONE ID no. 150484
REGION                    1..331
                          note = Functional Homolog of Ceres Clone ID no. 3964 at SEQ
                          ID NO. 154
REGION                    70..328
                          note = Pfam Name: Sulfotransfer_1 Pfam Description:
                          Sulfotransferase domain
source                    1..331
                          mol_type = protein
                          organism = Arabidopsis thaliana
SEQUENCE: 278
MGEKDIPRNL KEEEEEEEEN QSEETKSLIS SLPSDIDCSG TKLYKYQGCW YDKDILQAIL    60
NFNKNFQPQE TDIIVASFPK SGTTWLKALT FALAQRSKHT SDNHPLLTHN PHELVPYLEL   120
DLYLKSSKPD LTKLPSSSPR LFSTHMSFDA LKVPLKESPC KIVYVCRNVN DVLISLWCFE   180
NSMSGENNLS LEALFESLCS GVNLCGPLWE NVLGYWRGSL EDPKHVLFLR YEELKTEPRV   240
QIKRLAEFLD CPFTKEEEDS GGVDKILELC SLRNLSGLEI NKTGSLSEGV SFKSFFRKGE   300
VGDWKSYMTP EMENKIDMIV EEKLQGSGLK L                                  331

SEQ ID NO: 279            moltype = DNA  length = 1155
FEATURE                   Location/Qualifiers
misc_feature              1..1155
                          note = Ceres CLONE ID no.1368
misc_feature              1..1155
                          note = Encodes the peptide sequence at SEQ ID NO 280
```

```
source                  1..1155
                        mol_type = unassigned DNA
                        organism = Arabidopsis thaliana
SEQUENCE: 279
aaatcaccaa ccagtgacct aacaatggcc gttcctccat tattcttcct cctcacactc      60
ctctctctcc cttctcttct tatctccgcc ggtgcttcca atgcctatcc ttctattccc     120
ggaaccgctc ctatcgacgg aggtttcacc gatgaactta aacccattcg ccgtgaagtc     180
tacgggaatg gcaaaatcta tgacatcagt caccgttaca ctccggagat gccgtcgtgg     240
gactcatcgg aaggaatcgg acggttccta tggttagctg cgagtatgaa gaacggatcc     300
cttgctaata actctgaaat gaagattccc acgcacactg gtactcatgt tgattcacct     360
ggtcacgtct atgacaagta ttacgatgct ggctttgatg ttgactcgct tgatcttcaa     420
gtcctcaatg gtcttgcgtt gttggttgat gttccaaagg ataagaacat tactgctgaa     480
gtgatgaaat ctcttcacat tccaaaagga gttagtcgtg tgcttttcag aacattgaac     540
actgacaggc gtcttatgtt caagaaagaa tttgatacaa gctatgtcgg attcatgaag     600
gatggtgcgc aatggttggt agacaacaca gacatcaaac ttgttgggat tgattatcta     660
tcagtagctg catatgatga tcttattcca tcccacctag tattcctaaa agaccgggag     720
actatactcg tgraggggtt gaagctggat ggtgtgaagg caggactcta ctctgtccat     780
tgcttaccct ctaagactgg tggagcagaa gggtctccaa ttcgttgcat cctcatcgat     840
tgattctctc ccatcacaaa cctgccaaat ccgaaattgt ccgtaatcaa aagcttgctt     900
agcttatgaa ctgaatatca gtttgtgcta gatttatgca accaatatgg agattgaagt     960
aggaagaaat aagagagatg cagagaagac caagttgatg ataatgaagc accgaagaaa    1020
aaagattttt catttctatg tatatgtcaa taaataaatt aaaaattctc ttaatctgtc    1080
aaggttgtac taattatcaa ataggaaaaa gttcataaca tataaatcct tgttgaaata    1140
ggttttttgtt ttccc                                                    1155

SEQ ID NO: 280         moltype = AA  length = 272
FEATURE                Location/Qualifiers
REGION                 1..272
                       note = Ceres CLONE ID no. 1368
REGION                 1..272
                       note = Functional Homolog of Ceres CLONE ID no. 8686 at SEQ
                        ID NO. 80
REGION                 58..258
                       note = Pfam Name: Cyclase Pfam Description: Putative cyclase
source                 1..272
                       mol_type = protein
                       organism = Arabidopsis thaliana
SEQUENCE: 280
MAVPPLFFLL TLLSLPSLLI SAGASNAYPS IPGTAPIDGG FTDELKPIRR EVYGNGKIYD      60
ISHRYTPEMP SWDSSEGIGR FLWLAASMKN GSLANNSEMK IPTHTGTHVD SPGHVYDKYY     120
DAGFDVDSLD LQVLNGLALL VDVPKDKNIT AEVMKSLHIP KGVSRVLFRT LNTDRRLMFK     180
KEFDTSYVGF MKDGAQWLVD NTDIKLVGID YLSVAAYDDL IPSHLVFLKD RETILVEGLK     240
LDGVKAGLYS VHCLPLRLVG AEGSPIRCIL ID                                   272

SEQ ID NO: 281         moltype = DNA  length = 1273
FEATURE                Location/Qualifiers
misc_feature           1..1273
                       note = Ceres CLONE ID no.124067
misc_feature           1..1273
                       note = Encodes the peptide sequence at SEQ ID NO 282
source                 1..1273
                       mol_type = unassigned DNA
                       organism = Arabidopsis thaliana
SEQUENCE: 281
accaacacac aaagattcca ttacaaataa acaattttca tatatatcta taacaaaaaa      60
aaacaatggc gacctcaagc atgaagagca ttccaatggc gatcccaagt ttctccatgt     120
gtcacaagct cgagctcctt aaagaaggca aaactcgcga cgtcccgaaa gccgaagaag     180
atgaagggct aagctgcgag ttccaagaga tgttggattc tcttcctaag agagaggat      240
ggagaactcg ttacctttac ctattccaag ggttttggtg ccaagccaaa gagattcaag     300
ccatcatgtc tttccaaaaa catttccaat ccctcgaaaa cgacgtcgtt ctcgccacca     360
tacctaaatc cggtacaacc tggctaaaag cttaactttt caccatcctt aaccgtcacc     420
ggtttgatcc ggttgcctcg agtaccaacc accctctttt cacttccaac cctcatgacc     480
ttgtaccttt cttcgagtac aagctttacg ccaacggaga tgttcccgat ctctcgggtc     540
tagccagtcc aagaacgttc gcaacccact taccgttcct tccttaaag gaaacgatcg     600
agaaacccgg tgtgaaggtc gtgtacttgt gccggaaccc gtttgacaca ttcatctctt     660
cgtggcatta ccaacaac atcaaatccg agtcagtgag cccagtcttg ctagaccaag     720
cttttgatct gtattgccgg ggagtgatcg ggtttggccc gttttgggaa cacatgttgg     780
gatactggag agagagcttg aagagaccag agaaagtctt ctttttaagg tacgaggatt     840
tcaaagacga catccgaacc aacttgaaga ggctcgaac tttcttagag cttccttca     900
ccgaagaaga ggaacgaaag ggagttgtga aggctatcgc cgagctgtgt agcttcgaga     960
atctgaagaa gttggaggtg aacaagtcaa acaagtcgat caagaacttt gagaatcgat    1020
tcttgtttcg gaaggagaa gtgagtgatt gggttaacta tttgtcacct tcacaagtgg    1080
aaagattgtc agccttagtg gatgacaagt taggtggatc tggtctcact ttcaggtgaa    1140
gctaaaatata aggccacgtg ccccattttc tactcttgtt ctgagggcct actatatacg    1200
ttaagctaag ttaaggcagt tgtattgttg ttacagatag acatcgaagc aacgtaacgt    1260
ccataattaa gtc                                                       1273

SEQ ID NO: 282         moltype = AA  length = 359
FEATURE                Location/Qualifiers
```

```
REGION                  1..359
                        note = Ceres CLONE ID no. 124067
REGION                  1..359
                        note = Functional Homolog of Ceres Clone ID no. 3964 at SEQ
                         ID NO. 154
REGION                  91..353
                        note = Pfam Name: Sulfotransfer_1 Pfam Description:
                         Sulfotransferase domain
source                  1..359
                        mol_type = protein
                        organism = Arabidopsis thaliana
SEQUENCE: 282
MATSSMKSIP MAIPSFSMCH KLELLKEGKT RDVPKAEEDE GLSCEFQEML DSLPKERGWR      60
TRYLYLFQGF WCQAKEIQAI MSFQKHFQSL ENDVVLATIP KSGTTWLKAL TFTILNRHRF     120
DPVASSTNHP LFTSNPHDLV PFFEYKLYAN GDVPDLSGLA SPRTFATHLP FGSLKETIEK     180
PGVKVVYLCR NPFDTFISSW HYTNNIKSES VSPVLLDQAF DLYCRGVIGF GPFWEHMLGY     240
WRESLKRPEK VFFLRYEDLK DDIETNLKRL ATFLELPFTE EEERKGVVKA IAELCSFENL     300
KKLEVNKSNK SIKNFENRFL FRKGEVSDWV NYLSPSQVER LSALVDDKLG GSGLTFRLS      359

SEQ ID NO: 283          moltype = DNA  length = 845
FEATURE                 Location/Qualifiers
misc_feature            1..845
                        note = Ceres ANNOT ID no.870567
misc_feature            1..845
                        note = Encodes the peptide sequence at SEQ ID NO 284
source                  1..845
                        mol_type = unassigned DNA
                        organism = Arabidopsis thaliana
SEQUENCE: 283
aataagaaaa tcaaaatctt tactcgtttg aaatttgtaa tccattacct gtcatcgttg      60
acttgtcaag aagaaacaaa tcaactctaa aaagaaaaat gttgttcatc gaaatcgaag     120
cttgacagta ttcaaaatca gattcgagat gagctgcgac ggaggcaaac cggcgccggc     180
gaaactaggc gacgaacaac tagcggagct ccgggagata ttccgatcat ttgaccagaa     240
caaggatgga agtttgacgg agctcgagtt aggctcactt ctaagatctc tcggtctaaa     300
gccgagttca gaccaactcg acacattgat ccagaaagca gatcggaata acaacggact     360
ggtcgagttc tccgagttcg tcgccctcgt cgagccagat ctggtcaagt gtccttacac     420
ggatgatcag cttaaagcca tctttagaat gtttgaccgc gatggaaacg gttacataac     480
ggcggcggag ttagcccatt cgatggcgaa gctaggtcac gcgttgacgg cggaggagtt     540
aacggcgaatg atcaaagaag ctgatcgaga cggcgatggt tgtattgatt tccaagagtt     600
tgttcaagcg attacttcag ctgcgtttga taatgcttgg ggttgaagaa agaaaggtat     660
atatatacat agtttgaaat acttgtgttt tgttttttg gcttcatcct caaatcaaag      720
acatttggaa gtatatgtgt gtaggtgcga ttccatggaa aatgtgtgtt atttattgtt     780
tcatattatt cttttgatgaa atttttgatag cttgaagaga aagctatcat tgttggtttt     840
agggc                                                                 845

SEQ ID NO: 284          moltype = AA  length = 165
FEATURE                 Location/Qualifiers
REGION                  1..165
                        note = Ceres ANNOT ID no. 870567
REGION                  1..165
                        note = Functional Homolog of Ceres Clone ID no. 29658 at
                         SEQ ID NO. 123
REGION                  56..84
                        note = Pfam Name: efhand Pfam Description: EF hand
source                  1..165
                        mol_type = protein
                        organism = Arabidopsis thaliana
SEQUENCE: 284
MSCDGGKPAP AKLGDEQLAE LREIFRSFDQ NKDGSLTELE LGSLLRSLGL KPSQDQLDTL       60
IQKADRNNNG LVEFSEFVAL VEPDLVKCPY TDDQLKAIFR MFDRDGNGYI TAAELAHSMA     120
KLGHALTAEE LTGMIKEADR DGDGCIDFQE FVQAITSAAF DNAWG                     165

SEQ ID NO: 285          moltype = DNA  length = 1248
FEATURE                 Location/Qualifiers
misc_feature            1..1248
                        note = Ceres ANNOT ID no.864284
misc_feature            1..1248
                        note = Encodes the peptide sequence at SEQ ID NO 286
source                  1..1248
                        mol_type = unassigned DNA
                        organism = Arabidopsis thaliana
SEQUENCE: 285
gttcacttaa caaacaaga accaaaaaaa atggatgaga aagatattct aaggaacttg       60
agggaagaag aagaagaaga agaagaaaat caaagcgaag aaaccaaaat tttgatctct     120
tcacttcctt gggagataga ttaccttggg aacaagcttt tcaagtacca aggatattgg     180
tactacgaag acgttctcca atcaatccc aatatacact cgagttttca gccacaagaa      240
accgatatag ttgttgcttc tttctacaaa tcgggcacga cttggctcaa agcactcaca     300
tttgcactcg ttcaacgatc aaaacactcg ttagaagatc atcatcatcc tctgctatct     360
cataacccctc atgagatagt accgtacctc gagctagatc tgtatctcaa cagctcaaaa     420
```

```
ccggacttga ccaagttctt atcatcatca tcatcatcat catctccgag attgttctca  480
actcatatgt ccttggacgc gcttaaacta cccttgaaga agtctccttg caaggtagtg  540
tacgtgtgca ggaacgtgaa agacgtgttg gtgtcacttt ggtgtttcct caatgccaac  600
aagggagtag aatggggaga ttttagccaa aatgaaagaa tcattcgagc ggagaattat  660
tctttcaagg ctatatttga gtcattctgc aacggagtta ccctacacgg tcccttttgg  720
gaccatgcac agagctattg gcgaggcagc ttggaagatc ctaagcattt tcttttcatg  780
aggtacgagg agttgaaagc ggagcctcgt actcaggtca agagacttgc agagttcttg  840
gattgtccca tcactaagga agaggaagat agcggaactg tagacaagat cttggaactt  900
tgctctctaa gtaatttaag cagtttggag atcaacaaaa ctggatcctt gggtggagta  960
gattacaaga cttatttccg taaaggacaa gttggtgact ggaagagtta tatgacctct  1020
gaaatggtaa ataaaatcga tatgatcgtc gaggagaaac tcaaaggttc cggtttgaaa  1080
ttctagaatt atgcgtgtgc tttgtgaaga actgcagaaa aagtgttctt gaatgcgtta  1140
tttaataata aaagttacat tgtcatatat ataactttga tgtatcatta caactgatgt  1200
gtggtttttg ttctctttga tgttgcaata aaaaccttct ttacttct                 1248
```

| | | |
|---|---|---|
| SEQ ID NO: 286 | moltype = AA length = 351 | |
| FEATURE | Location/Qualifiers | |
| REGION | 1..351 | |
| | note = Ceres ANNOT ID no. 864284 | |
| REGION | 1..351 | |
| | note = Functional Homolog of Ceres Clone ID no. 3964 at SEQ ID NO. 154 | |
| REGION | 70..348 | |
| | note = Pfam Name: Sulfotransfer_1 Pfam Description: Sulfotransferase domain | |
| source | 1..351 | |
| | mol_type = protein | |
| | organism = Arabidopsis thaliana | |

SEQUENCE: 286

```
MDEKDILRNL REEEEEEEEN QSEETKILIS SLPWEIDYLG NKLFKYQGYW YYEDVLQSIP   60
NIHSSFQPQE TDIVVASFYK SGTTWLKALT FALVQRSKHS LEDHHHPLLS HNPHEIVPYL  120
ELDLYLNSSK PDLTKFLSSS SSSSSPRLFS THMSLDALKL PLKKSPCKVV YVCRNVKDVL  180
VSLWCFLNAN KGVEWGDFSQ NEKIIRAENY SFKAIFESFC NGVTLHGPFW DHAQSYWRGS  240
LEDPKHFLFM RYEELKAEPR TQVKRLAEFL DCPFTKEEED SGTVDKILEL CSLSNLSSLE  300
INKTGSLGGV DYKTYFRKGQ VGDWKSYMTS EMVNKIDMIV EEKLKGSGLK F           351
```

| | | |
|---|---|---|
| SEQ ID NO: 287 | moltype = DNA length = 1177 | |
| FEATURE | Location/Qualifiers | |
| misc_feature | 1..1177 | |
| | note = Ceres ANNOT ID no.858178 | |
| misc_feature | 1..1177 | |
| | note = Encodes the peptide sequence at SEQ ID NO 288 | |
| source | 1..1177 | |
| | mol_type = unassigned DNA | |
| | organism = Arabidopsis thaliana | |

SEQUENCE: 287

```
atagagagct taagcaaaag atctcatact ttcaagattg atcgatctct caagtctcaa   60
caatgtcatc atcatcatca gttcctgctt acttgggaga tgaagatctg acacaagaaa  120
caagagctct gatctcttct cttcctaaag agaaaggttg gttagtgagt gaaatatatg  180
aattccaagg actttggcac acacaagcta ttttacaagg aatcttgatc tgccaaaaac  240
gctttgaagc taaagattcc gacattatcc tcgtcactaa tcctaaatca ggtaccaatt  300
ggttaaaagc tcttgtcttt gctctcctta accgacacaa gtttccagtt cttcttctg   360
gtaaccatcc tcttctggtc accaatccaa accttcttgt gcccttcttg aaggagtt    420
actacgagtc cccagatttc gatttctcca gtttgccttc tccaagactg atgaacacgc  480
acatatcgca tctttcgctc cccgagtctg ttaagagctg gtcttgtaag attgtgtatt  540
gttgtaggaa ccctaaggac atgtttgtgt ccttatggca ttttgggaaa aagctagctc  600
ctgaggaaac cgcggattat cctatcgaaa aagcggttga agcgttttgt gaagggaagt  660
ttataggtgg acccttttgg gatcatatat tggagtactg gtatgcaagc cgcgagaatc  720
cgaacaaggt cttgttttgt acttacgagg agctaaagaa gcagaccgaa gttgagatga  780
agcggatcgc ggagttcttg aatgtggct ttattgaaga agaagaagtg agagagattg  840
tgaagttgtg tagctttgag agtttaagta atttggaagt taacaaagaa gggaaattgc  900
caaatggaat agagactaaa actttcttta gaaaaggaga gattggagga tggagagata  960
cttttgagtga gtcattggca gaggaaattg atagaaccat tgaagagaag tttaaaggtt  1020
ctggtcttaa atttttcttct tgaatcaatc tttgaaactt ttctcatgt tcttgttttg  1080
cttcaattat gttattttctt gttttatata ttttctgct gttatgtttg tgtttgtgtt  1140
tatgaataaa atgaaataaa ttatgtttgt gtttttct                           1177
```

| | | |
|---|---|---|
| SEQ ID NO: 288 | moltype = AA length = 326 | |
| FEATURE | Location/Qualifiers | |
| REGION | 1..326 | |
| | note = Ceres ANNOT ID no. 858178 | |
| REGION | 1..325 | |
| | note = Functional Homolog of Ceres Clone ID no. 3964 at SEQ ID NO. 154 | |
| REGION | 65..321 | |
| | note = Pfam Name: Sulfotransfer_1 Pfam Description: Sulfotransferase domain | |
| source | 1..326 | |
| | mol_type = protein | |

```
                        organism = Arabidopsis thaliana
SEQUENCE: 288
MSSSSSVPAY LGDEDLTQET RALISSLPKE KGWLVSEIYE FQGLWHTQAI LQGILICQKR    60
FEAKDSDIIL VTNPKSGTTW LKALVFALLN RHKFPVSSSG NHPLLVTNPH LLVPFLEGVY   120
YESPDFDFSS LPSPRLMNTH ISHLSLPESV KSSSCKIVYC CRNPKDMFVS LWHFGKKLAP   180
EETADYPIEK AVEAFCEGKF IGGPFWDHIL EYWYASRENP NKVLFVTYEE LKKQTEVEMK   240
RIAEFLECGF IEEEVREIV  KLCSFESLSN LEVNKEGKLP NGIETKTFFR KGEIGGWRDT   300
LSESLAEEID RTIEEKFKGS GLKFSS                                       326

SEQ ID NO: 289          moltype = DNA  length = 486
FEATURE                 Location/Qualifiers
misc_feature            1..486
                        note = Ceres ANNOT ID no.842118
misc_feature            1..486
                        note = Encodes the peptide sequence at SEQ ID NO 123
source                  1..486
                        mol_type = unassigned DNA
                        organism = Arabidopsis thaliana
SEQUENCE: 289
atggcgtcaa caaaaccaac cgatcaaatc aaacaactca agatatcttc cgctcgtttc    60
gacatggaca aggacggaag cttaacgcag ctagaactcg ccgctcttct gcgttctctc   120
ggaatcaaac ctcgcagcga tcaaatctct ctttctgttga accaaatcga ccgtaacggt   180
aacggatccg tagagttcga cgagctggtc gtgtgcgatat tgccggatat aaacgaagag   240
gttttgataa atcaagaaca gttgatggag gttttccgtt cgtttgatcg tgacggaaac   300
ggttcaataa cggcggcgga acttgctggg tcaatggcta aatgggaca  tccgttgact   360
taccgtgaat aacggaaat gatgacggaa gctgattcta acggtgacgg tgttattagt    420
tttaatgagt tttctcatat tatggctaaa tcggctgctg attttcttgg attaaccgct   480
tcttga                                                             486

SEQ ID NO: 290          moltype = DNA  length = 633
FEATURE                 Location/Qualifiers
misc_feature            1..633
                        note = Ceres ANNOT ID no.566551
misc_feature            1..633
                        note = Encodes the peptide sequence at SEQ ID NO 291
source                  1..633
                        mol_type = unassigned DNA
                        organism = Arabidopsis thaliana
SEQUENCE: 290
atggcggcga acgattcttc aaatgctatt gacatcgacg ggaatctcga ctccgattcg    60
aatcttaaca ctgacggtga cgaagcgacc gataatgatt cctcgaaggc attggttact   120
atccctgctc cagccgtttg tcttttccgg ttcgccggag atgctgctgg tggcgccgtt   180
atgggctcta tcttcggata tggttcagga ttgttcaaga agaaaggctt caaaggatca   240
tttgcagatg cagggcagtc tgctaagact tttgctgttt tatctggagt ccacagtttg   300
gttgtttgcc ttctgaagca aatccgaggc aaagatgacg ccattaatgt tggagtagca   360
gggtgttgca ctggtcttgc tcttagtttc cctggtgctc cacaggctct tctacagagt   420
tgtctcacgt ttggggcatt ctctttttatt cttgagggac tcaacaaaag acaaacagct   480
ttggcacact cggtctcgtt gagacaccaa accggactgt tccaagatca tcatcgtgct   540
ttaccactct ctcttgctct cccgatccct gaagaaatca aaggagcctt tcttctttc    600
tgcaagtcct tagctaaacc aaggaagttc taa                               633

SEQ ID NO: 291          moltype = AA  length = 210
FEATURE                 Location/Qualifiers
REGION                  1..210
                        note = Ceres ANNOT ID no. 566551
REGION                  1..210
                        note = Functional Homolog of Ceres CLONE ID no. 965405 at
                         SEQ ID NO. 172
REGION                  40..158
                        note = Pfam Name: Tim17 Pfam Description: Tim17/Tim22/Tim23
                         family
source                  1..210
                        mol_type = protein
                        organism = Arabidopsis thaliana
SEQUENCE: 291
MAANDSSNAI DIDGNLDSDS NLNTDGDEAT DNDSSKALVT IPAPAVCLFR FAGDAAGGAV    60
MGSIFGYGSG LFKKKGFKGS FADAGQSAKT FAVLSGVHSL VVCLLKQIRG KDDAINVGVA   120
GCCTGLALSF PGAPQALLQS CLTFGAFSFI LEGLNKRQTA LAHSVSLRHQ TGLFQDHHRA   180
LPLSLALPIP EEIKGAFSSF CKSLAKPRKF                                   210

SEQ ID NO: 292          moltype = DNA  length = 1323
FEATURE                 Location/Qualifiers
misc_feature            1..1323
                        note = Genomic Sequence Of Ceres ANNOT ID no. 566551
misc_feature            1..1323
                        note = Encodes the peptide sequence at SEQ ID NO 291
source                  1..1323
                        mol_type = unassigned DNA
                        organism = Arabidopsis thaliana
```

```
SEQUENCE: 292
tggcggcgaa cgattcttca aatgctattg acatcgacgg gaatctcgac tccgattcga    60
atcttaacac tgacggtgac gaagcgaccg ataatgattc ctcgaaggca ttggttacta   120
tccctgctcc agccgtttgt cttttccggt tcgccggaga tgctgctggt ggcgccgtta   180
tgggctctat cttcggatat ggtgctcttc ttctttctat tttgtttctt ctattgcttg   240
gttttatctg ctattgcttt actctctgat agtgaattga gaattactgg caaacaattg   300
agtttgtact cttttcttca tttaagttga tttcaaaaca tgtttcgtgg ataagggttt   360
gagaaatcat agttgtttta gcagactagc cttttgagtt attttcagga gtaatctaga   420
tttaggggat tcaacattcc tcaagtttgg ttatgttttg ctcctggaag ctatagaatt   480
gaattagctt agttttcatt aaagagcgtc aatgtgataa gattggctac tgatttgatt   540
acgatgatgg aattgtgaaa tattatctca ctatataagt tgggattcag gttcaggatt   600
gttcaagaag aaaggcttca aaggatcatt tgcagatgca gggcagtctg ctaaggtacc   660
cctcatcttt atgctatagc atatatatgc ttattgttcc aagaaactga gtaatttgct   720
aattttttgt tcaagacttt tgctgttttta tctggagtcc acagtttggt tgtttgcctt   780
ctgaagcaaa tccgaggcaa agatgacggt gagactcttc agattgcttc cttcttgtgt   840
aaatgattag ttttttacatg aacttgtaat ctctctccta cttatattgc ttttgttctt   900
tttttacagc cattaatgtt ggagtagcag ggtgttgcac tggtcttgct cttagtttcc   960
ctggtaatcc aaatccatta tgctcattct gatttctact ttggcgttat gtatcatatc  1020
aaagatgcaa tcatcacaga gaggagagct aatagattct tcttatatg gccttttta  1080
caggtgctcc acaggctctt ctacagagtt gtctcacgtt tggggcattc tcttttattc  1140
ttgagggact caacaaaaga caaacagctt ggcacactc ggtctcgttg agacaccaaa   1200
ccggactgtt ccaagatcat catcgtgctt taccactctc tcttgctctc ccgatccctg   1260
aagaaatcaa aggagccttt tcttctttct gcaagtcctt agctaaacca aggaagttct  1320
aat                                                                1323

SEQ ID NO: 293         moltype = DNA  length = 486
FEATURE                Location/Qualifiers
misc_feature           1..486
                       note = Genomic Sequence Of Ceres ANNOT ID no. 842118
misc_feature           1..486
                       note = Encodes the peptide sequence at SEQ ID NO 123
source                 1..486
                       mol_type = unassigned DNA
                       organism = Arabidopsis thaliana
SEQUENCE: 293
tggcgtcaac aaaaccaacc gatcaaatca aacaactcaa agatatcttc gctcgtttcg    60
acatggacaa ggacggaagc ttaacgcagc tagaactcgc cgctcttctg cgttctctcg   120
gaatcaaacc tcgcagcgat caaatctctc ttctgttgaa ccaaatcgac cgtaacggta   180
acggatccgt agagttcgac gagctggtcg tggcgatatt gccggatata aacgaagagg   240
ttttgataaa tcaagaacag ttgatggagg ttttccgttc gtttgatcgt gacgttaaacg   300
gttcaataac ggcggcggaa cttgctgggt caatggctaa aatgggacat ccgttgactt   360
accgtgaatt aacggaaatg atgacggaag ctgattctaa cggtgacggt gttattagtt   420
ttaatgagtt ttctcatatt atggctaaat cggctgctga ttttcttgga ttaaccgctt   480
cttgat                                                              486

SEQ ID NO: 294         moltype = DNA  length = 1177
FEATURE                Location/Qualifiers
misc_feature           1..1177
                       note = Genomic Sequence Of Ceres ANNOT ID no. 858178
misc_feature           1..1177
                       note = Encodes the peptide sequence at SEQ ID NO 288
source                 1..1177
                       mol_type = unassigned DNA
                       organism = Arabidopsis thaliana
SEQUENCE: 294
catagagagc ttaagcaaaa gatctcatac tttcaagatt gatcgatctc tcaagtctca    60
acaatgtcat catcatcatc agttcctgct tacttgggag atgaagatct gacacaagaa   120
acaagagctc tgatctcttc tcttcctaaa gagaaaggtt ggttagtgag tgaaatatat   180
gaattccaag gactttggca cacacaagct attttacaag gacatcttgat ctgccaaaaa   240
cgctttgaag ctaaagattc cgacattatc ctcgtcacta atcctaaatc aggtaccact   300
tggttaaaag ctcttgtctt tgctctcctt aaccgacaca agtttccagt tcttcttcct   360
ggtaaccatc ctcttctggt caccaatcca caccttcttg tgcccttctt ggaaggagtt   420
tactacgagt ccccagattt cgatttctcc agtttgcctt ctccaagact gatgaacacg   480
cacatatcgc atctttcgct ccccgagtct gttaagagct cgtcttgtaa gattgtgtat   540
tgttgtagga accctaagga catgtttgtg tccttatggc attttgggaa aaagctagct   600
cctgaggaaa ccgcggatta tcctatcgaa aaagcggttg aagcgttttg tgaagggaag   660
tttataggtg gacccttttg ggatcatata ttggagtact ggtatgcaag ccgcgagaat   720
ccgaacaagg tcttgtttgt tacttacgag gagctaaaga agcagaccga agttgagatg   780
aagcggatcg cggagttctt ggaatgtggc tttattgaag aagaagaagt gagagagatt   840
gtgaagttgt gtagctttga gagtttaagt aatttggaag ttaacaaaga agggaaattg   900
ccaaatggaa tagagactaa aacttttcttt agaaaggag agattggagg atggagagat   960
actttgagtg agtcattggc agaggaaatt gatagaacca ttgaagagaa gtttaaaggt  1020
tctggtctta aattttcttc ttgaatcaat cttttgaaact tgttctcatg ttcttgtttt  1080
gcttcaatta tgtttattct tgttttatat atttttctgc tgttatgttt gtgtttgtgt  1140
ttatgaataa aatgaaataa attatgtttg tgttttc                            1177

SEQ ID NO: 295         moltype = DNA  length = 1248
FEATURE                Location/Qualifiers
misc_feature           1..1248
```

|         |                                                           |
| ------- | --------------------------------------------------------- |
|         | note = Genomic Sequence Of Ceres ANNOT ID no. 864284      |
| misc_feature | 1..1248                                              |
|         | note = Encodes the peptide sequence at SEQ ID NO 286      |
| source  | 1..1248                                                   |
|         | mol_type = unassigned DNA                                 |
|         | organism = Arabidopsis thaliana                           |

SEQUENCE: 295

```
ttcacttaac aaaacaagaa ccaaaaaaaa tggatgagaa agatattcta aggaacttga   60
gggaagaaga agaagaagaa gaagaaaatc aaagcgaaga aaccaaaatt ttgatctctt  120
cacttcctig ggagatagat taccttggga acaagctttt caagtaccaa ggatattggt  180
actacgaaga cgttctccaa tcaatcccca atatacactc gagttttcag ccacaagaaa  240
ccgatatagt tgttgcttct ttctacaaat cgggcacgac ttggctcaaa gcactcacat  300
ttgcactcgt tcaacgatca aaacactcgt tagaagatca tcatcatcct ctgctatctc  360
ataaccctca tgagatagta ccgtacctcg agctagatct gtatctcaac agctcaaaac  420
cggacttgac caagttctta tcatcatcat catcatcatc atctccgaga ttgttctcaa  480
ctcatatgtc cttggacgcg cttaaactac ccttgaagaa gtctccttgc aaggtagtgt  540
acgtgtgcag gaacgtgaaa gacgtgttgg tgtcactttg gtgtttcctc aatgccaaca  600
agggagtaga atgggggagat tttagccaaa atgaaaagat cattcgagcg gagaattatt  660
ctttcaaggc tatatttgag tcattctgca acggagttac cctacacggt cccttttggg  720
accatgcaca gagctattgg cgaggcagct tggaagatcc taagcatttt cttttcatga  780
ggtacgagga gttgaaagcg gagcctcgta ctcaggtcaa gagacttgca gagttcttgg  840
attgtccatt cactaaggaa gaggaagata gcggaactgt agacaagatc ttggaacttt  900
gctctctaag taatttaagc agtttggaga tcaacaaaac tggatccttg ggtggagtag  960
attacaagac ttatttccgt aaaggacaag ttggtgactg gaaagagttat atgacctctg 1020
aaatggtaaa taaaatcgat atgatcgtcg aggagaaact caaaggttcc ggtttgaaat 1080
tctagaatta tgcgtgtgct ttgtgaagaa ctgcagaaaa agtgttcttg aatgcgttat 1140
ttaataataa aagttacatt gtcatatata taactttgat gtatcattac aactgatgtg 1200
tggtttttgt tctctttgat gttgcaataa aaaccttctt tacttcta             1248
```

|         |                                                           |
| ------- | --------------------------------------------------------- |
| SEQ ID NO: 296 | moltype = DNA   length = 845                       |
| FEATURE | Location/Qualifiers                                       |
| misc_feature | 1..845                                               |
|         | note = Genomic Sequence Of Ceres ANNOT ID no. 870567      |
| misc_feature | 1..845                                               |
|         | note = Encodes the peptide sequence at SEQ ID NO 284      |
| source  | 1..845                                                    |
|         | mol_type = unassigned DNA                                 |
|         | organism = Arabidopsis thaliana                           |

SEQUENCE: 296

```
ataagaaaat caaatctttt actcgtttga aatttgtaat ccattacctg tcatcgttga   60
cttgtcaaga agaaacaaat caactctaaa agaaaaatg ttgttcatcg aaatcgaagc  120
ttgacagtat tcaaaatcag attcgagatg agctgcgacg gaggcaaacc ggcgccggcg  180
aaactaggcg acgaacaact agcggagctc cgggagatat ctgatcatt tgaccagaac  240
aaggatggaa gtttgacgga gctcgagtta ggctcacttc taagatctct cggtctaaag  300
ccgagtcaag accaactcga cacattgatc cagaaagcag atcggaataa caacggactg  360
gtcgagttct ccgagttcgt cgccctcgtc gagccagatc tggtcaagtg tccttacacg  420
gatgatcagc ttaaagccat ctttagaatg tttgaccgcg atggaaacgg ttacataacg  480
gcggcggagt tagcccattc gatggcgaag ctaggtcacg cgttgacggc ggaggagtta  540
acgggaatga tcaaagaagc tgatcgagac ggcgatggtt gtattgattt ccaagagttt  600
gttcaagcga ttacttcagc tgcgtttgat aatgcttggg gttgaagaaa gaaaggtata  660
tatatacata gttttgaaata cttgtgttt gttttttttgg cttcatcctc aaatcaaaga  720
catttggaag tatatgtgtg taggtgcgat tccatggaaa atgtgtgtta tttattgttt  780
catattattc tttgatgaaa ttttgatagc ttgaagaaga agctatcatt gttggtttta  840
gggca                                                              845
```

|         |                                                           |
| ------- | --------------------------------------------------------- |
| SEQ ID NO: 297 | moltype = DNA   length = 2020                      |
| FEATURE | Location/Qualifiers                                       |
| misc_feature | 1..2020                                              |
|         | note = Ceres CLONE ID no.1792902                          |
| misc_feature | 1..2020                                              |
|         | note = Encodes the peptide sequence at SEQ ID NO 298      |
| source  | 1..2020                                                   |
|         | mol_type = unassigned DNA                                 |
|         | organism = Panicum virgatum                               |

SEQUENCE: 297

```
gtcactctcg gcactgctcc cagctgttgc gacctccgaa catccaaggc tcctgcaccc   60
ctgtcagtcc tagctccagc caaaaatcgt tggctcccgc tgcctgctcc tccgccttgc  120
acctcccatg accttccacg cgacatgatt gcattgcagg ccctgcgga gctcagctgt  180
cctcccacgc cgctgacgcc ttcttgttgc ctccacgctg ctcgctcaa ccgaaaggcg  240
cttcctctct tgcttccgc ggaaggattt ggcgatttat tcatctacta aagttgcatc  300
tctcttgtgc gtggtgattg tttcgaggag cgtggagcgg agccatgggg aagaaggca  360
agtggttcgg cgcggtcaag aaagtgttca gccctgaatc caaggagaag aaggaggaga  420
ggcagaggag gaaatcagca gctagcaacc tactccact agatctgacc ccgtcgacct  480
ccttgaagt caatgttttcg gtgccacccc ctccagctcc tccggctctt caccagatta  540
aggaggtcag gatccctgaa gctgagcagg agcagagcca gcacatcacc gtagaggagg  600
cccctgctgc cctgcacag gcgtcggtgc ttccacctgg tgtgcaagt gaagagcttg  660
ctgcaatcaa gatccagact gccttccgag gttacctggc aaggagggca ctgcgagcgc  720
tgcgggggcct tgttcgattg aagtcattgg ttgagggtga ttcagttagg cgtcaatctg  780
caagcactct gcgctgtatg cagactctat cgcgggtgca gtcacaaata cgttctagga  840
```

```
gagcaaagat gtctgaggag aaccaggccc tccagcgcca gctcctactg aagcaggaac   900
tggagaattt caggatgggt gagaactggg atgacagcac tcaatccaaa gagcaaatcg   960
aggcgagcct aataagcagg caagaggcag cgattagaag agaaagagcg cttgcatatg  1020
catttttcaca tcagtggaag agcacgtcga ggtctgtcaa cccaatgttt gtagacccaa  1080
acaacttgca gtggggctgg agctggctgg agcgctggat ggctgcaaaa ccttgggagg  1140
gccgcaatgg gactgataag gagagcaatg ttgaccgtgg atccgttaag agcatgagct  1200
tgaaccttgg agagggtgag atcactaaag ctttcaaccg ccgggactca aagccagaaa  1260
agccatcccc gccaactcca aaactgaccc gtccagcctc caggcaatcc ccttcaacgc  1320
cctccgctaa agtagcgcca atacctgtga ggagaaaatc cgtcacgcca aagaatgggc  1380
tttcacatgt ggatgacgat gcgagaagtg tgttcagtgt gcagtctgag cgaccaagga  1440
ggcacagtat agccacctcg actgtgcggg acgatgagag tctcgcaagc tcccatcac   1500
tcccaagtta tatggttccc acagaatctg caagggcgaa gtctcgtctc cagggatcag  1560
cattgaataa tggtgcagag acaccagaga aggaagctc tgctgaccg gtcaagaaaa  1620
ggttgtcctt tcaaggtgga acagcgctg cctcaccaat gcgacggcat tctggtcctc  1680
ccaaggtggg gagtgcggtg aaggatattg ttgccccacc acagccagag gccttggtga  1740
tcaatggtgg aagcaagtga ctcatgacaa gtaccaggag ggtaaagcgg acaatgaata  1800
tatattttat ccatgaagaa aggttaacgt gatatcagct ctatgagtga tttgaattgt  1860
tttccagtta cgaccacatt gtttgctcta taagattcac agtacctgcc agttgattcc  1920
attcgttgtt tctgtaaaac aagtaccggt tcgtcactag aatcagtgat gtttgtatgt  1980
aaacaggtct tctatttatg taaaaaaaaa aaaaaaaaa                         2020

SEQ ID NO: 298          moltype = AA   length = 471
FEATURE                 Location/Qualifiers
REGION                  1..471
                        note = Ceres CLONE ID no. 1792902
REGION                  104..124
                        note = Pfam Name: IQ Pfam Description: IQ
                        calmodulin-binding motif
REGION                  1..471
                        note = Functional Homolog of Ceres Ceres Clone ID no.
                        375578 at SEQ ID NO. 252 with e-value of 1.90e-67 and
                        BLAST sequence identity of 51.7
source                  1..471
                        mol_type = protein
                        organism = Panicum virgatum
SEQUENCE: 298
MGKKGKWFGA VKKVFSPESK EKKEERQRRK SAASNPTPLD LTPSTSLEVN VSVPPPPAPP   60
ALHQIKEVRI PEAEQEQSKH ITVEEAPAAP AQASVLPPGV PSEELAAIKI QTAFRGYLAR  120
RALRALRGLV RLKSLVEGDS VRRQSASTLR CMQTLSRVQS QIRSRRAKMS EENQALQRQL  180
LLKQELENFR MGENWDDSTQ SKEQIEASLI SRQEAAIRRE RALAYAFSHQ WKSTSRSVNP  240
MFVDPNNLQW GWSWLERWMA AKPWEGRNGT DKESNVDRGS VKSMSLNLGE GEITKAFNRR  300
DSKPEKPSPP TPKLTRPASR QSPSTPSAKV APIPVRRKSV TPKNGLSHVD DDARSVFSVQ  360
SERPRRHSIA TSTVRDDESL ASSPSLPSYM VPTESARAKS RLQGSALNNG AETPEKGSSA  420
GPVKKRLSFQ GGTAAASPMR RHSGPPKVGS AVKDIVAPPQ PEALVINGGS K           471

SEQ ID NO: 299          moltype = DNA   length = 1880
FEATURE                 Location/Qualifiers
misc_feature            1..1880
                        note = Ceres CLONE ID no.1919901
misc_feature            1..1880
                        note = Encodes the peptide sequence at SEQ ID NO 300
source                  1..1880
                        mol_type = unassigned DNA
                        organism = Gossypium hirsutum
SEQUENCE: 299
aactttctt agttatcctc tgcaaatgcc aacctgttct tttattatta ttttccgcca    60
tttttgctct ctttcaagca ttttttttt gcctagatcc acttctctct ctttgattt    120
taattactgc atttttgttt taatacacaa taagaacaac taagagatag aatgtgactt   180
atcaatcttt taactgagat ctgtgagaat ttttctatgt accaaggaat tatttacaga   240
tgggaaaaa aggtggctgg ctttctattg tgaagaaagc tttgagccct gaatccaaga   300
aatctcagca ccaaactcca aagccaaaga aaaatggtt cggaaaaagc aaaaatttga   360
gccctgtgtc tgtgcctgaa gaaactgaag tgataactga agatgcaaag ctaaagaag   420
ctgaaaacga acaaagcaaa catgcctact ctgtggctct tgccaccgct gtggcggccg   480
aggcagcggt ggcagctgct caggcggctg ctgaagttgt ccgtctcact tctcagccga   540
gccatctggg gaagtcaaag gaggaaatag ctgctatcag gattcaaaca gcatttcgtg   600
gatatttggc taggagggca ctgcgagctt tgagagggtt ggtaaggttg aaatcgttga   660
tcagagggca atccgtcaaa cgccaagcaa ctacaacgtt aagatgcatg cagactctag   720
ctcgtctgca gtctgagatt tctgcaagga ggattagaat gtcagaagag aaccaggctc   780
ttcagcgcca gcttcaacag aaatgccaga aagagctcga gaagttgaga gctcccatga   840
gagaagactg gaacgatagt acacagtcga aggagcagat cgaagcaaga caacaaaata   900
agcaaggagc tactatgaaa agggaaagag cattggctta tgcatactgt caccagcgat   960
cgtggaagaa ctgttctaga tcagtgaatc aaacatttat ggatccgagt aattcacact  1020
gggggttgga ttggttagag cgatggatgg cagccccgacc atgggaagtc caaagcacaa  1080
ctgataacaa tgaccgtggc tcagtcaaga gtatgagtgc ttgttcgata tctataagtg  1140
aaatcagcag agcttattct cgaagagatc ttaacatga taacaaacca tctccaacac  1200
ctcagaagtc aagtcgagtt cctagccgcc agtctccatc gactccacct tcaaaggcac  1260
cttcgatttc atccggtttct ggtaaaacaa gactgccaag tccgagagga agtcaatggg  1320
gagggtatga agactcaagg agcatactca gtacccggtc tgatcgttat aggagacata  1380
gcattgcagg gtcctcaatg agagacgatg agagcctac aagctcacct gcagttccaa  1440
```

```
gttatatggc accaacacag tccacaaagg ccaggtccca cataccaagc cccttaggaa  1500
gtggcacacc agataggaga gtggcagggt ctgcaaagaa acggcttttg ttcccagcat  1560
ccccagccag tagtaggaga cattcagagc ctcctaaagt ggacataagt gaggctagaa  1620
agaatcagca tgcaccaagc aatggaaggc aagtggcttg gtgaagagtg caacaaaagt  1680
tagattgaat aaacatggaa gggttatttc aacttgagt tcttgtagtg tggttgtgat  1740
tatcttttc ttcctaggtt ttatgattat taattataa agggttactt ttttctgggt  1800
gagatttagt ttattgtttg tggttgacaa acattcttaa aaatcttcaa gtttagtttc  1860
aattcatgaa atttgtaatt                                              1880

SEQ ID NO: 300           moltype = AA   length = 474
FEATURE                  Location/Qualifiers
REGION                   1..474
                         note = Ceres CLONE ID no. 1919901
REGION                   109..129
                         note = Pfam Name: IQ Pfam Description: IQ
                           calmodulin-binding motif
REGION                   1..474
                         note = Functional Homolog of Ceres Clone ID no. 375578 at
                           SEQ ID NO. 252 with e-value of 1.10e-62 and BLAST sequence
                           identity of 54.8
source                   1..474
                         mol_type = protein
                         organism = Gossypium hirsutum
SEQUENCE: 300
MGKKGGWLSI VKKALSPESK KSQHQTPKPK KKWFGKSKNL SPVSVPEETE VITEDAKLKE   60
AENEQSKHAY SVALATAVAA EAAVAAAQAA AEVVRLTSQP RHLGKSKEEI AAIRIQTAFR  120
GYLARRALRA LRGLVRLKSL IRGQSVKRQA TTTLRCMQTL ARLQSEISAR RIRMSEENQA  180
LQRQLQQKCQ KELEKLRAPM REDWNDSTQS KEQIEARQQN KQGATMKRER ALAYAYCHQR  240
SWKNCSRSVN QTFMDPSNSH WGWSWLERWM AARPWEVQST TDNNDRGSVK SMGACSISIS  300
EISRAYSRRD LNNDNKPSPT PQKSSRVPSR QSPSTPPSKA PSISSVSGKT RLPSPRGSQW  360
GGYEDSRSIL STRSDRYRRH SIAGSSMRDD ESLTSSPAVP SYMAPTQSTK ARSHIPSPLG  420
SGTPDRRVAG SAKKRLLFPA SPASSRRHSE PPKVDISEAR KNQHAPSNGR QVAW        474

SEQ ID NO: 301           moltype = AA   length = 476
FEATURE                  Location/Qualifiers
REGION                   1..476
                         note = Ceres CLONE ID no. 228069
REGION                   1..476
                         note = Functional Homolog of Ceres Clone ID no. 375578 at
                           SEQ ID NO. 252
source                   1..476
                         mol_type = protein
                         note = Zea mays subsp. mays
                         organism = Zea mays
SEQUENCE: 301
MGKKGKWFGA VKKVFSPESK EKKEERLRRK SAASNPAPVD LTPSTSLEVN VSVPPPPAPP   60
PVPRQTDEVR VPEAEQEQSS HVTLEEAPAA AAAPAQASVL AIKIQTAFRG GAPTEELA    120
YLARRALRAL RGLVRLKSLV EGNSVKRQSA STLRCMQTLS RVQSQIRSRR AKMSEENQAL  180
QRQLLLKQEL ENFRMGENWD DSTQSKEQIE ASLISRQEAA IRRERALAYA FSHQWKSTSR  240
SANPMFVDPN NLQWGWSWLE RWMAAKPWEG RNGTDKESNI DRGSVKNMSL NLGVGEGEIT  300
KAFNRRDSKP EKPSPPTPKP ARPASRQSPS TPSARVAPIP ARRKSSTPKN GLSQVDDDVR  360
SVLSVQSERP RRHSIATTST MRDDESLASS PSLPSYMVPT ESARAKSRTA TANGAETPEK  420
GGSAGPVKKR LSFQGGAAAA SPMRRHSGPP KVESAVKDIA APPQPEALVA NGGGSK      476

SEQ ID NO: 302           moltype = AA   length = 217
FEATURE                  Location/Qualifiers
REGION                   1..217
                         note = Ceres CLONE ID no. 335348
REGION                   1..217
                         note = Ceres Seed Line ID no. ME10681
source                   1..217
                         mol_type = protein
                         note = Zea mays subsp. mays
                         organism = Zea mays
SEQUENCE: 302
MGKKGKWFGA VKKVFSPESK EKKEESNIDR GSVKSMSLNL GEGEITKAFN RRDSKLEKPS   60
PPTPRPARPT SRHSPLTPSA RVAPIPARRK SVTPKNGLSQ VDDDARSVLS VQSERPRRHS  120
IATSTVRDDE SLTSSPSLPS YMVPTESARA KSRLQGSAMA NGAETPEKGG STGPAKKRLS  180
FQGGTAAASP MRRHSGPPKV EIAPPQPEAL VVNGGSK                           217

SEQ ID NO: 303           moltype = AA   length = 474
FEATURE                  Location/Qualifiers
REGION                   1..474
                         note = Public GI ID no. 54306075
source                   1..474
                         mol_type = protein
                         organism = Oryza sativa
SEQUENCE: 303
MGKKGKWFGA VKKVFSPESK EKKEERLRRK LAASNPNPPD LTPSASLEVN VSVPPPPPPP   60
```

```
PVQQIEEVKV PEVEQEQSKH VTVEAVPEAV PVPAQTSSLP PGVSREEQAT IKIQTAFRGY   120
LARRALRALR GLVRLKSLVE GNSVKRQAAS TLRCMQTLAR VQSQIRSRRL KMSEENQALQ   180
RQLLLKQELE SLRMGEQWDD STQSKEQIEA SLISRQEAAV RRERALAYAF SHQWKSTSRS   240
VNPMFVDPNN PQWGWSWLER WMAAKPWEGR AGTDKESNLD RASAKSASLN LGEGEITKAF   300
NRRGSKPDKS SPTTPKLTRP ASRQSPSTPS AKVSPIFAKK KSATPKNGLS QVDDDAKSVF   360
SVQSERPRRH SIATSTVRDD ESLASSPSVP SYMAPTKSAR AKLRLQGSAV TDGAETPPEK   420
VASVGSVKKK LSFQAGMAPP SPMRRHSGPP KVEVVKDIAE PPQPEALVIN GGSK         474

SEQ ID NO: 304            moltype = AA   length = 193
FEATURE                   Location/Qualifiers
REGION                    1..193
                          note = Synthesized Sequence
REGION                    1..193
                          note = Fragment of Ceres CLONE ID no. 335348
source                    1..193
                          mol_type = protein
                          organism = synthetic construct
SEQUENCE: 304
ESNIDRGSVK SMSLNLGEGE ITKAFNRRDS KLEKPSPPTP RPARPTSRHS PLTPSARVAP    60
IPARRKSVTP KNGLSQVDDD ARSVLSVQSE RPRRHSIATS TVRDDESLTS SPSLPSYMVP   120
TESARAKSRL QGSAMANGAE TPEKGGSTGP AKKRLSFQGG TAAASPMRRH SGPPKVEIAP   180
PQPEALVVNG GSK                                                     193

SEQ ID NO: 305            moltype = AA   length = 200
FEATURE                   Location/Qualifiers
REGION                    1..200
                          note = Synthesized Sequence
REGION                    1..200
                          note = Fragment of Ceres CLONE ID no. 228069
source                    1..200
                          mol_type = protein
                          organism = synthetic construct
SEQUENCE: 305
ESNIDRGSVK NMSLNLGVGE GEITKAFNRR DSKPEKPSPP TPKPARPASR QSPSTPSARV    60
APIPARRKSS TPKNGLSQVD DDVRSVLSVQ SERPRRHSIA TTSTMRDDES LASSPSLPSY   120
MVPTESARAK SRTATANGAE TPEKGGSAGP VKKRLSFQGG AAAASPMRRH SGPPKVESAV   180
KDIAAPPQPE ALVANGGGSK                                              200

SEQ ID NO: 306            moltype = AA   length = 189
FEATURE                   Location/Qualifiers
REGION                    1..189
                          note = Synthesized Sequence
REGION                    1..189
                          note = Fragment of Ceres CLONE ID no. 375578
source                    1..189
                          mol_type = protein
                          organism = synthetic construct
SEQUENCE: 306
DPKERAVTKN ASTSAVRVPV SRAISIQRPA TPNKSSRPPS RQSLSTPPSK TPSASGKARP    60
ASPRNSWLYK EDDLRSITSI RSERPRRQST GGGSVRDDTS LTSTPPLPSY MQSTESARAK   120
SRYRSLLLTE KLEVPERAPL AHSVVKKRLS FPVVEKPSVV PTEKPRERVR RHSDPPKVDP   180
ATLKDAPAA                                                          189

SEQ ID NO: 307            moltype = AA   length = 193
FEATURE                   Location/Qualifiers
REGION                    1..193
                          note = Synthesized Sequence
REGION                    1..193
                          note = Fragment of Ceres CLONE ID no. 229668
source                    1..193
                          mol_type = protein
                          organism = synthetic construct
SEQUENCE: 307
ESNIDRGSVK SMSLNLGEGE ITKAFNRRDS KLEKPSPPTP RPARPTSRHS PLTPSARVAP    60
IPARRKSVTP KNGLSQVDDD ARSVLSVQSE RPRRHSIATS TVRDDESLTS SPSLPSYMVP   120
TESARAKSRL QGSAMANGAE TPEKGGSTGP AKKRLSFQGG TAAASPMRRH SGPPKVEIAP   180
PQPEALVVNG GSK                                                     193

SEQ ID NO: 308            moltype = AA   length = 199
FEATURE                   Location/Qualifiers
REGION                    1..199
                          note = Synthesized Sequence
REGION                    1..199
                          note = Fragment of Public GI ID no. 54306075
source                    1..199
                          mol_type = protein
                          organism = synthetic construct
SEQUENCE: 308
ESNLDRASAK SASLNLGEGE ITKAFNRRGS KPDKSSPTTP KLTRPASRQS PSTPSAKVSP    60
```

```
IFAKKKSATP KNGLSQVDDD AKSVFSVQSE RPRRHSIATS TVRDDESLAS SPSVPSYMAP    120
TKSARAKLRL QGSAVTDGAE TPPEKVASVG SVKKKLSFQA GMAPPSPMRR HSGPPKVEVV    180
KDIAEPPQPE ALVINGGSK                                                199

SEQ ID NO: 309          moltype = AA   length = 188
FEATURE                 Location/Qualifiers
REGION                  1..188
                        note = Synthesized Sequence
REGION                  1..188
                        note = Fragment of Public GI ID no. 56202321
source                  1..188
                        mol_type = protein
                        organism = synthetic construct
SEQUENCE: 309
DPKDHYSTKN PSTSASRTYV PRAISIQRPA TPNKSSRPPS RQSPSTPPSR VPSVTGKIRP    60
ASPRDSWLYK EDDLRSITSI RSERPRRQST GGASVRDDAS LTSTPALPSY MQSTESARAK    120
SRYRSLLTDR FEVPERVPLV HSSIKKRLSF PVADKPNGEH ADKLMERGRR HSDPPKVDPA    180
SLKDVPVS                                                             188

SEQ ID NO: 310          moltype = AA   length = 199
FEATURE                 Location/Qualifiers
REGION                  1..199
                        note = Synthesized Sequence
REGION                  1..199
                        note = Fragment of Ceres CLONE ID. 1792902
source                  1..199
                        mol_type = protein
                        organism = synthetic construct
SEQUENCE: 310
ESNVDRGSVK SMSLNLGEGE ITKAFNRRDS KPEKPSPPTP KLTRPASRQS PSTPSAKVAP    60
IPVRRKSVTP KNGLSHVDDD ARSVFSVQSE RPRRHSIATS TVRDDESLAS SPSLPSYMVP    120
TESARAKSRL QGSALNNGAE TPEKGSSAGP VKKRLSFQGG TAAASPMRRH SGPPKVGSAV    180
KDIVAPPQPE ALVINGGSK                                                 199

SEQ ID NO: 311          moltype = AA   length = 200
FEATURE                 Location/Qualifiers
REGION                  1..200
                        note = Synthesized Sequence
REGION                  1..200
                        note = Fragment of Ceres CLONE ID no. 1727738
source                  1..200
                        mol_type = protein
                        organism = synthetic construct
SEQUENCE: 311
KESNIDRGSV KSMSLNLGEG EITKAFNRRD SKPEKPSPPT PKLTRPASRQ SPSTPSAKVA    60
PIPARRKSAT PENGLSHVDD DARSVFSVQS ERPRRHSIAT STVQDNESLA SSPSLPSYMV    120
PTESARAKSR LQGSALTNGA ETPEKGSSAG PVKKRLSFQG GTAAASPMRR HSGPPKVDSA    180
VKDIVAPPQP EALVINGGSK                                                200

SEQ ID NO: 312          moltype = AA   length = 471
FEATURE                 Location/Qualifiers
REGION                  1..471
                        note = Ceres CLONE ID no. 1727738
REGION                  1..471
                        note = Functional Homolog of Ceres Clone ID no. 375578 at
                          SEQ ID NO. 252
source                  1..471
                        mol_type = protein
                        organism = Panicum virgatum
SEQUENCE: 312
MGKKGKWFGA VKKVFSPESK EKKEERQRRK SAASNPTPRD LTPSTSLEVN VSVPPPPAPP    60
ALHQIEEIRA PEAEQEQSKH VTVEEAPAAP AQASVLPPGV PSEELAAIKI QTAFRGYLAR    120
RALRALRGLV RLKSLVEGDS VRRQSASTLR CMQTLSRVQS QIRSRRAKMS EENQALQRQL    180
LLKQELENFR MGENWDDSTQ SKEQIEASLI SRQEAAIRRE RALAYAFSHQ WKSTSRSVNP    240
MFVDPNNLQW GWSWLERWMA AKPWEGCNGA DKESNIDRGS VKSMSLNLGE GEITKAFNRR    300
DSKPEKPSPP TPKLTRPASR QSPSTPSAKV APIPARRKSA TPENGLSHVD DDARSVFSVQ    360
SERPRRHSIA TSTVQDNESL ASSPSLPSYM VPTESARAKS RLQGSALTNG AETPEKGSSA    420
GPVKKRLSFQ GGTAAASPMR RHSGPPKVDS AVKDIVAPPQ PEALVINGGS K             471

SEQ ID NO: 313          moltype = DNA   length = 1806
FEATURE                 Location/Qualifiers
misc_feature            1..1806
                        note = Ceres CLONE ID no. 228069
misc_feature            1..1806
                        note = Encodes the peptide sequence at SEQ ID NO 301
source                  1..1806
                        mol_type = unassigned DNA
                        note = Zea mays subsp. mays
                        organism = Zea mays
```

-continued

```
SEQUENCE: 313
gagccgcgga ggagcagcgg cgcatcgcaa cactaaccaa agtcctcctc tccaggtgcc   60
gagccagggt gactgttccg aggagcgtgg cgtggaccca tggggaagaa gggcaagtgg  120
ttcggtgccg tcaagaaggt cttcagcccc gaatccaagg agaagaaaga ggagaggcta  180
aggaggaaat cagcagctag caacccagca ccggtagatc tgaccccatc tacctccctg  240
gaagtcaatg tttcggtgcc accccctccg gctcctcctc cagttcctcg ccagaccgac  300
gaggtcaggg tccccgaagc cgagcaggag cagagcaagc atgtcaccct ggaggaggcc  360
cctgctgctg ctgctgcccc agcacaggcg tcggtgctgc cacctggtgc gccaaccgaa  420
gagctcgccg caatcaagat ccagaccgcc ttccgaggtt acctggcaag gagggcacta  480
agagcactac gaggccttgt acgattgaag tcattggttg agggtaattc agttaagcgt  540
caatctgcaa gcactctgcg ctgtatgcaa actctatcgc gggtgcagtc acaaatacga  600
tctaggagag caaagatgtc cgaggagaac caggccctcc aacgccagct cctacttaaa  660
caggaactgg agaatttcag aatgggtgag aactgggacg cagcactcca atccaaggag  720
caaatcgagg caagcctaat aagcaggcaa gaggcagcga taagaagaga aagagctctt  780
gcatatgcat tttcacatca gtggaagagc acatcaagat ctgcgaaccc aatgttgta   840
gacccaaata acttgcagtg gggctggagc tggttggagc gctggatggc agcaaaacct  900
tgggagggac gcaatgggac cgacaaggag agcaacattg atcgcggctc cgtcaagaat  960
atgagcttga accttggagt tggagagggt gagatcacaa aagcttttca ccgccgggac 1020
tcaaagccag agaagccatc accaccgact ccaaaaccgg cccgtccagc ttccaggcaa 1080
tccccttcga cgccctctgc tagagtggcc ccaatacctg cgaggaggaa atccagcacg 1140
ccaaagaatg ggctttcaca ggtggacgat gacgtgagga gcgtgctcag tgtgcagtct 1200
gagcgaccaa ggaggcacag catagccacg acgtcgacca gtgggacga tgagagccta 1260
gcgagctccc cgtcgctccc gagctacatg gttcccacag aatctgcgag gccaaatct  1320
cgcacagcaa cggccaatgg cgcagagacg cctgagaaag gaggctctgc tggaccagtc 1380
aagaagaggt tgtctttcca aggtggagct gcggctgcct caccgatgcg acggcattct 1440
ggccctccca aggtggagag cgctgtgaag gacattgcag cctcaccaca gcctgaggcc 1500
ttggtagcca atggtggtgg aagcaagtga cttgtattga caagttccag gatggggag  1560
cgggttatgg tcttatggag ggacatgttt catccgtgaa cagaagttaa gagtggtgcc 1620
ggatctacga atggtttgaa ttgttttccc gttacaacca cattgtttgc tgtataagat 1680
tcactgtacc tgccagttgg ttccatttgt tgttttctgt aaaacaaaca tcaatttgtc 1740
actagaatct gtgatgcttg tatgtaaaca ggtcctctat ttatgtgagc catatatttc 1800
attttc                                                            1806

SEQ ID NO: 314          moltype = DNA  length = 1083
FEATURE                 Location/Qualifiers
misc_feature            1..1083
                        note = Ceres CLONE ID no. 335348
misc_feature            1..1083
                        note = Encodes the peptide sequence at SEQ ID NO 302
source                  1..1083
                        mol_type = unassigned DNA
                        note = Zea mays subsp. mays
                        organism = Zea mays
SEQUENCE: 314
aaccccgcc gtatcggtct tgttcgttgt cctgccagat acagataggt ggctaccact    60
ggctcgcgtg acctgttggc ttgcttgctc ctctccaggt tcaggcaggg gagagtgcct  120
gtttcagggg ggcgtggagc ggagccggag ccatgggaga gaaggggcaag tggttcggcg  180
ccgtcaagaa ggtcttcagc cctgaatcca aggagaagaa agaggagagc aacattgacc  240
ggggatccgt taagagcatg agcttgaacc ttggagaggg tgagatcaca aaagcttca   300
accgccggga ctcaaagcta gaaaagccat cgccgccaac tccaagaccg gcccgtccaa  360
cttccaggca ttcccctttg acgccctctg ctagagtgga ccgataccct gcgaggagaa  420
aatctgtcac gcccaagaac gggctttcac aggtggacga tgacgcgagg agcgtgctca  480
gtgtgcagtc tgagcggcca aggaggcaca gtatagccac ctcgactgtg cgggacgacg  540
agagcctcac gagctccccg tcgctcccaa gctacatggt tcccacgaaa tctgcaaggg  600
ccaaatctcg cctccagggt tcagcaatgg ccaatggcgc agagacct agaaaaggag   660
gctcaactgg accagccaag aagaggttat ccttccaggg tggaactgcg gctgcctcgc  720
caatgcgacg acattctggt cctcccaagg tggagatcgc gccaccacaa ccagaggcct  780
tggtagtcaa tggtggaagc aagtgacaca tatgtgatga gtaccaggat gagaaacgga  840
ttatgaagat attagtttca ttttcatcca tgaataagaag ttaaaagtgg tatcatatct  900
atgaatggtt tcaattgttt tctgttaca accacattat ttgctatata cgattcacag  960
tacctgccag ttgattccat tggttgtttc tgtaaaacaa atatcaattt gtcactagaa 1020
tctgtgatgt ttgtatgtaa acagatcctc tatttatgtg agacatatat ttcttttctt 1080
tcg                                                              1083

SEQ ID NO: 315          moltype = DNA  length = 2024
FEATURE                 Location/Qualifiers
misc_feature            1..2024
                        note = Ceres CLONE ID no. 1727738
misc_feature            1..2024
                        note = Encodes the peptide sequence at SEQ ID NO 312
source                  1..2024
                        mol_type = unassigned DNA
                        organism = Panicum virgatum
SEQUENCE: 315
gttctctctc cctcgtcact ctcgccactg ctcccagctg ttgcgacctc cgatcatcca   60
aggtcctgc accccgtca gtcctagctc cagccaaaaa tcgttggctt ccgctgcctg   120
ctcctccgcc ttgcacctcc catgaccttc cacgcgacat gattgcattg caggcccctg   180
cggagctcag tgtcctccca cgccgctgac gccttcttgt tgcctcccg ctgctgcgca  240
caaccgaaag ggccttcctc tcttcctttg cttccgcgga aagatttggc gatttgttca  300
```

-continued

```
tctactaaag ttgcatctct cttggtgatt gtttcgagga gtgtggagtg gagccatggg  360
gaagaagggc aagtggttcg gcgcggtcaa gaaagtgttc agccctgaat ccaaggagaa  420
gaaggaggag aggcagagga ggaaatcagc agctagcaac cctactccac gagatctgac  480
cccgtcgacc tccttggaag tcaatgtttc ggtgccaccc cctccagctc ctccggcect  540
tcaccagatt gaggaaatca gggccectga agctgagcag gagcagagca agcacgtcac  600
cgtagaggag gctcctgctg cccctgcaca ggcgtcggtg ctgccacctg gtgtgccaag  660
tgaagagctt gctgcaatca agattcagac tgccttccga ggttacctgg caaggagggc  720
actgcgagcg ctgcggggcc ttgttcgatt gaaatcattg gttgagggtg attcagttag  780
gcgtcaatct gcaagcactc ttcgctgtat gcagactcta tcgcgggtgc agtcacaaat  840
acgttctagg agagcaaaga tgtctgagga gaaccaggcc cttcagcgcc agctcctact  900
gaagcaggaa ctggagaatt tcaggatggg tgagaactgg gatgacagca ctcaatccaa  960
agagcaaatc gaggcaagcc taataagcag gcaagaggca gcgattagaa gagaaagagc  1020
gcttgcatat gcattttcac atcagtggaa gagcacttcg agatctgtca acccaatgtt  1080
tgtagaccca aacaacttgc agtggggctg gagctggttg gagcgctgga tggctgcaaa  1140
accttgggag ggctgcaatg gggctgataa ggagagcaac attgaccgtg gatctgttaa  1200
gagcatgagc ttgaaccttg gagagggtga gatcacaaaa gctttcaacc gccgggactc  1260
aaagccagaa aagccatcac cgccaactcc aaaactaacc cgtccagcct ccaggcaatc  1320
cccttcgacg ccctctgcta aagtagcgcc aatacctgct aggagaaaat ccgccacgcc  1380
agagaatgcg ctttcacatg tggatgacga tgcgagaagt gtgttcagcg tgcagtctga  1440
gcgaccaagg aggcacagta tagccacctc gactgtgcag gacaatgaga gtctcgcaag  1500
ctccccatca ctcccaagtt acatggttcc cacagaatct gcaagggcga agtctcgtct  1560
ccagggatca gcattgacta atggtgcaga gacaccagag aaaggaagct ctgctggacc  1620
ggtcaagaaa aggttgtcat ttcaaggtgg aacagcggct gcctccaccaa tgcgacggca  1680
ttctggtcct cccaaggtgg acagtgcggt gaaggatatt gttgcccac cacagccaga  1740
ggccttggtg atcaatggtg gaagcaagtg actcatacca ggaggggaaa gcggattatg  1800
aatatatatt ttatcgatga agaaaggtta acgtgatatc agctcaatga gtgatttgaa  1860
ttgttttctt acgaccacat tgtttgctct ataagattcg cagtacctgc cagttgattc  1920
cattcgttgt ttctgtaaaa caagtatcgg ttcgtcacta gaatcaatga agtttgtatg  1980
taaacaggtc ttctatttat gtgagccata tatttcttct tctg              2024
```

What is claimed is:

1. A plant cell transformed with a recombinant nucleic acid molecule, wherein the recombinant nucleic acid molecule comprises a promoter operably linked to a nucleic acid, wherein the promoter and the nucleic acid are heterologous to each other, wherein said nucleic acid comprises a nucleotide sequence selected from the group consisting of:
   (a) a nucleotide sequence that encodes a protein comprising an amino acid sequence that has at least 95% amino acid sequence identity to the amino acid sequence of SEQ ID NO: 106;
   (b) a nucleotide sequence that encodes a protein that comprises the amino acid sequence of SEQ ID NO: 106;
   (c) a nucleotide sequence comprising the polynucleotide sequence of SEQ ID NO:105, wherein the nucleotide sequence encodes the protein as set forth in SEQ ID NO: 6; and
   (d) a nucleotide sequence comprising a polynucleotide sequence that has at least 95% nucleotide sequence identity to the nucleotide sequence as set forth in SEQ ID NO:105 and encodes a protein having the functional activity of SEQ ID NO: 6, and
   wherein a transformed plant produced from said transformed plant cell expresses said protein of parts (a), (b), (c) or (d) and exhibits increased salt tolerance as compared to a control plant of the same species that does not comprise said recombinant nucleic acid and is grown under identical growth conditions.

2. A transgenic plant comprising the transformed plant cell of claim 1, wherein the transgenic plant exhibits increased tolerance to salinity as compared to a control plant of the same species that does not comprise the recombinant nucleic acid molecule and is grown under identical growth conditions.

3. A progeny of the transgenic plant of claim 2, wherein said progeny comprises the recombinant nucleic acid molecule and has increased salt tolerance as compared a control plant of the same species that does not comprise said recombinant nucleic acid molecule and is grown under identical growth conditions.

4. A seed from a transgenic plant according to claim 2, wherein the seed is transgenic and comprises the recombinant nucleic acid molecule.

5. A vegetative tissue from a transgenic plant according to claim 2, wherein said vegetative tissue comprises the recombinant nucleic acid molecule.

6. A food product comprising the vegetative tissue of claim 5, wherein said food product comprises the recombinant nucleic acid molecule.

7. A feed product comprising a vegetative tissue from a transgenic plant according to claim 2, wherein the feed product comprises the nucleic acid molecule.

8. A product comprising a vegetative tissue from a transgenic plant according to claim 2 used for the conversion into fuel or chemical feedstocks, wherein the product comprises the recombinant nucleic acid molecule.

9. The transgenic plant of claim 2, wherein the nucleotide sequence encodes a protein that comprises the amino acid sequence of SEQ ID NO:106.

10. The transgenic plant of claim 2, wherein the nucleotide sequence encodes a protein comprising an amino acid sequence having at least 97% amino acid sequence identity to the amino acid sequence of SEQ ID NO:106.

11. The transgenic plant of claim 2, wherein the nucleotide sequence comprising the polynucleotide sequence of SEQ ID NO:105.

12. The transgenic plant of claim 2, wherein the nucleotide sequence has at least 97% nucleotide sequence identity to the nucleotide sequence as set forth in SEQ ID NO: 105, and encodes a protein having the functional activity of SEQ ID NO: 106.

13. The transgenic plant of claim 2, wherein the nucleotide sequence has at least 99% nucleotide sequence identity to the nucleotide sequence as set forth in SEQ ID NO: 105, and encodes a protein having the functional activity of SEQ ID NO: 106.

14. The transgenic plant of claim 2, wherein the nucleotide sequence encodes a protein that comprises an amino acid sequence having at least 99% amino acid sequence identity to the amino acid sequence of SEQ ID NO: 106.

15. The transgenic plant of claim 2, wherein the nucleotide sequence comprises the polynucleotide sequence of SEQ ID NO:105.

* * * * *